(12) United States Patent
Demont et al.

(10) Patent No.: US 8,697,725 B2
(45) Date of Patent: Apr. 15, 2014

(54) TETRAHYDROQUINOLINE DERIVATIVES AND THEIR PHARMACEUTICAL USE

(75) Inventors: Emmanuel Hubert Demont, Stevenage (GB); Neil Stuart Garton, Stevenage (GB); Romain Luc Marie Gosmini, Les Ulis (FR); Thomas George Christopher Hayhow, Stevenage (GB); Jonathan Seal, Stevenage (GB); David Matthew Wilson, Stevenage (GB); Michael David Woodrow, Stevenage (GB)

(73) Assignee: GlaxoSmithKline LLC, Philadelphia, PA (US)

( * ) Notice: Subject to any disclaimer, the term of this patent is extended or adjusted under 35 U.S.C. 154(b) by 70 days.

(21) Appl. No.: 13/501,159

(22) PCT Filed: Nov. 3, 2010

(86) PCT No.: PCT/EP2010/066693
§ 371 (c)(1),
(2), (4) Date: Apr. 10, 2012

(87) PCT Pub. No.: WO2011/054841
PCT Pub. Date: May 12, 2011

(65) Prior Publication Data
US 2012/0208798 A1 Aug. 16, 2012

(30) Foreign Application Priority Data
Nov. 2, 2009 (GB) .................. 0919431.7

(51) Int. Cl.
*A61K 31/04* (2006.01)
*C07D 215/38* (2006.01)

(52) U.S. Cl.
USPC .......................... 514/312; 546/159

(58) Field of Classification Search
USPC .......................... 546/159; 514/312
See application file for complete search history.

(56) References Cited

FOREIGN PATENT DOCUMENTS

EP 0987251 A1 3/2000
WO 2009084693 A1 7/2009

OTHER PUBLICATIONS

Denis, Discov Med, Dec. 2010, vol. 10(55), pp. 489-499.*
Mertz, PNAS, Oct. 2011, vol. 108, No. 40, pp. 16669-16674.*
Manzo, F., et al; Histone acetyltransferase inhibitors and preclinical studies; Expert Opin Ther Patents; Jun. 2009; 19, No. 6; 761-774.

* cited by examiner

*Primary Examiner* — D M Seaman
(74) *Attorney, Agent, or Firm* — Robert H. Brink

(57) ABSTRACT

Tetrahydroquinoline compounds of formula (I)

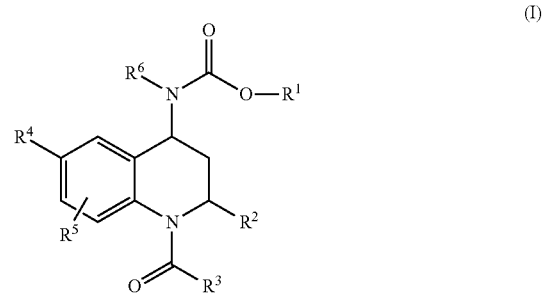

and salts thereof, pharmaceutical compositions containing such compounds and their use in therapy.

17 Claims, No Drawings

TETRAHYDROQUINOLINE DERIVATIVES AND THEIR PHARMACEUTICAL USE

CROSS-REFERENCE TO RELATED APPLICATIONS

This application is filed pursuant to 35 USC 371 as a United States National Phase Application of International Patent Application Serial No. PCT/EP2010/066693 filed on Nov. 3, 2010, which claims priority from 0919431.7 filed on Nov. 5, 2009 in the United Kingdom.

FIELD OF THE INVENTION

The present invention relates to tetrahydroquinoline derivatives, pharmaceutical compositions containing such compounds and to their use in therapy.

BACKGROUND OF THE INVENTION

The genomes of eukaryotic organisms are highly organised within the nucleus of the cell. The long strands of duplex DNA are wrapped around an octomer of histone proteins (most usually comprising two copies of histones H2A, H2B H3 and H4) to form a nucleosome. This basic unit is then further compressed by the aggregation and folding of nucleosomes to form a highly condensed chromatin structure. A range of different states of condensation are possible, and the tightness of this structure varies during the cell cycle, being most compact during the process of cell division. Chromatin structure plays a critical role in regulating gene transcription, which cannot occur efficiently from highly condensed chromatin. The chromatin structure is controlled by a series of post translational modifications to histone proteins, notably histones H3 and H4, and most commonly within the histone tails which extend beyond the core nucleosome structure. These modifications include acetylation, methylation, phosphorylation, ubiquitinylation, SUMOylation. These epigenetic marks are written and erased by specific enzymes, which place the tags on specific residues within the histone tail, thereby forming an epigenetic code, which is then interpreted by the cell to allow gene specific regulation of chromatin structure and thereby transcription.

Histone acetylation is most usually associated with the activation of gene transcription, as the modification loosens the interaction of the DNA and the histone octomer by changing the electrostatics. In addition to this physical change, specific proteins bind to acetylated lysine residues within histones to read the epigenetic code. Bromodomains are small (~110 amino acid) distinct domains within proteins that bind to acetylated lysine resides commonly but not exclusively in the context of histones. There is a family of around 50 proteins known to contain bromodomains, and they have a range of functions within the cell.

The BET family of bromodomain containing proteins comprises 4 proteins (BRD2, BRD3, BRD4 and BRD-t) which contain tandem bromodomains capable of binding to two acetylated lysine residues in close proximity, increasing the specificity of the interaction. BRD2 and BRD3 are reported to associate with histones along actively transcribed genes and may be involved in facilitating transcriptional elongation (Leroy et al, Mol. Cell. 2008 30(1):51-60), while BRD4 appears to be involved in the recruitment of the pTEF-β complex to inducible genes, resulting in phosphorylation of RNA polymerase and increased transcriptional output (Hargreaves et al, Cell, 2009 138(1): 129-145). It has also been reported that BRD4 or BRD3 may fuse with NUT (nuclear protein in testis) forming novel fusion oncogenes, BRD4-NUT or BRD3-NUT, in a highly malignant form of epithelial neoplasia (French et al. Cancer Research, 2003, 63, 304-307 and French et al. Journal of Clinical Oncology, 2004, 22 (20), 4135-4139). Data suggests that BRD-NUT fusion proteins contribute to carcinogensesis (Oncogene, 2008, 27, 2237-2242). BRD-t is uniquely expressed in the testes and ovary. All family members have been reported to have some function in controlling or executing aspects of the cell cycle, and have been shown to remain in complex with chromosomes during cell division—suggesting a role in the maintenance of epigenetic memory. In addition some viruses make use of these proteins to tether their genomes to the host cell chromatin, as part of the process of viral replication (You et al Cell, 2004 117(3):349-60).

Japanese patent application JP2008-156311 discloses a benzimidazole derivative which is said to be a BRD2 bromodomain binding agent which has utility with respect to virus infection/proliferation.

Patent application WO2009084693 discloses a series of thienotriazolodiazepiene derivatives that are said to inhibit the binding between an acetylated histone and a bromodomain containing protein which are said to be useful as anti-cancer agents.

A novel class of compounds have been found which inhibit the binding of bromodomains with its cognate acetylated proteins, more particularly a class of compounds that inhibit the binding of BET family bromodomains to acetylated lysine residues. Such compounds will hereafter be referred to as "bromodomain inhibitors".

SUMMARY OF THE INVENTION

In a first aspect of the present invention, there is provided a compound of formula (I) or a salt thereof, more particularly a pharmaceutically acceptable salt thereof.

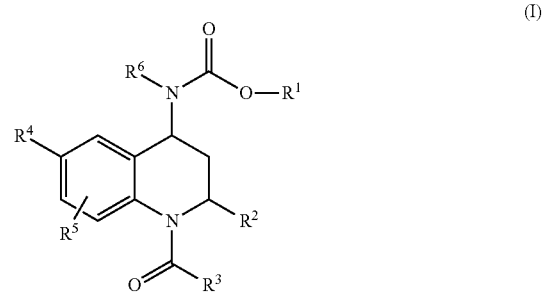

(I)

In a second aspect of the present invention, there is provided a pharmaceutical composition comprising a compound of formula (I) or a pharmaceutically acceptable salt thereof and one or more pharmaceutically acceptable carriers, diluents or excipients.

In a third aspect of the present invention, there is provided a compound of formula (I), or a pharmaceutically acceptable salt thereof for use in therapy, in particular in the treatment of diseases or conditions for which a bromodomain inhibitor is indicated.

In a fourth aspect of the present invention, there is provided a method of treating diseases or conditions for which a bromodomain inhibitor is indicated in a subject in need thereof which comprises administering a therapeutically effective amount of a compound of formula (I) or a pharmaceutically acceptable salt thereof.

In a fifth aspect of the present invention, there is provided the use of a compound of formula (I), or a pharmaceutically acceptable salt thereof in the manufacture of a medicament for the treatment of diseases or conditions for which a bromodomain inhibitor is indicated.

DETAILED DESCRIPTION OF THE INVENTION

The present invention relates to compounds of formula (I) or a salt thereof.

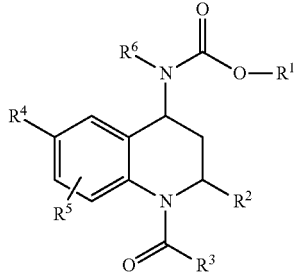
(I)

in which
$R^1$ is $C_{1-6}$alkyl, $C_{3-7}$cycloalkyl or benzyl;
$R^2$ is $C_{1-4}$alkyl;
$R^3$ is $C_{1-4}$alkyl;
$R^4$ is (i) halogen;
   (ii) hydroxy; or
   (iii) a group of formula (iii)

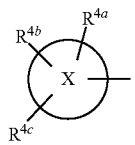
(iii)

in which
X is aryl or heteroaryl;
$R^{4a}$ is hydrogen, $C_{1-4}$alkyl or is a group L-Y in which L is a single bond or a $C_{1-6}$alkylene group and Y is OH, OMe, $CO_2H$, $CO_2C_{1-6}$alkyl, CN or $NR^7R^8$;
$R^7$ and $R^8$ are independently hydrogen, a heterocyclyl ring, $C_{1-6}$alkyl optionally substituted by hydroxy or a heterocyclyl ring; or
$R^7$ and $R^8$ combine together to form a heterocyclyl ring optionally substituted by $C_1$ alkyl, $CO_2C_{1-6}$alkyl, $NH_2$ or oxo;
$R^{4b}$ and $R^{4c}$ are independently hydrogen, halogen, $C_{1-6}$alkyl or $C_{1-6}$alkoxy;
$R^5$ is hydrogen, halogen, $C_{1-6}$alkyl or $C_{1-6}$alkoxy;
$R^6$ is hydrogen or $C_{1-4}$alkyl.

In one embodiment there is provided a compound of formula (I) or a salt thereof

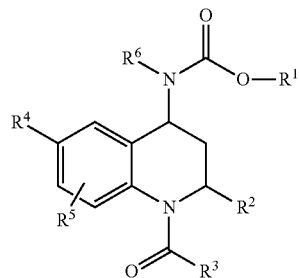
(I)

in which
$R^1$ is $C_{1-6}$alkyl, $C_{3-7}$cycloalkyl or benzyl;
$R^2$ is $C_{1-4}$alkyl;
$R^3$ is $C_{1-4}$alkyl;
$R^4$ is (i) halogen;
   (ii) hydroxy; or
   (iii) a group of formula (iii)

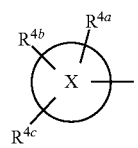
(iii)

in which
X is aryl or heteroaryl;
$R^{4a}$ is hydrogen, $C_{1-4}$alkyl or is a group L-Y in which L is a single bond or a $C_{1-6}$alkylene group and Y is OH, $CO_2H$, CN or $NR^7R^8$;
$R^7$ and $R^8$ are independently hydrogen, a heterocyclyl ring, $C_{1-6}$alkyl optionally substituted by hydroxy or a heterocyclyl ring; or
$R^7$ and $R^8$ combine together to form a heterocyclyl ring optionally substituted by $C_{1-6}$alkyl, $CO_2C_{1-6}$alkyl, $NH_2$ or oxo;
$R^{4b}$ and $R^{4c}$ are independently hydrogen, halogen, $C_{1-6}$alkyl or $C_{1-6}$alkoxy;
$R^5$ is hydrogen, halogen, $C_{1-6}$alkyl or $C_{1-6}$alkoxy;
$R^6$ is hydrogen or $C_{1-4}$alkyl.

In one embodiment the invention provides compounds of formula (I) with cis relative stereochemistry across the tetrahydroquinoline ring in respect of the substituents in the 2 and 4 position on the ring. In one embodiment the compound of formula (I) or a salt thereof is the (2S,4R) enantiomer.

In one embodiment $R^1$ is methyl, ethyl, isopropyl, cyclobutyl or benzyl. In one embodiment $R^{1a}$ is isopropyl.

In one embodiment $R^2$ is methyl.
In one embodiment $R^3$ is methyl.

For compounds of formula (I) in which $R^4$ is a group of formula (iii) and X is heteroaryl, the heteroaryl group may be attached to the rest of the molecule via a carbon atom or when present a suitable nitrogen atom.

In one embodiment $R^4$ is a group of formula (iii) in which X is phenyl or is a heteroaryl group selected from the group consisting of pyridyl, furanyl, pyrazolyl, thiazolyl, pyridazinyl, pyrazinyl and pyrimidinyl. In a further embodiment $R^4$ is a group of formula (i) in which P is phenyl or pyridyl.

In a further embodiment $R^4$ is a group of formula (iii) in which X is a heteroaryl group selected from the group consisting of imidazolyl, triazolyl, oxadiazolyl and thiadiazolyl.

In a further embodiment $R^4$ is a group of formula (iii) and $R^{4a}$ is a group L-Y wherein L is a single bond, $CH_2$ or $CH_2CH_2$ and Y is a group $NR^7R^8$ in which $R^7$ and $R^8$ are independently hydrogen or $C_{1-6}$alkyl.

In a further embodiment $R^4$ is a group of formula (iii) and $R^{4a}$ is a group L-Y wherein L is a single bond, $CH_2$ or $CH_2CH_2$ and Y is a group $NR^7R^8$ in which $R^7$ and $R^8$ combine together to form a heterocyclyl ring selected from the group consisting of pyrrolidinyl, piperidinyl, piperazinyl, morpholinyl, azepinyl and diazapinyl; said rings being optionally substituted by $C_{1-6}$alkyl, $CO_2C_{1-6}$alkyl, $NH_2$ or oxo.

In a further embodiment $R^4$ is a group of formula (iii) and $R^{4a}$ is a group L-Y wherein L is a single bond, $CH_2$ or $CH_2CH_2$ and Y is a $CO_2H$ group In a further embodiment $R^4$ is a group of formula (iii) and $R^{4a}$ is a group L-Y wherein L is $CH_2$ or $CH_2CH_2$ and Y is OH.

In one embodiment $R^{4b}$ is hydrogen or methyl.
In one embodiment $R^{4c}$ is hydrogen or methyl.
In one embodiment $R^5$ is hydrogen.
In one embodiment $R^6$ is hydrogen.

In a particular embodiment of the invention there is a provided a compound of formula (Ia) or a salt thereof.

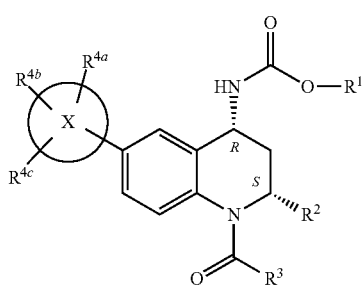

(Ia)

in which
$R^1$, $R^2$, $R^3$, $R^{4a-4c}$ and X are as defined in formula (I) and wherein S and R denote the stereochemistry at the adjacent chiral centre.

In one embodiment X is a compound of formula (Ia) or a salt thereof in which X is phenyl or pyridyl.

While the embodiments for each variable have generally been listed above separately for each variable, this invention is intended to include all combinations of embodiments described hereinabove including salts thereof.

Specific compounds according to the invention include Examples 1-123 as described herein or a salt thereof.

Particular compounds according to the invention are:
1-methylethyl((2S,4R)-1-acetyl-2-methyl-6-{4-[(methylamino)methyl]phenyl}-1,2,3,4-tetrahydro-4-quinolinyl)carbamate;
1-methylethyl {(2S,4R)-1-acetyl-2-methyl-6-[6-(1-piperazinyl)-3-pyridinyl]-1,2,3,4-tetrahydro-4-quinolinyl}carbamate;
1-methylethyl {(2S,4R)-1-acetyl-2-methyl-6-[4-(1-piperidinylmethyl)phenyl]-1,2,3,4-tetrahydro-4-quinolinyl}carbamate;
1-methylethyl((2S,4R)-1-acetyl-2-methyl-6-{1-[2-(methylamino)ethyl]-1H-pyrazol-4-yl}-1,2,3,4-tetrahydro-4-quinolinyl)carbamate;
(2S,4R)-1-Acetyl-6-bromo-2-methyl-1,2,3,4-tetrahydro-4-quinolinamine;
1-Methylethyl[(2S,4R)-1-acetyl-2-methyl-6-(5-methyl-1,2,4-oxadiazol-3-yl)-1,2,3,4-tetrahydro-4-quinolinyl]carbamate;
1-Methylethyl[(2S,4R)-1-acetyl-2-methyl-6-(1H-1,2,3-triazol-4-yl)-1,2,3,4-tetrahydro-4-quinolinyl]carbamate;
1-Methylethyl {(2S,4R)-1-acetyl-6-[5-(aminomethyl)-1,2,4-oxadiazol-3-yl]-2-methyl-1,2,3,4-tetrahydro-4-quinolinyl}carbamate;
{4-[(2S,4R)-1-Acetyl-2-methyl-4-({[(1-methylethyl)oxy]carbonyl}amino)-1,2,3,4-tetrahydro-6-quinolinyl]phenyl}acetic acid;
1-Methylethyl[(2S,4R)-1-acetyl-2-methyl-6-(5-methyl-1,3,4-thiadiazol-2-yl)-1,2,3,4-tetrahydro-4-quinolinyl]carbamate;
1-Methylethyl {(2S,4R)-1-acetyl-6-[3-(aminomethyl)-1,2,4-oxadiazol-5-yl]-2-methyl-1,2,3,4-tetrahydro-4-quinolinyl}carbamate;
1-Methylethyl {(2S,4R)-1-acetyl-6-[3-(2-aminoethyl)-1,2,4-oxadiazol-5-yl]-2-methyl-1,2,3,4-tetrahydro-4-quinolinyl}carbamate;
1-Methylethyl((2S,4R)-1-acetyl-2-methyl-6-{3-[2-(methylamino)ethyl]-1,2,4-oxadiazol-5-yl}-1,2,3,4-tetrahydro-4-quinolinyl)carbamate;
1-Methylethyl[(2S,4R)-1-acetyl-6-(4-aminophenyl)-2-methyl-1,2,3,4-tetrahydro-4-quinolinyl]carbamate;
1-Methylethyl((2S,4R)-1-acetyl-2-methyl-6-{4-[(2-oxo-1-piperazinyl)methyl]phenyl}-1,2,3,4-tetrahydro-4-quinolinyl)carbamate;
1-Methylethyl {(2S,4R)-1-acetyl-6-[1-(3-aminopropyl)-1H-1,2,3-triazol-4-yl]-2-methyl-1,2,3,4-tetrahydro-4-quinolinyl}carbamate;
1-Methylethyl {(2S,4R)-1-acetyl-6-[1-(2-hydroxyethyl)-1H-1,2,3-triazol-4-yl]-2-methyl-1,2,3,4-tetrahydro-4-quinolinyl}carbamate;
{4-[(2S,4R)-1-Acetyl-2-methyl-4-({[(1-methylethyl)oxy]carbonyl}amino)-1,2,3,4-tetrahydro-6-quinolinyl]-1H-1,2,3-triazol-1-yl}acetic acid;
1-Methylethyl {(2S,4R)-1-acetyl-6-[5-(2-aminoethyl)-1,2,4-oxadiazol-3-yl]-2-methyl-1,2,3,4-tetrahydro-4-quinolinyl}carbamate;
1-Methylethyl((2S,4R)-1-acetyl-6-{5-[2-(dimethylamino)ethyl]-1,2,4-oxadiazol-3-yl}-2-methyl-1,2,3,4-tetrahydro-4-quinolinyl)carbamate;
1-Methylethyl {(2S,4R)-1-acetyl-6-[1-(2-aminoethyl)-1H-1,2,3-triazol-4-yl]-2-methyl-1,2,3,4-tetrahydro-4-quinolinyl}carbamate;
1-Methylethyl((2S,4R)-1-acetyl-6-{1-[2-(dimethylamino)ethyl]-1H-1,2,3-triazol-4-yl}-2-methyl-1,2,3,4-tetrahydro-4-quinolinyl)carbamate;
1-Methylethyl((2S,4R)-1-acetyl-6-{1-[3-(dimethylamino)propyl]-1H-1,2,3-triazol-4-yl}-2-methyl-1,2,3,4-tetrahydro-4-quinolinyl)carbamate;
1-Methylethyl[(2S,4R)-1-acetyl-2-methyl-6-(1-methyl-1H-imidazol-5-yl)-1,2,3,4-tetrahydro-4-quinolinyl]carbamate;
1-Methylethyl[(2S,4R)-1-acetyl-2-methyl-6-(1-methyl-1H-imidazol-4-yl)-1,2,3,4-tetrahydro-4-quinolinyl]carbamate;
1-Methylethyl[(2S,4R)-1-acetyl-2-methyl-6-(4-methyl-1H-imidazol-1-yl)-1,2,3,4-tetrahydro-4-quinolinyl]carbamate;
1-Methylethyl {(2S,4R)-1-acetyl-6-[1-(2-aminoethyl)-1H-imidazol-4-yl]-2-methyl-1,2,3,4-tetrahydro-4-quinolinyl}carbamate;
1-Methylethyl[(2S,4R)-1-acetyl-6-(1H-imidazol-2-yl)-2-methyl-1,2,3,4-tetrahydro-4-quinolinyl]carbamate;
1-Methylethyl[(2S,4R)-1-acetyl-2-methyl-6-(2-methyl-1H-imidazol-1-yl)-1,2,3,4-tetrahydro-4-quinolinyl]carbamate;

1-Methylethyl[(2S,4R)-1-acetyl-2-methyl-6-(2-methylphenyl)-1,2,3,4-tetrahydro-4-quinolinyl]carbamate;
1-Methylethyl[(2S,4R)-1-acetyl-2-methyl-6-phenyl-1,2,3,4-tetrahydro-4-quinolinyl]carbamate;
1-Methylethyl {(2S,4R)-1-acetyl-6-[4-(2-hydroxyethyl)phenyl]-2-methyl-1,2,3,4-tetrahydro-4-quinolinyl}carbamate;
1-Methylethyl {(2S,4R)-1-acetyl-6-[4-(2-aminoethyl)phenyl]-2-methyl-1,2,3,4-tetrahydro-4-quinolinyl}carbamate;
1-Methylethyl((2S,4R)-1-acetyl-2-methyl-6-{4-[2-(methylamino)ethyl]phenyl}-1,2,3,4-tetrahydro-4-quinolinyl)carbamate;
{4-[(2S,4R)-1-Acetyl-2-methyl-4-({[(1-methylethyl)oxy]carbonyl}amino)-1,2,3,4-tetrahydro-6-quinolinyl]phenyl}acetic acid;
1-Methylethyl[(2S,4R)-1-acetyl-2-methyl-6-(2-pyridinyl)-1,2,3,4-tetrahydro-4-quinolinyl]carbamate;
3-{4-[(2S,4R)-1-Acetyl-2-methyl-4-({[(1-methylethyl)oxy]carbonyl}amino)-1,2,3,4-tetrahydro-6-quinolinyl]phenyl}propanoic acid;
1-Methylethyl[(2S,4R)-1-acetyl-2-methyl-6-(4-methyl-1H-imidazol-1-yl)-1,2,3,4-tetrahydro-4-quinolinyl]carbamate;
1-methylethyl[(2S,4R)-1-acetyl-2-methyl-6-(5-methyl-1H-imidazol-1-yl)-1,2,3,4-tetrahydro-4-quinolinyl]carbamate;
1-Methylethyl {(2S,4R)-1-acetyl-2-methyl-6-[5-(1-piperazinyl methyl)-1,3-thiazol-2-yl]-1,2,3,4-tetrahydro-4-quinolinyl}carbamate;
1-Methylethyl((2S,4R)-1-acetyl-2-methyl-6-{1-[(methyloxy)methyl]-1H-pyrazol-4-yl}-1,2,3,4-tetrahydro-4-quinolinyl)carbamate;
1-Methylethyl((2S,4R)-1-acetyl-2-methyl-6-{1-[2-(methyloxy)ethyl]-1H-pyrazol-4-yl}-1,2,3,4-tetrahydro-4-quinolinyl)carbamate;
1-Methylethyl {(2S,4R)-1-acetyl-6-[1-(2-hydroxyethyl)-1H-pyrazol-4-yl]-2-methyl-1,2,3,4-tetrahydro-4-quinolinyl}carbamate;
1-Methylethyl {(2S,4R)-1-acetyl-6-[1-(2-hydroxy-2-methylpropyl)-1H-pyrazol-4-yl]-2-methyl-1,2,3,4-tetrahydro-4-quinolinyl}carbamate;
1-Methylethyl[(2S,4R)-1-acetyl-6-bromo-2-methyl-1,2,3,4-tetrahydro-4-quinolinyl]carbamate;
1-Methylethyl((2S,4R)-1-acetyl-2-methyl-6-{3-[(methylamino)methyl]phenyl}-1,2,3,4-tetrahydro-4-quinolinyl)carbamate;
4-[(2S,4R)-1-Acetyl-2-methyl-4-({[(1-methylethyl)oxy]carbonyl}amino)-1,2,3,4-tetrahydro-6-quinolinyl]benzoic acid;
1-Methylethyl {(2S,4R)-1-acetyl-6-[3,4-bis(methyloxy)phenyl]-2-methyl-1,2,3,4-tetrahydro-4-quinolinyl}carbamate;
4-[(2S,4R)-1-Acetyl-2-methyl-4-({[(1-methylethyl)oxy]carbonyl}amino)-1,2,3,4-tetrahydro-6-quinolinyl]-3-methylbenzoic acid;
1-Methylethyl((2S,4R)-1-acetyl-2-methyl-6-{4-[(4-piperidinylamino)methyl]phenyl}-1,2,3,4-tetrahydro-4-quinolinyl)carbamate;
1-Methylethyl[(2S,4R)-1-acetyl-6-(2,4-dimethyl-1H-imidazol-1-yl)-2-methyl-1,2,3,4-tetrahydro-4-quinolinyl]carbamate;
1-Methylethyl[(2S,4R)-1-acetyl-6-(4-cyanophenyl)-2-methyl-1,2,3,4-tetrahydro-4-quinolinyl]carbamate;
1,1-Dimethylethyl {(2S,4R)-1-acetyl-6-[1-(2-hydroxyethyl)-1H-1,2,3-triazol-4-yl]-2-methyl-1,2,3,4-tetrahydro-4-quinolinyl}carbamate; and
1-Methylethyl((2S,4R)-1-acetyl-6-{1-[2-(dimethylamino)ethyl]-1H-pyrazol-4-yl}-2-methyl-1,2,3,4-tetrahydro-4-quinolinyl)carbamate; or a salt thereof.

Throughout the present specification, unless otherwise stated:

the term "halogen" is used to describe a group selected from fluorine, chlorine or bromine;

the terms "$C_{1-4}$alkyl" and "$C_{1-6}$alkyl" are used to describe a group or a part of the group comprising a linear or branched alkyl group containing from 1 to 4 or 1 to 6 carbon atoms respectively. Suitable examples of such groups include methyl, ethyl, propyl, isopropyl, n-butyl, isobutyl, t-butyl, pentyl and hexyl;

the term "$C_{1-6}$alkylene" is used to describe a divalent radical comprising a linear or branched alkyl group containing from 1 to 6 carbon atoms. Suitable examples of such groups include methylene (—$CH_2$—), ethylene (—$CH_2CH_2$—) and propylene (—$CH_2CH_2CH_2$—);

the term "$C_{1-6}$alkoxy" is used to describe a group wherein an oxygen atom is bound to the rest of the molecule and to the above mentioned $C_{1-6}$alkyl group. Suitable examples include methoxy, ethoxy, propoxy, isopropoxy, n-butoxy, isobutoxy, t-butoxy, pentoxy and hexoxy;

the term "heterocyclyl" or "heterocyclyl ring" is used to describe a saturated 4-7 membered monocyclic ring containing one or two heteroatoms selected from nitrogen, oxygen and sulphur. Suitable examples include azetidinyl, pyrrolidinyl, piperidinyl, piperazinyl, morpholinyl, azepinyl, diazapinyl, tetrahydrofuranyl and tetrahydropyranyl;

the term "heteroaryl" is used to describe an aromatic or a benzofused aromatic ring containing 1 to 3 heteroatoms selected from oxygen, nitrogen and sulphur. Suitable examples of such aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such benzofused aromatic rings include quinolinyl, isoquinolinyl, indolyl, benzofuryl, benzothienyl, benzimidazolyl and benzoxazolyl;

the term "$C_{3-7}$cycloalkyl" is used to describe a non-aromatic carbocyclic ring containing at least three and at most seven carbon atoms. Examples of $C_{3-7}$cycloalkyl include cyclopropyl, cyclobutyl, cyclopentyl, cyclohexyl and cycloheptyl.

The term "aryl" is used to describe an aromatic hydrocarbon ring such as phenyl or naphthyl.

the term "substituted" refers to substitution with the named substituent or substituents, multiple degrees of substitution, which may be the same or different, being allowed unless otherwise stated. When the substituent is on a ring comprising a heteroatom (e.g. substituents $R^{4a-4c}$ on the group of formula (iii) in which X is a heteroaryl) the substituent may be located on a carbon or a heteroatom, if the latter is appropriate.

It will be appreciated that the present invention covers compounds of formula (I) as the free base and as salts thereof, for example as a pharmaceutically acceptable salt thereof. In one embodiment the invention relates to compounds of formula (I) or a pharmaceutically acceptable salt thereof.

Because of their potential use in medicine, salts of the compounds of formula (I) are desirably pharmaceutically acceptable. Suitable pharmaceutically acceptable salts can include acid or base addition salts. As used herein, the term 'pharmaceutically acceptable salt' means any pharmaceutically acceptable salt or solvate of a compound of the invention, which upon administration to the recipient is capable of providing (directly or indirectly). For a review on suitable salts see Berge et al., J. Pharm. Sci., 66:1-19, (1977). Typically, a pharmaceutically acceptable salt may be readily prepared by using a desired acid or base as appropriate. The resultant salt may precipitate from solution and be collected by filtration or may be recovered by evaporation of the solvent.

A pharmaceutically acceptable base addition salt can be formed by reaction of a compound of formula (I) with a suitable inorganic or organic base, (e.g. triethylamine, ethanolamine, triethanolamine, choline, arginine, lysine or histidine), optionally in a suitable solvent, to give the base addition salt which is usually isolated, for example, by crystallisation and filtration. Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

A pharmaceutically acceptable acid addition salt can be formed by reaction of a compound of formula (I) with a suitable inorganic or organic acid (such as hydrobromic, hydrochloric, sulphuric, nitric, phosphoric, succinc, maleic, acetic, propionic, fumaric, citric, tartaric, lactic, benzoic, salicylic, glutamaic, aspartic, p-toluenesulfonic, benzenesulfonic, methanesulfonic, ethanesulfonic, naphthalenesulfonic such as 2-naphthalenesulfonic, or hexanoic acid), optionally in a suitable solvent such as an organic solvent, to give the salt which is usually isolated for example by crystallisation and filtration. A pharmaceutically acceptable acid addition salt of a compound of formula (I) can comprise or be for example a hydrobromide, hydrochloride, sulfate, nitrate, phosphate, succinate, maleate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g. 2-naphthalenesulfonate) or hexanoate salt.

Other non-pharmaceutically acceptable salts, e.g. formates, oxalates or trifluoroacetates, may be used, for example in the isolation of the compounds of formula (I), and are included within the scope of this invention.

The invention includes within its scope all possible stoichiometric and non-stoichiometric forms of the salts of the compounds of formula (I).

It will be appreciated that many organic compounds can form complexes with solvents in which they are reacted or from which they are precipitated or crystallized. These complexes are known as "solvates". For example, a complex with water is known as a "hydrate". Solvents with high boiling points and/or capable of forming hydrogen bonds such as water, xylene, N-methylpyrrolidinone, methanol and ethanol may be used to form solvates. Methods for identification of solvates include, but are not limited to, NMR and microanalysis. Solvates of the compounds of formula (I) are within the scope of the invention.

The invention includes within its scope all possible stoichiometric and non-stoichiometric forms of the solvates of the compounds of formula (I).

The invention encompasses all prodrugs, of the compound of the invention, which upon administration to the recipient is capable of providing (directly or indirectly) the compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives.

The compounds of formula (I) may be in crystalline or amorphous form. Furthermore, some of the crystalline forms of the compounds of formula (I) may exist as polymorphs, which are included within the scope of the present invention. Polymorphic forms of compounds of formula (I) may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

Compounds described herein contain chiral atoms so that optical isomers, e.g. enantiomers or diastereoisomers may be formed. Accordingly, the present invention encompasses all isomers of the compounds of formula (I) whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Separation of isomers may be achieved by conventional techniques known to those skilled in the art, e.g. by fractional crystallisation, chromatography or HPLC.

Certain compounds of formula (I) may exist in one of several tautomeric forms. It will be understood that the present invention encompasses all tautomers of the compounds of formula (I) whether as individual tautomers or as mixtures thereof.

It will be appreciated from the foregoing that included within the scope of the invention are solvates, isomers and polymorphic forms of the compounds of formula (I) and salts thereof.

The compounds of formula ( ) and salts thereof may be made by a variety of methods, including standard chemistry. Any previously defined variable will continue to have the previously defined meaning unless otherwise indicated. Illustrative general synthetic methods are set out below and then specific compounds of formula (I) or salts thereof are prepared in the working Examples.

The present invention further provides a process for the preparation of a compound of formula (I) or a salt thereof which comprises a process selected from (a), (b), (c), (d) or (e) in which:

(a) comprises reacting a compound of formula (II)

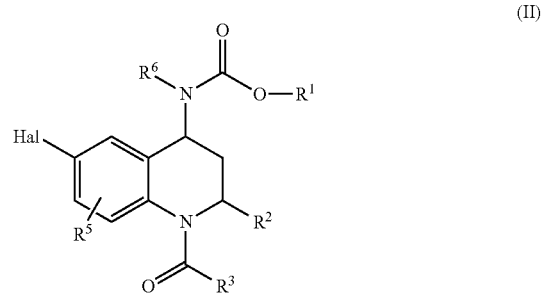

(II)

in which $R^1$, $R^2$, $R^3$, $R^5$ and $R^6$ are as defined in formula (I) and Hal is halogen with a compound of formula (IIIa) or (IIIb) or a protected derivative thereof

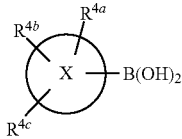
(IIIa)

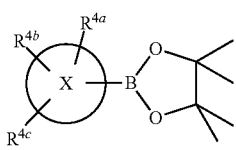
(IIIb)

in which $R^{4a}$, $R^{4b}$, $R^{4c}$ and X are as defined in formula (I);

(b) comprises reacting a compound of formula (IVa) or (IVb)

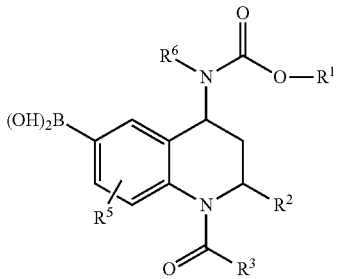
(IVa)

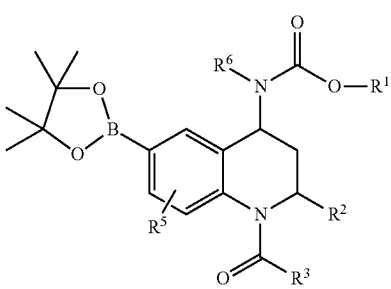
(IVb)

in which $R^1$, $R^2$, $R^3$, $R^5$ and $R^6$ is as defined in formula (I) with a compound of formula (V)

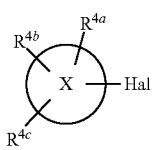
(V)

in which $R^{4a}$, $R^{4b}$ and $R^{4c}$ are as defined in formula (I) and Hal is halogen;

(c) comprises the reaction of a compound of formula (VI)

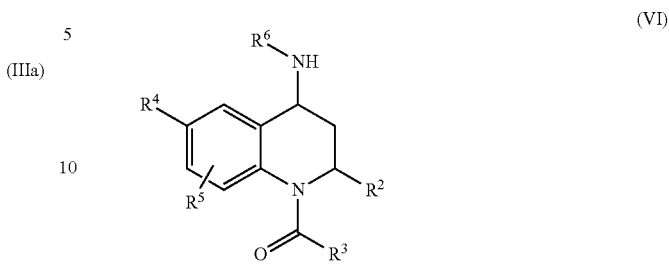
(VI)

in which $R^2$, $R^3$, $R^4$, $R^5$ and $R^6$ are as defined in formula (I) with a compound of formula (VII)

$$R^1OC(O)Hal \quad (VII)$$

in which $R^1$ is as defined in formula (I) and Hal is halogen;

(d) comprises, for compounds in which $R^{4a}$ is a group L-Y wherein L is $CH_2$ and Y is $NR^aR^b$, the reductive amination of a compound of formula (VIII)

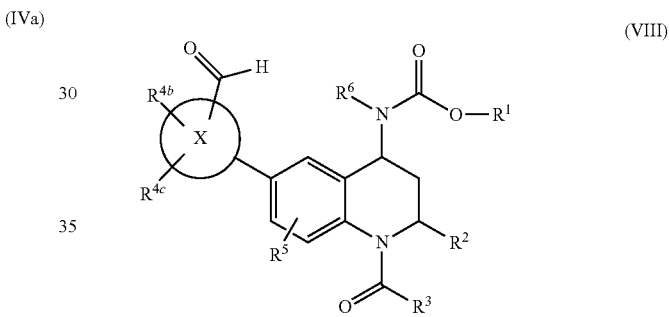
(VIII)

in which $R^1$, $R^2$, $R^3$, $R^{4b}$, $R^{4c}$, $R^5$, $R^6$ and X are as defined in formula (I) with a compound of formula (IX) or a protected derivative thereof $$NHR^7R^8 \quad (IX)$$

in which $R^7$ and $R^8$ are as defined in formula (I);

(e) comprises reaction of a compound of formula (X)

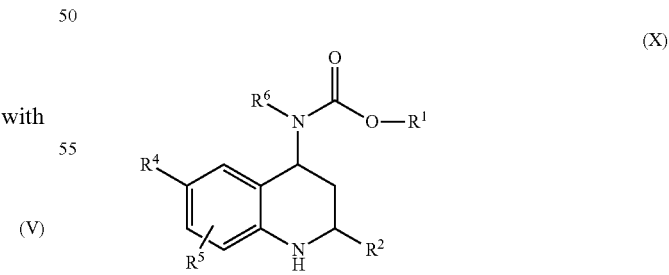
(X)

in which $R^1$, $R^2$, $R^4$, $R^5$ and $R^6$ are as defined in formula (I) with a compound of formula (XI)

$$R^3C(O)Hal \quad (XI)$$

in which $R^3$ is as defined in formula (I) and Hal is halogen.

Process (a)

For process (a), a suitable halogen is bromo. This reaction may be carried out by stirring a compound of formula (II) with the boronic acid of formula (III) in the presence of a suitable catalyst such as Pd(PPh$_3$)$_4$, a base such as aqueous sodium or potassium carbonate and a suitable solvent, for example, DME, ethanol or toluene at a non-extreme temperature such as reflux, for example 85° C., for a period of, for example 5 to 24 hours such as about 12 hours.

A compound of formula (II), for example in which L$^1$ is bromo, may be prepared by a method as described in Scheme 1.

Scheme 1

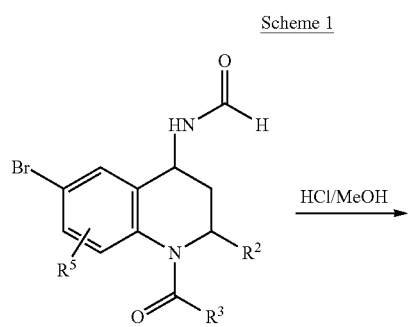

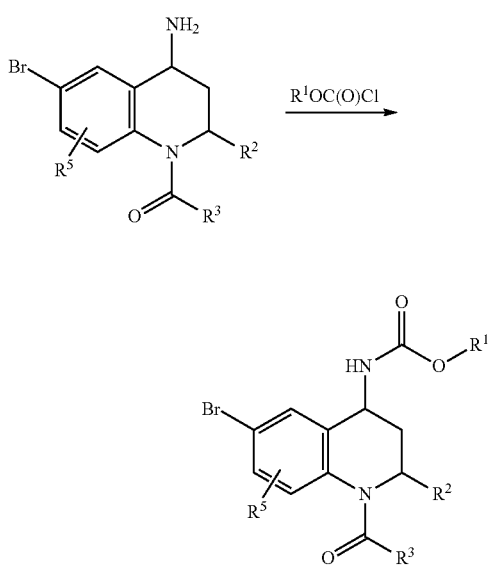

It will be appreciated that the compounds of formula (II) may be in racemic form or as a stereospecific isomer. By way of illustration, a stereospecific synthesis of a compound of formula (II) is provided in Scheme 2.

Scheme 2

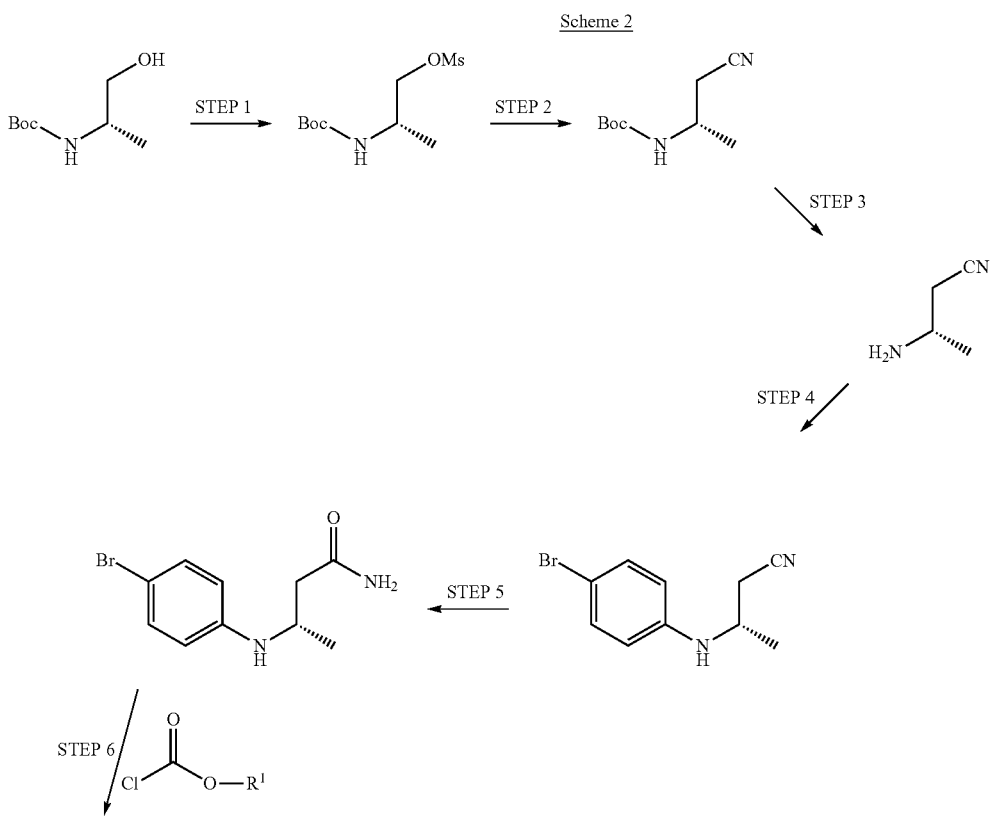

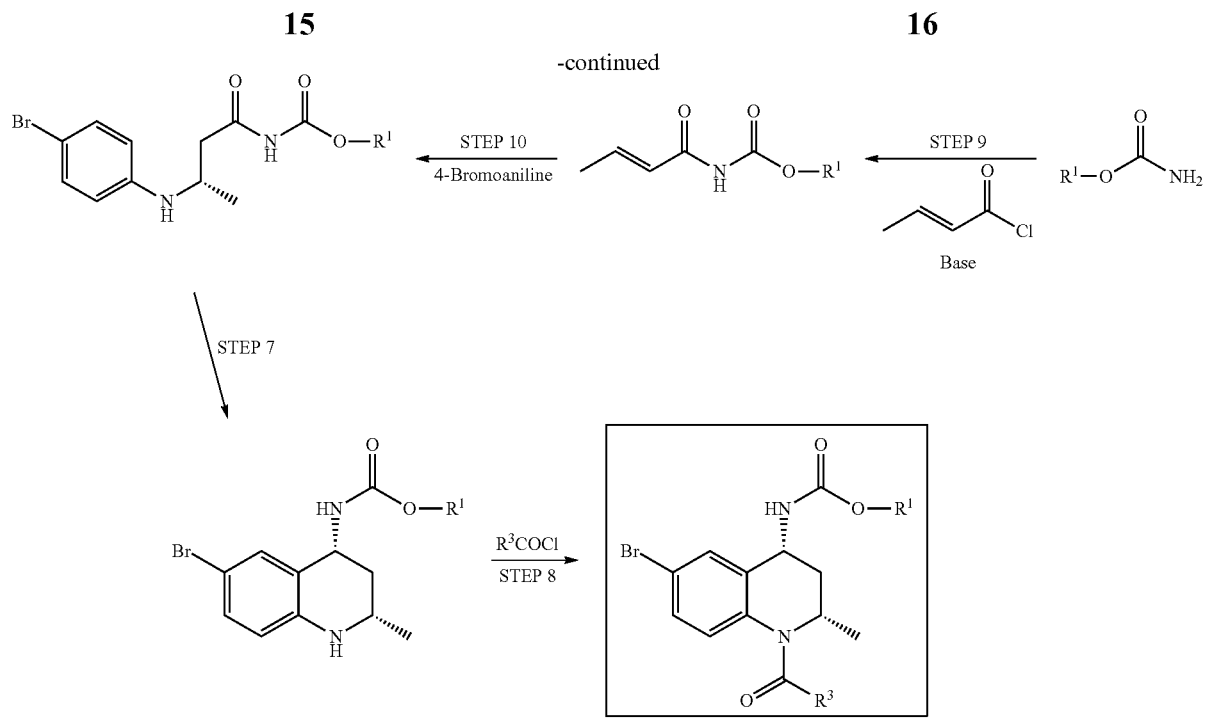

In respect of steps shown in FIG. 2 the following reactions conditions may be utilised.

Step 1 may be carried out by treating with a suitable reagent such as methane sulfonyl chloride, in the presence of a suitable base, such as TMEDA, in a suitable solvent, such as ethyl acetate, at a suitable temperature, such as 0° C., for a period of for example 1 hour.

Step 2 may be carried out with a suitable source of cyanide, such as tetrabutylammonium cyanide, which may be formed in situ from tetrabutylammonium bromide and sodium cyanide, in a suitable solvent, such as DMF, at a suitable temperature, such as 40° C.

Step 3 may be carried out in the presence of a suitable strong acid, such as methanesulfonic acid or TFA, in a suitable solvent such as THF or DCM, at a suitable temperature such as room temperature to 60° C., for a period of, for example, 3 to 24 hours.

Step 4 may be carried out by coupling with 1,4-dibromobenzene or 1,4-iodobromobenzene, under Buchwald coupling conditions in the presence of a suitable catalyst, such as palladium (II) acetate, and a suitable ligand, such as 2-Dicyclohexylphosphino-2'-(N,N-dimethylamino)biphenyl, in the presence of a suitable base, such as cesium carbonate, optionally in the presence of a suitable catalyst such as phenylboronic acid, in a suitable solvent, such as toluene, at an elevated temperature, such as 80° C., for a suitable period, such as 18 hours. Alternatively this may be carried out in two steps, firstly by coupling with bromobenzene as previously described, followed by treating with a brominating agent, for example N-bromosuccinimide, in a suitable solvent such as DMF at a suitable temperature, such as 0° C., for a suitable period, for example less than 1 hour, such as 20 minutes.

Step 5 may be carried out with a suitable acid, such as sulphuric acid, in a suitable solvent, such as toluene, at a suitable temperature, such as 60° C., for a suitable period, such as 2 hours.

Step 6 may be carried out with a suitable base, such as Lithium tert-butoxide, in a suitable solvent, such as ethyl acetate or THF, at a suitable temperature, such as 0° C., for a suitable period, for example less than 1 hour, such as 20 minutes.

Step 7 may be carried out with a suitable reducing agent, such as sodium borohydride, in the presence of a suitable lewis acid, such as magnesium chloride, in a suitable solvent, such as ethanol, at a suitable temperature, such as −5° C., followed by treatment with a suitable acid, such as hydrochloric acid.

Step 8 may be carried out by stirring with an acid chloride $R_3COCl$ in the presence of pyridine in a suitable solvent, such as DCM, at a reduced temperature such as 0° C., for less than 4 hours such as about 2 hours.

Step 9 may be carried out in the presence of a suitable base such as n-butyllithium, in a suitable solvent such as THF, at a suitable temperature such as −78° C.

Step 10 may be carried out in the presence of a suitable catalyst such as (R-BINAP)ditriflatebis(acetonitrile)palladium(II) in a suitable solvent such as toluene, at a suitable temperature such as room temperature for a suitable time such as 18-24 hours, as described in Eur. J. Org. Chem., 2004, p. 959-964.

Compounds of formula (IIIa) or (IIIb) are either commercially available or can be prepared by methods described herein or by analogous procedures thereto.

Process (b)

For process (a), a suitable halogen is bromo. This reaction may be carried out under similar conditions to those described in Process (a).

Compounds of formula (IVa), (IVb) and (V) are either commercially available or can be prepared by methods described herein or by analogous procedures thereto.

Process (c)

For process (a), a suitable halogen is chloro. This reaction may be carried out in a suitable solvent (e.g. DCM) in the presence of a suitable base (e.g. an organic base such as diisopropylethylamine) at a non-extreme temperature such as room temperature.

Compounds of formula (VI) can be prepared in accordance with the procedure outlined in Scheme 3.

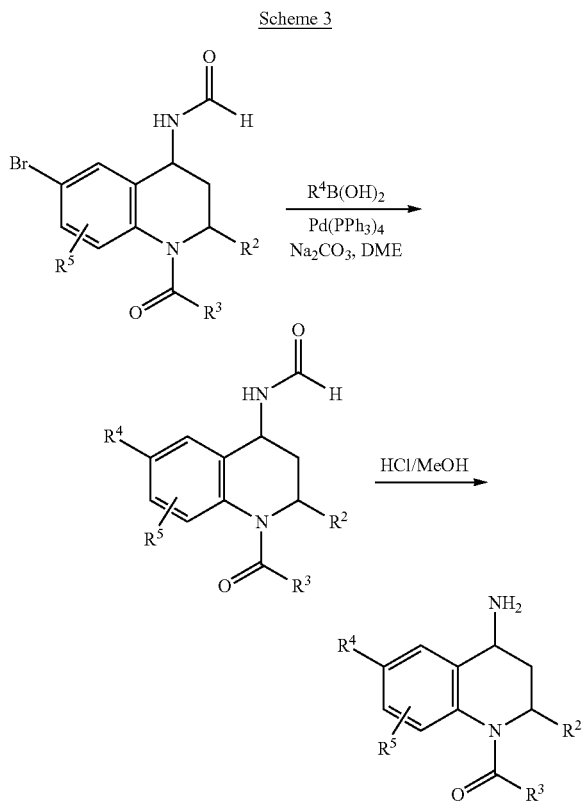

Compounds of formula (VII) are either commercially available or can be prepared by methods described herein or by analogous procedures thereto.

Process (d)

This reaction may be carried out by stirring the compound of formula (VIII) with the amine reagent of formula (IX) in the presence of a reducing agent such as a hydride, for example sodium borohydride or tri-acetoxysodium borohydride, and a catalytic amount of acetic acid in a suitable solvent, such as DCM at a non-extreme temperature, for example room temperature.

Compounds of formula (VIII), in which X is phenyl, may be prepared by the representative procedure outlined in Scheme 4

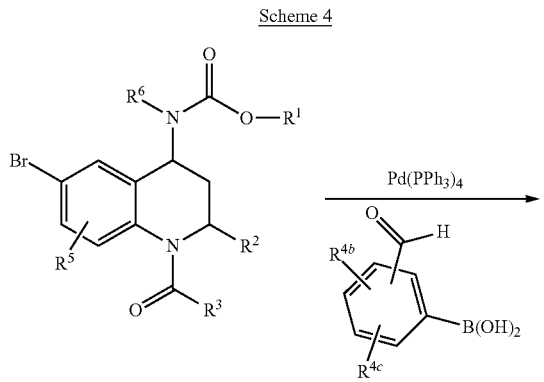

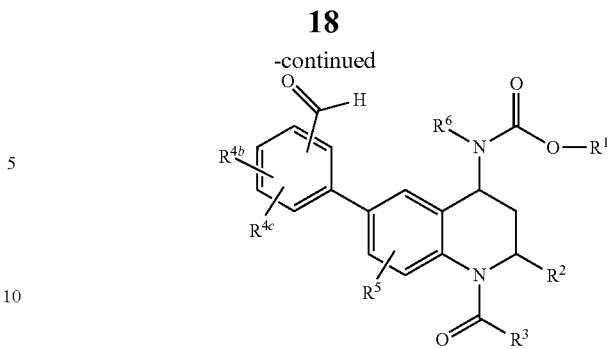

Process (e)

For process (e), a suitable halogen is chloro. This reaction may be carried out under similar conditions to those described in Process (c).

Compounds of formula (X), and (XI) are either commercially available or can be prepared by methods described herein or by analogous procedures thereto.

It will be appreciated by those skilled in the art that it may be advantageous to protect one or more functional groups of the compounds described in processes (a)-(e). Examples of protecting groups and the means for their removal can be found in T. W. Greene 'Protective Groups in Organic Synthesis' (4th edition, J. Wiley and Sons, 2006). Suitable amine protecting groups include acyl (e.g. acetyl, carbamate (e.g. 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid in dioxane or trifluoroacetic acid in dichloromethane) or reductively (e.g. hydrogenolysis of a benzyl or benzyloxycarbonyl group or reductive removal of a 2',2',2'-trichloroethoxycarbonyl group using zinc in acetic acid) as appropriate. Other suitable amine protecting groups include trifluoroacetyl (—COCF$_3$) which may be removed by base catalysed hydrolysis.

It will be appreciated that in any of the routes (a)-(e) described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Certain intermediate compounds described above are believed to be novel and therefore form a yet further aspect of the invention. Particular intermediate compounds of the invention are compounds of formula (II), compounds of formula (VI), compounds of formula (VIII) and compounds of formula (X).

The compounds of formula (I) and salts thereof are bromodomain inhibitors, and thus are believed to have potential utility in the treatment of diseases or conditions for which a bromodomain inhibitor is indicated.

The present invention thus provides a compound of formula (I) or a pharmaceutically acceptable salt thereof for use in therapy. The compound of formula (I) or pharmaceutically salt thereof can be used in the treatment of diseases or conditions for which a bromodomain inhibitor is indicated.

The present invention thus provides a compound of formula (I) or a pharmaceutically acceptable salt thereof for use in the treatment of any diseases or conditions for which a bromodomain inhibitor is indicated.

Also provided is the use of a compound of formula (I) or a pharmaceutically acceptable salt thereof in the manufacture of a medicament for the treatment of diseases or conditions for which a bromodomain inhibitor is indicated.

Also provided is a method of treating diseases or conditions for which a bromodomain inhibitor is indicated in a subject in need thereof which comprises administering a therapeutically effective amount of compound of formula (I) or a pharmaceutically acceptable salt thereof.

Suitably the subject in need thereof is a mammal, particularly a human.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

Bromodomain inhibitors are believed to be useful in the treatment of a variety of diseases or conditions related to systemic or tissue inflammation, inflammatory responses to infection or hypoxia, cellular activation and proliferation, lipid metabolism, fibrosis and in the prevention and treatment of viral infections.

Bromodomain inhibitors may be useful in the treatment of a wide variety of chronic autoimmune and inflammatory conditions such as rheumatoid arthritis, osteoarthritis, acute gout, psoriasis, systemic lupus erythematosus, multiple sclerosis, inflammatory bowel disease (Crohn's disease and Ulcerative colitis), asthma, chronic obstructive airways disease, pneumonitis, myocarditis, pericarditis, myositis, eczema, dermatitis, alopecia, vitiligo, bullous skin diseases, nephritis, vasculitis, atherosclerosis, Alzheimer's disease, depression, retinitis, uveitis, scleritis, hepatitis, pancreatitis, primary biliary cirrhosis, sclerosing cholangitis, Addison's disease, hypophysitis, thyroiditis, type I diabetes and acute rejection of transplanted organs.

Bromodomain inhibitors may be useful in the treatment of a wide variety of acute inflammatory conditions such as acute gout, giant cell arteritis, nephritis including lupus nephritis, vasculitis with organ involvement such as glomerulonephritis, vasculitis including giant cell arteritis, Wegener's granulomatosis, Polyarteritis nodosa, Behcet's disease, Kawasaki disease, Takayasu's Arteritis, vasculitis with organ involvement and acute rejection of transplanted organs.

Bromodomain inhibitors may be useful in the prevention or treatment of diseases or conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria and SIRS associated with viral infections such as influenza, herpes zoster, herpes simplex and coronavirus.

Bromodomain inhibitors may be useful in the prevention or treatment of conditions associated with ischaemia-reperfusion injury such as myocardial infarction, cerebro-vascular ischaemia (stroke), acute coronary syndromes, renal reperfusion injury, organ transplantation, coronary artery bypass grafting, cardio-pulmonary bypass procedures, pulmonary, renal, hepatic, gastro-intestinal or peripheral limb embolism.

Bromodomain inhibitors may be useful in the treatment of disorders of lipid metabolism via the regulation of APO-A1 such as hypercholesterolemia, atherosclerosis and Alzheimer's disease.

Bromodomain inhibitors may be useful in the treatment of fibrotic conditions such as idiopathic pulmonary fibrosis, renal fibrosis, post-operative stricture, keloid formation, scleroderma and cardiac fibrosis.

Bromodomain inhibitors may be useful in the prevention and treatment of viral infections such as herpes virus, human papilloma virus, adenovirus and poxvirus and other DNA viruses.

Bromodomain inhibitors may be useful in the treatment of cancer, including hematological, epithelial including lung, breast and colon carcinomas, midline carcinomas, mesenchymal, hepatic, renal and neurological tumours.

In one embodiment the disease or condition for which a bromodomain inhibitor is indicated is selected from diseases associated with systemic inflammatory response syndrome, such as sepsis, burns, pancreatitis, major trauma, haemorrhage and ischaemia. In this embodiment the bromodomain inhibitor would be administered at the point of diagnosis to reduce the incidence of: SIRS, the onset of shock, multi-organ dysfunction syndrome, which includes the onset of acute lung injury, ARDS, acute renal, hepatic, cardiac and gastro-intestinal injury and mortality. In another embodiment the bromodomain inhibitor would be administered prior to surgical or other procedures associated with a high risk of sepsis, haemorrhage, extensive tissue damage, SIRS or MODS (multiple organ dysfunction syndrome). In a particular embodiment the disease or condition for which a bromodomain inhibitor is indicated is sepsis, sepsis syndrome, septic shock or endotoxaemia. In another embodiment, the bromodomain inhibitor is indicated for the treatment of acute or chronic pancreatitis. In another embodiment the bromodomain is indicated for the treatment of burns.

In one embodiment the disease or condition for which a bromodomain inhibitor is indicated is selected from herpes simplex infections and reactivations, cold sores, herpes zoster infections and reactivations, chickenpox, shingles, human papilloma virus, cervical neoplasia, adenovirus infections, including acute respiratory disease, poxvirus infections such as cowpox and smallpox and African swine fever virus. In one particular embodiment a bromodomain inhibitor is indicated for the treatment of Human papilloma virus infections of skin or cervical epithelia.

The term "diseases or conditions for which a bromodomain inhibitor is indicated", is intended to include any of or all of the above disease states.

In one embodiment, there is provided a method for inhibiting a bromodomain which comprises contacting the bromodomain with a compound of formula (I) or a pharmaceutically acceptable salt thereof.

While it is possible that for use in therapy, a compound of formula (I) as well as pharmaceutically acceptable salts thereof may be administered as the raw chemical, it is common to present the active ingredient as a pharmaceutical composition.

The present invention therefore provides in a further aspect a pharmaceutical composition comprising a compound of formula (I) or a pharmaceutically acceptable salt and one or more pharmaceutically acceptable carriers, diluents and/or excipients. The compounds of the formula (I) and pharmaceutically acceptable salts, are as described above. The carrier(s), diluent(s) or excipient(s) must be acceptable in the sense of being compatible with the other ingredients of the composition and not deleterious to the recipient thereof. In accordance with another aspect of the invention there is also provided a process for the preparation of a pharmaceutical composition including admixing a compound of formula (I), or a pharmaceutically acceptable salt thereof, with one or more pharmaceutically acceptable carriers, diluents or excipients. The pharmaceutical composition can be for use in the treatment of any of the conditions described herein.

Since the compounds of formula (I) and pharmaceutically acceptable salts thereof are intended for use in pharmaceutical compositions it will be readily understood that they are each preferably provided in substantially pure form, for example, at least 60% pure, more suitably at least 75% pure and preferably at least 85% pure, especially at least 98% pure (% in a weight for weight basis).

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered more than once a day. Preferred unit dosage compositions are those containing a daily dose or sub-dose (for administration more than once a day), as herein above recited, or an appropriate fraction thereof, of an active ingredient.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

In one embodiment the pharmaceutical composition is adapted for parenteral administration, particularly intravenous administration.

In one embodiment the pharmaceutical composition is adapted for oral administration.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders suitable for incorporating into tablets or capsules may be prepared by reducing the compound to a suitable fine size (e.g. by micronisation) and mixing with a similarly prepared pharmaceutical carrier such as an edible carbohydrate, for example, starch or mannitol. Flavoring, preservative, dispersing and coloring agent can also be present.

Capsules may be made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of formula (I) and pharmaceutically acceptable salts thereof can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The formulation can also be prepared to prolong or sustain the release as for example by coating or embedding particulate material in polymers, wax or the like.

The compounds of formula (I) and pharmaceutically acceptable salts thereof can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Dosage forms for nasal or inhaled administration may conveniently be formulated as aerosols, solutions, suspensions, gels or dry powders.

For compositions suitable and/or adapted for inhaled administration, it is preferred that the compound of formula (I) and pharmaceutically acceptable salts thereof are in a particle-size-reduced form e.g. obtained by micronisation. The preferable particle size of the size-reduced (e.g. micronised) compound or salt is defined by a D50 value of about 0.5 to about 10 microns (for example as measured using laser diffraction).

Aerosol formulations, e.g. for inhaled administration, can comprise a solution or fine suspension of the active substance in a pharmaceutically acceptable aqueous or non-aqueous solvent. Aerosol formulations can be presented in single or multidose quantities in sterile form in a sealed container, which can take the form of a cartridge or refill for use with an atomising device or inhaler. Alternatively the sealed container may be a unitary dispensing device such as a single dose nasal inhaler or an aerosol dispenser fitted with a metering valve (metered dose inhaler) which is intended for disposal once the contents of the container have been exhausted.

Where the dosage form comprises an aerosol dispenser, it preferably contains a suitable propellant under pressure such as compressed air, carbon dioxide or an organic propellant such as a hydrofluorocarbon (HFC). Suitable HFC propellants include 1,1,1,2,3,3,3-heptafluoropropane and 1,1,1,2-tetrafluoroethane. The aerosol dosage forms can also take the form of a pump-atomiser. The pressurised aerosol may contain a solution or a suspension of the active compound. This may require the incorporation of additional excipients e.g. co-solvents and/or surfactants to improve the dispersion characteristics and homogeneity of suspension formulations. Solution formulations may also require the addition of co-solvents such as ethanol.

For pharmaceutical compositions suitable and/or adapted for inhaled administration, the pharmaceutical composition may be a dry powder inhalable composition. Such a composition can comprise a powder base such as lactose, glucose, trehalose, mannitol or starch, the compound of formula (I) or a pharmaceutically acceptable salt thereof (preferably in particle-size-reduced form, e.g. in micronised form), and optionally a performance modifier such as L-leucine or another amino acid and/or metals salts of stearic acid such as magnesium or calcium stearate. Preferably, the dry powder inhalable composition comprises a dry powder blend of lactose e.g. lactose monohydrate and the compound of formula (I) or salt thereof. Such compositions can be administered to the patient using a suitable device such as the DISKUS® device, marketed by GlaxoSmithKline which is for example described in GB 2242134 A.

The compounds of formula (I) and pharmaceutically acceptable salts thereof may be formulated as a fluid formulation for delivery from a fluid dispenser, for example a fluid dispenser having a dispensing nozzle or dispensing orifice through which a metered dose of the fluid formulation is dispensed upon the application of a user-applied force to a pump mechanism of the fluid dispenser. Such fluid dispensers are generally provided with a reservoir of multiple metered doses of the fluid formulation, the doses being dispensable upon sequential pump actuations. The dispensing nozzle or orifice may be configured for insertion into the nostrils of the user for spray dispensing of the fluid formulation into the nasal cavity. A fluid dispenser of the aforementioned type is described and illustrated in WO-A-2005/044354.

A therapeutically effective amount of a compound of formula (I) or a pharmaceutically acceptable salt thereof will depend upon a number of factors including, for example, the age and weight of the animal, the precise condition requiring treatment and its severity, the nature of the formulation, and the route of administration, and will ultimately be at the discretion of the attendant physician or veterinarian. In the pharmaceutical composition, each dosage unit for oral or parenteral administration preferably contains from 0.01 to 3000 mg, more preferably 0.5 to 1000 mg, of a compound of the invention calculated as the free base. Each dosage unit for nasal or inhaled administration preferably contains from 0.001 to 50 mg, more preferably 0.01 to 5 mg, of a compound of the formula (I) or a pharmaceutically acceptable salt thereof, calculated as the free base.

The pharmaceutically acceptable compounds of formula (I) or a pharmaceutically acceptable salt thereof can be administered in a daily dose (for an adult patient) of, for example, an oral or parenteral dose of 0.01 mg to 3000 mg per day or 0.5 to 1000 mg per day, or a nasal or inhaled dose of 0.001 to 50 mg per day or 0.01 to 5 mg per day, of the compound of the formula (I) or a pharmaceutically acceptable salt thereof, calculated as the free base. This amount may be given in a single dose per day or more usually in a number (such as two, three, four, five or six) of sub-doses per day such that the total daily dose is the same. An effective amount of a salt thereof, may be determined as a proportion of the effective amount of the compound of formula (I) per se.

The compounds of formula (I) and pharmaceutically acceptable salts thereof may be employed alone or in combination with other therapeutic agents. Combination therapies according to the present invention thus comprise the administration of at least one compound of formula (I) or a pharmaceutically acceptable salt thereof, and the use of at least one other pharmaceutically active agent. Preferably, combination therapies according to the present invention comprise the administration of at least one compound of formula (I) or a pharmaceutically acceptable salt thereof, and at least one other pharmaceutically active agent. The compound(s) of formula (I) and pharmaceutically acceptable salts thereof and the other pharmaceutically active agent(s) may be administered together in a single pharmaceutical composition or separately and, when administered separately this may occur simultaneously or sequentially in any order. The amounts of the compound(s) of formula (I) and pharmaceutically acceptable salts thereof and the other pharmaceutically active agent(s) and the relative timings of administration will be selected in order to achieve the desired combined therapeutic effect. Thus in a further aspect, there is provided a combination comprising a compound of formula (I) or a pharmaceutically acceptable salt thereof and at least one other pharmaceutically active agent.

Thus in one aspect, the compound of formula (I) or a pharmaceutically acceptable salt thereof and pharmaceutical compositions comprising a compound of formula (I) or a pharmaceutically acceptable salt thereof may be used in combination with or include one or more other therapeutic agents, for example selected from antibiotics, anti-virals, glucocorticosteroids, muscarinic antagonists and beta-2 agonists.

It will be appreciated that when the compound of formula (I) or a pharmaceutically acceptable salt thereof is administered in combination with other therapeutic agents normally administered by the inhaled, intravenous, oral or intranasal route, that the resultant pharmaceutical composition may be administered by the same routes. Alternatively the individual components of the composition may be administered by different routes.

One embodiment of the invention encompasses combinations comprising one or two other therapeutic agents.

It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical composition and thus pharmaceutical compositions comprising a combination as defined above together with a pharmaceutically acceptable diluent or carrier represent a further aspect of the invention.

The compounds of formula (I) and pharmaceutically acceptable salts thereof may be prepared by the methods described below or by similar methods. Thus the following Intermediates and Examples serve to illustrate the preparation of the compounds of formula (I) and pharmaceutically acceptable salts thereof, and are not to be considered as limiting the scope of the invention in any way.

General Experimental Details

All temperatures referred to are in ° C.

ABBREVIATIONS

AcOH refers to acetic acid
BINAP refers to 2,2'-bis(diphenylphosphino)-1,1'-binaphthyl
BOC refers to tert-butoxycarbonyl
CV refers to column volumes
DCM refers to dichloromethane
1,2-DCE refers to 1,2-dichloroethane
DIPEA refers to diisopropylethylamine
DMSO refers to dimethylsulfoxide.
DMF refers to N,N-dimethylformamide
Ether refers to diethyl ether
$Et_2O$ refers to diethyl ether
EtOAc refers to ethyl acetate
FMOC refers to 9-fluorenylmethoxycarbonyl
HATU refers to O-(7-azabenzotriazol-1-yl)-N,N,N',N'-tetramethyluronium hexafluorophosphate
HPLC refers to high performance liquid chromatography
IPA refers to propan-2-ol
i-$Pr_2O$ refers to di-isopropyl ether
$LiAlH_4$ refers to lithium aluminium hydride
MDAP refers to Mass directed autoprep refers preparative mass directed HPLC
MeCN refers to acetonitrile
MeOH refers to methanol
$MgSO_4$ refers to magnesium sulfate
Mp refers to melting point
r.t. refers to room temperature
Rt refers to retention time
$Na_2SO_4$ refers to sodium sulphate
TMEDA refers to tetramethylethylenediamine
TFA refers to trifluoroacetic acid
THF refers to tetrahydrofuran
TLC refers to thin layer chromatography Experimental details of LC-MS methods A-F as referred to herein are as follows:

LC/MS (Method A) was conducted on an Acquity UPLC BEH C18 column (50 mm×2.1 mm i.d. 1.7 μm packing diameter) at 40 degrees centigrade, eluting with 10 mM Ammonium Bicarbonate in water adjusted to pH 10 with Ammonia solution (Solvent A) and Acetonitrile (Solvent B) using the following elution gradient 0-1.5 min 1-97% B, 1.5-1.9 min 97% B, 1.9-2.0 min 100% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

LC/MS (Method B) was conducted on an Acquity UPLC BEH C18 column (50 mm×2.1 mm i.d. 1.7 μm packing diameter) at 40 degrees centigrade, eluting with 0.1% v/v solution of Formic Acid in Water (Solvent A) and 0.1% v/v solution of Formic Acid in Acetonitrile (Solvent B) using the following elution gradient 0-1.5 min 3-100% B, 1.5-1.9 min 100% B, 1.9-2.0 min 3% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

LC/MS (Method C) was conducted on an Acquity UPLC BEH C18 column (50 mm×2.1 mm i.d. 1.7 μm packing diameter) at 40 degrees centigrade, eluting with 0.1% v/v solution of Trifluoroacetic Acid in Water (Solvent A) and 0.1% v/v solution of Trifluoroacetic Acid in Acetonitrile (Solvent B) using the following elution gradient 0-1.5 min 3-100% B, 1.5-1.9 min 100% B, 1.9-2.0 min 3% B at a flow rate of 1 ml/min. The UV detection was a summed signal from wavelength of 210 nm to 350 nm. The mass spectra were recorded on a Waters ZQ Mass Spectrometer using Positive Electrospray. Ionisation data was rounded to the nearest integer.

LC/MS (Method D) was conducted on a Supelcosil LCABZ+PLUS column (3 μm, 3.3 cm×4.6 mm ID) eluting with 0.1% $HCO_2H$ and 0.01 M ammonium acetate in water (solvent A), and 95% acetonitrile and 0.05% $HCO_2H$ in water (solvent B), using the following elution gradient 0-0.7 minutes 0% B, 0.7-4.2 minutes 0→100% B, 4.2-5.3 minutes 100% B, 5.3-5.5 minutes 100→0% B at a flow rate of 3 mL/minute. The mass spectra (MS) were recorded on a Fisons VG Platform mass spectrometer using electrospray positive ionisation [(ES+ve to give $[M+H]^+$ and $[M+NH_4]^+$ molecular ions] or electrospray negative ionisation [(ES−ve to give $[M-H]-$ molecular ion] modes. Analytical data from this apparatus are given with the following format: $[M+H]^+$ or $[M-H]^-$.

LC/MS (Method E) was conducted on a Chromolith Performance RP 18 column (100×4.6 mm id) eluting with 0.01 M ammonium acetate in water (solvent A) and 100% acetonitrile (solvent B), using the following elution gradient 0-4 minutes 0-100% B, 4-5 minutes 100% B at a flow rate of 5 ml/minute. The mass spectra (MS) were recorded on a micromass Platform-LC mass spectrometer using atmospheric pressure chemical positive ionisation[AP+ve to give MH+ molecular ions] or atmospheric pressure chemical negative ionisation [AP−ve to give (M−H)− molecular ions] modes. Analytical data from this apparatus are given with the following format: $[M+H]^+$ or $[M-H]^-$.

LC/MS (Method F) was conducted on an Sunfire C18 column (30 mm×4.6 mm i.d. 3.5 μm packing diameter) at 30 degrees centigrade, eluting with 0.1% v/v solution of Trifluoroacetic Acid in Water (Solvent A) and 0.1% v/v solution of Trifluoroacetic Acid in Acetonitrile (Solvent B) using the following elution gradient 0-0.1 min 3% B, 0.1-4.2 min 3-100% B, 4.2-4.8 min 100% B, 4.8-4.9 min 100-3% B, 4.9-5.0 min 3% B at a flow rate of 3 ml/min. The UV detection was an averaged signal from wavelength of 210 nm to 350 nm and mass spectra were recorded on a mass spectrometer using positive electrospray ionization. Ionisation data was rounded to the nearest integer.

LC/MS (Method G) was conducted on an Acquity UPLC BEH C18 column (50 mm×2.1 mm i.d. 1.7 μm packing diameter) at 40 degrees centigrade, eluting with 0.1% v/v solution of Formic Acid in Water (Solvent A) and 0.1% v/v solution of Formic Acid in Acetonitrile (Solvent B) using the following elution gradient 0-1.5 min 1-97% B, 1.5-1.9 min 97% B, 1.9-2.0 min 97 to 100% B at a flow rate of 1 ml/min. The UV detection was a summed signal from wavelength of 210 nm to 350 nm. The mass spectra were recorded on a Waters ZQ Mass Spectrometer using Alternate-scan Positive and Negative Electrospray. Ionisation data was rounded to the nearest integer.

LC/HRMS: Analytical HPLC was conducted on a Uptisphere-hsc column (3 μm 33×3 mm id) eluting with 0.01M ammonium acetate in water (solvent A) and 100% acetonitrile (solvent B), using the following elution gradient 0-0.5 minutes 5% B, 0.5-3.75 minutes 5→100% B, 3.75-4.5 100% B, 4.5-5 100→5% B, 5-5.5-5% B at a flow rate of 1.3 mL/minute. The mass spectra (MS) were recorded on a micromass LCT mass spectrometer using electrospray positive ionisation[ES+ve to give $MH^+$ molecular ions] or electrospray negative ionisation[ES−ve to give (M−H)− molecular ions] modes.

TLC (thin layer chromatography) refers to the use of TLC plates sold by Merck coated with silica gel 60 F254.

"Mass directed autoprep"/"preparative mass directed HPLC" was conducted on a system such as; a Waters FractionLynx system comprising of a Waters 600 Gradient pump, a Waters 2767 inject/collector, a Waters Reagent manager, a Gilson Aspec-waste collector, a Gilson 115 post-fraction UV detector and a Computer System. The column used is typically a Supelco LCABZ++ column whose dimensions are 20 mm internal diameter by 100 mm in length. The stationary phase particle size is 5 μm. A flow rate was used of 20 mL/min with either 0.1% formic acid or trifluoroacetic acid in water (solvent A) and 0.1% formic or trifluoroacetic acid in acetonitrile (solvent B) using the appropriate elution gradient. Mass spectra were recorded on Micromass ZQ mass spectrometer using electrospray positive and negative mode, alternate scans. The software used was MassLynx 4.0 or using equivalent alternative systems.

Method Formate
LC Conditions
The HPLC analysis was conducted on either a Sunfire C18 column (100 mm×19 mm, i.d 5 μm packing diameter) or a Sunfire C18 column (150 mm×30 mm, i.d. 5 μm packing diameter) at ambient temperature.
The solvents employed were:
A=0.1% v/v solution of formic acid in water
B=0.1% v/v solution of formic acid in acetonitrile
Run as a gradient over either 15 or 25 min (extended run) with a flow rate of 20 ml/min (100 mm×19 mm, i.d 5 μm packing diameter) or 40 ml/min (150 mm×30 mm, i.d. 5 μm packing diameter).
The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.50 sec
Inter scan delay: 0.20 sec Method HpH
LC Conditions
The HPLC analysis was conducted on either an Xbridge C18 column (100 mm×19 mm, i.d 5 μm packing diameter) or a Xbridge C18 column (100 mm×30 mm, i.d. 5 μm packing diameter) at ambient temperature.
The solvents employed were:
A=10 mM ammonium bicarbonate in water, adjusted to pH10 with ammonia solution
B=acetonitrile
Run as a gradient over either 15 or 25 min (extended run) with a flow rate of 20 ml/min (100 mm×19 mm, i.d 5 μm packing diameter) or 40 ml/min (100 mm×30 mm, i.d 5 μm packing diameter).
The UV detection was a summed signal from wavelength of 210 nm to 350 nm.
MS Conditions
MS: Waters ZQ
Ionisation mode: Alternate-scan positive and negative electrospray
Scan range: 100 to 1000 AMU
Scan time: 0.50 sec
Inter scan delay: 0.20 sec Method TFA
LC Conditions
The HPLC analysis was conducted on either a Sunfire C18 column (100 mm×19 mm, i.d. 5 μm packing diameter) or Sunfire C18 column (150 mm×30 mm, i.d. 5 μm packing diameter) at ambient temperature.
The solvents employed were:
A=0.1% v/v solution of trifluoroacetic acid in water
B=0.1% v/v solution of trifluoroacetic in acetonitrile
Run as a gradient over either 15 or 25 min (extended run) with a flow rate of 20 ml/min (100 mm×19 mm, i.d 5 μm packing diameter) or 40 ml/min (150 mm×30 mm, i.d 5 μm packing diameter).
The UV detection was a summed signal from wavelength of 210 nm to 350 nm.
MS Conditions
  MS: Waters ZQ
  Ionisation mode: Positive electrospray
  Scan range: 100 to 1000 AMU
  Scan time: 0.50 sec
  Inter scan delay: 0.20 sec Silica chromatography techniques include either automated (Flashmaster or Biotage SP4) techniques or manual chromatography on pre-packed cartridges (SPE) or manually-packed flash columns.

Microwave chemistry was typically performed in sealed vessels, irradiating with a suitable microwave reactor system, such as a Biotage Initiator™ Microwave Synthesiser.

When the name of a commercial supplier is given after the name of a compound or a reagent, for instance "compound X (Aldrich)" or "compound X/Aldrich", this means that compound X is obtainable from a commercial supplier, such as the commercial supplier named.

Similarly, when a literature or a patent reference is given after the name of a compound, for instance compound Y (EP 0 123 456), this means that the preparation of the compound is described in the named reference.

The names of the above mentioned Examples have been obtained using the compound naming programme "ACD Name Pro 6.02".

Intermediate 1

[4-(1-piperidinylmethyl)phenyl]boronic acid hydrochloride

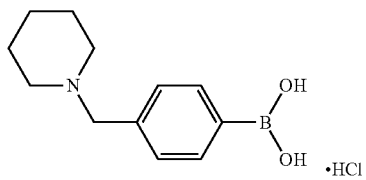 [SMILES: OB(O)c1ccc(CN2CCCCC2)cc1 ; Cl]

4-Formylphenylboronic acid (5 g, 33.3 mmol, available from Aldrich) was stirred in Dichloromethane (DCM) (50 mL) under nitrogen and Sodium triacetoxyborohydride (10.60 g, 50.0 mmol) added. The mixture was stirred overnight and evaporated to dryness. The residue was diluted in MeOH:water (4:1, ~50 ml), applied to a 70 g SCX cartridge and the mixture eluted with MeOH (500 ml) and then 2M ammonia in MeOH (400 ml). The neutral and basic fractions were evaporated to dryness separately. The neutral fraction was redissolved in MeOH:water (4:1, ~50 ml), applied to a 70 g SCX cartridge and the mixture eluted with MeOH (500 ml) and then 2M ammonia in MeOH (400 ml). The basic fraction was evaporated to dryness, combined with the other basic fraction and dissolved in toluene (100 ml) and HCl in IPA (10 mL, 50.0 mmol) added. The mixture was stirred for 10 mins, evaporated to give a pale yellow oil and stirred in diethyl ether (100 ml) over the weekend. The mixture was filtered, washed (diethyl ether (25 ml)) and dried to give a white powder (8.24 g). LCMS (Method C): Rt 0.45, MH+=220

Intermediate 2

(cis)-1-acetyl-2-methyl-6-[4-(1-piperidinylmethyl) phenyl]-1,2,3,4-tetrahydro-4-quinolinamine

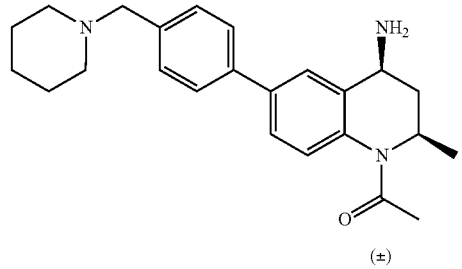 [SMILES: CC(=O)N1c2ccc(-c3ccc(CN4CCCCC4)cc3)cc2[C@@H](N)C[C@H]1C]

To a suspension of {(cis)-1-acetyl-2-methyl-6-[4-(1-piperidinylmethyl)phenyl]-1,2,3,4-tetrahydro-4-quinolinyl}formamide (for a preparation see Intermediate 30) (109 g, 0.27 mol) in MeOH (1 L) was added 6N HCl (136 mL, 0.8 mol). The resulting homogenous mixture was stirred at reflux for 2 hours and concentrated under vacuo. The residue was taken up in water (1 L) and washed with DCM (100 mL). The aqueous phase was basified with NaHCO$_3$ and the organic materials were extracted with DCM (2×0.5 L) dried over Na$_2$SO$_4$ and concentrated to dryness. After heating of the residue in DCM (100 mL) and iPr$_2$O (1 L) and filtration the title compound was obtained as a white precipitate (70 g, 70%)

LC/MS (Method E) m/z 378 [M+H]$^+$, Rt=2.19 min.

Intermediate 3

5-bromo-N-methyl-2-pyridinamine

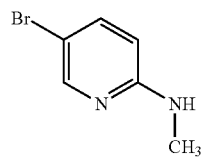

NaH (47.3 mg, 1.971 mmol) and 5-bromo-2-pyridinamine (310 mg, 1.792 mmol, available from Aldrich) were added to N,N-Dimethylformamide (DMF) (7 mL) and stirred in an ice bath for 30 mins. The reaction mixture was then allowed to warm to room temperature and methyl iodide (0.123 mL, 1.971 mmol) was added and the reaction mixture stirred for 24 hr. The reaction mixture was partitioned between DCM (20 mL) and water (20 mL) and the organic layer washed with more water (20 mL) before being dried through an hydrophobic frit and concentrated. The residue was dissolved in DCM and purified by SP4 on a 25+S silica cartridge using a gradient of 10%-40% EtOAc in cyclohexane. Appropriate fractions were collected and concentrated to yield the desired product as a white solid (79.1 mg). LCMS (Method C): Rt 0.39, MH+=187

Intermediate 4

(cis)-1-acetyl-6-bromo-2-methyl-1,2,3,4-tetrahydro-4-quinolinamine hydrochloride

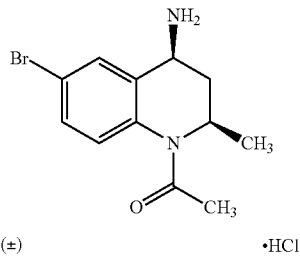 [SMILES: CC(=O)N1c2ccc(Br)cc2[C@@H](N)C[C@H]1C ; Cl]

cis-1-acetyl-6-bromo-2-methyl-1,2,3,4-tetrahydro-4-quinolinamine (for a preparation see Intermediate 45) (45.53 g, 161 mmol) was dissolved in Methanol (160 ml) and HCl (5M solution in 2-propanol) (40 ml, 200 mmol) was slowly added over 10 mins. After a further 10 mins of stirring, the orange solution was concentrated down. Ether (250 mL) was added to the orange gummy solid and the suspension was stirred for 1 h. After this time, a pale yellow powdery suspension had formed. The mixture was left sitting overnight, then the yellow solid was filtered off and the solid was washed with ether and dried in the vacuum oven to yield a white solid—cis-1-acetyl-6-bromo-2-methyl-1,2,3,4-tetrahydro-4-quinolinamine hydrochloride (46.65 g, 146 mmol, 91% yield).

LCMS (Method B): Rt 0.46, MH+=285

Intermediate 5

(cis)-1-acetyl-2-ethyl-6-[4-(1-piperidinylmethyl)phenyl]-1,2,3,4-tetrahydro-4-quinolinamine

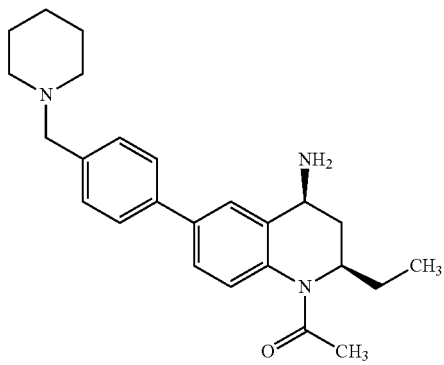

{1-acetyl-2-ethyl-6-[4-(1-piperidinylmethyl)phenyl]-1,2,3,4-tetrahydro-4-quinolinyl}formamide (for a preparation see Intermediate 6) (1.00 g, 2.026 mmol) was dissolved in Ethanol (20 ml), mixed with 5M hydrochloric acid (1.216 ml, 6.08 mmol) and stirred under reflux at 85° C. for 24 hours. The mixture was loaded onto a 5 g SCX-column, eluting with MeOH (70 mL), followed by 2M MeOH/NH3 (70 mL). Product-containing fractions were evaporated to dryness to give a yellow solid (1.242 g). The residue was purified on a 40+S Biotage silica column, eluting with DCM:2M MeOH/NH3 (1:0 to 19:1). Product-containing fractions were evaporated to dryness to give a pale yellow solid (0.782 g). LCMS (Method C): Rt 0.57, MH+=392

Intermediate 6

{(cis)-1-acetyl-2-ethyl-6-[4-(1-piperidinylmethyl)phenyl]-1,2,3,4-tetrahydro-4-quinolinyl}formamide

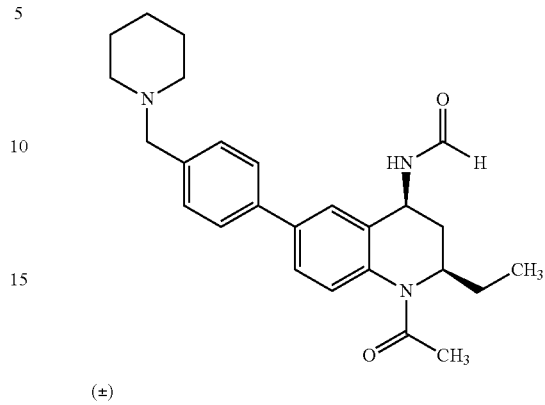

((cis)-1-acetyl-6-bromo-2-ethyl-1,2,3,4-tetrahydro-4-quinolinyl)formamide (for a preparation see Intermediate 44) (1 g, 3.08 mmol) and [4-(1-piperidinylmethyl)phenyl]boronic acid (1.572 g, 6.15 mmol, Intermediate 1) were mixed with Ethanol (8 mL), Toluene (8.00 mL). potassium carbonate (1.402 g, 10.15 mmol) and tetrakis(triphenylphosphine)palladium(0) (0.355 g, 0.308 mmol) were added and the mixture was stirred under nitrogen, at reflux at 110° C. After 3 hours, another sample of tetrakis(triphenylphosphine)palladium(0) (0.355 g, 0.308 mmol) was added and the reaction was left to stir overnight. The reaction was evaporated to dryness. The residue was diluted with DCM (150 mL), washed (water (150 mL), sat. sodium bicarbonate (200 mL), brine (200 mL)), dried (sodium sulfate), filtered and evaporated to dryness to give a black solid which was loaded onto an 20 g SCX-column, eluting with MeOH (120 mL) followed by MeOH/NH3 (300 mL). Product-containing fractions were evaporated to dryness to give a dark red solid which was purified on a 40+S Biotage silica column, eluting with DCM: 2M MeOH/NH3 (1:0 to 19:1). Product-containing fractions were evaporated to dryness to give a yellow/orange solid (1.00 g).

LCMS (Method B): Rt 0.67, MH+=420

Intermediate 7

1-methylethyl[(cis)-1-acetyl-6-(4-formylphenyl)-2-methyl-1,2,3,4-tetrahydro-4-quinolinyl]carbamate

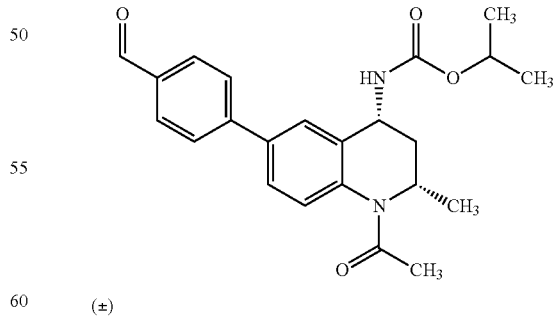

1-methylethyl[(cis)-1-acetyl-6-bromo-2-methyl-1,2,3,4-tetrahydro-4-quinolinyl]carbamate (for a preparation see Example 61) (1.6 g, 4.33 mmol), potassium carbonate (1.198 g, 8.67 mmol), tetrakis(triphenylphosphine)palladium(0) (0.250 g, 0.217 mmol) and (4-formylphenyl)boronic acid (0.780 g, 5.20 mmol) were dissolved in Ethanol (10 mL) and Toluene (10 mL). The reaction mixture was degassed for 30 min then stirred and heated under nitrogen for 1 hr at 100° C. The reaction mixture was filtered and the solvent evaporated under vacuum. The residue was partitioned between ethyl acetate (50 ml) and water (50 ml). The organic layer was dried through a hydrophobic frit and concentrated in vacuo. The residue was dissolved with dichloromethane and purified by SP4 on a 40+M silica cartridge using a gradient 20-75% ethyl acetate in cyclohexane. The appropriate fractions were combined and evaporated in vacuo to give the required product (1.4 g) as a yellow solid. LCMS (Method B): Rt 0.99, MH+=395

Intermediate 8

1,1-dimethylethyl 4-({4-[(cis)-1-acetyl-2-methyl-4-({[(1-methylethyl)oxy]carbonyl}amino)-1,2,3,4-tetrahydro-6-quinolinyl]phenyl}methyl)-1-piperazinecarboxylate

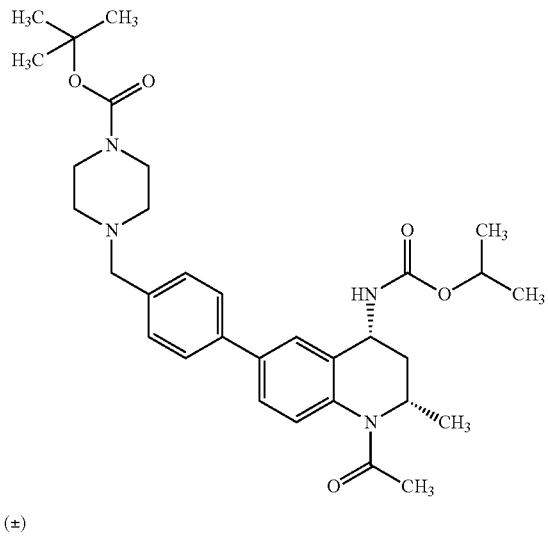 [SMILES: CC(=O)N1c2ccc(-c3ccc(CN4CCN(C(=O)OC(C)(C)C)CC4)cc3)cc2[C@H](NC(=O)OC(C)C)C[C@@H]1C]

(±)

1-methylethyl[(cis)-1-acetyl-6-(4-formylphenyl)-2-methyl-1,2,3,4-tetrahydro-4-quinolinyl]carbamate (for a preparation see Intermediate 7) (95 mg, 0.241 mmol) was dissolved in Dichloromethane (DCM) (2 mL) and to this was added tert-butyl 1 piperazinecarboxylate (67.3 mg, 0.361 mmol) as a solid and the resulting solution stirred under nitrogen for 40 min. sodium triacetoxyborohydride (66.4 mg, 0.313 mmol) was added and stirred as a suspension over the weekend. The reaction was quenched with ammonium chloride (2 ml). The organics were separated and the aqueous reextracted with DCM (5 ml). The combined organics were washed with water (5 ml) and reduced in vacuo to give a colourless solid. (135 mg). The solid was dissolved in DCM and loaded onto a 12+M silica cartridge for automated flash chromatography. A gradient of 20 to 100% ethyl acetate in iso-hexane over 10 CV was used and the appropriate fractions reduced in vacuo to give a colourless oil which was dried on high vac overnight (98 mg).

LCMS (Method A): Rt=1.32, MH+=565

Intermediate 9

1,1-dimethylethyl 4-[({4-[(cis)-1-acetyl-2-methyl-4-({[(1-methylethyl)oxy]carbonyl}amino)-1,2,3,4-tetrahydro-6-quinolinyl]phenyl}methyl)amino]-1-piperidinecarboxylate

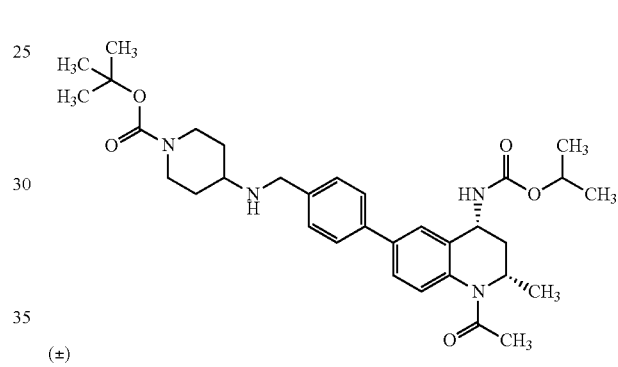

(±)

This was prepared in a similar manner to Example 19, using 1,1-dimethylethyl 4-amino-1-piperidinecarboxylate (48.0 mg, 0.24 mmol, available from Apollo Scientific) and purifying with a gradient of 20 to 100% ethyl acetate in petrol over 10 CV to give the desired product (70 mg). LCMS (Method A): Rt=1.24, MH+=579

Intermediate 10

1-methylethyl[(cis)-1-acetyl-6-(4-{[4-({[(1,1-dimethylethyl)oxy]carbonyl}amino)-1-piperidinyl]methyl}phenyl)-2-methyl-1,2,3,4-tetrahydro-4-quinolinyl]carbamate

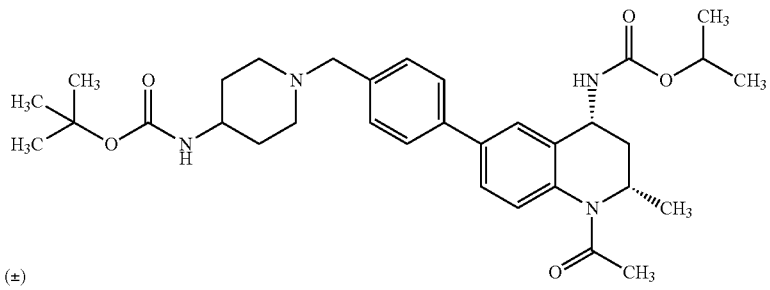 [SMILES: CC(=O)N1c2ccc(-c3ccc(CN4CCC(NC(=O)OC(C)(C)C)CC4)cc3)cc2[C@H](NC(=O)OC(C)C)C[C@@H]1C]

(±)

This was prepared in a similar manner to Example 19, using 1,1-dimethylethyl 4-piperidinylcarbamate (48.0 mg, 0.24 mmol, available from Acros) and purifying with a gradient of 20 to 100% ethyl acetate in petrol over 10 CV to give the desired product (70 mg). LCMS (Method A): Rt=1.26, MH+=579

Intermediate 11

1,1-dimethylethyl 4-({4-[(cis)-1-acetyl-2-methyl-4-({[(1-methylethyl)oxy]carbonyl}amino)-1,2,3,4-tetrahydro-6-quinolinyl]phenyl}methyl)hexahydro-1H-1,4-diazepine-1-carboxylate

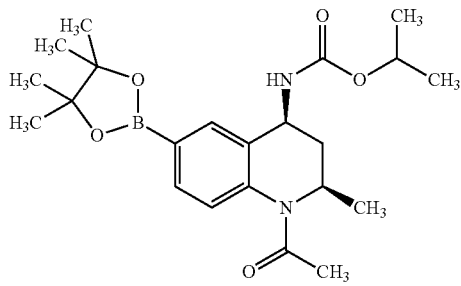

(±)

This was prepared in a similar manner to Example 19, using 1,1-dimethylethyl hexahydro-1H-1,4-diazepine-1-carboxylate (48.0 mg, 0.24 mmol, available from Aldrich) and purifying with a gradient of 20 to 100% ethyl acetate in petrol over 10 CV to give the desired product (70 mg). LCMS (Method A): Rt=1.36, MH+=579

Intermediate 12

1-methylethyl[(cis)-1-acetyl-2-methyl-6-(4,4,5,5-tetramethyl-1,3,2-dioxaborolan-2-yl)-1,2,3,4-tetrahydro-4-quinolinyl]carbamate

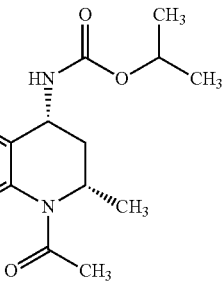

(±)

To a solution of in 1,4-Dioxane (4 mL) were added 1-methylethyl[(cis)-1-acetyl-6-bromo-2-methyl-1,2,3,4-tetrahydro-4-quinolinyl]carbamate (for a preparation see Example 61) (200 mg, 0.542 mmol), bis(pinacolato)diboron (275 mg, 1.083 mmol, Aldrich), Pd(dppf)Cl2 (39.6 mg, 0.054 mmol, Apollo) and potassium acetate (159 mg, 1.625 mmol). The mixture was degassed by bubbling nitrogen through the solution for 30 minutes. The reaction was then stirred and heated at 100° C. for 24 hours. When analysed by LC MS, no starting material was found. The reaction mixture was concentrated and then dissolved in DCM and purified by SP4 on a 25+S silica cartridge using a gradient of 10-60% EtOAc in cyclohexane. The appropriate fractions were collected and concentrated to yield an off white solid containing the desired product (170 mg). This was used without any further purification. LCMS (Method C): Rt=1.12, MH+=417

Intermediate 13

1,1-dimethylethyl 4-(5-iodo-2-pyrazinyl)-1-piperazinecarboxylate

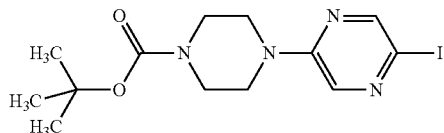

In a 5 mL round bottomed flask were mixed: 1,1-dimethylethyl 1-piperazinecarboxylate (110 mg, 0.590 mmol, available from Fluke), 2-bromo-5-iodopyrazine (140 mg, 0.491 mmol, available from Apollo) and Dipea (0.112 mL, 0.639 mmol) in Tert-Butanol (2 mL). The reaction was stirred and heated under reflux at 100° C. for 40 hr. The reaction mixture was partitioned between EtOAc (20 mL) and water (20 mL) and the organic layer washed with brine (20 mL) before being dried through an hydrophobic frit and concentrated. The samples were dissolved in 1:1 MeOH:DMSO 2×1 mL and purified by MDAP. The solvent was evaporated in vacuo to give the required product 1,1-dimethylethyl 4-(5-iodo-2-pyrazinyl)-1-piperazinecarboxylate (98.6 mg) LCMS (Method C): Rt=1.20, MH+=391

Intermediate 14

1,1-dimethylethyl 4-(6-chloro-3-pyridazinyl)-1-piperazinecarboxylate

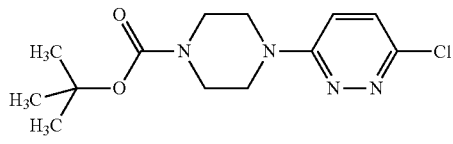 [SMILES: CC(C)(C)OC(=O)N1CCN(c2ccc(Cl)nn2)CC1]

In a microwave vial were mixed: 1,1-dimethylethyl 1-piperazinecarboxylate (135 mg, 0.725 mmol, available from Fluke), 3,6-dichloropyridazine (90 mg, 0.604 mmol, available from Alfa Aesar) and DIPEA (0.137 mL, 0.785 mmol) in Tert-Butanol (2 mL). The reaction was stirred and heated in an Emrys Optimizer microwave at 100° C. for 20 mins then for 30 mins at 150° C. The reaction mixture was partitioned between EtOAc (20 mL) and water (20 mL) and the organic layer washed with brine (20 mL) before being dried through an hydrophobic frit and concentrated. The residue was dissolved in DCM and purified by SP4 on a 12+M silica cartridge using a gradient of 10-50% EtOAc in cyclohexane. The appropriate fractions were collected and concentrated to yield the desired product as a white solid, 1,1-dimethylethyl 4-(6-chloro-3-pyridazinyl)-1-piperazinecarboxylate (114.2 mg). LCMS (Method C): Rt=0.85, MH+=299

Intermediate 15

[2-(4-bromo-1H-pyrazol-1-yl)ethyl]dimethylamine

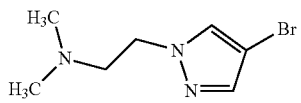

4-bromopyrazole (100 mg, 0.680 mmol, available from Aldrich), cesium carbonate (333 mg, 1.021 mmol) and 1-bromo-2-chloroethane (0.085 mL, 1.021 mmol, available from Aldrich) were suspended in N,N-Dimethylformamide (DMF) (2 mL) and heated to 60° C. under microwave conditions in a Biotage Initiator for 1 hour. 2M dimethylamine in THF (1.701 mL, 3.40 mmol) added and the mixture allowed to stand over the weekend. The mixture was heated to 60° C. under microwave conditions in a Biotage Initiator for 1 hour, then to 100° C. under microwave conditions in a Biotage Initiator for 2 hours. The mixture was filtered, evaporated to 13 mbar, loaded on to a 5 g SCX cartridge and eluted with MeOH (25 ml) followed by 2M methanolic ammonia (25 ml). The basic fraction was evaporated to a colourless oil (99 mg). LCMS (Method C): Rt=0.43, MH+=218

Intermediate 16

1-[2-(4-bromo-1H-pyrazol-1-yl)ethyl]piperidine 4-bromo-1-(2-chloroethyl)-1H-pyrazole (see Intermediate 29 for a preparation) (120 mg, 0.573 mmol), potassium carbonate (158 mg, 1.146 mmol) and Piperidine (0.113 mL, 1.146 mmol) was stirred in Acetonitrile (2 mL) and heated to 60° C. for five days. The mixture was fully dissolved in MeOH/water and loaded on to a 10 g SCX cartridge. The SCX cartridge was eluted with MeOH (100 ml), followed by 2M methanolic ammonia (50 ml). The basic fractions were evaporated to dryness to give the desired product (101 mg). LCMS (Method A): Rt=1.04, MH+=260

Intermediate 17

1,1-dimethylethyl {1-[2-(4-bromo-1H-pyrazol-1-yl)ethyl]-4-piperidinyl}carbamate

This was prepared in a similar manner to Intermediate 16, using 1,1-dimethylethyl 4-piperidinylcarbamate (229 mg, 1.146 mmol, available from Aldrich).
LCMS (Method A): Rt=1.07, MH+=375

Intermediate 18

1,1-dimethylethyl 4-[2-(4-bromo-1H-pyrazol-1-yl)ethyl]-1-piperazinecarboxylate

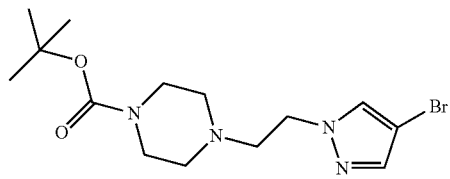 [SMILES: CC(C)(C)OC(=O)N1CCN(CCn2cc(Br)cn2)CC1]

This was prepared in a similar manner to Intermediate 16, using 1,1-dimethylethyl 1-piperazinecarboxylate (213 mg, 1.146 mmol, available from Aldrich). LCMS (Method A): Rt=1.12, MH+=359

Intermediate 19

1,1-dimethylethyl 4-(5-bromo-2-pyrimidinyl)-1-piperazinecarboxylate

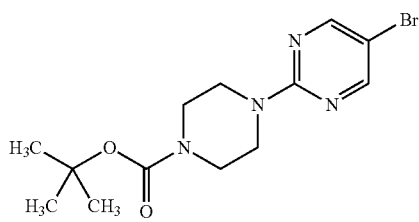 [SMILES: CC(C)(C)OC(=O)N1CCN(c2ncc(Br)cn2)CC1]

In a microwave vial were mixed: 1,1-dimethylethyl 1-piperazinecarboxylate (110 mg, 0.589 mmol, available from Fluke), 5-bromo-2-chloropyrimidine (95 mg, 0.491 mmol, available from Lancaster) and DIPEA (0.112 mL, 0.638 mmol) in tert-butanol (2 mL). The reaction was stirred and heated in an Emrys Optimizer microwave at 150° C. for 0.5 hr. The reaction mixture was partitioned between EtOAc (20 mL) and water (20 mL) and the organic layer washed with brine (20 mL) before being dried through an hydrophobic frit and concentrated to yield the desired product (162.3 mg)
LCMS (Method C): Rt=1.26, MH+=343

Intermediate 20

1-methylethyl[(cis)-1-acetyl-6-(4-formyl-2-furanyl)-2-methyl-1,2,3,4-tetrahydro-4-quinolinyl]carbamate

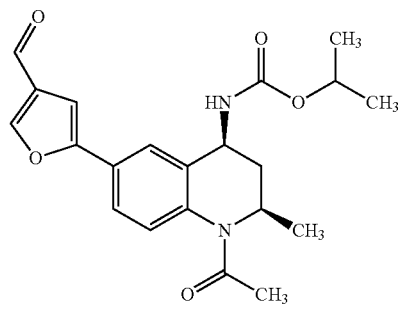

(±)

1-methylethyl (1-acetyl-6-bromo-2-methyl-1,2,3,4-tetrahydro-4-quinolinyl)carbamate (for a preparation see Example 61) (150 mg, 0.406 mmol) was mixed with potassium carbonate (112 mg, 0.812 mmol), tetrakis(triphenylphosphine)palladium(0) (23.47 mg, 0.020 mmol) and (4-formyl-2-furanyl)boronic acid (68.2 mg, 0.487 mmol, available from Frontier scientific), dissolved in ethanol (1 mL) and toluene (1 mL) and stirred under nitrogen at 90° C. for 2.5 days. The reaction A was partitioned between distilled water (20 mL) and EtOAc (60 mL). The aqueous layer was extracted with EtOAc (2×60 mL) and the organic fractions were combined, washed (brine (50 mL)), dried (sodium sulfate) and evaporated to dryness to give a dark brown solid (184 mg) which was purified using MDAP. Product-containing fractions were evaporated to dryness to give a yellow/brown solid (32 mg).

LCMS (Method C): Rt=0.91, MH+=385

Intermediate 21

1-methylethyl[(cis)-1-acetyl-6-(5-formyl-2-furanyl)-2-methyl-1,2,3,4-tetrahydro-4-quinolinyl]carbamate

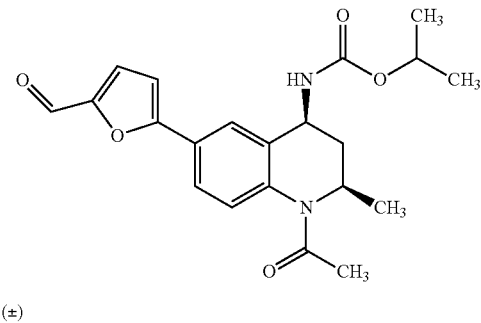 [SMILES: CC(=O)N1c2ccc(-c3ccc(C=O)o3)cc2[C@@H](NC(=O)OC(C)C)C[C@H]1C]

(±)

This was prepared in a similar manner to Intermediate 7, using 5-formyl-2-furanyl)boronic acid (68.2 mg, 0.487 mmol, available from Aldrich), and purifying on a 25+S Biotage silica column, eluting with cyclohexane:EtOAc (1:0 to 13:20). Product-containing fractions were evaporated to dryness to give a dark brown solid (18 mg).

LCMS (Method C): Rt=0.90, MH+=385

Intermediate 22

1-methylethyl((cis)-1-acetyl-6-{1-[2-(1,3-dioxo-1,3-dihydro-2H-isoindol-2-yl)ethyl]-1H-pyrazol-4-yl}-2-methyl-1,2,3,4-tetrahydro-4-quinolinyl)carbamate

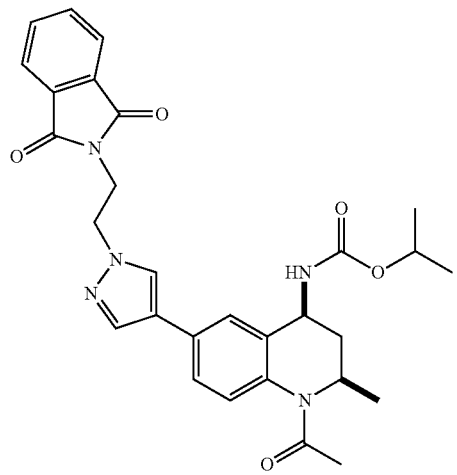

(±)

2-[2-(4-bromo-1H-pyrazol-1-yl)ethyl]-1H-isoindole-1,3(2H)-dione (for a preparation see Intermediate 28) (80 mg, 0.250 mmol) and 1-methylethyl[1-acetyl-2-methyl-6-(4,4,5,5-tetramethyl-1,3,2-dioxaborolan-2-yl)-1,2,3,4-tetrahydro-4-quinolinyl]carbamate (Intermediate 12, 150 mg, 0.360 mmol) were mixed with potassium carbonate (69.1 mg, 0.500 mmol) and tetrakis(triphenylphosphine)palladium(0) (14.44 mg, 0.012 mmol), dissolved in ethanol (1 mL) and toluene (1 mL) and stirred under nitrogen at 90° C. for 1 hour. The mixture was partitioned between distilled water (20 mL) and EtOAc (60 mL). The aqueous layer was extracted with EtOAc (60 mL) and the organic fractions were combined, washed (brine, 30 mL), dried (MgSO$_4$), filtered and evaporated to dryness to give a yellow solid which was loaded on to a 12+M Biotage silica column and eluted with cyclohexane:ethyl acetate (3:1 to 1:2). Product-containing fractions were evaporated to dryness to give a solid (39 mg). LCMS (Method C): Rt=0.95, MH+=530

Intermediate 23

5-bromo-2-(1-piperidinylmethyl)pyridine

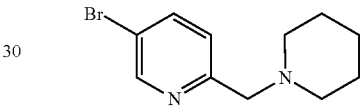

Lithium aluminium hydride in 1M THF (1.858 mL, 1.858 mmol) was cooled to 0° C. 5-bromo-2-(1-piperidinylcarbonyl)pyridine (for a preparation see Intermediate 25) (250 mg, 0.929 mmol) was dissolved in THF (7 mL) and added dropwise to the LiAlH$_4$ under nitrogen and stirred. After addition to the reductant, the solution was warmed to room temperature. After 1 hour the reactions were filtered, washed with EtOAc (3×10 mL) and evaporated to dryness to give a brown/yellow solid (159 mg). This was purified on a 25+S Biotage silica column, eluting with DCM:2M MeOH/NH$_3$ (1:0 to 97:3). Product-containing fractions were evaporated to dryness to give a dark yellow solid (61 mg).

LCMS (Method C): Rt=0.53, MH+=257

Intermediate 24

2-bromo-5-(1-piperidinylmethyl)pyridine

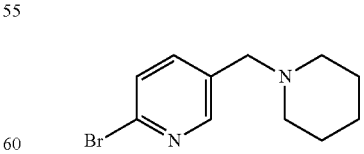

This was prepared in a similar manner to Intermediate 23, using 2-bromo-5-(1-piperidinylcarbonyl)pyridine (Intermediate 26, 250 mg, 0.929 mmol) to give the desired product as an brown/orange solid (141 mg). LCMS (Method C): Rt=0.48, MH+=255

Intermediate 25

5-bromo-2-(1-piperidinylcarbonyl)pyridine

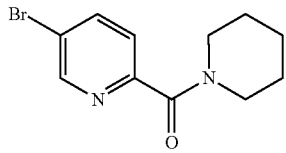 [SMILES: O=C(c1ccc(Br)cn1)N1CCCCC1]

5-bromo-2-pyridinecarboxylic acid (501 mg, 2.480 mmol, available from Apollo) was mixed with HATU (2358 mg, 6.20 mmol), DIPEA (1.625 mL, 9.30 mmol) and piperidine (0.307 mL, 3.10 mmol), dissolved in N,N-dimethylformamide (DMF) (22.5 mL) and stirred under nitrogen for 18 hours. The reaction was partitioned between distilled water (30 mL) and DCM (100 mL). The aqueous layer was extracted with DCM (2×70 mL) and the organic fractions were combined, washed (brine (2×50 mL)), dried (sodium sulfate), filtered and evaporated to dryness to give a dark brown solid (2.43 g). The crude product was purified on a 40+M Biotage silica column, eluting with cyclohexane:EtOAc (1:0 to 3:2, 19 CV). Product-containing fractions were evaporated to dryness to give a dark yellow solid (573 mg). LCMS (Method C): Rt=0.83, MH+=271

Intermediate 26

2-bromo-5-(1-piperidinylcarbonyl)pyridine

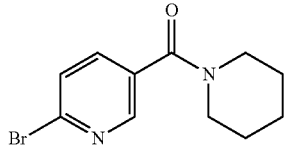 [SMILES: O=C(c1ccc(Br)nc1)N1CCCCC1]

This was prepared in a similar manner to Intermediate 25, using 6-bromo-nicotinic acid (501 mg, 2.480 mmol, available from Aldrich) to give the desired product as an white/yellow solid (506 mg) LCMS (Method C): Rt=0.80, MH+=271

Intermediate 27

1-[(2-bromo-1,3-thiazol-5-yl)methyl]piperidine

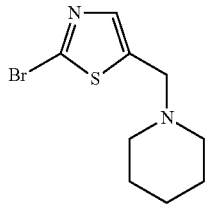 [SMILES: Brc1ncc(CN2CCCCC2)s1]

2-Bromo-5-formylthiazole (198 mg, 1.034 mmol, available from Fluorochem) was mixed with acetic acid (0.148 mL, 2.58 mmol) and Piperidine (0.128 mL, 1.292 mmol), dissolved in Dichloromethane (DCM) (9.5 mL) and stirred under nitrogen for 30 minutes. sodium triacetoxyborohydride (411 mg, 1.938 mmol) was added and the reaction was allowed to stir under nitrogen for 45 minutes. A second sample of sodium triacetoxyborohydride (411 mg, 1.938 mmol) was added and the reaction was left to stir under nitrogen for 4.5 days. The reaction was loaded onto a 5 g SCX-column, eluting with MeOH (40 mL) followed by 2M MeOH/NH$_3$ (40 mL). Product-containing fractions were evaporated to dryness to give a yellow solid. This was partitioned between sodium bicarbonate (20 mL) and EtOAc (100 mL). The aqueous layer was extracted with EtOAc (70 mL) and the organic fractions were combined, washed (brine (50 mL)), dried (sodium sulfate), filtered and evaporated to dryness to give a yellow solid (214 mg). This was purified on a 25+S Biotage silica column, eluting with DCM:2M MeOH/NH$_3$ (1:0 to 49:1, 22 CV). Product-containing fractions were evaporated to dryness to give a dark yellow solid (134 mg)

LCMS (Method C): Rt=0.47, MH+=263

Intermediate 28

2-[2-(4-bromo-1H-pyrazol-1-yl)ethyl]-1H-isoindole-1,3(2H)-dione

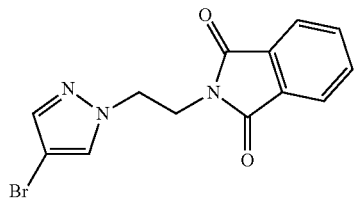 [SMILES: O=C1c2ccccc2C(=O)N1CCn1cc(Br)cn1]

4-bromo-1-(2-chloroethyl)-1H-pyrazole (for a preparation see Intermediate 29) (120 mg, 0.573 mmol) was mixed with potassium phthalimide (159 mg, 0.859 mmol), dissolved in N,N-Dimethylformamide (DMF) (4 mL) and stirred under nitrogen at 120° C. for 20 hours. The reaction was left to cool to room temperature and the product was partitioned between distilled water (20 mL) and EtOAc (60 mL). The aqueous layer was extracted with EtOAc (60 mL) and the organic fractions were combined, washed (brine, 30 mL), dried (MgSO4), filtered and evaporated to dryness to give a white solid. The product was purified on a 25+S Biotage silica column, eluting with cyclohexane:EtOAc (1:0 to 7:3). Product-containing fractions were evaporated to dryness to give a white solid (85 mg).

LCMS (Method C): Rt=0.91, MH+=320

Intermediate 29

4-bromo-1-(2-chloroethyl)-1H-pyrazole

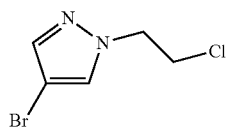

4-bromopyrazole (700 mg, 4.76 mmol, available from Aldrich), cesium carbonate (2328 mg, 7.14 mmol) and 1-bromo-2-chloroethane (0.592 ml, 7.14 mmol, available from Acros) were suspended in N,N-Dimethylformamide (DMF) (14 ml) and heated to 60° C. under microwave conditions in an Emrys Optimiser for 1 hour. The mixture was partitioned between water (20 ml) and ethyl acetate (60 ml). The aqueous layer was run off and the organic washed (water 3×10 ml), brine (10 ml)), dried (magnesium sulfate) and evaporated to dryness to give the desired product (868 mg).

LCMS (Method C): Rt=0.83, MH+=211

Intermediate 30

{(cis)-1-acetyl-2-methyl-6-[4-(1-piperidinylmethyl)phenyl]-1,2,3,4-tetrahydro-4-quinolinyl}formamide

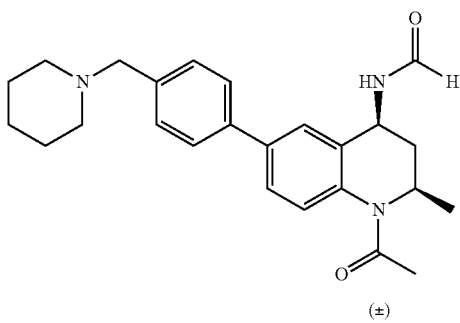 [SMILES: CC(=O)N1c2ccc(-c3ccc(CN4CCCCC4)cc3)cc2[C@@H](NC=O)C[C@H]1C]

To a solution of [1-acetyl-6-(4-formylphenyl)-2-methyl-1,2,3,4-tetrahydro-4-quinolinyl]formamide (for a preparation see Intermediate 48) (95 g, 0.25 mol) and piperidine (31 g, 0.3 mol) in solution in dichloroethane (2 L) were added at room temperature triacetoxysodiumborohydride (70 g, 0.33 mol) and acetic acid (33 g). After stirring 2 hours a t.l.c monitoring indicated the completion of the reaction and the mixture was poured into a saturated solution of NaHCO$_3$. The organic phase was extracted after addition of DCM (500 mL) and washed with brine (100 mL), dried over Na$_2$SO$_4$, filtered and evaporated to dryness. Trituration of the residue in a mixture of DCM/hexane afforded the title compound (109 g, 95.6%) as an off white solid. LC/MS (Method E) m/z 406 [M+H]$^+$, Rt=2.22 min;

Intermediate 31

(3S)-3-(phenylamino)butanenitrile

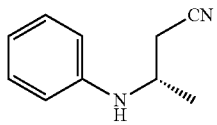

(3S)-3-aminobutanenitrile (8.6 g, 102 mmol, may be prepared as described in PCT Int. Appl., WO2005/100321), bromobenzene (16.16 ml, 153 mmol) and cesium carbonate (50.0 g, 153 mmol) were combined in Toluene (100 ml) under nitrogen were stirred for 45 mins. Phenylboronic acid (0.187 g, 1.534 mmol, Aldrich), palladium (II) acetate (0.188 g, 0.837 mmol, available from Aldrich) and 2-dicyclohexylphosphino-2'-(N,N-dimethylamino)biphenyl (0.443 g, 1.125 mmol, available from Aldrich) were combined in tetrahydrofuran (THF) (6.67 ml) under nitrogen and stirred for 45 mins. The THF solution was added to the toluene solution and the reaction heated to 80° C. overnight. The reaction mixture was cooled and partitioned between EtOAc (500 ml) and water (300 ml). The aqueous layer was reextracted with EtOAc (200 ml). The combined organic layers were washed with water and brine (500 ml each) and then dried with Na$_2$SO$_4$, filtered and concentrated to yield an orange oil. The crude product was taken up in the minimum of DCM, applied to a 330 g Companion XL column and eluted with 5% ethyl acetate in cyclohexane for 1 CV then 5-30% Ethyl Acetate over 12 CV then held at 30% for 3 CV; UV collection; 450 ml fractions. The product was isolated as an off-white solid (11.3526 g).

LCMS (Method B): Rt=0.87, MH+=161

Intermediate 32

(3S)-3-[(4-bromophenyl)amino]butanenitrile

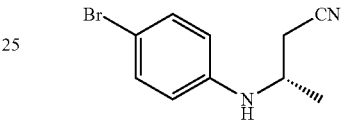

(3S)-3-(phenylamino)butanenitrile (for a preparation see Intermediate 31) (11.3526 g, 70.9 mmol) was taken up in N,N-dimethylformamide (DMF) (200 mL) under nitrogen and cooled in an ice-bath. NBS (12.61 g, 70.9 mmol) was added and the reaction stirred. After 20 mins, the reaction was partitioned between EtOAc (1000 ml) and water (500 ml). The organic layer was washed with 2M NaOH ×2, water and brine (500 ml each) and then dried with Na$_2$SO$_4$, filtered and concentrated to yield the product as a cream solid (17.3 g).

LCMS (Method B): Rt=1.05, MH+=239

Intermediate 33

(3S)-3-[(4-bromophenyl)amino]butanamide

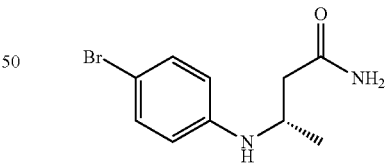

(3S)-3-[(4-bromophenyl)amino]butanenitrile (for a preparation see Intermediate 32) (17.3 g, 72.4 mmol) was taken up in Toluene (500 ml) and H$_2$SO$_4$ (19.28 ml, 362 mmol) added. The biphasic mixture was stirred at 60° C. After two hours, only a small amount of SM remained by LCMS so the reaction was diluted with water (500 ml) and the phases separated. The aqueous phase was basified with 10N NaOH and extracted with EtOAc (2×750 ml). The combined organics were dried with Na$_2$SO$_4$, filtered and concentrated to yield the product as a cream solid (17.5 g). LCMS (Method B): Rt=0.77, MH+=257

Intermediate 34

1-methylethyl {(3S)-3-[(4-bromophenyl)amino]butanoyl}carbamate

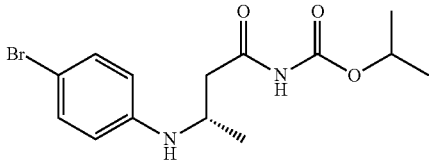 [SMILES: CC(C)OC(=O)NC(=O)C[C@H](C)Nc1ccc(Br)cc1]

(3S)-3-[(4-bromophenyl)amino]butanamide (for a preparation see Intermediate 33, 24.9 g, 97 mmol) was taken up in Ethyl acetate (850 mL) and cooled to <−9° C. (internal). Isopropyl chloroformate (116 mL, 116 mmol, Aldrich) was added followed by slow addition of Lithium tert-butoxide (18.61 g, 232 mmol) in Tetrahydrofuran (THF) (232 mL) keeping the temperature below 0° C. The reaction was stirred for 30 mins then checked by LCMS which showed a complete reaction. The mixture was partitioned between EtOAc (1000 ml) and 2N HCl (2000 ml). The organic layer was washed with brine (2000 ml) and then dried with Na2SO4, filtered and concentrated to yield the product as a brown oil (17.9 g)

LCMS (Method B): Rt=1.09, MH+=343

Alternative Method 1-methylethyl (2E)-2-butenoylcarbamate (Intermediate 49, 9.38 g, 54.8 mmol) was stirred in Toluene (281 ml) under nitrogen and (R-BINAP)ditriflatebis(acetonitrile)palladium(II) (Intermediate 50, 3.35 g, 3.01 mmol) added. The catalyst formed a gummy ball, the solution turned to an opaque yellow mixture and was stirred for 20 mins. 4-bromoaniline (14.14 g, 82 mmol) was added, the solution turned a clear light brown and the gummy catalyst dissolved further. The mixture was stirred overnight, Similarly a second batch of 1-methylethyl (2E)-2-butenoylcarbamate (Intermediate 49, 8.51 g, 49.7 mmol) was stirred in Toluene (255 ml) under nitrogen and (R-BINAP)ditriflatebis(acetonitrile)palladium(II) (3.04 g, 2.73 mmol) added. The catalyst formed a gummy ball, the solution turned to an opaque yellow mixture and was stirred for 20 mins. 4-bromoaniline (12.83 g, 74.6 mmol) was added, the solution turned a clear light brown and the gummy catalyst dissolved further. The mixture was stirred overnight. The two reaction mixtures were combined and loaded on to a 1.5 kg Isco silica Redisep column. The column was eluted with DCM:MeOH (0%->0.5%, 19 CV). The clean, product containing fractions were evaporated to a pale brown oil. The mixture was dried in a vacuum oven overnight at 40° C. to give a white solid (24.2 g, 67% overall).

LCMS (Method C): Rt=0.91, MH+=343. ee=92%.

Intermediate 35

1-methylethyl[(2S,4R)-6-bromo-2-methyl-1,2,3,4-tetrahydro-4-quinolinyl]carbamate

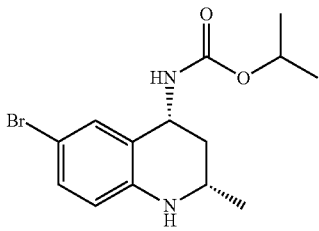 [SMILES: CC(C)OC(=O)N[C@@H]1C[C@H](C)Nc2ccc(Br)cc21]

1-methylethyl {(3S)-3-[(4-bromophenyl)amino]butanoyl}carbamate (for a preparation see Intermediate 34) (17.9 g, 52.2 mmol) was taken up in Ethanol (150 mL) and cooled to below −10° C. (internal) in a CO2/acetone bath. NaBH4 (1.381 g, 36.5 mmol) was added followed by Magnesium Chloride hexahydrate (11.35 g, 55.8 mmol) in Water (25 mL) keeping the temperature below −5° C. The mixture was allowed to stir at <0° C. for 1 hr then warmed to RT and stirred for an hour. The resulting thick suspension was poured into a mixture of citric acid (25.05 g, 130 mmol), HCl (205 mL, 205 mmol) and dichloromethane (DCM) (205 mL). The biphasic mixture was stirred at RT for 1 hr. LCMS showed no SM remained so the organic layer was extracted and dried with Na2SO4, filtered and concentrated to yield the product as a light brown solid (14.1 g). LCMS (Method B): Rt=1.13, MH+=327

Intermediate 36

1-methylethyl[(2S,4R)-1-acetyl-6-(4-formylphenyl)-2-methyl-1,2,3,4-tetrahydro-4-quinolinyl]carbamate

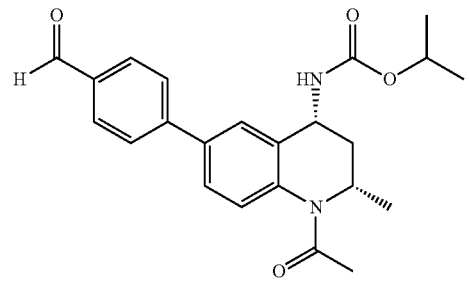 [SMILES: CC(=O)N1c2ccc(-c3ccc(C=O)cc3)cc2[C@H](NC(=O)OC(C)C)C[C@@H]1C]

1-methylethyl[(2S,4R)-1-acetyl-6-bromo-2-methyl-1,2,3,4-tetrahydro-4-quinolinyl]carbamate (for a preparation see Example 4) (1 g, 2.71 mmol), (4-formylphenyl)boronic acid (0.487 g, 3.25 mmol, available from Aldrich), Pd(Ph3P)4, (0.156 g, 0.135 mmol) and potassium carbonate (0.487 g, 3.52 mmol) were combined in dry Ethanol (7 ml) and dry toluene (7.00 ml) and the reaction mixture was de-gassed for 10 mins. The reaction mixture was heated at 85° C. overnight. The reaction mixture was allowed to cool to r.t. and concentrated. The crude reaction mixture was partitioned between water (15 ml) and ethyl acetate (5 ml) and stirred at r.t. for 30 mins. A light grey solid precipitated out and was filtered off, washed with water (5 ml) and dried in a vacuum oven to give 854 mg of grey solid. LCMS (Method B): Rt=1.00, MH+=395

Intermediate 37

1-methylethyl[(cis)-1-acetyl-6-(1-{2-[4-({[(1,1-dimethylethyl)oxy]carbonyl}amino)-1-piperidinyl]ethyl}-1H-pyrazol-4-yl)-2-methyl-1,2,3,4-tetrahydro-4-quinolinyl]carbamate

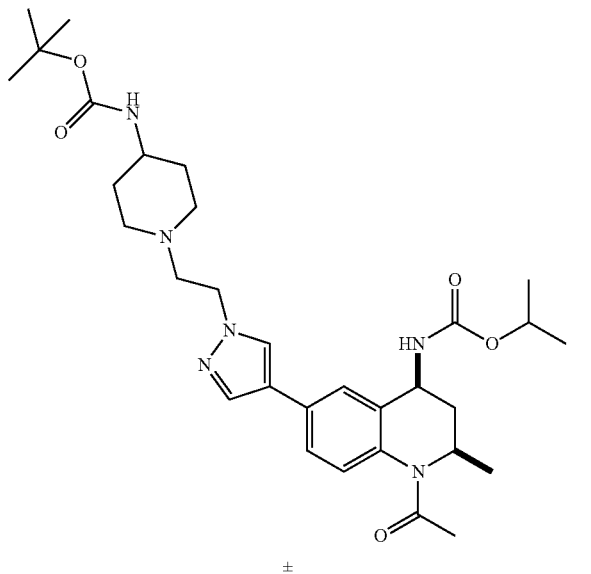 [SMILES: CC(=O)N1c2ccc(-c3cnn(CCN4CCC(NC(=O)OC(C)(C)C)CC4)c3)cc2[C@@H](NC(=O)OC(C)C)C[C@H]1C]

±

This was made in a similar manner to Example 46, using 1,1-dimethylethyl {1-[2-(4-bromo-1H-pyrazol-1-yl)ethyl]-4-piperidinyl}carbamate (for a preparation see Intermediate 17) (276 mg, 0.739 mmol). Purification was carried out on a 25+M Biotage silica column, eluting with a 0 to 6% gradient of 2M methanolic ammonia in DCM to give the desired compound (134 mg). LCMS (Method C): Rt=0.82, MH+=583

Intermediate 38

1,1-dimethylethyl 4-(2-{4-[(cis)-1-acetyl-2-methyl-4-({[(1-methylethyl)oxy]carbonyl}amino)-1,2,3,4-tetrahydro-6-quinolinyl]-1H-pyrazol-1-yl}ethyl)-1-piperazinecarboxylate

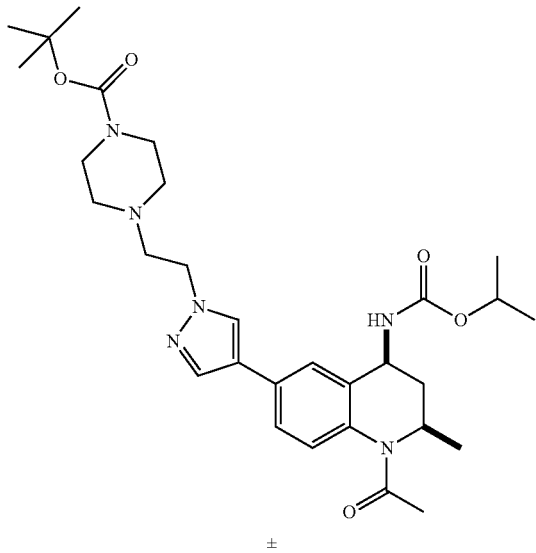 [SMILES: CC(=O)N1c2ccc(-c3cnn(CCN4CCN(C(=O)OC(C)(C)C)CC4)c3)cc2[C@@H](NC(=O)OC(C)C)C[C@H]1C]

±

This was made in a similar manner to Example 46, using 1,1-dimethylethyl 4-[2-(4-bromo-1H-pyrazol-1-yl)ethyl]-1-piperazinecarboxylate (for a preparation see Intermediate 18) (211 mg, 0.587 mmol). Purification was carried out on a 12+M Biotage silica column, eluting with a 0 to 4% gradient of 2M methanolic ammonia in DCM to give the desired compound (68 mg). LCMS (Method C): Rt=0.80, MH+=569

Intermediate 39

1-methylethyl[(cis)-1-acetyl-6-(2-formyl-1,3-thiazol-4-yl)-2-methyl-1,2,3,4-tetrahydro-4-quinolinyl]carbamate

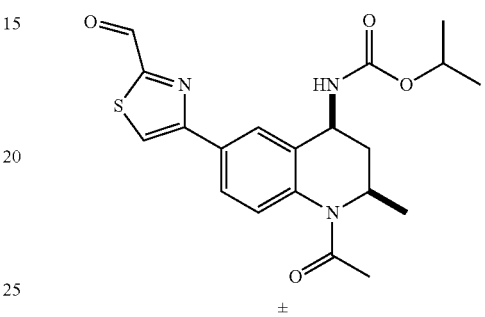

±

1-methylethyl[(cis)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 12) (50 mg, 0.120 mmol) was mixed with 4-bromo-1,3-thiazole-2-carbaldehyde (34.6 mg, 0.180 mmol, available from Frontier), potassium carbonate (33.2 mg, 0.240 mmol), tetrakis(triphenylphosphine)palladium(0) (6.94 mg, 6.01 μmol) and dissolved in ethanol (0.5 mL) and toluene (0.5 mL). The mixture was heated in a nitrogen-flushed microwave vial at 90° C. for 1 hour in a Biotage initiator and the mixture was left to cool to room temperature overnight. The residue was partitioned between distilled water (20 mL) and EtOAc (60 mL). The aqueous layer was extracted with EtOAc (60 mL) and the organic fractions were combined, washed (brine (50 mL)), dried (sodium sulfate), filtered and evaporated to dryness to give a yellow solid. This was purified on a 12+M Biotage silica column eluting with a 0-60% gradient of ethyl acetate in cyclohexane. Product-containing fractions were evaporated to dryness to give a clear, colourless solid (23 mg). LCMS (Method C): Rt=0.96, MH+=402

Intermediate 40

1-methylethyl[(cis)-1-acetyl-6-bromo-2-methyl-1,2,3,4-tetrahydro-4-quinolinyl]carbamate

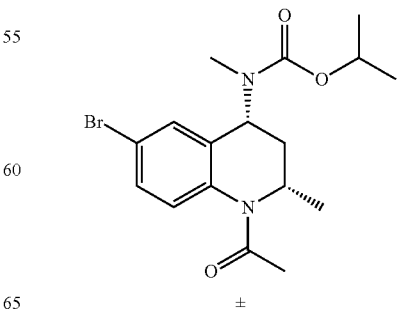

±

1-methylethyl[(cis)-1-acetyl-6-bromo-2-methyl-1,2,3,4-tetrahydro-4-quinolinyl]carbamate (for a preparation see Example 61, 125 mg, 0.339 mmol) was dissolved in N-methyl-2-pyrrolidone (NMP) (3 mL) and to this was added sodium hydride (60% in mineral oil) (14.9 mg, 0.621 mmol) and methyl iodide (0.021 mL, 0.339 mmol) the reaction was stirred overnight under nitrogen. More sodium hydride (60% in mineral oil) (2.5 mg) was added. Conversion was still not complete by LCMS analysis so more sodium hydride (2.5 mg) was added. The reaction was quenched with water (15 ml) and then diluted with ethyl acetate (30 ml). The organics were separated and aqueous reextracted with ethyl acetate (30 ml). The combined organics were washed with water (50 ml), passed through a phase separation cartridge and then reduced in vacuo to give a yellow oil (223 mg) dried under vacuum overnight. The oil was dissolved in DCM and loaded onto a 12+S silica cartridge for purification using a Biotage SP4 and a gradient of 10 to 45% ethyl acetate in cyclohexane. The appropriate fractions were combined and reduced in vacuo to give a slightly yellow oil (125 mg). LCMS (Method C): Rt=1.13, MH+=383

Intermediate 41

((cis)-6-bromo-6-methyl-1,2,3,4-tetrahydro-4-quinolinyl)formamide

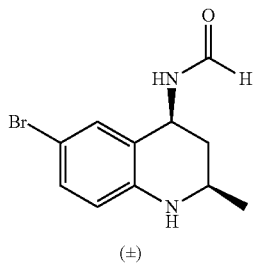

(±)

A 3 L, four neck flask under nitrogen atmosphere was charged with N-vinyl formamide (66.2 g, 0.946 mol) and dry THF (400 mL). BF$_3$.Et$_2$O (239 mL, 1.9 mol) were added dropwise at −5° C. to the milky mixture. After 15 minutes Intermediate 46 (150 g, 0.473 mol) in solution in THF (1 L) was added at −5° C. After 2 h, the mixture was slowly and carefully poured in a NaHCO$_3$ saturated solution (5 L). Ethyl acetate (2 L) was added and the mixture was transferred to a separatory funnel. The organic layer was separated and was washed 1×200 mL H$_2$O, 1×200 mL brine and dried (Na$_2$SO$_4$). The mixture was filtered and the solids washed 1×50 mL ethyl acetate. The filtrate was concentrated progressively until a precipitate appeared and the mixture cooled in an ice bath during 2 h. The precipitate was filtered through a Buchner funnel, and washed with 2×100 mL iPr$_2$O to deliver the title compound as a solid (71 g, 56%). LC/MS (Method E) m/z 269 and 271 [M+H]$^+$, Rt=2.29 min.

Intermediate 42

((cis)-6-bromo-2-ethyl-1,2,3,4-tetrahydro-4-quinolinyl)formamide

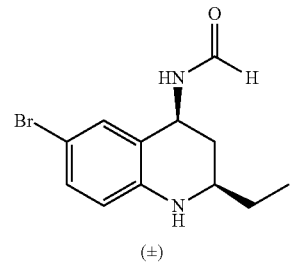 [SMILES: CC[C@@H]1C[C@H](NC=O)c2cc(Br)ccc2N1]

(±)

The titled compound was prepared by similar methods to that described for Intermediate 41 using Intermediate 47. LC/MS (Method E) m/z 284.98 [M+H]$^+$, Rt=2.6 min Intermediate 43

[(cis)-1-acetyl-6-bromo-2-methyl-1,2,3,4-tetrahydro-4-quinolinyl]formamide

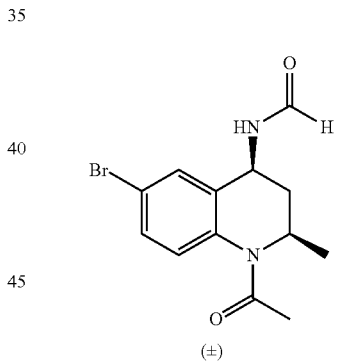

(±)

Acetyl chloride (21 mL, 0.29 mol) was added dropwise at 0° C. to a solution of ((cis)-6-bromo-2-methyl-1,2,3,4-tetrahydro-4-quinolinyl)formamide (for a preparation see Intermediate 41) (71 g, 0.26 mol) in a mixture of DCM (1 L) and pyridine (350 mL). After stirring 2 hours at 0° C. the mixture was poured into a mixture of crushed ice (2 kg) and concentrated HCl (450 mL). The product was extracted with DCM (1 L) washed with brine and dried over Na$_2$SO$_4$. Concentration under vacuo afforded the expected product as an off white solid (82 g, 100%).

$^1$H NMR (300 MHz, CHLOROFORM-d) δ ppm 0.98 (d, 3H) 1.15 (m, 1H) 1.95 (s, 3H) 2.4 (m, 1H) 4.7 (m, 1H) 4.85 (m, 1H) 5.8 (br d, 1H) 6.85 (d, 1H) 7.15 (s, 1H) 7.25 (d, 1H) 8.2 (s, 1H)

Intermediate 44

[(cis)-1-acetyl-6-bromo-2-ethyl-1,2,3,4-tetrahydro-4-quinolinyl]formamide

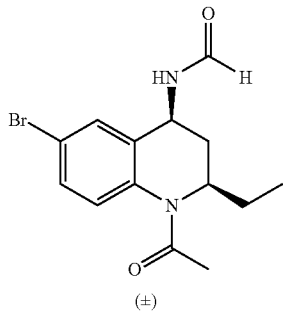 [SMILES: CC[C@@H]1C[C@H](NC=O)c2cc(Br)ccc2N1C(C)=O]

(±)

The title compound was prepared by similar methods to that described for Intermediate 43 using Intermediate 42. LC/MS (Method E) m/z 324.94 [M−H]⁻, Rt=2.38 min

Intermediate 45

(cis)-1-acetyl-6-bromo-2-methyl-1,2,3,4-tetrahydro-4-quinolinamine

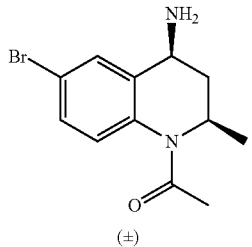 [SMILES: CC(=O)N1c2ccc(Br)cc2[C@@H](N)C[C@H]1C]

(±)

To a suspension of [(cis)-1-acetyl-6-bromo-2-methyl-1,2,3,4-tetrahydro-4-quinolinyl]formamide (for a preparation see Intermediate 43) (4 g, 12.9 mol) in MeOH (50 mL) was added 6N HCl (6.5 mL, 38.6 mmol). The resulting mixture was stirred at reflux for 3 hours and the medium was made basic by the addition of 2N NaOH. The MeOH was evaporated under reduced pressure and the organic material extracted with EtOAc (250 mL). The organic phase was washed with brine, dried over $Na_2SO_4$ and concentrated to dryness to afford the title compound as an oil (3.3 g, 91%); LC/MS (Method E) m/z 284 [M+H]⁺, Rt=2.18 min

Intermediate 46

[1-(1H-1,2,3-benzotriazol-1-yl)ethyl](4-bromophenyl)amine

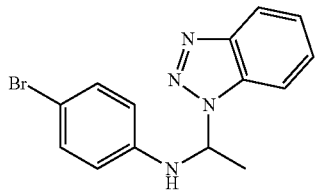 [SMILES: CC(Nc1ccc(Br)cc1)n1nnc2ccccc21]

To a suspension of benzotriazole (139 g, 1.16 mol) in toluene (2 L) in a 3 L, four neck flask under nitrogen atmosphere was added at room temperature a solution of 4-bromoaniline (200 g, 1.16 mol) in toluene (300 mL). Then, via an addition funnel was added drop wise acetaldehyde (64.7 ml, 1.17 mol) in solution in toluene (200 mL). The reaction mixture becomes progressively homogenous and then gives a precipitate. The resulting mixture is stirred for 12 hours under nitrogen atmosphere and then filtered. The precipitate is recrystallised in toluene to afford the title compound as a white solid (304 g, 82%).

1H NMR (300 MHz, CHLOROFORM-d) δ ppm 2.1 (m, 3H) 4.9 (m, 0.66; H) 5.15 (m, 0.33H) 6.5-6.9 (m, 3H) 7.2-8.2 (m, 7H)

Intermediate 47

[1-(1H-1,2,3-benzotriazol-1-yl)propyl](4-bromophenyl)amine

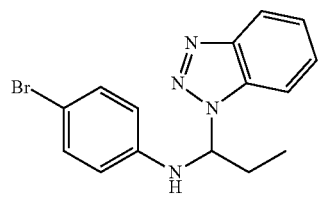 [SMILES: CCC(Nc1ccc(Br)cc1)n1nnc2ccccc21]

The title compound was prepared by similar methods to that described for Intermediate 46 using propionaldehyde and was isolated as a white powder. Mp: 132° C.

Intermediate 48

[(cis)-1-acetyl-6-(4-formylphenyl)-2-methyl-1,2,3,4-tetrahydro-4-quinolinyl]formamide

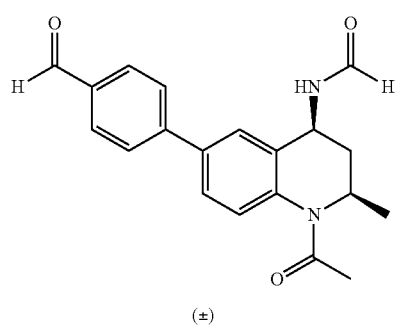 [SMILES: CC(=O)N1c2ccc(-c3ccc(C=O)cc3)cc2[C@@H](NC=O)C[C@H]1C]

(±)

To a solution of [(cis)-1-acetyl-6-bromo-2-methyl-1,2,3,4-tetrahydro-4-quinolinyl]formamide (for a preparation see Intermediate 43) (82 g, 0.263 mol) in DME (2 L) are added (4-formylphenyl)boronic acid (51.4 g, 0.34 mol) at room temperature. A 2N solution of $Na_2CO_3$ (527 mL, 1.05 mol) and tetrakis(triphenylphosphine)palladium(0) (8.2 g, 10% w/w) are added and the mixture is heated to reflux under a nitrogen atmosphere. After 2 hours, the reaction is complete and the mixture is concentrated under reduced pressure. The residue is taken up in water (1 L) and the darkened mixture is diluted with EtOAC (1 L) and transferred to a separatory funnel. A dark precipitate has formed and is isolated by filtration after separation of the organic phase. The organic layer is dried over $Na_2SO_4$ and delivers the title compound (37.5 g) as a yellow solid after concentration under reduced pressure and precipitation of the organic residue in a DCM/hexane mixture. The dark solid is taken up in a DCM/MeOH mixture and purified by flash chromatography on silica gel eluting with a 80/2 ratio of DCM/MeOH to afford the title compound (45 g) as a yellow brown solid. Mp: 85.6° C.

Intermediate 49

1-methylethyl (2E)-2-butenoylcarbamate

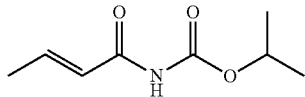

Isopropyl carbamate (30 g, 291 mmol, available from TCI) was charged to a 3 L Lara vessel and dry Tetrahydrofuran (THF) (150 ml) added. (2E)-2-butenoyl chloride (31.2 ml, 326 mmol, available from Aldrich) was added under nitrogen and the jacket cooled to −30° C. When the solution temperature reached −17° C. 1M Lithium tert-butoxide (655 ml, 655 mmol) was added by peristaltic pump over 2 hours, keeping the reaction temperature between −10° C. and −18° C. Once the addition was complete the mixture was complete the mixture was stirred for 30 mins and brought to 0° C. Diethyl ether (450 ml) and 1M HCl (375 ml) were added and the mixture brought to 20° C. with vigorous stirring. The stirring was stopped, the layers allowed to separate and the aqueous layer run off. Brine (375 ml) was added and the mixture stirred vigorously. The stirring was stopped, the layers allowed to separate and the aqueous layer run off. The organic layer was dried (magnesium sulfate), filtered and evaporated to a brown oil (60 g). The mixture was loaded on to a 40+M Biotage silica column and eluted with DCM:ethyl acetate (1:1 to 0:1, 10 CV). The product containing fractions were evaporated to dryness and loaded on to a 1500 g Redisep Isco silica column and eluted with a gradient of 0 to 40% ethyl acetate in cyclohexane. The clean, product containing fractions were evaporated to an off white solid (15.41 g). LCMS (Method C): Rt=0.68, MH+=172

Intermediate 50

(R-BI NAP)ditriflatebis(acetonitrile)palladium(II)

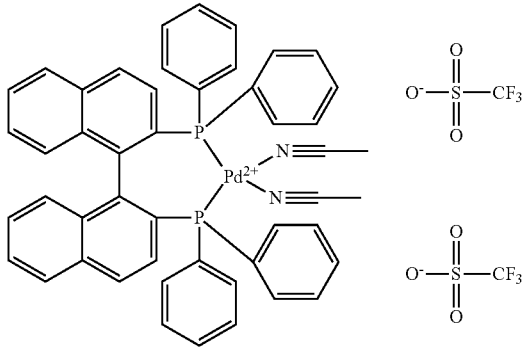

R-(+)-BINAP (6.08 g, 9.76 mmol, available from Avocado) was stirred in Dichloromethane (DCM) (626 ml) and Dichlorobis(acetonitrile)palladium (II) (2.5 g, 9.64 mmol, available from Aldrich) added. The mixture was stirred under nitrogen for 30 mins, the suspension had not become a solution and more DCM (100 ml) was added. The mixture was stirred for a further 30 mins and Silver triflate (5.00 g, 19.47 mmol, available from Aldrich) dissolved in Acetonitrile (250 ml) was added. The mixture changed from an orange cloudy suspension to a yellow suspension. The mixture was stirred for 1 hour, filtered through celite and evaporated to an orange solid. The residue was dried under vacuum (at approximately 14 mbar) at room temperature over the weekend to give the desired product (10.69 g).

$^1$H NMR (400 MHz, MeCN-d3) δ ppm 2.0 (s, 6H), 6.7 (d, 2H), 6.9 (br m, 4H), 7.1 (br t, 2H), 7.2 (t, 2H), 7.5-7.9 (m, 22H)

Intermediate 51

1-methylethyl[(2S,4R)-1-acetyl-2-methyl-6-(1-{2-[methyl(phenylmethyl)amino]ethyl}-1H-pyrazol-4-yl)-1,2,3,4-tetrahydro-4-quinolinyl]carbamate

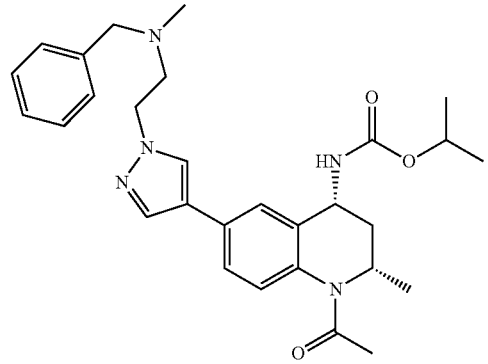 [SMILES: CC(=O)N1c2ccc(-c3cnn(CCN(C)Cc4ccccc4)c3)cc2[C@H](NC(=O)OC(C)C)C[C@@H]1C]

1-Methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (300 mg, 0.721 mmol, for a preparation see Intermediate 52), potassium carbonate (149 mg, 1.081 mmol) and 2-(4-bromo-1H-pyrazol-1-yl)-N-methyl-N-(phenylmethyl)ethanamine (317 mg, 1.078 mmol, for a preparation see Intermediate 53) were stirred in ethanol (3 mL) and toluene (3.00 mL). The mixture was degassed, tetrakis(triphenylphosphine)palladium(0) (41.6 mg, 0.036 mmol) added, the mixture degassed again and heated to reflux (90° C.) under nitrogen for 4.5 hours. The mixture was cooled to room temperature, loaded on to a 5 g SCX cartridge, eluted with MeOH (50 ml), 2M methanolic ammonia (25 ml) and the basic fractions evaporated to dryness. The residue was loaded on to a 12+M Biotage silica column and eluted with a gradient of 0 to 5% 2M methanolic ammonia in DCM. The product containing fractions were evaporated to a colourless gum (223 mg).

LCMS (Method C): Rt=0.78, MH+=504

Intermediate 52

1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate

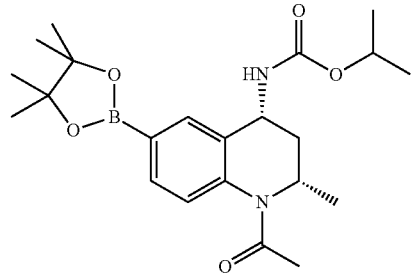 [SMILES: CC(=O)N1c2ccc(B3OC(C)(C)C(C)(C)O3)cc2[C@H](NC(=O)OC(C)C)C[C@@H]1C]

1-methylethyl[(2S,4R)-1-acetyl-6-bromo-2-methyl-1,2,3,4-tetrahydro-4-quinolinyl]carbamate (for a preparation see Example 4) (1 g, 2.71 mmol) was mixed with potassium acetate (0.399 g, 4.06 mmol), 4,4,4',4',5,5,5',5'-octamethyl-2,2'-bi-1,3,2-dioxaborolane (1.375 g, 5.42 mmol, available from Aldrich) and 1,1-bis(diphenylphosphino)ferrocene/dichloropalladium(II) (0.040 g, 0.054 mmol, available from Apollo Scientific), dissolved in dimethyl sulfoxide (20 ml) and stirred under nitrogen at 80° C. for 6 hours. The reaction was left to cool to room temperature overnight. The mixture was partitioned between distilled water (30 mL) and DCM (70 mL). The aqueous layer was extracted with DCM (50 mL) and the organic fractions were combined, washed with brine (50 mL), dried (MgSO4), filtered and evaporated to dryness to give a black liquid (4.119 g). The mixture was purified on a 40+M biotage silica column, eluting with a gradient of 10 to 40% Ethyl acetate in cyclohexane. Product-containing fractions were evaporated to dryness to give a clear, slightly yellow solid (1.498 g) which was used without further purification. LCMS (Method C): Rt=1.13, MH+=417

Intermediate 53

2-(4-bromo-1H-pyrazol-1-yl)-N-methyl-N-(phenylmethyl)ethanamine

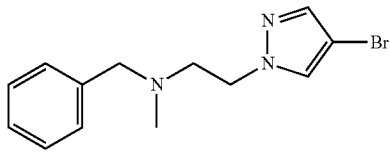 [SMILES: CN(CCn1cc(Br)cn1)Cc1ccccc1]

4-bromo-1-(2-chloroethyl)-1H-pyrazole (317 mg, 1.513 mmol, for a preparation see Intermediate 54) was dissolved in N,N-dimethylformamide (DMF) (5 mL) and cesium carbonate (740 mg, 2.270 mmol) added with N-methyl-1-phenylmethanamine (0.973 mL, 7.57 mmol, available from Aldrich). The mixture was heated to 80° C. for 3 hours then allowed to stir at 80° C. overnight. The mixture was cooled to room temperature and loaded on to a 20 g SCX cartridge. The SCX was eluted with MeOH (100 ml) and 2M methanolic ammonia (100 ml). The basic fraction was evaporated to a colourless oil, loaded on to a 25+M Biotage silica column and eluted with a gradient of 0 to 2.5% 2M methanolic ammonia in DCM. The product containing fractions were evaporated to a pale yellow oil (155 mg). LCMS (Method C): Rt=0.67, MH+=294

Intermediate 54

4-bromo-1-(2-chloroethyl)-1H-pyrazole

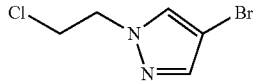

4-Bromopyrazole (700 mg, 4.76 mmol, available from Aldrich), cesium carbonate (2328 mg, 7.14 mmol, available from Aldrich) and 1-bromo-2-chloroethane (0.592 ml, 7.14 mmol, available from Acros) were suspended in N,N-dimethylformamide (DMF) (14 ml) and heated to 60° C. under microwave conditions in an Emrys Optimiser for 1 hour. The mixture was partitioned between water (20 ml) and ethyl acetate (60 ml). The aqueous layer was run off and the organic washed (water ×3 (10 ml), brine (10 ml)), dried (magnesium sulfate) and evaporated to dryness to give the desired compound (868 mg).

LCMS (Method C): Rt=0.84, MH+=211

Intermediate 55

(2S,4R)-1-Acetyl-6-bromo-2-methyl-1,2,3,4-tetrahydro-4-quinolinamine

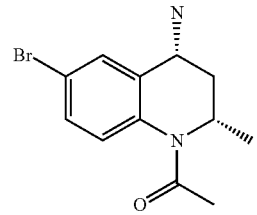 [SMILES: CC(=O)N1c2ccc(Br)cc2[C@H](N)C[C@@H]1C]

To a suspension of aluminium chloride (6.97 g, 52.3 mmol) in dichloromethane (DCM) (80 mL) at 0° C. under nitrogen was added 1-methylethyl[(2S,4R)-1-acetyl-6-bromo-2-methyl-1,2,3,4-tetrahydro-4-quinolinyl]carbamate (for a preparation, see Example 4) (5.08 g, 13.76 mmol) in DCM (10 mL). The resulting mixture was stirred for 30 min then triethylamine (23.01 mL, 165 mmol) in methanol (8 mL) was slowly added to the mixture. AcOEt (200 mL) was added and the resulting mixture was stirred at room temperature for 15 min. The precipitate formed was filtered off and rinsed with AcOEt then partitioned between a saturated NaHCO₃ aqueous solution and DCM (200 mL each). The biphasic mixture was vigorously stirred for 2 h. The two layers were separated and the organic phase was dried using a phase separator then concentrated in vacuo to give a first batch of (2S,4R)-1-acetyl-6-bromo-2-methyl-1,2,3,4-tetrahydro-4-quinolinamine. The aqueous layer was treated with another 200 mL of DCM and the resulting biphasic mixture was vigorously stirred for 20 min. The two layers were separated and the organic phase was dried using a phase separator then concentrated in vacuo to give a second batch of (2S,4R)-1-acetyl-6-bromo-2-methyl-1,2,3,4-tetrahydro-4-quinolinamine. Both batches were combined to give (2S,4R)-1-acetyl-6-bromo-2-methyl-1,2,3,4-tetrahydro-4-quinolinamine (3.65 g, 12.7 mmol, 93%) as white solid which was used in the next step without further purification.

LCMS (method A): Retention time 0.78 min, [M−H]−=281.21 (1 Br)

Intermediate 56

1-Methylethyl {(2S,4R)-1-acetyl-6-[hydroxyamino)(imino)methyl]-2-methyl-1,2,3,4-tetrahydro-4-quinolinyl}carbamate

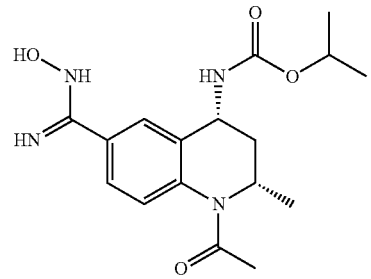 [SMILES: CC(=O)N1c2ccc(C(=N)NO)cc2[C@H](NC(=O)OC(C)C)C[C@@H]1C]

To a solution of 1-methylethyl[(2S,4R)-1-acetyl-6-cyano-2-methyl-1,2,3,4-tetrahydro-4-quinolinyl]carbamate (for a preparation, see Intermediate 57) (238 mg, 0.755 mmol) in ethanol (5 mL) at room temperature was added hydroxylamine (50 μl, 59.0 mmol) (50% w/w in water) and the resulting mixture was stirred at 80° C. for 16 h then cooled to room temperature. Most of the ethanol was removed in vacuo and the residue was dissolved with DCM. The organic phase was dried using a phase separator then concentrated in vacuo to give 1-methylethyl {(2S,4R)-1-acetyl-6-[hydroxyamino)(imino)methyl]-2-methyl-1,2,3,4-tetrahydro-4-quinolinyl}carbamate (263 mg, 0.755 mmol, 100% yield) as a white foam which was used in the next phase without further purification. LCMS (method A): Retention time 0.67 min, [M+H]+=349.08

Intermediate 57

1-Methylethyl[(2S,4R)-1-acetyl-6-cyano-2-methyl-1,2,3,4-tetrahydro-4-quinolinyl]carbamate

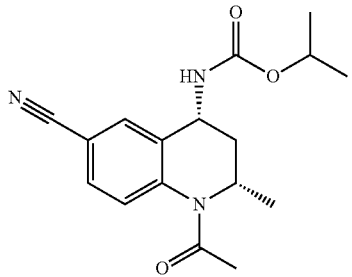

A solution of 1-methylethyl[(2S,4R)-1-acetyl-6-bromo-2-methyl-1,2,3,4-tetrahydro-4-quinolinyl]carbamate (for a preparation, see Example 4) (355 mg, 0.962 mmol) in N,N-dimethylformamide (DMF) (5 mL) at room temperature was degassed over 30 min under house vacuum and quenched several times with nitrogen. Tetrakis(triphenylphosphine)palladium(0) (116 mg, 0.1 mmol) and zinc(II) cyanide (153 mg, 1.3 mmol) were then added and the resulting yellow mixture was stirred under nitrogen at 100° C. for 5 h then cooled to room temperature. The insoluble were filtered off, rinsed with AcOEt then destroyed with bleach. The organic phase was washed with water. The aqueous phase was extracted with AcOEt. The combined organic phases were washed twice with water then brine, dried over MgSO4 and concentrated in vacuo. Purification of the residue by SP4 using a 10 G silica cartridge (gradient: 13 to 63% AcOEt in Hexanes) gave 1-methylethyl[(2S,4R)-1-acetyl-6-cyano-2-methyl-1,2,3,4-tetrahydro-4-quinolinyl]carbamate (238 mg, 0.755 mmol, 78% yield) as a white solid.

LCMS (method A): Retention time 0.88 min, [M+H]+=316.14

Intermediate 58

1-Methylethyl[(2S,4R)-1-acetyl-6-ethynyl-2-methyl-1,2,3,4-tetrahydro-4-quinolinyl]carbamate

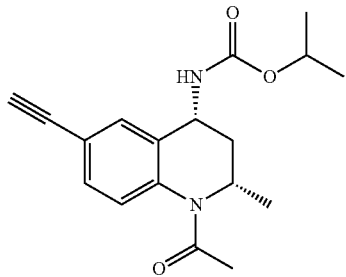 [SMILES: C#Cc1ccc2c(c1)[C@H](NC(=O)OC(C)C)C[C@H](C)N2C(C)=O]

To a solution of 1-methylethyl {(2S,4R)-1-acetyl-2-methyl-6-[(trimethylsilyl)ethynyl]-1,2,3,4-tetrahydro-4-quinolinyl}carbamate (for a preparation, see Intermediate 59) (216 mg, 0.559 mmol) in tetrahydrofuran (THF) (3 mL) at room temperature was added TBAF (1M in THF, 0.671 mL, 0.671 mmol) and the resulting black mixture was stirred at this temperature for 35 min. Most of the solvent was removed in vacuo and the residue dissolved in AcOEt. The organic phase was washed with a saturated NaHCO3 aqueous solution then twice with brine, dried over MgSO4 and concentrated in vacuo. Purification of the residue on SP4 using a 10 G silica cartridge (Gradient: 13 to 63% AcOEt in Hexanes) gave 1-methylethyl[(2S,4R)-1-acetyl-6-ethynyl-2-methyl-1,2,3,4-tetrahydro-4-quinolinyl]carbamate (156 mg, 0.496 mmol, 89% yield) as a very pale yellow foam.

LCMS (method A): Retention time 0.98 min, [M+H]+=315.14

Intermediate 59

1-Methylethyl {(2S,4R)-1-acetyl-2-methyl-6-[(trimethylsilyl)ethynyl]-1,2,3,4-tetrahydro-4-quinolinyl}carbamate

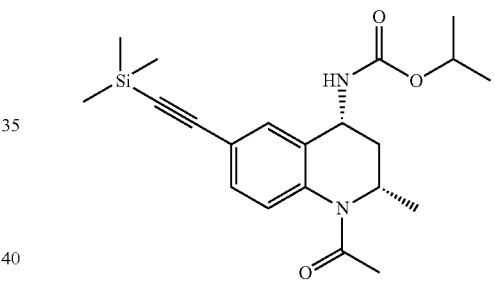

A flask was charged with 1,1-dimethylethyl[(2S,4R)-1-acetyl-6-bromo-2-methyl-1,2,3,4-tetrahydro-4-quinolinyl]carbamate (for a preparation, see Example 4) (4 g, 10.44 mmol), copper(I) iodide (0.199 g, 1.044 mmol) and bis(triphenylphosphine)palladium(II) chloride (0.733 g, 1.044 mmol) then filled with N,N-dimethylformamide (DMF) (60 mL). Triethylamine (58.2 mL, 417 mmol) and ethynyl(trimethyl)silane (29.7 mL, 209 mmol) were added and the resulting mixture was stirred for 20 h at 90° C. under nitrogen then cooled to room temperature. Most of the volatiles were removed in vacuo. The residue was partitioned between AcOEt and water/brine (1/1). The layers were separated and the aqueous phase was extracted with AcOEt. The combined organic phases were washed three times with water/brine (1/1), dried over MgSO4 then concentrated in vacuo. Purification of the residue by SP4 on a 100 G silica cartridge (gradient: 10 to 50% AcOEt in Hexanes) gave 1,1-dimethylethyl {(2S,4R)-1-acetyl-2-methyl-6-[(trimethylsilyl)ethynyl]-1,2,3,4-tetrahydro-4-quinolinyl}carbamate (3.4 g, 8.49 mmol, 81% yield) as a black foam.

LCMS (method A): Retention time 1.39 min, [M+H]+=400.19

Intermediate 60

1-Methylethyl((2S,4R)-1-acetyl-6-{5-[({[(1,1-dimethylethyl)oxy]carbonyl}amino)methyl]-1,2,4-oxadiazol-3-yl}-2-methyl-1,2,3,4-tetrahydro-4-quinolinyl)carbamate

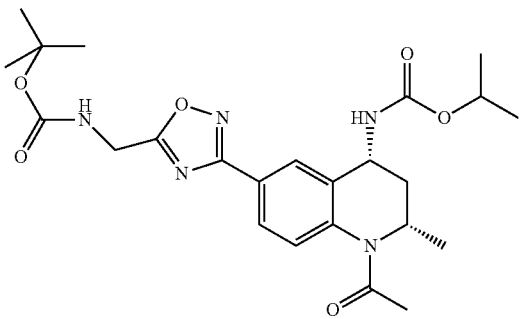 [SMILES: CC(=O)N1c2ccc(-c3noc(CNC(=O)OC(C)(C)C)n3)cc2[C@H](NC(=O)OC(C)C)C[C@@H]1C]

A flask was charged with N-{[(1,1-dimethylethyl)oxy]carbonyl}glycine (72.4 mg, 0.413 mmol) and HATU (170 mg, 0.448 mmol) then filled with N,N-dimethylformamide (DMF) (2 mL). DIPEA (0.180 mL, 1.033 mmol) was added and the resulting pale yellow solution was stirred for 5 min. 1-Methylethyl {(2S,4R)-1-acetyl-6-[(hydroxyamino)(imino)methyl]-2-methyl-1,2,3,4-tetrahydro-4-quinolinyl}carbamate (for a preparation, see Intermediate 56) (120 mg, 0.344 mmol) in N,N-dimethylformamide (DMF) (2 mL) was then added via syringe and the resulting mixture was stirred at room temperature for 1 h. The mixture was then stirred at 100° C. under nitrogen for 3.5 h then cooled to room temperature and dissolved in AcOEt. The organic phase was washed with water. The aqueous phase was extracted with AcOEt. The combined organic phases were washed three times with water then brine, dried over MgSO4 and concentrated in vacuo. Purification of the residue by SP4 on a 10 G silica cartridge (gradient 23 to 63% AcOEt in Hexanes) gave 1-methylethyl((2S,4R)-1-acetyl-6-{5-[({[(1,1-dimethylethyl)oxy]carbonyl}amino)methyl]-1,2,4-oxadiazol-3-yl}-2-methyl-1,2,3,4-tetrahydro-4-quinolinyl)carbamate (132 mg, 0.271 mmol, 79% yield) as a white foam. LCMS (method A): Retention time 1.07 min, [M−H]−=486.23

Intermediate 61

Ethyl {4-[(2S,4R)-1-acetyl-2-methyl-4-({[(1-methylethyl)oxy]carbonyl}amino)-1,2,3,4-tetrahydro-6-quinolinyl]phenyl}acetate

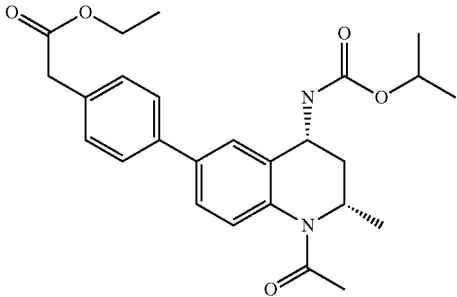 [SMILES: CCOC(=O)Cc1ccc(-c2ccc3c(c2)[C@H](NC(=O)OC(C)C)C[C@H](C)N3C(C)=O)cc1]

A flask was charged with ethyl (4-bromophenyl)acetate (0.174 mL, 1.000 mmol), 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation, see Intermediate 52) (416 mg, 1 mmol), potassium carbonate (415 mg, 3.00 mmol) and [1,1'-bis(diphenylphosphino)ferrocene]dichloropalladium(II) (73.2 mg, 0.100 mmol) then filled with 1,4-dioxane (6 mL) and water (2 mL) and flushed with nitrogen. The resulting mixture was stirred under microwave irradiation at 120° C. for 30 min then cooled to room temperature. Most of the 1,4-dioxane was removed in vacuo and the residue was partitioned between AcOEt and water. The layers were separated and the aqueous phase was extracted with AcOEt. The combined organic phases were washed with brine, dried over MgSO4 and concentrated in vacuo. Purification of the residue by SP4 on a 25 G silica cartridge (gradient: 5 to 25% of (10% MeOH in DCM) in DCM) gave ethyl {4-[(2S,4R)-1-acetyl-2-methyl-4-({[(1-methylethyl)oxy]carbonyl}amino)-1,2,3,4-tetrahydro-6-quinolinyl]phenyl}acetate (270 mg, 0.597 mmol, 59.7% yield).

LCMS (method A): Retention time 1.16 min, [M+H]+= 453.09.

Intermediate 62

1-Methylethyl((2S,4R)-1-acetyl-6-{3-[({[(1,1-dimethylethyl)oxy]carbonyl}amino)methyl]-1,2,4-oxadiazol-5-yl}-2-methyl-1,2,3,4-tetrahydro-4-quinolinyl)carbamate

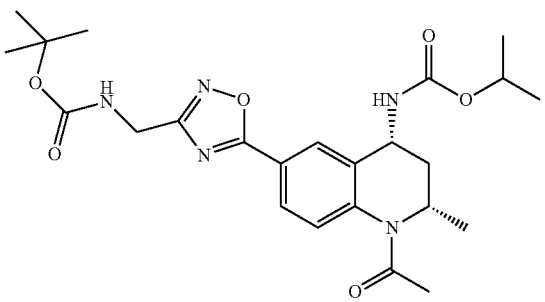 [SMILES: CC(=O)N1c2ccc(-c3nc(CNC(=O)OC(C)(C)C)no3)cc2[C@H](NC(=O)OC(C)C)C[C@@H]1C]

A flask was charged with (2S,4R)-1-acetyl-2-methyl-4-({[(1-methylethyl)oxy]carbonyl}amino)-1,2,3,4-tetrahydro-6-quinolinecarboxylic acid (for a preparation, see Intermediate 63) (100 mg, 0.3 mmol) and HATU (137 mg, 0.360 mmol) then filled with N,N-dimethylformamide (DMF) (2 mL) and the mixture was treated with DIPEA (0.157 mL, 0.900 mmol). The resulting mixture was stirred at room temperature for 5 min then 1,1-dimethylethyl[2-(hydroxyamino)-2-iminoethyl]carbamate (for a preparation, see Intermediate 64) (68.1 mg, 0.360 mmol) in N,N-dimethylformamide (DMF) (2 mL) was added. The resulting mixture was stirred at room temperature under nitrogen for 30 min, at 110° C. for 7 h then cooled to room temperature. The mixture was partitioned between AcOEt and water and the phases were separated. The aqueous phase was extracted three times with AcOEt and the combined organic phases were washed twice with water then brine, dried over MgSO4 and concentrated in vacuo. Purification of the residue by SP4 using a 10 G silica cartridge (gradient: 8 to 38% (10% MeOH in DCM) in DCM) gave 1-methylethyl((2S,4R)-1-acetyl-6-{3-[({[(1,1-dimethylethyl)oxy]carbonyl}amino)methyl]-1,2,4-oxadiazol-5-yl}-2-methyl-1,2,3,4-tetrahydro-4-quinolinyl)carbamate (70 mg, 0.144 mmol, 47.9% yield) as a pale yellow solid.

LCMS (method A): Retention time 1.06 min, [M+H]+= 488.14

Intermediate 63

(2S,4R)-1-Acetyl-2-methyl-4-({[(1-methylethyl)oxy]carbonyl}amino)-1,2,3,4-tetrahydro-6-quinolinecarboxylic acid

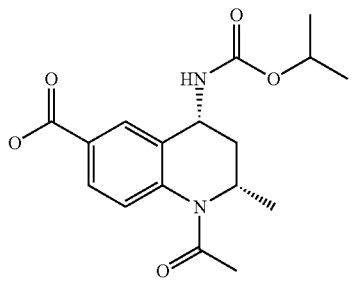 [SMILES: CC(=O)N1c2ccc(C(=O)O)cc2[C@H](NC(=O)OC(C)C)C[C@@H]1C]

Lithium hydroxide (0.365 g, 15.23 mmol) in water (5 mL) was added to a solution of butyl (2S,4R)-1-acetyl-2-methyl-4-({[(1-methylethyl)oxy]carbonyl}amino)-1,2,3,4-tetrahydro-6-quinolinecarboxylate (for a preparation, see Intermediate 65) (1.982 g, 5.08 mmol) in ethanol (5 ml) and the mixture was stirred for 16 h at this temperature then concentrated in vacuo. The aqueous residue was diluted with water (5 mL) and the aqueous phase was washed with Et$_2$O (10 mL). The aqueous layer was acidified with a 2M HCl aqueous solution (pH<2) and extracted with EtOAc (2×10 mL). The combined organic phases were dried over MgSO$_4$ and concentrated in vacuo to give (2S,4R)-1-acetyl-2-methyl-4-({[(1-methylethyl)oxy]carbonyl}amino)-1,2,3,4-tetrahydro-6-quinolinecarboxylic acid (1.45 g, 4.34 mmol, 85% yield) as a colourless crystalline solid LCMS (method A): Retention time 0.72 min, [M+H]+= 335.07

Intermediate 64

1,1-Dimethylethyl[2-(hydroxyamino)-2-iminoethyl]carbamate

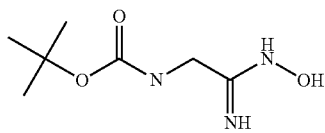

A flask was charged with 1,1-dimethylethyl(cyanomethyl)carbamate (1.562 g, 10 mmol) then filled with ethanol (15 mL) and hydroxylamine (50% w/w in water, 2.451 mL, 40.0 mmol) and the resulting mixture was stirred at 80° C. for 1.5 h then cooled to room temperature and concentrated in vacuo. The residue was dissolved in DCM and the organic phase was dried using a phase separator then concentrated in vacuo. Trituration of the residue in Et$_2$O gave 1,1-dimethylethyl[2-(hydroxyamino)-2-iminoethyl]carbamate (1.8 g, 9.51 mmol, 95% yield) as a white solid which was used in the next step without further purification.

Intermediate 65

Butyl (2S,4R)-1-acetyl-2-methyl-4-({[(1-methylethyl)oxy]carbonyl}amino)-1,2,3,4-tetrahydro-6-quinolinecarboxylate

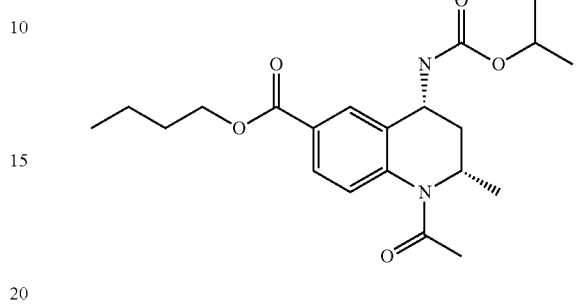

1-Methylethyl[(2S,4R)-1-acetyl-6-bromo-2-methyl-1,2,3,4-tetrahydro-4-quinolinyl]carbamate (for a preparation, see Example 4) (2.4 g, 6.50 mmol), N,N-dimethyl-4-pyridinamine (1.588 g, 13.00 mmol), trans-di-mu(m)-acetatobis[2-(di-o-tolylphosphino)benzyl]dipalladium(II) (Hermann's catalyst) (0.305 g, 0.325 mmol), 1-butanol (7.23 g, 97 mmol), molybdenum hexacarbonyl (0.858 g, 3.25 mmol), DIPEA (1.680 g, 13.00 mmol) were combined with 1,4-dioxane (2 mL) in 2 sealed 20 mL vials and the mixture was stirred at 180° C. for 30 min under microwave irradiation, then cooled to room temperature. The microwave seals were distinctly raised on completion of the reaction and the pressure was released by use of a 20 mL syringe and needle. The vials were opened and the black reaction mixtures were combined in a 250 mL conical flask, diluted with EtOAc (40 mL) and treated with water. The layers were separated and the organic phase was dried over MgSO$_4$ then concentrated in vacuo. Purification of the residue using SP4 on a 50 G silica cartridge (gradient: 0-100% AcOEt in Hexanes) gave butyl (2S,4R)-1-acetyl-2-methyl-4-({[(1-methylethyl)oxy]carbonyl}amino)-1,2,3,4-tetrahydro-6-quinolinecarboxylate (1.822 g, 4.67 mmol, 71.8% yield)

LCMS (method A): Retention time 1.13 min, [M+H]+= 391.11

Intermediate 66

1-Methylethyl((2S,4R)-1-acetyl-6-{3-[2-({[(1,1-dimethylethyl)oxy]carbonyl}amino)ethyl]-1,2,4-oxadiazol-5-yl}-2-methyl-1,2,3,4-tetrahydro-4-quinolinyl)carbamate

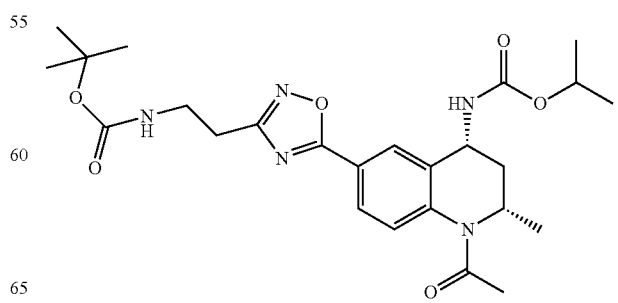

A flask was charged with (2S,4R)-1-acetyl-2-methyl-4-({[(1-methylethyl)oxy]carbonyl}amino)-1,2,3,4-tetrahydro-6-quinolinecarboxylic acid (for a preparation, see Intermediate 63) (100 mg, 0.3 mmol) and HATU (137 mg, 0.360 mmol) then filled with N,N-dimethylformamide (DMF) (2 mL) and DIPEA (0.157 mL, 0.900 mmol). The resulting mixture was stirred at room temperature for 5 min then 1,1-dimethylethyl [2-(hydroxyamino)-2-iminoethyl]carbamate (for a preparation, see Intermediate 67) (68.1 mg, 0.360 mmol) in N,N-dimethylformamide (DMF) (2 mL) was added. The resulting mixture was stirred at this temperature under nitrogen for 30 min, at 110° C. for 7 h then cooled to room temperature. The mixture was partitioned between AcOEt and water and the phases were separated. The aqueous phase was extracted three times with AcOEt and the combined organic were washed twice with water then brine, dried over MgSO₄ and concentrated in vacuo. Purification of the residue by SP4 using 10 G silica cartridge, (gradient: 8 to 38% (10% MeOH in DCM) in DCM) gave 1-methylethyl((2S,4R)-1-acetyl-6-{3-[2-({[(1,1-dimethylethyl)oxy]carbonyl}amino)ethyl]-1,2,4-oxadiazol-5-yl}-2-methyl-1,2,3,4-tetrahydro-4-quinolinyl)carbamate (60 mg, 0.120 mmol, 39.9% yield) as a pale yellow solid. LCMS (method A): Retention time 1.04 min, [M+H-Boc]+=402.0

Intermediate 67

1,1-Dimethylethyl[3-(hydroxyamino)-3-iminopropyl]carbamate

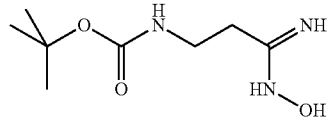

A flask was charged with 1,1-dimethylethyl (2-cyanoethyl)carbamate (1.702 g, 10 mmol) then filled with ethanol (20 mL) and hydroxylamine (50% w/w in water, 2.451 mL, 40.0 mmol). The resulting mixture was stirred at 80° C. for 90 min then cooled to room temperature and concentrated in vacuo. The residue was dissolved in DCM and the organic phase was dried using a phase separator then concentrated in vacuo. Trituration of the residue with Et₂O gave 1,1-dimethylethyl [3-(hydroxyamino)-3-iminopropyl]carbamate (1.87 g, 9.20 mmol, 92% yield) as a white solid which was in the next step without further purification.

Intermediate 68

1-Methylethyl[(2S,4R)-1-acetyl-6-(3-{2-[{[(1,1-dimethylethyl)oxy]carbonyl}(methyl)amino]ethyl}-1,2,4-oxadiazol-5-yl)-2-methyl-1,2,3,4-tetrahydro-4-quinolinyl]carbamate

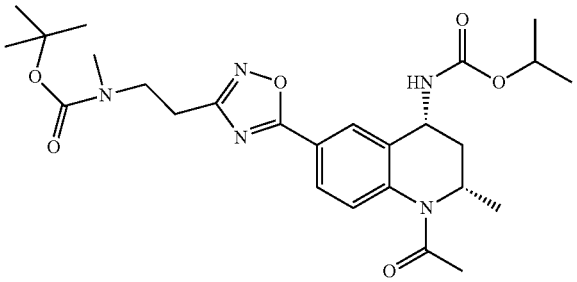 [SMILES: CC(=O)N1c2ccc(-c3nc(CCN(C)C(=O)OC(C)(C)C)no3)cc2[C@H](NC(=O)OC(C)C)C[C@@H]1C]

A flask was charged with (2S,4R)-1-acetyl-2-methyl-4-({[(1-methylethyl)oxy]carbonyl}amino)-1,2,3,4-tetrahydro-6-quinolinecarboxylic acid (for a preparation, see Intermediate 63) (100 mg, 0.3 mmol) and HATU (137 mg, 0.360 mmol) then filled with N,N-dimethylformamide (DMF) (2 mL) and DIPEA (0.157 mL, 0.900 mmol). The resulting mixture was stirred at room temperature for 5 min then 1,1-dimethylethyl [2-(hydroxyamino)-2-iminoethyl]carbamate (for a preparation, see Intermediate 69) (68.1 mg, 0.360 mmol) in N,N-dimethylformamide (DMF) (2 mL) was added. The resulting mixture was stirred at room temperature under nitrogen for 30 min, at 110° C. for 7 h then cooled to room temperature. The mixture was partitioned between AcOEt and water and the phases were separated. The aqueous phase was extracted three times with AcOEt and the combined organic were washed twice with water then brine, dried over MgSO₄ and concentrated in vacuo. Purification of the residue by SP4 using a 10 G silica cartridge (gradient: 8 to 38% (10% MeOH in DCM) in DCM) gave 1-methylethyl[(2S,4R)-1-acetyl-6-(3-{2-[{[(1,1-dimethylethyl)oxy]carbonyl}methyl)amino]ethyl}-1,2,4-oxadiazol-5-yl)-2-methyl-1,2,3,4-tetrahydro-4-quinolinyl]carbamate (67 mg, 0.130 mmol, 43.3% yield) as a pale yellow solid. LCMS (method A): Retention time 1.11 min, [M+H]+=516.1

Intermediate 69

1,1-Dimethylethyl[(3Z)-3-(hydroxyamino)-3-iminopropyl]methylcarbamate

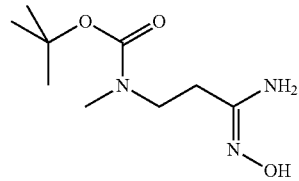

hydroxylamine (40% w/w in water, 4.44 g, 53.7 mmol) was added to a solution of 1,1-dimethylethyl (2-cyanoethyl)methylcarbamate (for a preparation see Intermediate 70) (3.3 g, 17.91 mmol) in ethanol (20 mL) and the mixture was heated at reflux for 2 h, then cooled to room temperature and concentrated in vacuo. The residue was dissolved in DCM (50 mL) and the organic phase was washed with water (50 mL), dried over MgSO4 and concentrated in vacuo to give 1,1-dimethylethyl[(3Z)-3-(hydroxyamino)-3-iminopropyl]methylcarbamate (3.52 g, 16.20 mmol, 90% yield) as colourless gum.

Intermediate 70

1,1-Dimethylethyl (2-cyanoethyl)methylcarbamate

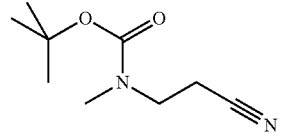

Bis(1,1-dimethylethyl)dicarbonate (27.6 mL, 119 mmol) in DCM (40 mL) was added dropwise to a solution of 3-(methylamino)propanenitrile (10 g, 119 mmol) in DCM (200 mL) at room temperature and the mixture was stirred at this temperature for 2 h, then washed with a 0.5M HCl aqueous solution, water and brine, dried over MgSO₄ and concentrated in vacuo to give 1,1-dimethylethyl (2-cyanoethyl)methylcarbamate (19.8 g, 107 mmol, 90% yield).

Intermediate 71

1,1-Dimethylethyl 4-({4-[(2S,4R)-1-acetyl-2-methyl-4-({[(1-methylethyl)oxy]carbonyl}amino)-1,2,3,4-tetrahydro-6-quinolinyl]phenyl}methyl)-3-oxo-1-piperazinecarboxylate

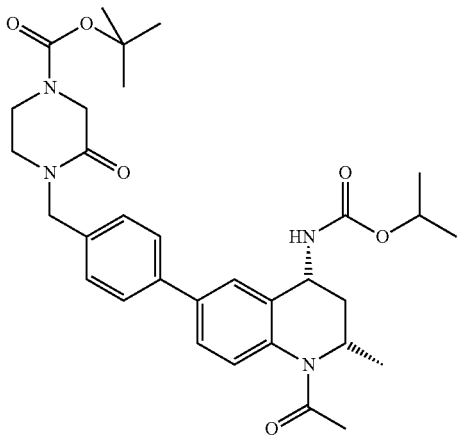

A flask was charged with 1,1-dimethylethyl 4-[(4-bromophenyl)methyl]-3-oxo-1-piperazinecarboxylate (for a preparation, see Intermediate 72) (111 mg, 0.3 mmol), 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation, see Intermediate 52) (250 mg, 0.600 mmol), potassium carbonate (124 mg, 0.900 mmol) and [1,1'-bis(diphenylphosphino)ferrocene]dichloropalladium(II) (21.95 mg, 0.030 mmol) then filled with 1,4-dioxane (3 mL) and water (1 mL) and flushed with nitrogen. The resulting mixture was stirred under microwave irradiation at 120° C. for 30 min then cooled to room temperature. Most of the 1,4-dioxane was removed in vacuo and the residue was partitioned between AcOEt and water. The layers were separated and the aqueous phase was extracted with AcOEt. The combined organic phases were washed with brine, dried over MgSO$_4$ and concentrated in vacuo. Purification of the residue by SP4 using a 25 G silica cartridge (gradient: 5 to 25% (10% MeOH in DCM) in DCM) gave 1,1-dimethylethyl 4-({4-[(2S,4R)-1-acetyl-2-methyl-4-({[(1-methylethyl)oxy]carbonyl}amino)-1,2,3,4-tetrahydro-6-quinolinyl]phenyl}methyl)-3-oxo-1-piperazinecarboxylate (180 mg, 0.311 mmol, 104% yield) which was used in the next step without further purification.

LCMS (method A): Retention time 1.03 min, [M−H]−= 577.38

Intermediate 72

1,1-Dimethylethyl 4-[(4-bromophenyl)methyl]-3-oxo-1-piperazinecarboxylate

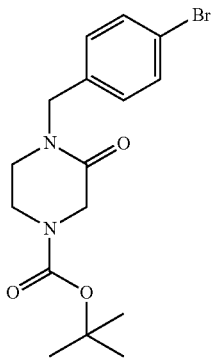 [SMILES: CC(C)(C)OC(=O)N1CCN(Cc2ccc(Br)cc2)C(=O)C1]

To a solution of 1,1-dimethylethyl 3-oxo-1-piperazinecarboxylate (500 mg, 2.497 mmol) in N,N-dimethylformamide (DMF) (8 mL) at room temperature under nitrogen was added sodium hydride (60% w/w in mineral oil, 120 mg, 3.00 mmol) and the resulting suspension was stirred at this temperature for 30 min. 1-Bromo-4-(bromomethyl)benzene (749 mg, 3.00 mmol) in DMF (5 mL) was then added via syringe. The resulting mixture was stirred at room temperature for 1.5 h then partitioned between AcOEt and water. The layers were separated and the aqueous phase was extracted three times with AcOEt. The combined organic phases were washed three times with brine, dried over MgSO$_4$ and concentrated in vacuo. Purification of the residue by SP4 using a 25 G silica cartridge (gradient: 13 to 63% AcOEt in Hexanes) gave 1,1-dimethylethyl 4-[(4-bromophenyl)methyl]-3-oxo-1-piperazinecarboxylate (763 mg, 2.066 mmol, 83% yield) as an oil which solidified to a white solid over 16 h.

LCMS (method A): Retention time 1.14 min, [M+H]+= 370.95 (1 Br)

Intermediate 73

1-Methylethyl((2S,4R)-1-acetyl-6-{1-[3-({[(1,1-dimethylethyl)oxy]carbonyl}amino)propyl]-1H-1,2,3-triazol-4-yl}-2-methyl-1,2,3,4-tetrahydro-4-quinolinyl)carbamate

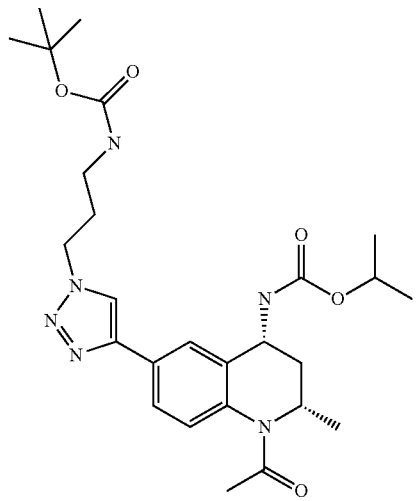 [SMILES: CC(=O)N1c2ccc(-c3cn(CCCNC(=O)OC(C)(C)C)nn3)cc2[C@H](NC(=O)OC(C)C)C[C@@H]1C]

To a solution of 1-methylethyl[(2S,4R)-1-acetyl-6-ethynyl-2-methyl-1,2,3,4-tetrahydro-4-quinolinyl]carbamate (for a preparation, see Intermediate 58) (250 mg, 0.795 mmol) in a mixture of N,N-dimethylformamide (DMF) (4.5 mL) and methanol (0.500 mL) were successively added 1,1-dimethylethyl (3-azidopropyl)carbamate (for a preparation, see Intermediate 74) (318 mg, 1.590 mmol) and copper(I) iodide (7.57 mg, 0.040 mmol). The resulting mixture was stirred at 100° C. under microwave irradiation for 2 h, and then cooled to room temperature and partitioned between EtOAc and brine. The two layers were separated and the aqueous phase was extracted with EtOAc (3×). The combined organic layers were washed with brine, dried over a Na$_2$SO$_4$ cartridge and concentrated in vacuo. Purification of the residue by SP4 column using a 10 G silica cartridge (gradient: 2 to 10% MeOH in DCM) gave 1-methylethyl((2S,4R)-1-acetyl-6-{1-[3-({[(1,1-dimethylethyl)oxy]carbonyl}amino)propyl]-1H-1,2,3-triazol-4-yl}-2-methyl-1,2,3,4-tetrahydro- 4-quinolinyl)carbamate (514 mg, 0.999 mmol, 126%) as a viscous yellow oil which was used in the next step without further purification.

LCMS (method A): Retention time 0.96 min, [M+H]+= 515.23

Intermediate 74

1,1-Dimethylethyl (3-azidopropyl)carbamate

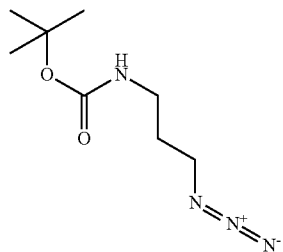

To a solution of 1,1-dimethylethyl (3-hydroxypropyl)carbamate (1.612 g, 9.2 mmol) in toluene (40 mL) cooled with an ice bath was added triethylamine (1.282 mL, 9.20 mmol) then methanesulfonyl chloride (0.717 mL, 9.20 mmol) and the resulting mixture was stirred for 15 min. Tetrabutylammonium bromide (0.297 g, 0.920 mmol) was then added followed by a solution of sodium azide (5 g, 77 mmol) in water (20 mL) and the resulting mixture was stirred at 60° C. for 7 h then cooled to room temperature and diluted with Et$_2$O (150 mL). The two layers were separated and the organic phase was washed with water then brine, dried over MgSO$_4$ and concentrated in vacuo. Purification of the residue by SP4 using a 25 G silica cartridge gave 1,1-dimethylethyl (3-azidopropyl)carbamate (1.27 g, 6.34 mmol, 68.9% yield) as a colourless oil.

Intermediate 75

Methyl {4-[(2S,4R)-1-acetyl-2-methyl-4-({[(1-methylethyl)oxy]carbonyl}amino)-1,2,3,4-tetrahydro-6-quinolinyl]-1H-1,2,3-triazol-1-yl}acetate

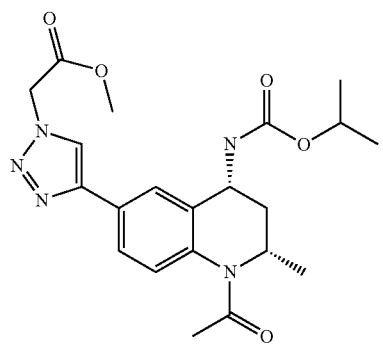 [SMILES: COC(=O)Cn1cc(-c2ccc3c(c2)[C@H](NC(=O)OC(C)C)C[C@H](C)N3C(C)=O)nn1]

To a solution of 1-methylethyl[(2S,4R)-1-acetyl-6-ethynyl-2-methyl-1,2,3,4-tetrahydro-4-quinolinyl]carbamate (for a preparation, see Intermediate 58) (408 mg, 1.298 mmol) in N,N-dimethylformamide (DMF) (8 mL) and methanol (0.9 mL) were successively added methyl azidoacetate (299 mg, 2.60 mmol) and copper(I) iodide (12.36 mg, 0.065 mmol). The resulting mixture was stirred at 100° C. under microwave irradiation for 2 h then cooled to room temperature and partitioned between brine and AcOEt. The layers were separated. The aqueous phase was extracted with EtOAc (3×) and the combined organic layers were washed with brine, dried over a Na$_2$SO$_4$ cartridge and concentrated in vacuo. Purification of the residue on SP4 using a 25 G silica cartridge (gradient: 2 to 10% MeOH in DCM) gave methyl {4-[(2S,4R)-1-acetyl-2-methyl-4-({[(1-methylethyl)oxy]carbonyl}amino)-1,2,3,4-tetrahydro-6-quinolinyl]-1H-1,2,3-triazol-1-yl}acetate (468 mg, 1.046 mmol, 96%) as a viscous yellow oil.

LCMS (method A): Retention time 0.81 min, [M+H]+= 430.15

Intermediate 76

1-Methylethyl((2S,4R)-1-acetyl-6-{5-[2-({[(1,1-dimethylethyl)oxy]carbonyl}amino)ethyl]-1,2,4-oxadiazol-3-yl}-2-methyl-1,2,3,4-tetrahydro-4-quinolinyl)carbamate

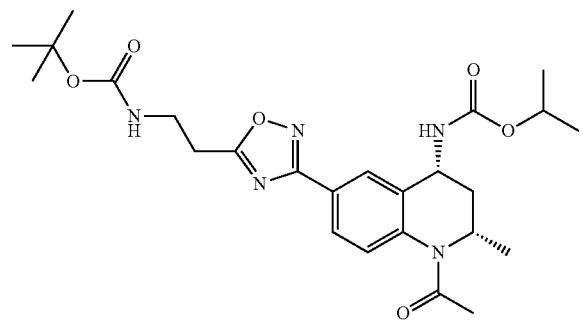 [SMILES: CC(=O)N1c2ccc(-c3noc(CCNC(=O)OC(C)(C)C)n3)cc2[C@H](NC(=O)OC(C)C)C[C@@H]1C]

A flask was charged with N-{[(1,1-dimethylethyl)oxy]carbonyl}-β-alanine (227 mg, 1.200 mmol) and HATU (494 mg, 1.300 mmol) then filled with N,N-dimethylformamide (DMF) (5 mL). DIPEA (0.524 mL, 3.00 mmol) was added and the resulting pale yellow solution was stirred for 5 min. 1-Methylethyl {(2S,4R)-1-acetyl-6-[(hydroxyamino)(imino)methyl]-2-methyl-1,2,3,4-tetrahydro-4-quinolinyl}carbamate (for a preparation, see Intermediate 56) (348 mg, 1 mmol) in N,N-dimethylformamide (DMF) (5 mL) was then added via syringe. The resulting mixture was stirred at room temperature for 30 min, at 110° C. for 5 h then cooled to room temperature and partitioned between AcOEt and water/brine (1/1). The layers were separated and the aqueous phase was extracted with AcOEt. The combined organic phases were washed with water/brine (1/1) (3×) then dried over MgSO$_4$ and concentrated in vacuo. Purification of the residue by SP4 using 25 G silica cartridge (gradient: 23 to 73% AcOEt in Hexanes), gave 1-methylethyl((2S,4R)-1-acetyl-6-{5-[2-({[(1,1-dimethylethyl)oxy]carbonyl}amino)ethyl]-1,2,4-oxadiazol-3-yl}-2-methyl-1,2,3,4-tetrahydro-4-quinolinyl)carbamate (260 mg, 0.518 mmol, 51.8% yield) as a pale orange foam. LCMS (method G): Retention time 1.04 min, [M+H]+=502.0

Intermediate 77

1-Methylethyl((2S,4R)-1-acetyl-6-{1-[2-({[(1,1-dimethylethyl)oxy]carbonyl}amino)ethyl]-1H-1,2,3-triazol-4-yl}-2-methyl-1,2,3,4-tetrahydro-4-quinolinyl)carbamate

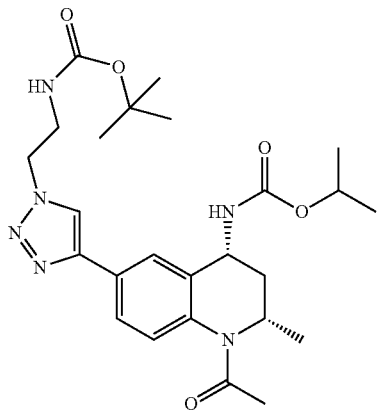 [SMILES: CC(=O)N1c2ccc(-c3cn(CCNC(=O)OC(C)(C)C)nn3)cc2[C@H](NC(=O)OC(C)C)C[C@@H]1C]

A flask was charged with 1-methylethyl[(2S,4R)-1-acetyl-6-ethynyl-2-methyl-1,2,3,4-tetrahydro-4-quinolinyl]carbamate (for a preparation, see Intermediate 58) (80 mg, 0.254 mmol) and copper(I) iodide (2.423 mg, 0.013 mmol) then filled with N,N-dimethylformamide (DMF) (1.8 mL) and methanol (0.200 mL). 1,1-Dimethylethyl (2-azidoethyl)carbamate (for a preparation, see Intermediate 78) (95 mg, 0.509 mmol) was added and the resulting mixture was stirred under microwave irradiation at 100° C. for 2 h then cooled to room temperature. The reaction mixture was partitioned between EtOAc and brine and the layers were separated. The aqueous phase was extracted with EtOAc (3×) and the combined organic phases were washed with brine, dried over a $Na_2SO_4$ cartridge and concentrated in vacuo. Purification of the residue on SP4 using a 10 G silica cartridge (gradient: 5 to 25% (10% MeOH in DCM) in DCM) gave 1-methylethyl((2S,4R)-1-acetyl-6-{1-[2-({[(1,1-dimethylethyl)oxy]carbonyl}amino)ethyl]-1H-1,2,3-triazol-4-yl}-2-methyl-1,2,3,4-tetrahydro-4-quinolinyl)carbamate (108 mg, 0.216 mmol, 85% yield) as a pale yellow foam. LCMS (method A): Retention time 0.95 min, [M+H]+=501.26

Intermediate 78

1,1-Dimethylethyl (2-azidoethyl)carbamate

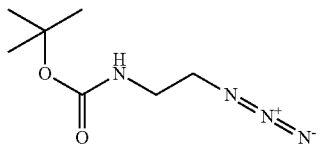

To a solution of 1,1-dimethylethyl (2-hydroxyethyl)carbamate (1.483 g, 9.2 mmol) in toluene (40 mL) cooled with an ice bath was added triethylamine (1.282 mL, 9.20 mmol) then methanesulfonyl chloride (0.717 mL, 9.20 mmol) and the resulting mixture was stirred for 5 min at this temperature then tetrabutylammonium bromide (0.297 g, 0.920 mmol) was added followed by a solution of sodium azide (5 g, 77 mmol) in water (20 mL). The resulting mixture was stirred at 60° C. for 3 h then cooled to room temperature and diluted with $Et_2O$ (150 mL). The organic layer was washed with water then brine, dried over $MgSO_4$ and concentrated in vacuo. Purification of the residue by SP4 using a 50G silica cartridge gave 1,1-dimethylethyl (2-azidoethyl)carbamate (456 mg, 2.449 mmol, 26.6% yield) as a colourless oil.

Intermediate 79

1-Methylethyl((2S,4R)-1-acetyl-6-{1-[2-({[(1,1-dimethylethyl)oxy]carbonyl}amino)ethyl]-1H-imidazol-4-yl}-2-methyl-1,2,3,4-tetrahydro-4-quinolinyl)carbamate

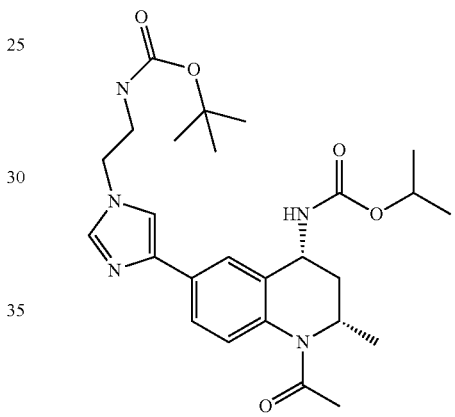

A mixture of 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 52) (333 mg, 0.80 mmol), 1,1-dimethylethyl[2-(4-iodo-1H-imidazol-1-yl)ethyl]carbamate (for a preparation see Intermediate 80) (270 mg, 0.8 mmol), potassium carbonate (443 mg, 3.2 mmol) and tetrakis(triphenylphosphine)palladium(0) (46 mg, 0.040 mmol) in toluene (10 ml) and ethanol (10 ml) was refluxed under nitrogen for 16 h then cooled to room temperature and the insoluble were filtered off. Potassium carbonate (443 mg, 3.2 mmol) and tetrakis(triphenylphosphine)palladium(0) (46 mg, 0.040 mmol) were added to the filtrate and the resulting mixture refluxed for 7 h then cooled to room temperature and the insoluble filtered off. The resulting solution was concentrated in vacuo. Purification of the residue by flash chromatography on silica gel (gradient: 0 to 6% MeOH in DCM) gave 1-methylethyl((2S,4R)-1-acetyl-6-{1-[2-({[(1,1-dimethylethyl)oxy]carbonyl}amino)ethyl]-1H-imidazol-4-yl}-2-methyl-1,2,3,4-tetrahydro-4-quinolinyl)carbamate (47 mg, 0.094 mmol, 12%) as a light brown solid.

LCMS (method G): Retention time 0.73 min, [M+H]+=500.1

Intermediate 80

1,1-Dimethylethyl[2-(4-iodo-1H-imidazol-1-yl)ethyl]carbamate

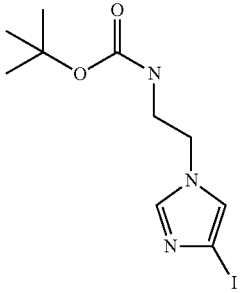 [SMILES: CC(C)(C)OC(=O)NCCn1cnc(I)c1]

A solution of 1,1-dimethylethyl[2-(2,4,5-triiodo-1H-imidazol-1-yl)ethyl]carbamate (for a preparation see Intermediate 81) (1.15 g, 1.95 mmol) in dry THF (20 mL) was cooled to −40° C. and treated with ethylmagnesium bromide (3.0 M in $Et_2O$, 1.3 mL, 3.9 mmol) added dropwise. The reaction mixture was stirred at −40° C. for 20 min then treated with water (1 mL) and the resulting mixture was allowed to warm to room temperature then was diluted with $Et_2O$ (20 mL). The organic phase was washed with water then brine, dried over $MgSO_4$ and concentrated in vacuo. Purification of the residue by flash chromatography on silica gel (gradient: 0 to 4% MeOH in DCM) gave 1,1-dimethylethyl[2-(4-iodo-1H-imidazol-1-yl)ethyl]carbamate (270 mg, 0.801 mmol, 41%) as a brown oil which was used in the next step without further purification.

LCMS (method G): Retention time 0.62 min, [M+H]+=337.9

Intermediate 81

1,1-Dimethylethyl[2-(2,4,5-triiodo-1H-imidazol-1-yl)ethyl]carbamate

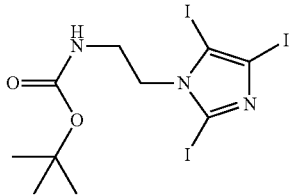 [SMILES: CC(C)(C)OC(=O)NCCn1c(I)nc(I)c1I]

Sodium hydride, (60% in mineral oil, 90 mg, 2.24 mmol) was added portionwise to a stirred solution of 2,4,5-triiodoimidazole (1 g, 2.24 mmol) in dry DMF (10 mL) at room temperature under nitrogen. After complete addition the reaction mixture was stirred at room temperature for 15 min. The mixture was then treated with 1,1-dimethylethyl (2-bromoethyl)carbamate (503 mg, 2.24 mmol). The resulting mixture was stirred at 100° C. for 16 h then cooled to room temperature and partitioned between $Et_2O$ (50 mL) and water (50 mL). The two layers were separated and the aqueous phase was extracted with $Et_2O$ (50 mL). The combined organic phases were washed with brine, dried over $MgSO_4$ and concentrated in vacuo. Purification of the residue by flash chromatography on silica gel (gradient: 0 to 5% MeOH in DCM) gave a yellow oil which was further purified by flash chromatography on silica gel (gradient: 30 to 60% AcOEt in Hexanes) to give 1,1-dimethylethyl[2-(2,4,5-triiodo-1H-imidazol-1-yl)ethyl]carbamate (580 mg, 0.985 mmol, 44%) as a colourless oil. LCMS (method G): Retention time 1.04 min, [M+H]+=590.9

Intermediate 82

Ethyl 1-[(cis)-1-acetyl-2-methyl-4-({[(1-methylethyl)oxy]carbonyl}amino)-1,2,3,4-tetrahydro-6-quinolinyl]-1H-imidazole-4-carboxylate

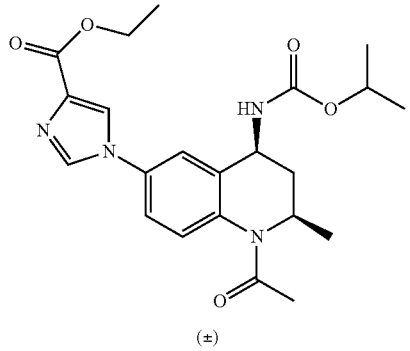 [SMILES: CCOC(=O)c1cn(-c2ccc3c(c2)[C@@H](NC(=O)OC(C)C)C[C@@H](C)N3C(C)=O)cn1]

(±)

Acetic anhydride (20 mL) was added to ethyl 1-[(cis)-2-methyl-4-({[(1-methylethyl)oxy]carbonyl}amino)-1,2,3,4-tetrahydro-6-quinolinyl]-1H-imidazole-4-carboxylate (for a preparation see intermediate 83) (3.5 g, 9.06 mmol). The resulting mixture was stirred at room temperature for 24 h then most of the solvent was removed in vacuo. The residue was dissolved in AcOEt (30 mL) and washed repeatedly with a saturated $NaHCO_3$ aqueous solution until the later was basic. The organic phase was then washed with water and brine, dried over $MgSO_4$ and concentrated in vacuo. Purification of the residue by flash chromatography on silica gel (gradient: 0 to 5% MeOH in DCM) gave ethyl 1-[(cis)-1-acetyl-2-methyl-4-({[(1-methylethyl)oxy]carbonyl}amino)-1,2,3,4-tetrahydro-6-quinolinyl]-1H-imidazole-4-carboxylate (3.8 g, 8.87 mmol, 98%) as a colourless foam. LCMS (method G): Retention time 0.83 min, [M+H]+=429.11

Intermediate 83

Ethyl 1-[(cis)-2-methyl-4-({[(1-methylethyl)oxy]carbonyl}amino)-1,2,3,4-tetrahydro-6-quinolinyl]-1H-imidazole-4-carboxylate

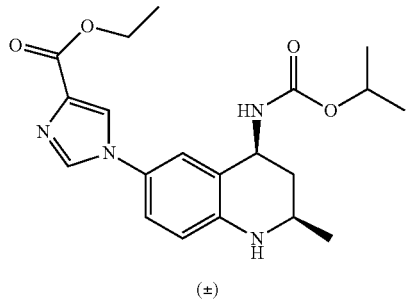 [SMILES: CCOC(=O)c1cn(-c2ccc3c(c2)[C@@H](NC(=O)OC(C)C)C[C@@H](C)N3)cn1]

(±)

A solution of ethyl 1-(4-{[1-methyl-3-({[(1-methylethyl)oxy]carbonyl}amino)-3-oxopropyl]amino}phenyl)-1H-imidazole-4-carboxylate (for a preparation see intermediate 84) (5 g, 12.4 mmol) in ethanol (80 mL) was cooled to −15° C. The solution was treated with sodium borohydride (423 mg, 11.2 mmol) followed by a solution of magnesium chloride (2.78 g, 13.7 mmol) in water (15 mL) maintaining the temperature below −10° C. The mixture was stirred below 0° C. for 1 h then at room temperature for 1 h. The suspension formed was poured onto a stirred mixture of citric acid (4.89 g, 25.5 mmol), HCl (1M in water, 130 mL) and DCM (65 mL). The resulting mixture was stirred vigorously for 30 min and the layers were separated. The aqueous phase was basified by the addition of solid K$_2$CO$_3$ (CARE: gas evolved) and extracted with AcOEt (4×70 mL). The combined organic phases were washed with water then brine, dried over MgSO$_4$ and concentrated in vacuo to give ethyl 1-[(cis)-2-methyl-4-({[(1-methylethyl)oxy]carbonyl}amino)-1,2,3,4-tetrahydro-6-quinolinyl]-1H-imidazole-4-carboxylate (3.6 g, 9.32 mmol, 75%) as a colourless foam which was used in the next step without further purification.

LCMS (method G): Retention time 0.92 min, [M+H]+= 387.13

Intermediate 84

Ethyl 1-(4-{[1-methyl-3-({[(1-methylethyl)oxy]carbonyl}amino)-3-oxopropyl]amino}phenyl)-1H-imidazole-4-carboxylate

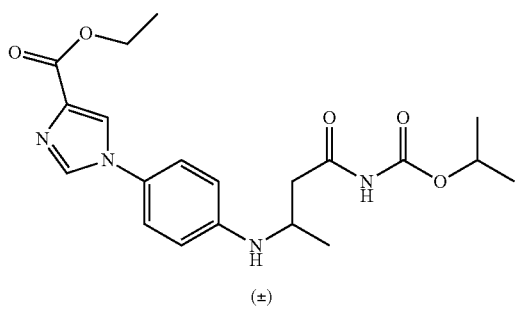 [SMILES: CCOC(=O)c1cn(-c2ccc(NC(C)CC(=O)NC(=O)OC(C)C)cc2)cn1]

(±)

A mixture of ethyl 1-(4-aminophenyl)-1H-imidazole-4-carboxylate (for a preparation see intermediate 85) (9.4 g, 40.6 mmol), 1-methylethyl (2E)-2-butenoylcarbamate (for a preparation see intermediate 49) (6.96 g, 40.6 mmol), and yttrium nitrate hexahydrate (1.56 g, 4.06 mmol) in dry acetonitrile (200 mL) was stirred at 60° C. for 48 h then cooled to room temperature and concentrated in vacuo. The residue was suspended in AcOEt (250 mL) and the organic phase was washed with water (×2) then brine, dried over MgSO$_4$ and concentrated in vacuo. Purification of the residue by flash chromatography on silica gel (gradient: 60-100% AcOEt in Hexanes followed by 0 to 5% methanol in AcOEt) gave ethyl 1-(4-{[1-methyl-3-({[(1-methylethyl)oxy]carbonyl}amino)-3-oxopropyl]amino}phenyl)-1H-imidazole-4-carboxylate (5 g, 12.42 mmol, 31%) as a colourless gum.

LCMS (method A): Retention time 0.86 min, [M-H]-= 401.25

Intermediate 85

Ethyl 1-(4-aminophenyl)-1H-imidazole-4-carboxylate

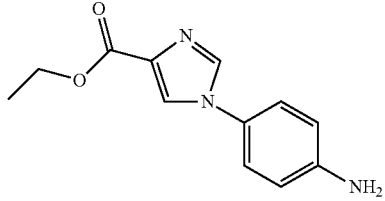 [SMILES: CCOC(=O)c1cn(-c2ccc(N)cc2)cn1]

Palladium(0) (10% w/w on carbon, 50% wet, 1.25 g, 47.8 mmol) was added to a solution of ethyl 1-(4-nitrophenyl)-1H-imidazole-4-carboxylate (for a preparation see Intermediate 86) (12.5 g, 47.8 mmol) and ammonium formate (7.54 g, 120 mmol) in ethanol (250 mL). The reaction mixture was refluxed for 4 h then cooled to room temperature and filtered through celite. The solvent was removed in vacuo to give ethyl 1-(4-aminophenyl)-1H-imidazole-4-carboxylate (9.41 g, 40.7 mmol, 85%) as a colourless oil.

LCMS (method G): Retention time 0.55 min, [M+H]+= 232.09

Intermediate 86

Ethyl 1-(4-nitrophenyl)-1H-imidazole-4-carboxylate

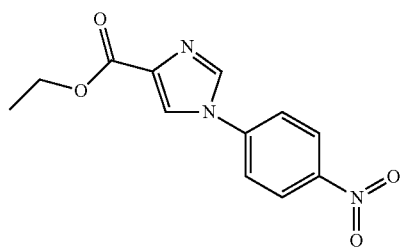 [SMILES: CCOC(=O)c1cn(-c2ccc([N+](=O)[O-])cc2)cn1]

A mixture of ethyl 1H-imidazole-4-carboxylate (8 g, 57.1 mmol), 4-fluoro-1-nitrobenzene (8.05 g, 57.1 mmol) and potassium carbonate (8.68 g, 62.8 mmol) in acetonitrile (100 mL) was stirred at 60° C. for 16 h then cooled to room temperature and most the solvent was removed in vacuo. The residue was partitioned between AcOEt (200 mL) and water (150 mL) and the layers were separated. The organic phase was dried over MgSO$_4$ and concentrated in vacuo. Purification of the residue by flash chromatography on silica gel (gradient: 0 to 5% MeOH in DCM) gave ethyl 1-(4-nitrophenyl)-1H-imidazole-4-carboxylate (12.53 g, 48.0 mmol, 84%) as a yellow oil.

LCMS (method G): Retention time 0.80 min, [M+H]+= 262.0

Intermediate 87

1-Methylethyl((2S,4R)-1-acetyl-6-{4-[2-({[(1,1-dimethylethyl)oxy]carbonyl}amino)ethyl]phenyl}-2-methyl-1,2,3,4-tetrahydro-4-quinolinyl)carbamate

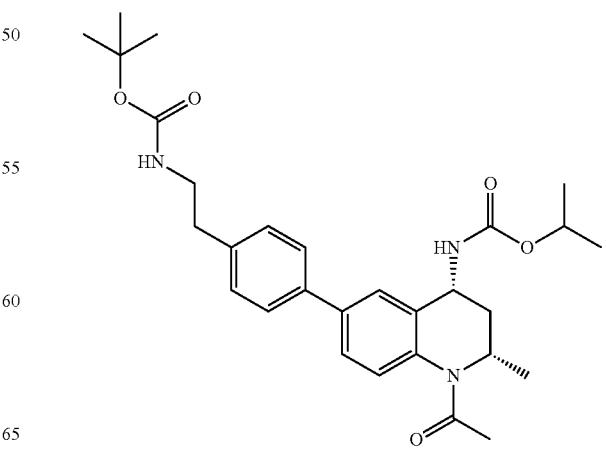

A mixture of 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 52) (125 mg, 0.300 mmol), 1,1-dimethylethyl[2-(4-bromophenyl)ethyl]carbamate (90 mg, 0.300 mmol), potassium carbonate (104 mg, 0.751 mmol) and tetrakis(triphenylphosphine)palladium(0) (17.35 mg, 0.015 mmol) was degassed under house vacuum for 15 min and quenched several times with nitrogen, then was then stirred at 100° C. under nitrogen for 50 min before being cooled to room temperature. Most of the solvent was removed in vacuo and the residue was partitioned between AcOEt (20 mL) and water (15 mL). The layers were separated and the aqueous phase was extracted with AcOEt (15 mL). The combined organic phases were washed with brine (15 mL), dried over MgSO4 and concentrated in vacuo. Purification of the residue by flash chromatography on silica gel (gradient: 50 to 75% AcOEt in Hexanes) gave 1-methylethyl((2S,4R)-1-acetyl-6-{4-[2-({[(1,1-dimethylethyl)oxy]carbonyl}amino)ethyl]phenyl}-2-methyl-1,2,3,4-tetrahydro-4-quinolinyl)carbamate (50 mg, 0.093 mmol, 31%) as a colourless oil.

LCMS (method G): Retention time 1.16 min, [M+H-Boc]+=410.3

Intermediate 88

1,1-Dimethylethyl {(cis)-4-[2-methyl-4-({[(1-methylethyl)oxy]carbonyl}amino)-1,2,3,4-tetrahydro-6-quinolinyl]-1H-imidazol-1-yl}acetate

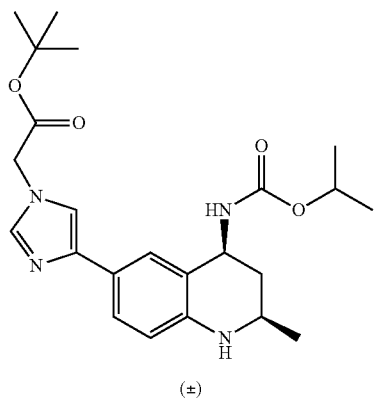 [SMILES: CC(C)OC(=O)N[C@H]1C[C@@H](C)Nc2ccc(-c3cn(CC(=O)OC(C)(C)C)cn3)cc21]

(±)

A solution of 1,1-dimethylethyl[4-(4-{[1-methyl-3-({[(1-methylethyl)oxy]carbonyl}amino)-3-oxopropyl]amino}phenyl)-1H-imidazol-1-yl]acetate (for a preparation see intermediate 89) (980 mg, 2.21 mmol) in ethanol (20 mL1) was cooled to −15° C. The solution was treated with sodium borohydride (75 mg, 1.98 mmol) followed by magnesium chloride (1M in water, 2.43 mL, 2.43 mmol) maintaining the temperature below −10° C. The reaction mixture was stirred at a temperature lower than 0° C. for 1 h then at room temperature for 1 h. The suspension formed was poured onto a stirred mixture of citric acid (1.06 g, 5.51 mmol), HCl (1M in water, 25 mL) and DCM (15 mL). The resulting mixture was stirred at room temperature for 30 min and the layers were separated. The aqueous layer was basified by the addition of solid K2CO3 then was extracted with AcOEt (3×20 mL). The combined organic phases (DCM+EtOAc) were washed with water then brine, dried over MgSO4 and concentrated in vacuo. Purification of the residue by flash chromatography on silica gel (gradient: 0 to 2% MeOH in DCM) gave 1,1-dimethylethyl {(cis)-4-[2-methyl-4-({[(1-methylethyl)oxy] carbonyl}amino)-1,2,3,4-tetrahydro-6-quinolinyl]-1H-imidazol-1-yl}acetate (645 mg, 1.505 mmol, 68%) as an orange oil.

LCMS (method G): Retention time 0.79 min, [M+H]+=429.3

Intermediate 89

1,1-Dimethylethyl[4-(4-{[1-methyl-3-({[(1-methylethyl)oxy]carbonyl}amino)-3-oxopropyl]amino}phenyl)-1H-imidazol-1-yl]acetate

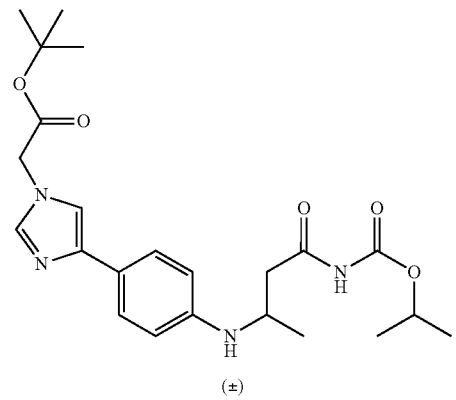 [SMILES: CC(CC(=O)NC(=O)OC(C)C)Nc1ccc(-c2cn(CC(=O)OC(C)(C)C)cn2)cc1]

(±)

DBU (1.0 g, 993 µl, 6.59 mmol) was added to a stirred solution of 1,1-dimethylethyl[4-(4-aminophenyl)-1H-imidazol-1-yl]acetate (for a preparation see Intermediate 90) (1.8 g, 6.59 mmol) and 1-methylethyl (2E)-2-butenoylcarbamate (for a preparation see intermediate 49) (1.41 g, 8.23 mmol) in acetonitrile (25 mL). The reaction mixture was stirred at 50° C. for 48 h then cooled to room temperature and most of the solvent was removed in vacuo. Purification of the residue by flash chromatography on silica gel (gradient: 0 to 5% MeOH in AcOEt) gave 1,1-dimethylethyl[4-(4-{[1-methyl-3-({[(1-methylethyl)oxy]carbonyl}amino)-3-oxopropyl]amino}phenyl)-1H-imidazol-1-yl]acetate (980 mg, 2.205 mmol, 33%) as an orange oil. LCMS (method G): Retention time 0.80 min, [M+H]+=445.4

Intermediate 90

1,1-Dimethylethyl[4-(4-aminophenyl)-1H-imidazol-1-yl]acetate

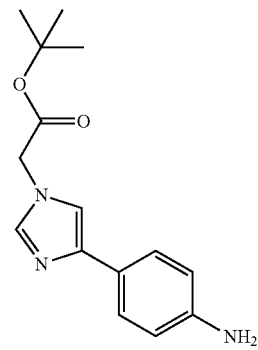 [SMILES: CC(C)(C)OC(=O)Cn1cnc(-c2ccc(N)cc2)c1]

Palladium (10% w/w on carbon, 50% wet, 300 mg, 2.82 mmol) was added to a solution of 1,1-dimethylethyl[4-(4-nitrophenyl)-1H-imidazol-1-yl]acetate (for a preparation see intermediate 91) (3.0 g, 9.89 mmol) and ammonium formate (1.56 g, 24.73 mmol) in ethanol (50 mL). The reaction mixture was refluxed for 4 h then cooled to room temperature. Ammonium formate (1 g) and palladium (10% w/w on carbon, 50% wet, 100 mg, 0.94 mmol) were added and the resulting mixture was refluxed for 2 h then was cooled to 40° C. and filtered through celite whilst still warm. Most of the solvent was removed in vacuo from the filtrate to give 1,1-dimethylethyl[4-(4-aminophenyl)-1H-imidazol-1-yl]acetate (2.44 g, 8.93 mmol, 90%) as a yellow solid which was used in the next step without further purification.

LCMS (method G): Retention time 0.57 min, [M+H]+= 274.1

Intermediate 91

1,1-Dimethylethyl[4-(4-nitrophenyl)-1H-imidazol-1-yl]acetate

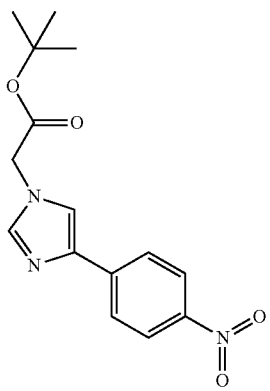 [SMILES: CC(C)(C)OC(=O)Cn1cnc(-c2ccc([N+](=O)[O-])cc2)c1]

A mixture of 4-(4-nitrophenyl)-1H-imidazole (for a preparation see Intermediate 92) (3.5 g, 18.5 mmol), 1,1-dimethylethyl bromoacetate (3.61 g, 2.73 mL, 18.5 mmol), and potassium carbonate (5.11 g, 37.0 mmol) in DMF (50 mL) was stirred at 50° C. for 16 h then was cooled to room temperature and partitioned between AcOEt (100 mL) and water (100 mL). The layers were separated and the organic phase was washed with water then brine, dried over MgSO$_4$ and concentrated in vacuo. Purification of the residue by flash chromatography on silica gel (gradient: 25 to 50% AcOEt in Hexanes) gave 1,1-dimethylethyl[4-(4-nitrophenyl)-1H-imidazol-1-yl]acetate (3.01 g, 9.92 mmol, 54%) as an orange solid. LCMS (method G): Retention time 0.93 min, [M+H]+= 304.0

Intermediate 92

4-(4-Nitrophenyl)-1H-imidazole

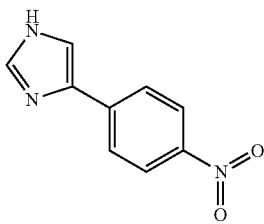 [SMILES: O=[N+]([O-])c1ccc(-c2c[nH]cn2)cc1]

A mixture of 2-bromo-1-(4-nitrophenyl)ethanone (15 g, 61.5 mmol) and formamide (100 mL) was stirred at 150° C. for 3 days then was cooled to approximately 40° C. and poured onto ice/water (approximately 700 mL). The mixture was stirred for 30 min and the solid formed was filtered off, washed with water and dried to give 4-(4-nitrophenyl)-1H-imidazole (7.0 g, 37.0 mmol, 60%) as a brown solid which was used in the next step without further purification. LCMS (method G): Retention time 0.46 min, [M+H]+=190.0

Intermediate 93

1,1-Dimethylethyl 3-{(cis)-4-[2-methyl-4-({[(1-methylethyl)oxy]carbonyl}amino)-1,2,3,4-tetrahydro-6-quinolinyl]-1H-imidazol-1-yl}propanoate

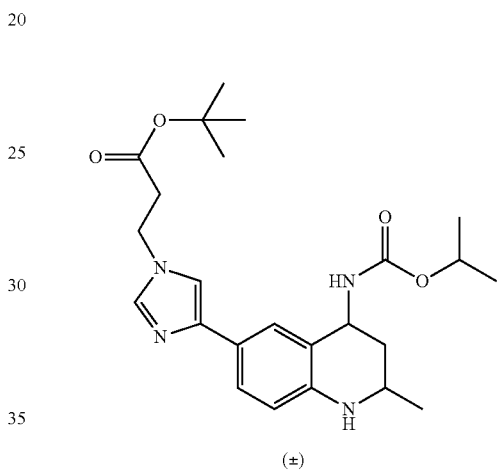

(±)

A solution of 1,1-dimethylethyl 3-[4-(4-{[1-methyl-3-({[(1-methylethyl)oxy]carbonyl}amino)-3-oxopropyl]amino}phenyl)-1H-imidazol-1-yl]propanoate (for a preparation see Intermediate 95) (1.53 g, 3.34 mmol) in ethanol (20 mL) was cooled to −15° C. then treated with sodium borohydride (114 mg, 3.0 mmol) followed by magnesium chloride (1M in water, 3.67 mL, 3.67 mmol) maintaining the temperature below −10° C. The mixture obtained was stirred at a temperature lower than 0° C. for 1 h then at room temperature for 1 h. The suspension formed was poured onto a stirred mixture of citric acid (1.6 g, 8.34 mmol), HCl (1M in water, 25 mL) and DCM (15 mL) and the mixture obtained was stirred at room temperature for 30 min. The layers were separated and the aqueous phase was basified by the addition of solid K$_2$CO$_3$ then was extracted with AcOEt (3×20 mL). The combined organic phases (DCM+EtOAc) were washed with water then brine dried over MgSO$_4$ and concentrated in vacuo. Purification of the residue by flash chromatography on silica gel (gradient: 0 to 2% MeOH in DCM) gave 1,1-dimethylethyl 3-{(cis)-4-[2-methyl-4-({[(1-methylethyl)oxy]carbonyl}amino)-1,2,3,4-tetrahydro-6-quinolinyl]-1H-imidazol-1-yl}propanoate (1.46 g, 3.30 mmol, 99%) as an orange oil.

LCMS (method G): Retention time 0.77 min, [M+H]+= 443.3

Intermediate 94

1-[(Methyloxy)methyl]-4-(4,4,5,5-tetramethyl-1,3,2-dioxaborolan-2-yl)-1H-pyrazole

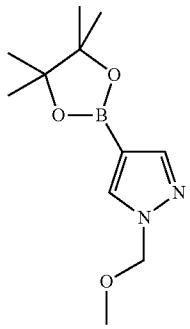 [SMILES: COCn1cc(B2OC(C)(C)C(C)(C)O2)cn1]

4-(4,4,5,5-tetramethyl-1,3,2-dioxaborolan-2-yl)-1H-pyrazole (10.00 g, 51.5 mmol) was dissolved in acetonitrile (40 mL) and stirred at 35° C. for 5 min under nitrogen atmosphere then cooled to room temperature. Iodomethyl methyl ether (21.83 mL, 258 mmol) and potassium carbonate (35.6 g, 258 mmol) were added and the resulting mixture was stirred at 35° C. for 3 h then cooled to room temperature. The insoluble material was filtered off and the filtrate was concentrated in vacuo. The residue was dissolved in EtOAc and the organic phase was washed with water, dried over MgSO4 and concentrated in vacuo. Purification of the residue by SP4 using a 100 G silica cartridge (gradient: 0 to 50% AcOEt in hexanes) gave 1-[(methyloxy)methyl]-4-(4,4,5,5-tetramethyl-1,3,2-dioxaborolan-2-yl)-1H-pyrazole (6.45 g, 50% pure by LCMS, 26%) as a yellow liquid which was used in the next step without further purification.

LCMS (method G): Retention time 0.85 min, [M+H]+= 238.8

Intermediate 95

1,1-Dimethylethyl 3-[4-(4-{[1-methyl-3-({[(1-methylethyl)oxy]carbonyl}amino)-3-oxopropyl]amino}phenyl)-1H-imidazol-1-yl]propanoate

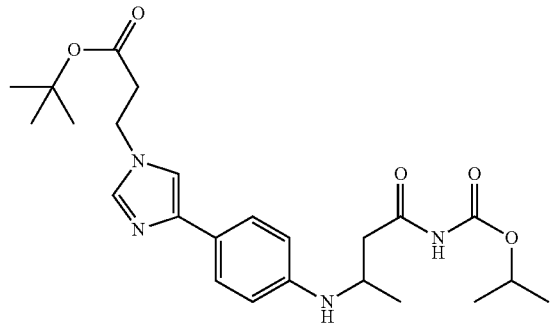 [SMILES: CC(CC(=O)NC(=O)OC(C)C)Nc1ccc(-c2cn(CCC(=O)OC(C)(C)C)cn2)cc1]

DBU (954 mg, 944 µl, 6.26 mmol) was added to a stirred solution of 1,1-dimethylethyl 3-[4-(4-aminophenyl)-1H-imidazol-1-yl]propanoate (for a preparation see Intermediate 96) (1.8 g, 6.26 mmol) and 1-methylethyl (2E)-2-butenoylcarbamate (for a preparation see Intermediate 49) (1.34 g, 7.83 mmol) in acetonitrile (25 mL). The reaction mixture was stirred at 50° C. for 48 h then was cooled to room temperature and most of the solvent was removed in vacuo. Purification of the residue by flash chromatography on silica gel (gradient: 0 to 5% MeOH in AcOEt) gave 1,1-dimethylethyl 3-[4-(4-{[1-methyl-3-({[(1-methylethyl)oxy]carbonyl}amino)-3-oxopropyl]amino}phenyl)-1H-imidazol-1-yl]propanoate (1.53 g, 3.34 mmol, 53%) as an orange oil.

LCMS (method G): Retention time 0.78 min, [M+H]+= 459.4

Intermediate 96

1,1-Dimethylethyl 3-[4-(4-aminophenyl)-1H-imidazol-1-yl]propanoate

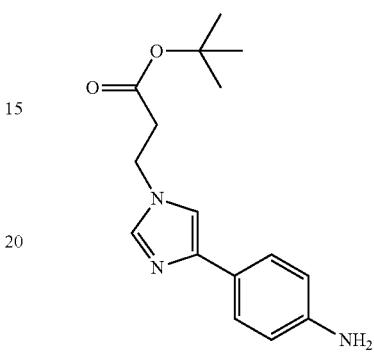

Palladium (10% w/w on carbon, 50% wet, 260 mg, 2.443 mmol) was added to a solution of 1,1-dimethylethyl 3-[4-(4-nitrophenyl)-1H-imidazol-1-yl]propanoate (for a preparation see Intermediate 97) (2.6 g, 8.19 mmol) and ammonium formate (1.29 g, 20.48 mmol) in ethanol (50 mL). The reaction mixture was refluxed for 4 h then was cooled to approximately 40° C. and filtered through celite whilst still warm. Most of the solvent was removed in vacuo from the filtrate to give 1,1-dimethylethyl 3-[4-(4-aminophenyl)-1H-imidazol-1-yl]propanoate (1.8 g, 6.26 mmol, 76%) as a yellow solid.

LCMS (method G): Retention time 0.60 min, [M+H]+= 288.1

Intermediate 97

1,1-Dimethylethyl 3-[4-(4-nitrophenyl)-1H-imidazol-1-yl]propanoate

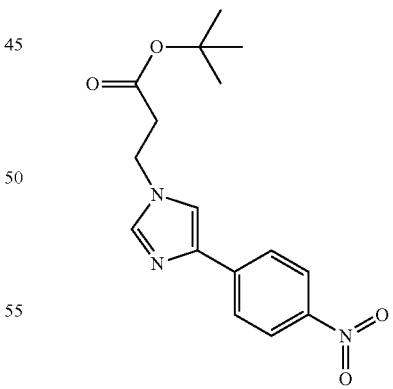

A mixture of 4-(4-nitrophenyl)-1H-imidazole (for a preparation see Intermediate 120) (3.5 g, 18.5 mmol), 1,1-dimethylethyl 2-propenoate (2.37 g, 2.71 mL, 18.5 mmol) and DBU (2.82 g, 2.79 mL, 18.5 mmol) in DMF (50 mL) was stirred at 50° C. for 16 h then was cooled to room temperature and partitioned between AcOEt (100 mL) and water (100 mL). The layers were separated and the organic phase was washed with water then brine, dried over MgSO$_4$ and concentrated in vacuo. Purification of the residue by flash chromatography on silica gel (gradient: 25 to 50% AcOEt in hexanes) gave 1,1-dimethylethyl 3-[4-(4-nitrophenyl)-1H-imidazol-1-yl]propanoate (2.6 g, 8.19 mmol, 44%) as an orange solid. LCMS (method G): Retention time 0.90 min, [M+H]+=318.0

Intermediate 98

1,1-Dimethylethyl[2-(4-bromophenyl)ethyl]methyl-carbamate

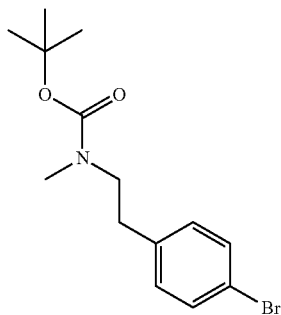 [SMILES: CN(CCc1ccc(Br)cc1)C(=O)OC(C)(C)C]

Sodium hydride (60% in mineral oil, 134 mg, 3.35 mmol) was added portionwise to a solution of 1,1-dimethylethyl[2-(4-bromophenyl)ethyl]carbamate (for a preparation see Intermediate 99) (914 mg, 3.04 mmol) in tetrahydrofuran (THF) (25 mL). The reaction mixture was stirred at room temperature for 15 min, then methyl iodide (0.952 mL, 15.22 mmol) was slowly added to the mixture which was stirred under nitrogen for a further 2 h. An extra portion of methyl iodide (0.952 mL, 15.22 mmol) was then added to the mixture which was stirred at the same temperature for 2 more hours before being treated with methanol (1 mL). Most of the solvent was removed in vacuo and the residue partitioned between AcOEt (50 mL) and water (30 mL). The layers were separated and the aqueous phase was extracted with AcOEt (20 mL). The combined organic phases were washed with brine, dried over MgSO$_4$ and concentrated in vacuo. Purification of the residue by flash chromatography on silica gel (gradient: 5 to 15% AcOEt in Hexanes) gave 1,1-dimethylethyl[2-(4-bromophenyl)ethyl]methylcarbamate (566 mg, 1.801 mmol, 59%) as a colourless oil. LCMS (method G): Retention time 1.35 min, [M+H]+=315.9 (1 Br)

Intermediate 99

1,1-Dimethylethyl[2-(4-bromophenyl)ethyl]carbamate

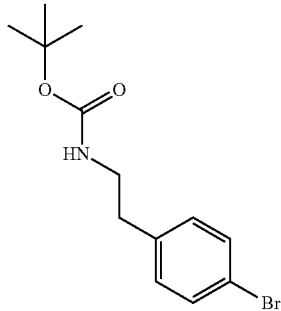 [SMILES: CC(C)(C)OC(=O)NCCc1ccc(Br)cc1]

Bis(1,1-dimethylethyl) dicarbonate (240 mg, 1.100 mmol) was added to a mixture of [2-(4-bromophenyl)ethyl]amine 2-(4-bromophenyl)ethanamine (200 mg, 1.000 mmol) and DIPEA (0.524 mL, 3.00 mmol) in dichloromethane (DCM) (5 mL). The resulting mixture was stirred under nitrogen at room temperature for 2 h then concentrated in vacuo. The residue was partitioned between AcOEt (20 mL) and water (15 mL) and the layers were separated. The aqueous phase was extracted with AcOEt (15 mL). The combined organic phases were washed with brine (15 mL), dried over MgSO$_4$ and concentrated in vacuo. Purification of the residue by flash chromatography on silica gel (gradient: 5 to 25% AcOEt in hexanes) gave 1,1-dimethylethyl[2-(4-bromophenyl)ethyl]carbamate (256 mg, 0.853 mmol, 85%) as a white solid.

LCMS (method G): Retention time 1.22 min, [M+H-t-Bu]+=244.0 (1 Br)

Intermediate 100

Ethyl {4-[(2S,4R)-1-acetyl-2-methyl-4-({[(1-methylethyl)oxy]carbonyl}amino)-1,2,3,4-tetrahydro-6-quinolinyl]phenyl}acetate

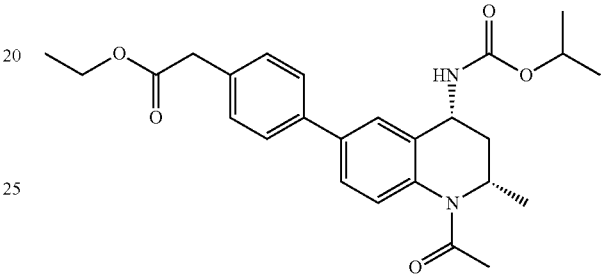

A mixture of 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 52) (100 mg, 0.240 mmol), ethyl (4-bromophenyl)acetate (70.1 mg, 0.288 mmol), potassium carbonate (100 mg, 0.721 mmol) and tetrakis(triphenylphosphine)palladium (0) (13.88 mg, 0.012 mmol) was degassed under house vacuum and quenched several times with nitrogen, and then was heated at 100° C. for 1 h before being cooled to room temperature and partitioned between AcOEt (60 mL) and water (30 mL). The layers were separated and the organic phase was washed with brine, dried on MgSO$_4$ and concentrated in vacuo. Purification of the residue by flash chromatography on silica gel (gradient: 5 to 25% AcOEt in hexanes) gave ethyl {4-[(2S,4R)-1-acetyl-2-methyl-4-({[(1-methylethyl)oxy]carbonyl}amino)-1,2,3,4-tetrahydro-6-quinolinyl]phenyl}acetate (33.9 mg, 0.075 mmol, 31%) as a colourless solid.

LCMS (method G): Retention time 1.12 min, [M+H]+=453.1

Intermediate 101

Ethyl 3-{4-[(2S,4R)-1-acetyl-2-methyl-4-({[(1-methylethyl)oxy]carbonyl}amino)-1,2,3,4-tetrahydro-6-quinolinyl]phenyl}propanoate

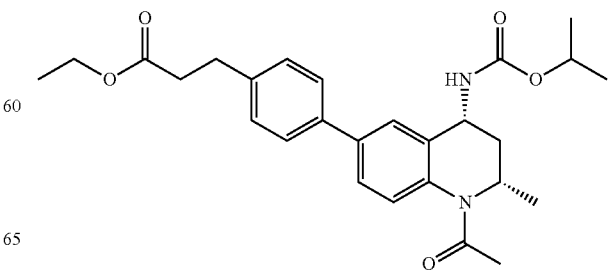

A mixture of 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 52) (100 mg, 0.240 mmol), phenylmethyl 3-(4-bromophenyl)propanoate (92 mg, 0.288 mmol), potassium carbonate (100 mg, 0.721 mmol) and tetrakis(triphenylphosphine)palladium(0) (13.88 mg, 0.012 mmol) in ethanol (2.5 mL) and toluene (2.500 mL) was degassed for 15 min under house vacuum and quenched several times with nitrogen, and then was heated at 100° C. for 1 h before being cooled to room temperature and partitioned between AcOEt (35 mL) and water (20 mL). The layers were separated and the aqueous phase was extracted with AcOEt (15 mL). The combined organic phases were washed with brine (15 mL), dried over MgSO$_4$ and concentrated in vacuo. Purification of the residue by flash chromatography on silica gel (gradient: 40 to 70% AcOEt in Hexanes) gave a residue which was further purified by MDAP (modifier: formic acid) to give ethyl 3-{4-[(2S,4R)-1-acetyl-2-methyl-4-({[(1-methylethyl)oxy]carbonyl}amino)-1,2,3,4-tetrahydro-6-quinolinyl]phenyl}propanoate (39.7 mg, 0.085 mmol, 35%) as a white solid.

LCMS (method G): Retention time 1.16 min, [M+H]+=467.3

Intermediate 102

1,1-Dimethylethyl[(cis)-2-methyl-6-(4-methyl-1H-imidazol-1-yl)-1,2,3,4-tetrahydro-4-quinolinyl]carbamate

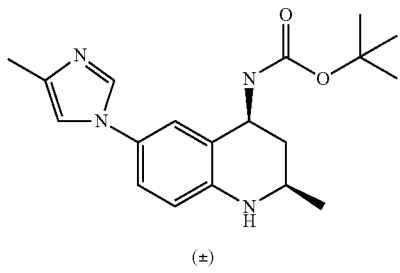 [SMILES: Cc1cn(-c2ccc3c(c2)[C@@H](NC(=O)OC(C)(C)C)C[C@@H](C)N3)cn1]

(±)

Sodium borohydride (29 mg, 0.767 mmol) was added to a solution of 1,1-dimethylethyl (3-{[4-(4-methyl-1H-imidazol-1-yl)phenyl]amino}butanoyl)carbamate (for a preparation see Intermediate 103) (340 mg, 0.949 mmol) in ethanol (6 mL) cooled at −15° C. (cold bath: ethanol/card ice). Magnesium chloride hexahydrate (202 mg, 0.996 mmol) in water (1 mL) was then slowly added keeping the temperature below 10° C.). The mixture was then stirred at 0° C. for 45 min and at room temperature for 45 min before being poured onto a stirred mixture of citric acid (456 mg, 2.371 mmol), HCl (1M in water, 10 mL) and DCM (5 mL). The resulting mixture was stirred for 30 min at room temperature then the layers were separated. The aqueous phase was basified with solid K$_2$CO$_3$ and extracted twice with AcOEt (25 mL). The combined organic phases were washed with water then brine, dried over MgSO$_4$ and concentrated in vacuo. Purification of the residue by flash chromatography on silica gel (gradient: 4 to 8% MeOH in DCM) gave 1,1-dimethylethyl [(cis)-2-methyl-6-(4-methyl-1H-imidazol-1-yl)-1,2,3,4-tetrahydro-4-quinolinyl]carbamate (273 mg, 0.797 mmol, 84%) as a white solid.

LCMS (method A): Retention time 1.02 min, [M+H]+=343.19

Intermediate 103

1,1-Dimethylethyl (3-{[4-(4-methyl-1H-imidazol-1-yl)phenyl]amino}butanoyl)carbamate

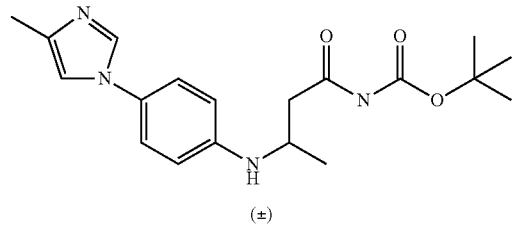 [SMILES: Cc1cn(-c2ccc(NC(C)CC(=O)NC(=O)OC(C)(C)C)cc2)cn1]

(±)

A mixture of 4-(4-methyl-1H-imidazol-1-yl)aniline (for a preparation see Intermediate 104) (500 mg, 2.89 mmol), 1,1-dimethylethyl (2E)-2-butenoylcarbamate (for a preparation see Intermediate 105) (615 mg, 3.32 mmol) and yttrium(III) nitrate hexahydrate (111 mg, 0.289 mmol) in acetonitrile (2 mL) was heated at 50° C. for 15 h. An extra portion of yttrium(III) nitrate hexahydrate (111 mg, 0.289 mmol) was added to the mixture which was stirred for 7 more hours before being cooled to room temperature. Half of the solvent was removed in vacuo and the residue was partitioned between AcOEt (40 mL) and a saturated NaHCO$_3$ aqueous solution (20 mL). The layers were separated and the organic phase was washed with brine (15 mL). The combined aqueous phases were extracted with AcOEt (35 mL) and the combined organic were dried over MgSO$_4$ and concentrated in vacuo. Purification of the residue by flash chromatography on silica gel (gradient: 4 to 8% MeOH in DCM) gave a residue which was further purified by flash chromatography on silica gel (gradient: 60-95% AcOEt in Hexanes) to give 1,1-dimethylethyl (3-{[4-(4-methyl-1H-imidazol-1-yl)phenyl]amino}butanoyl)carbamate (343 mg, 0.956 mmol, 33%) as a colourless sticky solid. LCMS (method A): Retention time 0.94 min, [M+H]+=359.12

Intermediate 104

4-(4-Methyl-1H-imidazol-1-yl)aniline

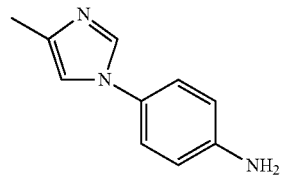

Ammonium formate (2.202 g, 34.9 mmol) and palladium (10% w/w on carbon, 50% wet, 0.473 g, 4.44 mmol) were added to a solution 4-methyl-1-(4-nitrophenyl)-1H-imidazole (4.73 g, 23.28 mmol) in ethanol (150 mL) and the resulting mixture was refluxed under nitrogen for 1 h then cooled to room temperature. An extra portion of ammonium formate (2.202 g, 34.9 mmol) was then added and the resulting mixture was refluxed for a further hour then cooled to room temperature and filtered through celite. Most of the solvent was removed in vacuo and the residue was loaded on a 50 g SCX column which was eluted with MeOH (5 CV) then with 2N NH$_3$ in MeOH (5 CV). The ammonia fractions were combined and concentrated in vacuo to give 4-(4-methyl-1H-imidazol-1-yl)aniline (3.92 g, 21.06 mmol, 90%) as a yellow solid.

LCMS (method G): Retention time 0.61 min, [M+H]+= 164.03

Intermediate 105

1,1-Dimethylethyl (2E)-2-butenoylcarbamate

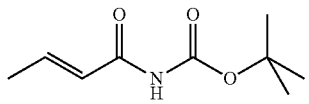

1,1-Dimethylethyl carbamate (5 g, 42.7 mmol) was dissolved in tetrahydrofuran (THF) (100 mL) In a 500 mL 3 necks round bottom flask and cooled at −78° C. under nitrogen. n-Butyl lithium (1.6 M in THF, 26.7 mL, 42.7 mmol) and (2E)-2-butenoyl chloride (4.55 mL, 42.7 mmol) were added in slow successive additions as follow: 1) n-Butyl lithium: 13.4 mL and (2E)-2-butenoyl chloride 2.28 mL; 2) n-Butyl lithium: 6.8 mL and (2E)-2-butenoyl chloride 1.14 mL; 3) n-Butyl lithium: 3.34 mL and (2E)-2-butenoyl chloride 0.57 mL; 4) n-Butyl lithium: 1.67 mL and (2E)-2-butenoyl chloride 0.28 mL (2x). A five to ten min waiting time was observed between each double addition, and the final mixture was stirred for an extra 30 minutes period at −78° C. The temperature was kept below −60° C. during the additions. The reaction mixture was then slowly poured into a stirred saturated NaHCO3 aqueous solution (250 mL). The aqueous layer was extracted with AcOEt (2×250 mL). The combined organic phases were washed with brine (150 mL), dried over MgSO4 and concentrated in vacuo. Purification of the residue by flash chromatography on silica gel (gradient: 50 to 100% AcOEt in Hexanes) gave 1,1-dimethylethyl (2E)-2-butenoylcarbamate (2.21 g, 11.93 mmol, 28%) as a white solid.

LCMS (method G): Retention time 0.61 min, [M+H]+= 164.03

Intermediate 106

1-Methylethyl[(2S,4R)-1-acetyl-6-(5-formyl-1,3-thiazol-2-yl)-2-methyl-1,2,3,4-tetrahydro-4-quinolinyl]carbamate

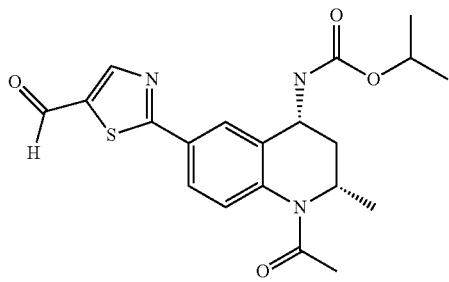 [SMILES: CC(=O)N1c2ccc(-c3ncc(C=O)s3)cc2[C@H](NC(=O)OC(C)C)C[C@@H]1C]

1-Methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 52) (108 mg, 0.259 mmol), 2-bromo-1,3-thiazole-5-carbaldehyde (74.7 mg, 0.389 mmol), sodium bicarbonate (32.7 mg, 0.389 mmol) and tetrakis(triphenylphosphine)palladium(0) (30.0 mg, 0.026 mmol) were stirred at 100° C. in 1,2-dimethoxyethane (DME) (4 mL) under nitrogen for 16 h then cooled to room temperature. A saturated NaHCO3 aqueous solution (1 mL) was added and the resulting mixture was stirred at 100° C. for 4 h then cooled to room temperature and concentrated in vacuo. The residue was dissolved in DCM and the organic phase was filtered through celite then concentrated in vacuo to give 1-methylethyl [(2S,4R)-1-acetyl-6-(5-formyl-1,3-thiazol-2-yl)-2-methyl-1,2,3,4-tetrahydro-4-quinolinyl]carbamate (104 mg, 0.259 mmol, 100%) which was used in the next step without further purification. LCMS (method G): Retention time 0.91 min, [M+H]+=402.0

Intermediate 107

Methyl 4-[(2S,4R)-1-acetyl-2-methyl-4-({[(1-methylethyl)oxy]carbonyl}amino)-1,2,3,4-tetrahydro-6-quinolinyl]benzoate

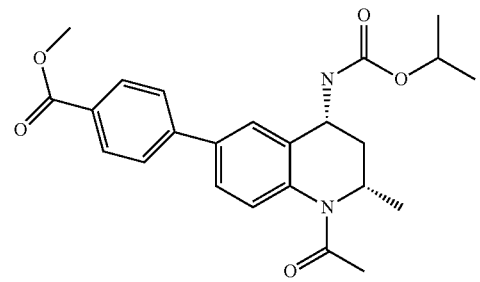 [SMILES: COC(=O)c1ccc(-c2ccc3c(c2)[C@H](NC(=O)OC(C)C)C[C@H](C)N3C(C)=O)cc1]

A flask was charged with methyl 4-(4,4,5,5-tetramethyl-1,3,2-dioxaborolan-2-yl)benzoate (0.355 g, 1.354 mmol), 1-methylethyl[(2S,4R)-1-acetyl-6-bromo-2-methyl-1,2,3,4-tetrahydro-4-quinolinyl]carbamate (for a preparation see Example 4) (0.5 g, 1.354 mmol), a saturated NaHCO3 aqueous solution (1.5 mL, 1.354 mmol) and bis(diphenylphosphino)ferrocene]dichloropalladium(II)-DCM adduct (0.111 g, 0.135 mmol) then filled with 1,4-dioxane (7 mL). The resulting mixture was degassed by bubbling nitrogen in to it, stirred at 100° C. for 1 hr under microwave irradiation then cooled to room temperature. The reaction mixture was filtered through celite and concentrated in vacuo. The residue was partitioned between EtOAC (30 mL) and water (30 mL) and the layers were separated. The organic phase was washed with brine (25 mL) dried over MgSO4 and concentrated in vacuo to give methyl 4-[(2S,4R)-1-acetyl-2-methyl-4-({[(1-methylethyl)oxy]carbonyl}amino)-1,2,3,4-tetrahydro-6-quinolinyl]benzoate (0.47 g, 1.11 mmol, 82%) which was used in the next step without further purification LCMS (method A): Retention time 1.09 min, [M+H]+= 425.19

Intermediate 108

Methyl 4-[(2S,4R)-1-acetyl-2-methyl-4-({[(1-methylethyl)oxy]carbonyl}amino)-1,2,3,4-tetrahydro-6-quinolinyl]-3-methylbenzoate

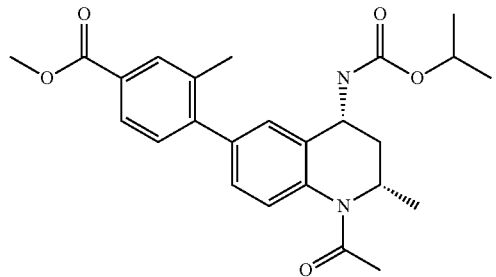 [SMILES: COC(=O)c1ccc(-c2ccc3c(c2)[C@H](NC(=O)OC(C)C)C[C@H](C)N3C(C)=O)c(C)c1]

A flask was charged with methyl 3-methyl-4-(4,4,5,5-tetramethyl-1,3,2-dioxaborolan-2-yl)benzoate (0.449 g, 1.625 mmol), 1-methylethyl[(2S,4R)-1-acetyl-6-bromo-2-methyl-1,2,3,4-tetrahydro-4-quinolinyl]carbamate (for a preparation see Example 4) (0.5 g, 1.354 mmol), sodium bicarbonate (saturated solution) (1.5 mL, 1.354 mmol) and bis(diphenylphosphino)ferrocene]dichloropalladium(II)-DCM adduct (0.111 g, 0.135 mmol) then filled with 1,4-dioxane (7 mL). The resulting mixture was degassed by bubbling nitrogen in to it, stirred at 100° C. for 1 hr under microwave irradiation then cooled to room temperature. The reaction mixture was filtered through celite and concentrated in vacuo. The residue was partitioned between EtOAC (30 mL) and water (30 mL) and the layers were separated. The organic phase was washed with brine (25 mL) dried over $MgSO_4$ and concentrated in vacuo. Purification of the residue by flash chromatography on silica gel (gradient: 0 to 60% AcOEt in hexanes) gave methyl 4-[(2S,4R)-1-acetyl-2-methyl-4-({[(1-methylethyl)oxy]carbonyl}amino)-1,2,3,4-tetrahydro-6-quinolinyl]-3-methylbenzoate (337 mg, 0.769 mmol, 56.8%) as a light yellow solid.

LCMS (method A): Retention time 1.12 min, [M+H]+= 439.17

Intermediate 109

1,1-Dimethylethyl 4-[({4-[(2S,4R)-1-acetyl-2-methyl-4-({[(1-methylethyl)oxy]carbonyl}amino)-1,2,3,4-tetrahydro-6-quinolinyl]phenyl}methyl)amino]-1-piperidinecarboxylate

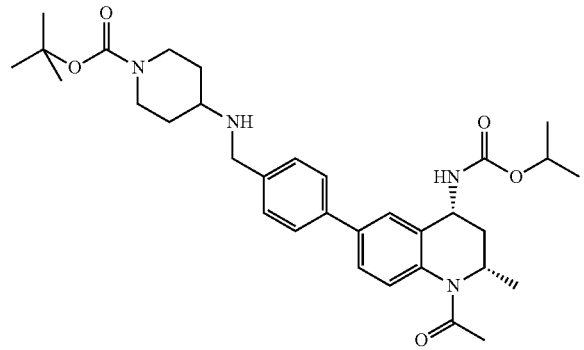 [SMILES: CC(=O)N1c2ccc(-c3ccc(CNC4CCN(C(=O)OC(C)(C)C)CC4)cc3)cc2[C@H](NC(=O)OC(C)C)C[C@@H]1C]

A mixture of 1-methylethyl[(2S,4R)-1-acetyl-6-(4-formylphenyl)-2-methyl-1,2,3,4-tetrahydro-4-quinolinyl]carbamate (for a preparation see intermediate 36) (500 mg, 1.268 mmol) and 1,1-dimethylethyl 4-amino-1-piperidinecarboxylate (400 mg, 1.997 mmol) in dichloromethane (DCM) (15 ml) was stirred 45 min at room temperature under nitrogen before being treated portionwise with sodium triacetoxyborohydride (457 mg, 2.155 mmol). The resulting mixture was stirred at room temperature for 20 h then treated with a saturated $NH_4Cl$ aqueous solution (8 mL) and diluted with water (10 mL). The layers were separated and the aqueous phase was washed with DCM (2×10 mL). The combined organic layers were dried over $Na_2SO_4$ then concentrated in vacuo. Purification of the residue by flash chromatography on silica gel (gradient: 1 to 10% MeOH in DCM) gave 1,1-dimethylethyl 4-[({4-[(2S,4R)-1-acetyl-2-methyl-4-({[(1-methylethyl)oxy]carbonyl}amino)-1,2,3,4-tetrahydro-6-quinolinyl]phenyl}methyl)amino]-1-piperidinecarboxylate (608 mg, 0.998 mmol, 79%) as a cream solid.

LCMS (method G): Retention time 0.84 min, [M+H]+= 579.3

Intermediate 110

1-Methylethyl {(2S,4R)-1-acetyl-6-[acetyl(2-oxopropyl)amino]-2-methyl-1,2,3,4-tetrahydro-4-quinolinyl}carbamate

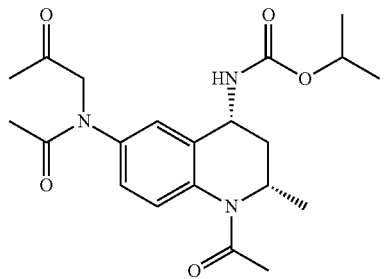 [SMILES: CC(=O)CN(C(C)=O)c1ccc2c(c1)[C@H](NC(=O)OC(C)C)C[C@H](C)N2C(C)=O]

1-Methylethyl {(2S,4R)-1-acetyl-2-methyl-6-[(2-oxopropyl)amino]-1,2,3,4-tetrahydro-4-quinolinyl}carbamate (for a preparation see Intermediate 111) (200 mg, 0.553 mmol) was dissolved in acetic anhydride (1044 µl, 11.07 mmol) and the resulting mixture was stirred at room temperature under nitrogen for 1 h then partitioned between water (2 mL) and DCM (5 mL). The layers were separated and the organic phase washed with water, dried over $Na_2SO_4$ and concentrated in vacuo. Purification of the residue by flash chromatography on silica gel (gradient: 10 to 100% AcOEt in hexanes) gave 1-methylethyl {(2S,4R)-1-acetyl-6-[acetyl(2-oxopropyl)amino]-2-methyl-1,2,3,4-tetrahydro-4-quinolinyl}carbamate (130 mg, 0.274 mmol, 49%) as an orange oil.

LCMS (method G): Retention time 0.71 min, [M+H]+= 404.0

Intermediate 111

1-Methylethyl {(2S,4R)-1-acetyl-2-methyl-6-[(2-oxopropyl)amino]-1,2,3,4-tetrahydro-4-quinolinyl}carbamate

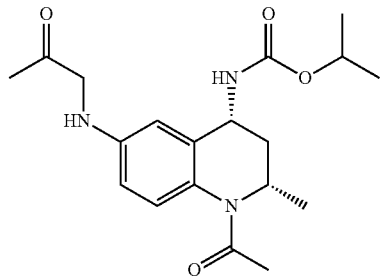 [SMILES: CC(=O)CNc1ccc2c(c1)[C@H](NC(=O)OC(C)C)C[C@H](C)N2C(C)=O]

To a solution of 1-methylethyl[(2S,4R)-1-acetyl-6-amino-2-methyl-1,2,3,4-tetrahydro-4-quinolinyl]carbamate (for a preparation see Intermediate 112) (1.46 g, 4.78 mmol) in acetone (15 mL) at 60° C. was added potassium carbonate (0.991 g, 7.17 mmol) and the resulting mixture was stirred at this temperature for 15 min. 1-Chloro-2-propanone (0.457 ml, 5.74 mmol) was added as well as sodium iodide (0.860 g, 5.74 mmol) and resulting mixture was stirred at 60° C. for 1 h then cooled to room temperature, filtered through celite and concentrated in vacuo. Purification of the residue by flash chromatography on silica gel (gradient: 10 to 100% AcOEt in Hexanes) gave 1-methylethyl {(2S,4R)-1-acetyl-2-methyl-6-[(2-oxopropyl)amino]-1,2,3,4-tetrahydro-4-quinolinyl}carbamate (1.11 g, 3.07 mmol, 64%) as an orange foamy solid.

LCMS (method G): Retention time 0.76 min, [M+H]+= 362.18

Intermediate 112

1-Methylethyl[(2S,4R)-1-acetyl-6-amino-2-methyl-1,2,3,4-tetrahydro-4-quinolinyl]carbamate

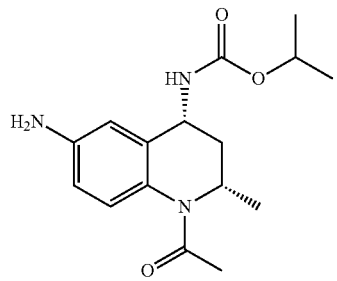 [SMILES: CC(=O)N1c2ccc(N)cc2[C@H](NC(=O)OC(C)C)C[C@@H]1C]

A mixture of 1-methylethyl[(2S,4R)-1-acetyl-6-bromo-2-methyl-1,2,3,4-tetrahydro-4-quinolinyl]carbamate (for a preparation see example 4) (2.71 g, 7.34 mmol) and copper(I) oxide (0.247 g, 1.726 mmol) in N,N-dimethylformamide (DMF) (5 mL) was treated with NH$_3$ (35% w/w in water) (5 mL, 258 mmol) and the resulting mixture was stirred at 110° C. for 5 h under microwave irradiation then cooled to room temperature and concentrated in vacuo. The residue was partitioned between water and AcOEt and the layers were separated. The aqueous phase was extracted with AcOEt (2×50 mL) and the combined organic phases were dried over MgSO$_4$ then concentrated in vacuo. Purification of the residue by flash chromatography on silica gel (gradient: 10 to 100% AcOEt in Hexanes) gave 1-methylethyl[(2S,4R)-1-acetyl-6-amino-2-methyl-1,2,3,4-tetrahydro-4-quinolinyl]carbamate (1.91 g, 6.25 mmol, 85%) as an orange foamy solid.

LCMS (method G): Retention time 0.56 min, [M+H]+= 306.15

Intermediate 113

1,1-Dimethylethyl[(2S,4R)-1-acetyl-6-ethynyl-2-methyl-1,2,3,4-tetrahydro-4-quinolinyl]carbamate

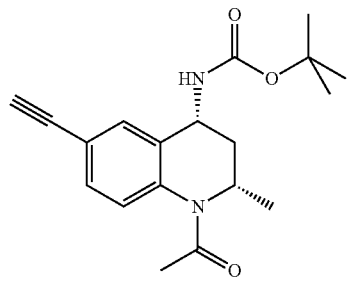 [SMILES: C#Cc1ccc2c(c1)[C@H](NC(=O)OC(C)(C)C)C[C@H](C)N2C(C)=O]

To a solution of 1,1-dimethylethyl {(2S,4R)-1-acetyl-2-methyl-6-[(trimethylsilyl)ethynyl]-1,2,3,4-tetrahydro-4-quinolinyl}carbamate (for a preparation see Intermediate 114) (3.4 g, 8.49 mmol) in tetrahydrofuran (THF) (50 mL) at room temperature was added TBAF (1M in THF, 8.49 mL, 8.49 mmol) and the resulting mixture was stirred at this temperature for 30 min then most of the solvent was removed in vacuo. The residue was partitioned between AcOEt and water/brine (1/1) and the layers were separated. The aqueous phase was extracted three times with AcOEt and the combined organic phases were washed with water/brine (1/1) which when combined were extracted twice with AcOEt. All organic phases were combined and dried over MgSO$_4$ then concentrated in vacuo. Purification of this residue by SP4 using a 50 G silica cartridge (gradient: 10 to 50% AcOEt in hexanes) gave 1,1-dimethylethyl[(2S,4R)-1-acetyl-6-ethynyl-2-methyl-1,2,3,4-tetrahydro-4-quinolinyl]carbamate (2.75 g, 8.37 mmol, 99% yield) as a yellow foam.

LCMS (method A): Retention time 1.06 min, [M+H]+= 329.15

Intermediate 114

1,1-Dimethylethyl {(2S,4R)-1-acetyl-2-methyl-6-[(trimethylsilyl)ethynyl]-1,2,3,4-tetrahydro-4-quinolinyl}carbamate

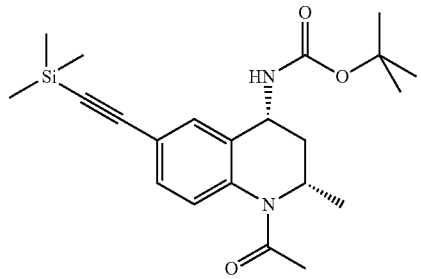 [SMILES: CC(=O)N1c2ccc(C#C[Si](C)(C)C)cc2[C@H](NC(=O)OC(C)(C)C)C[C@@H]1C]

A flask was charged with 1,1-dimethylethyl[(2S,4R)-1-acetyl-6-bromo-2-methyl-1,2,3,4-tetrahydro-4-quinolinyl]carbamate (for a preparation see example 63) (4 g, 10.44 mmol), copper(I) iodide (0.199 g, 1.044 mmol) and bis(triphenylphosphine)palladium(II) chloride (0.733 g, 1.044 mmol) then filled with N,N-dimethylformamide (DMF) (60 mL). Triethylamine (58.2 mL, 417 mmol) and ethynyl(trimethyl)silane (29.7 mL, 209 mmol) were added and the resulting mixture was stirred for 20 h at 90° C. under nitrogen then cooled to room temperature. Most of the solvent was removed in vacuo and the residue was partitioned between AcOEt and water/brine (1/1). The layers were separated and the aqueous phase was extracted with AcOEt. The combined organic phases were washed three times with water/brine (1/1), dried over MgSO$_4$ and concentrated in vacuo. Purification of this residue by SP4 using a 100 G silica cartridge (gradient: 10 to 50% AcOEt in Hexanes) gave 1,1-dimethylethyl {(2S,4R)-1-acetyl-2-methyl-6-[(trimethylsilyl)ethynyl]-1,2,3,4-tetrahydro-4-quinolinyl}carbamate (3.4 g, 8.49 mmol, 81% yield) as a black foam. LCMS (method A): Retention time 1.39 min, [M+H]+=401.19

Intermediate 115

N,N-Dimethyl-2-[4-(4,4,5,5-tetramethyl-1,3,2-dioxaborolan-2-yl)-1H-pyrazol-1-yl]ethanamine

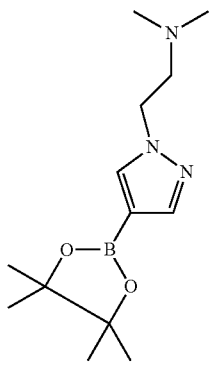

4-(4,4,5,5-Tetramethyl-1,3,2-dioxaborolan-2-yl)-1H-pyrazole (2 g, 10.31 mmol), cesium carbonate (6.72 g, 20.61 mmol) and 2-chloro-N,N-dimethylethanamine hydrochloride (2.227 g, 15.46 mmol) were suspended in acetonitrile (30 mL) and the mixture was heated at reflux for 5 h, then cooled to room temperature, diluted with $Et_2O$ and filtered. The filtrate was concentrated in vacuo to give N,N-dimethyl-2-[4-(4,4,5,5-tetramethyl-1,3,2-dioxaborolan-2-yl)-1H-pyrazol-1-yl]ethanamine dimethyl{2-[4-(4,4,5,5-tetramethyl-1,3,2-dioxaborolan-2-yl)-1H-pyrazol-1-yl]ethyl}amine (2.61 g, 9.84 mmol, 95% yield) as an amber oil which was used in the next step without further purification.

Intermediate 116

1-Methylethyl[(2S,4R)-1-acetyl-6-(4-{2-[{[(1,1-dimethylethyl)oxy]carbonyl}(methyl)amino]ethyl}phenyl)-2-methyl-1,2,3,4-tetrahydro-4-quinolinyl]carbamate

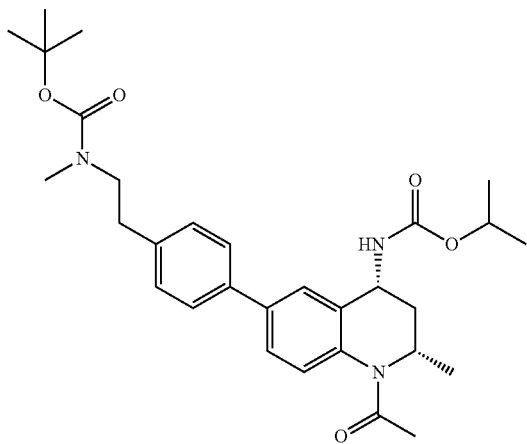 [SMILES: CC(=O)N1c2ccc(-c3ccc(CCN(C)C(=O)OC(C)(C)C)cc3)cc2[C@H](NC(=O)OC(C)C)C[C@@H]1C]

A mixture of 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 52) (150 mg, 0.360 mmol), 1,1-dimethylethyl[2-(4-bromophenyl)ethyl]methylcarbamate (for a preparation see Intermediate 98) (113 mg, 0.360 mmol), potassium carbonate (124 mg, 0.901 mmol) and tetrakis(triphenylphosphine)palladium(0) (20.82 mg, 0.018 mmol) was degassed under house vacuum for 15 min and quenched several times with nitrogen, then was then stirred at 100° C. under nitrogen for 50 min before being cooled to room temperature. Most of the solvent was removed in vacuo and the residue was partitioned between AcOEt (20 mL) and water (15 mL). The layers were separated and the aqueous phase was extracted with AcOEt (15 mL). The combined organic phases were washed with brine (15 mL), dried over $MgSO_4$ and concentrated in vacuo. Purification of the residue by flash chromatography on silica gel (gradient: 50 to 75% AcOEt in hexanes) gave 1-methylethyl [(2S,4R)-1-acetyl-6-(4-{2-[{[(1,1-dimethylethyl)oxy]carbonyl}methyl)amino]ethyl}phenyl)-2-methyl-1,2,3,4-tetrahydro-4-quinolinyl]carbamate (41.5 mg, 0.079 mmol, 22%) as a colourless oil. LCMS (method G): Retention time 1.26 min, [M+H-Boc]+=424.3

Intermediate 117

1-[2-(Methyloxy)ethyl]-4-(4,4,5,5-tetramethyl-1,3,2-dioxaborolan-2-yl)-1H-pyrazole

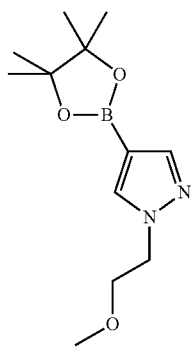 [SMILES: COCCn1cc(B2OC(C)(C)C(C)(C)O2)cn1]

A solution of 4-(4,4,5,5-tetramethyl-1,3,2-dioxaborolan-2-yl)-1H-pyrazole (10 g, 51.5 mmol) in ethanol (50 mL) was treated with KOH (3.47 g, 61.8 mmol) and 1-bromo-2-(methyloxy)ethane (5.81 mL, 61.8 mmol) at room temperature and the resulting mixture was stirred at 50° C. under nitrogen for 16 h then cooled to room temperature. 1-Bromo-2-(methyloxy)ethane (2 mL, 21.3 mmol) was added and the resulting mixture was stirred at 50° C. for 60 h then cooled to room temperature. The mixture was filtered through celite and the insoluble were washed with ethanol. The combined filtrate and washings were concentrated in vacuo. Purification of the residue on SP4 using a 100 G silica cartridge (gradient: 0 to 100% AcOEt in Hexanes) gave 1-[2-(methyloxy)ethyl]-4-(4,5,5-tetramethyl-1,3,2-dioxaborolan-2-yl)-1H-pyrazole (2.72 g, 10.25 mmol, 20%) as a yellow oil. LCMS (method G): Retention time 0.87 min, [M+H]+=252.9

Intermediate 118

2-[4-(4,4,5,5-tetramethyl-1,3,2-dioxaborolan-2-yl)-1H-pyrazol-1-yl]ethanol

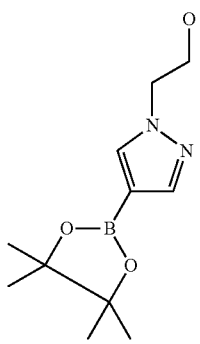 [SMILES: CC1(C)OB(c2cnn(CCO)c2)OC1(C)C]

A solution of 1,3-dioxolan-2-one (2.496 g, 28.3 mmol), 4-(4,4,5,5-tetramethyl-1,3,2-dioxaborolan-2-yl)-1H-pyrazole (5 g, 25.8 mmol) and sodium hydroxide (0.103 g, 2.58 mmol) in N,N-Dimethylformamide (DMF) (18 mL) was stirred at 140° C. for 16 h. then cooled to room temperature and treated with activated charcoal (200 mg). The resulting mixture was stirred at room temperature for 1 h then filtered through celite (10 g). The insoluble were washed with EtOAc (50 mL) and EtOH (50 mL). The combined filtrate and washings were concentrated in vacuo. Purification of the residue by flash chromatography on silica gel using a 50 G silica cartyridge (gradient: 0 to 40% MeOH in DCM) gave a residue which was further purified by SP4 using a 100 G silica cartridge (eluant: 0 to 20% MeOH in DCM) to give 2-[4-(4,4,5,5-tetramethyl-1,3,2-dioxaborolan-2-yl)-1H-pyrazol-1-yl] ethanol (5.58 g, 23.44 mmol, 91% yield) as a colourless oil which was used in the next step without further purification.

LCMS (method A): Retention time 0.68 min, [M+H]+= 239.13

Intermediate 119

2-methyl-1-[4-(4,4,5,5-tetramethyl-1,3,2-dioxaborolan-2-yl)-1H-pyrazol-1-yl]-2-propanol

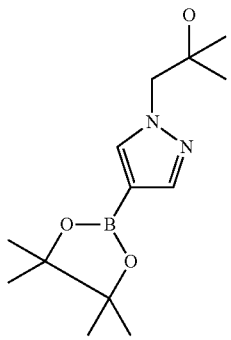 [SMILES: CC(C)(O)Cn1cc(B2OC(C)(C)C(C)(C)O2)cn1]

To a solution of 4-(4,4,5,5-tetramethyl-1,3,2-dioxaborolan-2-yl)-1H-pyrazole (1.5 g, 7.73 mmol) and cesium carbonate (3.78 g, 11.60 mmol) in N,N-dimethylformamide (DMF) (17 mL) was added 2,2-dimethyloxirane (1.717 mL, 19.33 mmol) and the resulting mixture was stirred at 110° C. for 1 h under microwave irradiation then cooled to room temperature and filtered through celite (50 g). The insoluble material was washed with EtOAc (20 mL) and MeOH (20 mL). The combined filtrate and washings were concentrated in vacuo. Purification of the residue by flash chromatography using a 50 G silica cartridge (gradient: 0 to 100% (20% MeOH in DCM) in DCM) gave 2-methyl-1-[4-(4,4,5,5-tetramethyl-1,3,2-dioxaborolan-2-yl)-1H-pyrazol-1-yl]-2-propanol (2.10 g, 7.89 mmol, 102% yield) as a cream solid which was used in the next step without further purification.

LCMS (method G): Retention time 0.81 min, [M+H]+= 266.8

Intermediate 120

4-(4-nitrophenyl)-1H-imidazole

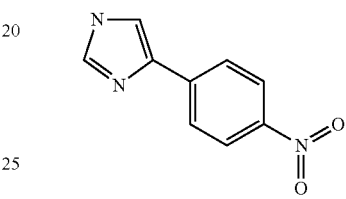

A mixture of 2'-bromo-4-nitroacetphenone (15 g, 61.5 mmol) and formamide (100 mL) was stirred at 150° C. for 3 days then cooled to approximately 40° C. and poured onto ice/water (approximately 700 mL). The resulting mixture was stirred for 30 min then the solid formed was filtered off, washed with water and dried to give 4-(4-nitrophenyl)-1H-imidazole (7.0 g, 37 mmol, 60%) as a brown solid.

LCMS (method G): Retention time 0.46 min, [M+H]+= 190.0

Example 1

1-methylethyl(((2S,4R)-1-acetyl-2-methyl-6-{4-[(methylamino)methyl]phenyl}-1,2,3,4-tetrahydro-4-quinolinyl)carbamate

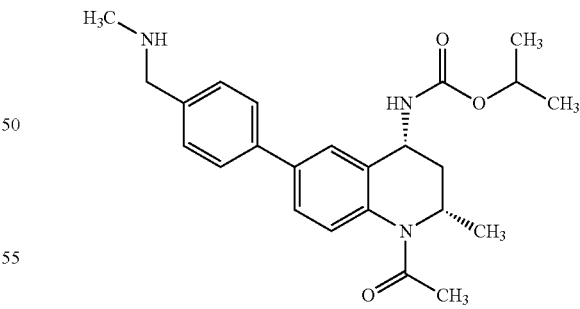

1-Methylethyl[(2S,4R)-1-acetyl-6-(4-formylphenyl)-2-methyl-1,2,3,4-tetrahydro-4-quinolinyl]carbamate (for a preparation see Intermediate 36) (100 mg, 0.254 mmol) was dissolved in methanol (3 mL) and 2M methylamine in THF (0.254 mL, 0.507 mmol) was added. The yellow solution was stirred under nitrogen at room temperature for 135 minutes at which point sodium borohydride (15.35 mg, 0.406 mmol) was added. The reaction was stirred for 1 h then left sitting overnight. The reaction was quenched with sat. aqueous sodium bicarbonate solution (1 mL) and EtOAc (8 mL) was added. A white solid was filtered off (bond elut reservoir) and found to be the desired product (34 mg). The filtrate was partitioned and the organic layer dried. Concentration of the organic layer gave 67 mg of a colourless residue which was applied to a silica 12+S Biotage column and purified eluting with a gradient of 1-5% methanolic ammonia in DCM. Concentration of the product containing fractions gave another batch of the desired product (52 mg).

LCMS (Method C): Rt 0.71, MH+=410

1H NMR(CHLOROFORM-d, 600 MHz): δ (ppm) 7.55 (d, J=8.1 Hz, 2H), 7.49 (d, J=7.9 Hz, 1H), 7.45 (br. s., 1H), 7.41 (d, J=7.9 Hz, 2H), 7.18 (d, J=7.3 Hz, 1H), 4.52-5.08 (m, 4H), 3.81 (s, 2H), 2.62 (ddd, J=12.5, 8.3, 4.5 Hz, 1H), 2.50 (s, 3H), 2.17 (s, 3H), 1.21-1.37 (m, 7H), 1.18 (d, J=6.4 Hz, 3H)

Example 2

1-methylethyl {(2S,4R)-1-acetyl-2-methyl-6-[6-(1-piperazinyl)-3-pyridinyl]-1,2,3,4-tetrahydro-4-quinolinyl}carbamate

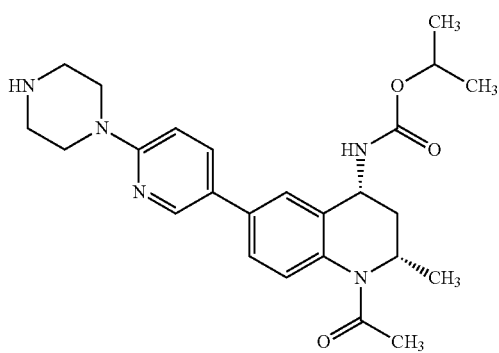 [SMILES: CC(=O)N1c2ccc(-c3ccc(N4CCNCC4)nc3)cc2[C@H](NC(=O)OC(C)C)C[C@@H]1C]

1-Methylethyl[(2S,4R)-1-acetyl-6-bromo-2-methyl-1,2,3,4-tetrahydro-4-quinolinyl]carbamate (for a preparation see Example 4) (1.09 g, 2.95 mmol), potassium carbonate (0.816 g, 5.90 mmol), tetrakis(triphenylphosphine)palladium(0) (0.171 g, 0.148 mmol) and 1,1-dimethylethyl 4-[5-(4,4,5,5-tetramethyl-1,3,2-dioxaborolan-2-yl)-2-pyridinyl]-1-piperazinecarboxylate (1.379 g, 3.54 mmol, available from Aldrich) were dissolved in ethanol (10 mL) and toluene (10 mL). The reaction mixture was degassed for 30 min then stirred and heated under nitrogen for 1 hr at 100° C. The reaction mixture was filtered and the solvent evaporated under vacuum. The residue was partitioned between dichloromethane (30 ml) and water (30 ml). The organic layer was dried through a hydrophobic frit and concentrated in vacuo. The residue (2.08 g) was dissolved with dichloromethane and purified by SP4 on a 40+M silica cartridge using a gradient of 30-80% EtOAc in cyclohexane. The appropriate fractions were combined and evaporated in vacuo to give a Boc protected intermediate. This was dissolved with methanol (10 ml) and treated with 2 ml of acetyl chloride, the resulting mixture was stirred at room temp for 1 hour. The reaction mixture was concentrated under reduced pressure and the residue was loaded on a 50 g SCX column which was previously conditioned with methanol. Columns was washed with methanol (3 CV) and eluted with 2N ammonia in methanol (3 CV). The appropriate fractions were combined and evaporated in vacuo to give the required product, yield 0.96 g as a white solid.

LCMS (Method B): Rt 0.59, MH+=452

1H NMR (DMSO-d6, 400 MHz): δ (ppm) 8.41 (d, J=2.0 Hz, 1H), 7.80 (dd, J=8.8, 2.3 Hz, 1H), 7.61 (d, J=8.5 Hz, 1H), 7.46-7.54 (m, 1H), 7.26-7.41 (m, 2H), 6.90 (d, J=8.9 Hz, 1H), 4.78-4.91 (m, 1H), 4.58-4.74 (m, 1H), 4.33-4.48 (m, 1H), 3.42-3.55 (m, 4H), 2.76-2.87 (m, 4H), 2.41-2.50 (m, 1H), 2.07 (s, 3H), 1.13-1.32 (m, 7H), 1.04 (d, J=6.1 Hz, 3H)

Example 3

1-methylethyl {(2S,4R)-1-acetyl-2-methyl-6-[4-(1-piperidinyl methyl)phenyl]-1,2,3,4-tetrahydro-4-quinolinyl}carbamate

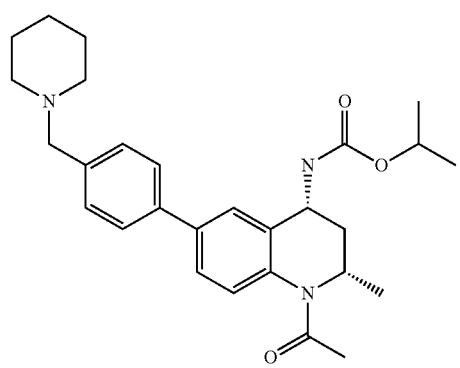 [SMILES: CC(=O)N1c2ccc(-c3ccc(CN4CCCCC4)cc3)cc2[C@H](NC(=O)OC(C)C)C[C@@H]1C]

1-Methylethyl[(2S,4R)-1-acetyl-6-bromo-2-methyl-1,2,3,4-tetrahydro-4-quinolinyl]carbamate (for a preparation see Example 4) (50 mg, 0.135 mmol), [4-(1-piperidinylmethyl)phenyl]boronic acid hydrochloride (for a preparation see Intermediate 1) (45.0 mg, 0.176 mmol), potassium carbonate (43.0 mg, 0.311 mmol) and tetrakis(triphenylphosphine)palladium(0) (7.82 mg, 6.77 µmol) were suspended in a mixture of Ethanol (0.5 ml) and Toluene (0.5 ml) and heated under microwave conditions in an Emrys Optimiser at 100° C. for 3 hours. Further tetrakis(triphenylphosphine)palladium(0) (7.82 mg, 6.77 µmol) added and the mixture heated at 90° C. thermally for 23 hours. The mixture was cooled to room temperature, loaded on to a 2 g SCX cartridge, eluted with MeOH (25 ml), 2M methanolic ammonia (25 ml) and the basic fractions evaporated to dryness. The residue was loaded on to a 12+M Biotage silica column and eluted with a gradient of 0 to 4% methanloic ammonia in DCM. The clean, product containing fractions were evaporated to a white solid (10 mg).

LCMS (Method C): Rt=0.77, MH+=464

Example 4

1-methylethyl[(2S,4R)-1-acetyl-6-bromo-2-methyl-1,2,3,4-tetrahydro-4-quinolinyl]carbamate

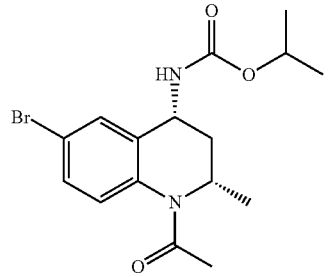 [SMILES: CC(=O)N1c2ccc(Br)cc2[C@H](NC(=O)OC(C)C)C[C@@H]1C]

1-Methylethyl[(2S,4R)-6-bromo-2-methyl-1,2,3,4-tetrahydro-4-quinolinyl]carbamate (for a preparation see Intermediate 35) (14.1 g, 43.1 mmol) was taken up in Dichloromethane (DCM) (400 mL) under nitrogen at RT. Pyridine (10.46 mL, 129 mmol) then Acetyl chloride (4.60 mL, 64.6 mmol) were added and the reaction stirred overnight. LCMS showed a complete reaction so it was partitioned between EtOAc (2000 ml) and sat. NaHCO3 (800 ml). The organic layer was extracted and washed with water and brine (1500 ml each) and then dried with Na2SO4, filtered and concentrated to yield a purple solid. The crude product was taken up in the minimum of DCM and applied to a 330 g Companion XL column and eluted with a gradient of 12-63% Ethyl Acetate in cyclohexane. Product containing fractions were collected as an off-white solid (12.37 g).

LCMS (Method B): Rt=1.03, MH+=369

[alpha]D=+281.1025° (T=20.7° C., 10 mm cell, c=0.508 g/100 ml, ethanol).

Example 5

1-methylethyl {(cis)-1-acetyl-2-methyl-6-[4-(1-piperidinylmethyl)phenyl]-1,2,3,4-tetrahydro-4-quinolinyl}carbamate Racemate of Example 3

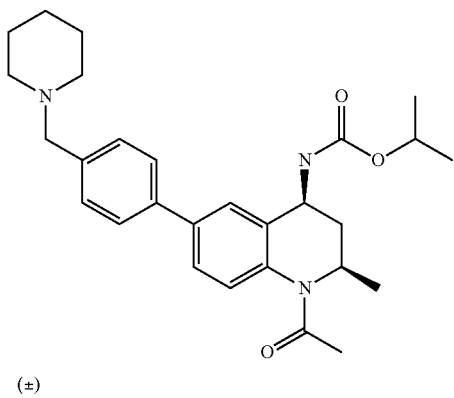 [SMILES: CC(=O)N1c2ccc(-c3ccc(CN4CCCCC4)cc3)cc2[C@@H](NC(=O)OC(C)C)C[C@H]1C]

(±)

1-Methylethyl[(cis)-1-acetyl-6-bromo-2-methyl-1,2,3,4-tetrahydro-4-quinolinyl]carbamate (for a preparation see Example 61) (1 g, 2.71 mmol), [4-(1-piperidinylmethyl)phenyl]boronic acid hydrochloride (for a preparation see Intermediate 1) (0.900 g, 3.52 mmol) and potassium carbonate (0.861 g, 6.23 mmol) were stirred in Ethanol (15.6 ml) and Toluene (15.6 ml) under nitrogen and the mixture degassed. tetrakis(triphenylphosphine)palladium(0) (0.156 g, 0.135 mmol) was added, the mixture degassed again and heated to 95° C. for 4 hours, and evaporated to dryness. The mixture was partitioned between ethyl acetate (50 ml) and water (10 ml). The aqueous layer (pH8) was run off and the organic washed (2× sat. sodium hydrogen carbonate (10 ml)), dried (sodium sulfate) and evaporated to a brown solid. The residue was loaded on to a 40+M Biotage silica column and eluted with DCM:2M Methanolic ammonia (0 to 4%). The clean, product containing fractions were evaporated to a beige solid (634 mg). The mixed fractions were applied to a 10 g SCX cartridge and eluted with MeOH (100 ml) and 2M methanolic ammonia (50 ml). The basic fractions were evaporated to give a second batch of material as a white solid (415 mg). LCMS (Method C): Rt 0.76 min, MH+464.

Example 6

1-methylethyl((cis)-1-acetyl-2-methyl-6-{4-[(methylamino)methyl]phenyl}-1,2,3,4-tetrahydro-4-quinolinyl)carbamate hydrochloride Racemate of Example 1

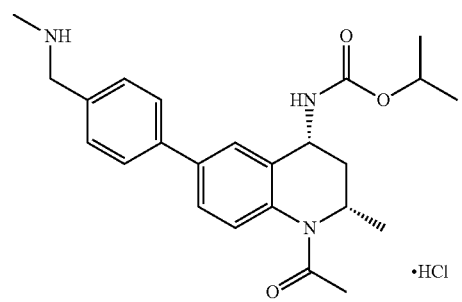

(±)

1-Methylethyl[(cis)-1-acetyl-6-(4-formylphenyl)-2-methyl-1,2,3,4-tetrahydro-4-quinolinyl]carbamate (for a preparation see Intermediate 7) (65 mg, 0.165 mmol) dissolved in dichloromethane (DCM) (2 mL) and to this was added 2.0M methylamine in methanol (0.124 mL, 0.247 mmol) and stirred for 30 min. Sodium triacetoxyborohydride (45.4 mg, 0.214 mmol) was added and left stirring under nitrogen over the weekend then quenched with saturated aqueous ammonia solution (2 ml). The layers were separated and the aqueous reextracted with DCM (3×10 ml). The combined organics were passed through a phase separation cartridge and reduced in vacuo to give an off white solid (52 mg). The aqueous was reduced in vacuo and then dissolved in water and reextracted with DCM though this yielded no further product. The crude mixture was dissolved in DCM and purified by SP4 on a 12+M silica cartridge using a gradient of 0 to 100% 0.5M methanolic ammonia in ethyl acetate. The relevant fractions were combined and reduced in vacuo to give a colourless film (27 mg). The film was dissolved in methanol and to this was added 1.25M HCl in methanol (2 equivalents, 0.106 ml) and reduced in vacuo to give a colourless solid (27 mg) LCMS (Method A): Rt=0.95, MH+=410

Example 7

1-methylethyl((cis)-1-acetyl-6-{4-[(dimethylamino)methyl]phenyl}-2-methyl-1,2,3,4-tetrahydro-4-quinolinyl)carbamate hydrochloride

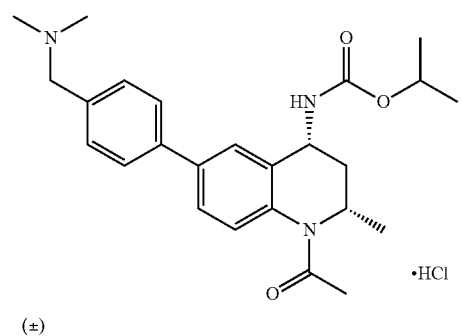 [SMILES: CC(=O)N1c2ccc(-c3ccc(CN(C)C)cc3)cc2[C@H](NC(=O)OC(C)C)C[C@@H]1C ; Cl]

(±)

This was prepared in a similar manner to Example 6, using 2M dimethylamine in THF (0.124 mL, 0.247 mmol) to give the desired product as a colourless solid (65 mg LCMS (Method A): Rt=1.10, MH+=424

Example 8

1,1-dimethylethyl 4-{5-[(cis)-1-acetyl-2-methyl-4-({[(1-methylethyl)oxy]carbonyl}amino)-1,2,3,4-tetrahydro-6-quinolinyl]-2-pyridinyl}-1-piperazinecarboxylate

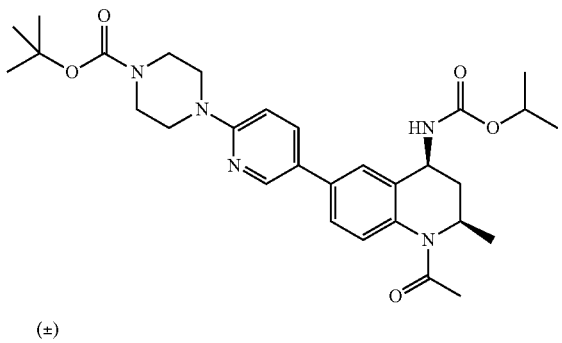 [SMILES: CC(=O)N1c2ccc(-c3ccc(N4CCN(C(=O)OC(C)(C)C)CC4)nc3)cc2[C@@H](NC(=O)OC(C)C)C[C@H]1C]

(±)

Example 9

1-methylethyl {(cis)-1-acetyl-2-methyl-6-[6-(1-piperazinyl)-3-pyridinyl]-1,2,3,4-tetrahydro-4-quinolinyl}carbamate hydrochloride

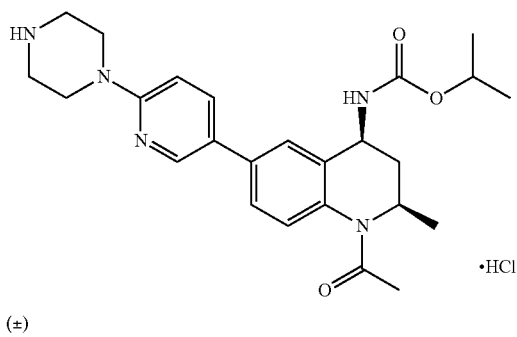 [SMILES: CC(=O)N1c2ccc(-c3ccc(N4CCNCC4)nc3)cc2[C@@H](NC(=O)OC(C)C)C[C@H]1C ; Cl]

(±)

Racemate of Example 2

In a carousel tube, 1-methylethyl[(cis)-1-acetyl-6-bromo-2-methyl-1,2,3,4-tetrahydro-4-quinolinyl]carbamate (Example 61, 80 mg, 0.217 mmol), potassium carbonate (59.9 mg, 0.433 mmol), tetrakis(triphenylphosphine)palladium(0) (12.52 mg, 10.83 μmol) and 1,1-dimethylethyl 4-[5-(4,4,5,5-tetramethyl-1,3,2-dioxaborolan-2-yl)-2-pyridinyl]-1-piperazinecarboxylate (101 mg, 0.26 mmol, available from Aldrich) were dissolved in Ethanol (0.5 mL) and Toluene (0.5 mL). The tubes were placed in a carousel and heated under nitrogen for 18 hr at 90° C. The reaction mixtures were filtered and the solvent evaporated before being taken up in DCM and purified by SP4 on a 12+M silica cartridge using a gradient of 12-62% EtOAc in cyclohexane. Appropriate fractions were collected and concentrated. 16 mg was removed for analysis, characterisation and testing of the protected product, Example 8, 1,1-dimethylethyl 4-{5-[(cis)-1-acetyl-2-methyl-4-({[(1-methylethyl)oxy]carbonyl}amino)-1,2,3,4-tetrahydro-6-quinolinyl]-2-pyridinyl}-1-piperazinecarboxylate. LCMS (Method C): Rt=0.88, MH+=552

The remaining 1,1-dimethylethyl 4-{5-[(cis)-1-acetyl-2-methyl-4-({[(1-methylethyl)oxy]carbonyl}amino)-1,2,3,4-tetrahydro-6-quinolinyl]-2-pyridinyl}-1-piperazinecarboxylate was dissolved in methanol and 0.5 mL acetyl chloride was added. Solvents were evaporated to yield Example 9, 1-methylethyl {(cis)-1-acetyl-2-methyl-6-[6-(1-piperazinyl)-3-pyridinyl]-1,2,3,4-tetrahydro-4-quinolinyl}carbamate hydrochloride as a pale yellow solid (40 mg). LCMS (Method C): Rt=0.59, MH+=452

Example 10

1-methylethyl {(cis)-1-acetyl-2-methyl-6-[6-(4-morpholinyl)-3-pyridinyl]-1,2,3,4-tetrahydro-4-quinolinyl}carbamate hydrochloride

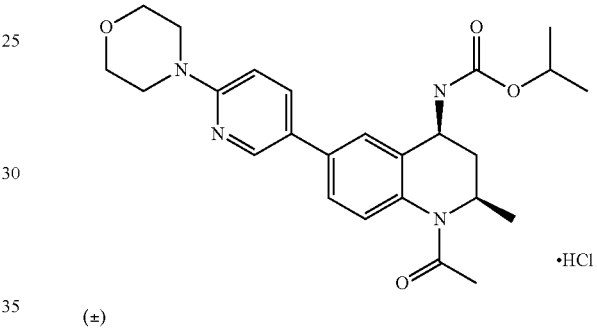

(±)

This was prepared in a similar manner as for Example 8, using 4-[5-(4,4,5,5-tetramethyl-1,3,2-dioxaborolan-2-yl)-2-pyridinyl]morpholine (Maybridge). To form a salt, the product was dissolved in MeOH, and HCl (0.217 mL, 0.217 mmol) 1M in ether was added. Solvents were evaporated to yield the title compound as a pale yellow solid (39.8 mg)
LCMS (Method C): Rt=0.68, MH+=453

Example 11

1-methylethyl {(cis)-1-acetyl-2-methyl-6-[6-(1-piperidinyl)-3-pyridinyl]-1,2,3,4-tetrahydro-4-quinolinyl}carbamate hydrochloride

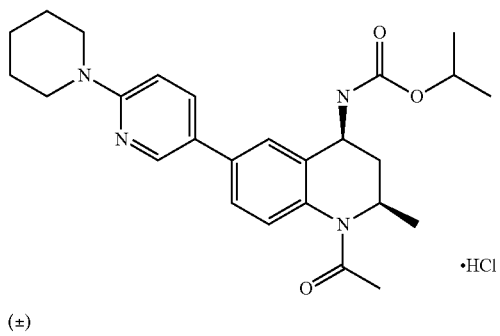 [SMILES: CC(=O)N1c2ccc(-c3ccc(N4CCCCC4)nc3)cc2[C@@H](NC(=O)OC(C)C)C[C@H]1C ; Cl]

(±)

This was prepared in a similar manner as for Example 10, using 2-(1-piperidinyl)-5-(4,4,5,5-tetramethyl-1,3,2-dioxaborolan-2-yl)pyridine (available from Frontier). To form a salt, the product was dissolved in MeOH, and HCl (0.217 mL, 0.217 mmol) 1M in ether was added. Solvents were evaporated to yield the title compound as a pale yellow solid (49.9 mg) LCMS (Method C): Rt=0.78, MH+=451

Example 12

1-methylethyl((cis)-1-acetyl-6-{4-[(4-amino-1-piperidinyl)methyl]phenyl}-2-methyl-1,2,3,4-tetrahydro-4-quinolinyl)carbamate dihydrochloride

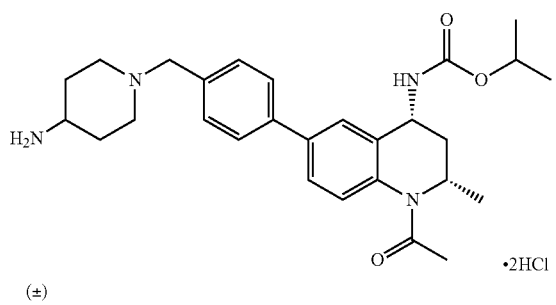 [SMILES: CC(=O)N1c2ccc(-c3ccc(CN4CCC(N)CC4)cc3)cc2[C@H](NC(=O)OC(C)C)C[C@@H]1C ; "·2HCl"]

(±)

1-Methylethyl[(cis)-1-acetyl-6-(4-{[4-({[(1,1-dimethylethyl)oxy]carbonyl}amino)-1-piperidinyl]methyl}phenyl)-2-methyl-1,2,3,4-tetrahydro-4-quinolinyl]carbamate (for a preparation see Intermediate 10) (79 mg, 0.137 mmol) was dissolved in Methanol (3 mL) and to this was added 1.25M HCl in methanol (1 mL, 1.250 mmol). The reaction vessel was sealed and heated in Emrys Optimiser microwave to 70° C. for 2 hr 30 min. After cooling the reaction was reduced in vacuo to give a colourless solid and placed under high vacuum for 1 hr. The material was transferred to a vial using methanol, concentrated, and then redissolved in ether and concentrated to give the desired compound as a colourless solid (67 mg). LCMS (Method 1): Rt=0.94, MH+=479

Example 13

1-methylethyl((cis)-1-acetyl-2-methyl-6-{4-[(4-piperidinylamino)methyl]phenyl}-1,2,3,4-tetrahydro-4-quinolinyl)carbamate dihydrochloride

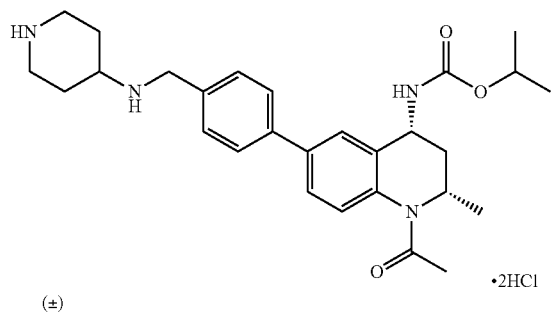 [SMILES: CC(=O)N1c2ccc(-c3ccc(CNC4CCNCC4)cc3)cc2[C@H](NC(=O)OC(C)C)C[C@@H]1C ; "·2HCl"]

(±)

1,1-Dimethylethyl 4-[({4-[(cis)-1-acetyl-2-methyl-4-({[(1-methylethyl)oxy]carbonyl}amino)-1,2,3,4-tetrahydro-6-quinolinyl]phenyl}methyl)amino]-1-piperidinecarboxylate (for a preparation see Intermediate 9) (70 mg, 0.121 mmol) was dissolved in Methanol (3 mL) and to this was added 1.25M HCl in methanol (1 ml, 1.250 mmol). The reaction vessel was sealed and heated in Emrys Optimiser microwave to 70° C. for 2 hr 30 min. After cooling the reaction was reduced in vacuo to give a colourless solid and placed under high vacuum for 1 hr, then transferred to a vial using methanol, concentrated, and then redissolved in ether and evaporated to give a colourless solid (66 mg). LCMS (Method A): Rt=0.89, MH+=479

Example 14

1-methylethyl((cis)-1-acetyl-6-{-4-[(1,1-dioxido-4-thiomorpholinyl)methyl]phenyl}-2-methyl-1,2,3,4-tetrahydro-4-quinolinyl)carbamate hydrochloride

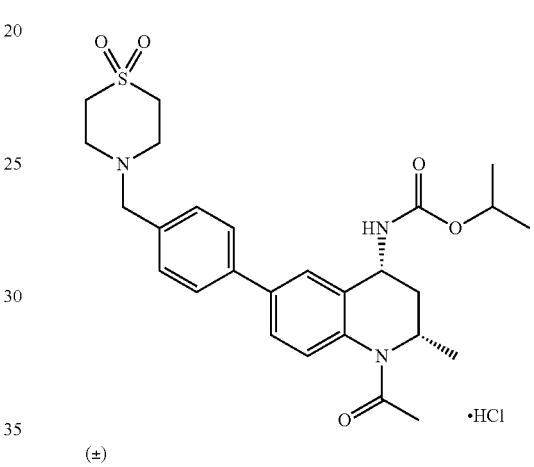

(±)

1-Methylethyl[(cis)-1-acetyl-6-(4-formylphenyl)-2-methyl-1,2,3,4-tetrahydro-4-quinolinyl]carbamate (for a preparation see Intermediate 7) (95 mg, 0.241 mmol) was dissolved in Dichloromethane (DCM) (2 mL) and to this was added thiomorpholine 1,1dioxide (48.8 mg, 0.361 mmol, available from Apollo) as a solid and the resulting solution stirred under nitrogen for 5 min. Sodium triacetoxyborohydride (66.4 mg, 0.313 mmol) was added and stirred as a suspension over the weekend. More sodium triacetoxyborohydride (25.5 mg, 0.241 mmol) added and left overnight. Further sodium triacetoxyborohydride (25.5 mg, 0.241 mmol) added. The reaction was quenched after a further 2 hours with aqueous ammonium chloride (4 ml). The layers were separated and the aqueous reextracted with DCM (2×5 ml). The combined organics were washed with water (15 ml) and then reduced in vacuo to give a white solid (106 mg).

Purification was attempted by SP4 on a silica cartridge using a gradient of 0.25 to 1.25% 2M methanolic ammonia, in ethyl acetate but the product and impurity eluted together. The fractions were reduced and then taken up in acetonitrile and purified using MDAP. The appropriate fractions were collected to isolate 29 mg of alcohol byproduct (see Example 15) along with the desired product as a white solid (40 mg) which was dissolved in methanol and to this was added 2 eqv. of 1.25M HCl in methanol and reduced in vacuo to give an off white solid (40 mg) LCMS (Method A): Rt=1.00, MH+=514

Example 15

1-methylethyl {(cis)-1-acetyl-6-[4-(hydroxymethyl)phenyl]-2-methyl-1,2,3,4-tetrahydro-4-quinolinyl}carbamate

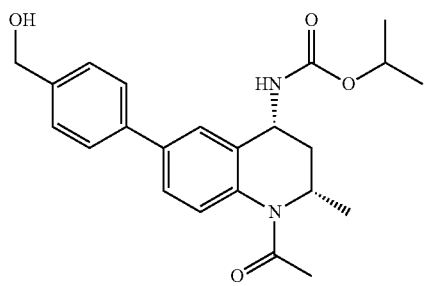

(±)

This was isolated as a byproduct in the formation of Example 14 through reduction of starting material. LCMS (Method A): Rt=0.93, MH+=397

Example 16

1-methylethyl {(cis)-1-acetyl-6-[4-(hexahydro-1H-1,4-diazepin-1-ylmethyl)phenyl]-2-methyl-1,2,3,4-tetrahydro-4-quinolinyl}carbamate dihydrochloride

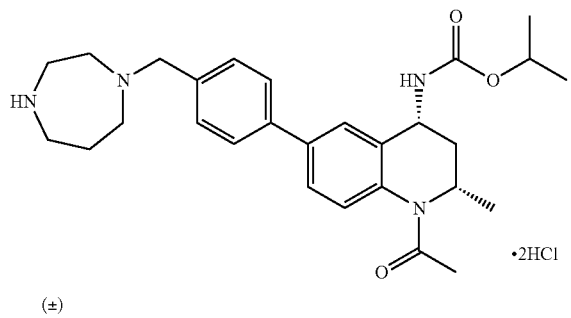 [SMILES: CC(=O)N1c2ccc(-c3ccc(CN4CCCNCC4)cc3)cc2[C@H](NC(=O)OC(C)C)C[C@@H]1C]

(±)

1,1-Dimethylethyl 4-({4-[(cis)-1-acetyl-2-methyl-4-({[(1-methylethyl)oxy]carbonyl}amino)-1,2,3,4-tetrahydro-6-quinolinyl]phenyl}methyl)hexahydro-1H-1,4-diazepine-1-carboxylate (for a preparation see Intermediate 11) (78 mg, 0.135 mmol) was dissolved in methanol (3 mL) and to this was added 1.25M HCl in methanol (1 mL, 1.250 mmol). The reaction vessel was sealed and heated in Emrys Optimiser microwave to 70° C. for 2 hr. After cooling the reaction was reduced in vacuo to give a colourless solid and placed under high vacuum for 1 hr. Transferred to vial using methanol, reduced, and then redissolved in ether to give a colourless solid (66 mg). LCMS (Method A): Rt=0.96, MH+=479

Example 17

1,1-dimethylethyl {(cis)-1-acetyl-2-methyl-6-[4-(1-piperidinyl methyl)phenyl]-1,2,3,4-tetrahydro-4-quinolinyl}carbamate

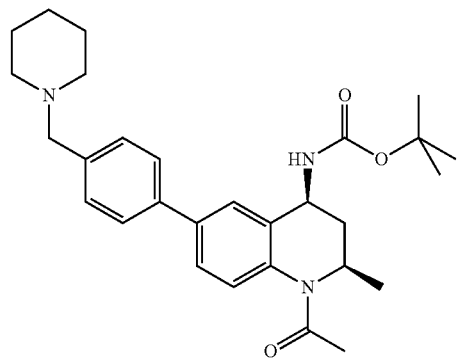

(±)

Di-tert-butyl dicarbonate (87 mg, 0.397 mmol, Aldrich) was stirred in dichloromethane (DCM) (3 mL) and (cis)-1-acetyl-2-methyl-6-[4-(1-piperidinylmethyl)phenyl]-1,2,3,4-tetrahydro-4-quinolinamine (for a preparation see Intermediate 2) (100 mg, 0.265 mmol) added. The mixture was stirred for 10 mins, and allowed to stand overnight. The mixture was purified by SP4 on a 12+M silica cartridge using a gradient of 0 to 5% 2M methanolic ammonia in dichloromethane. The clean product containing fractions were evaporated to a white solid (96 mg). LCMS (Method C): Rt=0.82, MH+=478

Example 18

1-methylethyl {(cis)-1-acetyl-2-methyl-6-[4-(1-piperidinylmethyl)-2-furanyl]-1,2,3,4-tetrahydro-4-quinolinyl}carbamate

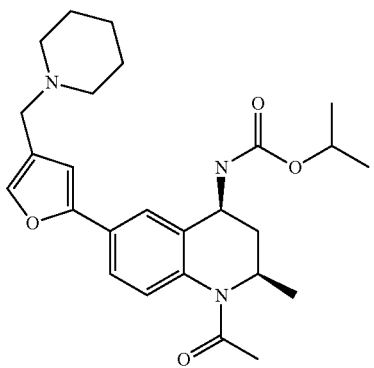

(±)

1-Methylethyl[(cis)-1-acetyl-6-(4-formyl-2-furanyl)-2-methyl-1,2,3,4-tetrahydro-4-quinolinyl]carbamate (for a preparation see Intermediate 20) (28 mg, 0.073 mmol) was dissolved in dichloromethane (DCM) (1 mL), mixed with piperidine (8.65 µL, 0.087 mmol) and acetic acid (8.34 µL, 0.146 mmol) and stirred under nitrogen for 30 minutes. Sodium triacetoxyborohydride (20.07 mg, 0.095 mmol) was added and the mixture was stirred again under nitrogen. After 16 hours reaction time the mixture was loaded onto a 2 g Flash SCX-column, eluting with MeOH (60 mL) followed by 2M MeOH/NH3 (60 mL). The product-containing fraction was evaporated to dryness to give a light brown solid (19 mg).

LCMS (Method C): Rt=0.75, MH+=454

Example 19

1-methylethyl((cis)-1-acetyl-2-methyl-6-{4-[(3-oxo-1-piperazinyl)methyl]phenyl}-1,2,3,4-tetrahydro-4-quinolinyl)carbamate hydrochloride

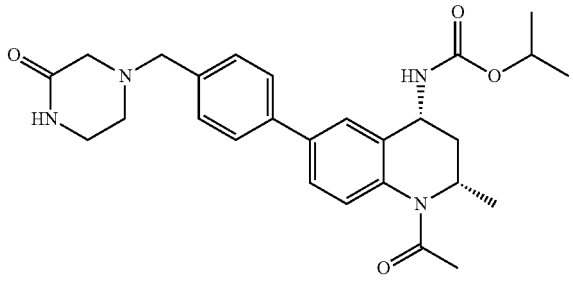

(±)  •HCl

To 2-piperazinone (3.60 mg, 0.240 mmol, available from Alfa Aesar) was added dichloromethane (DCM) (2 mL) and 1-methylethyl[(cis)-1-acetyl-6-(4-formylphenyl)-2-methyl-1,2,3,4-tetrahydro-4-quinolinyl]carbamate (for a preparation see Intermediate 7) (63 mg, 0.160 mmol) and stirred under nitrogen for 35 min. Sodium triacetoxyborohydride (44.0 mg, 0.208 mmol) was added and left stirring overnight. The reactions were quenched with the addition of ammonium chloride (1 ml). The layers were separated and the aqueous reextracted with DCM (5 ml). The combined organics were washed with water (5 ml) and then reduced in vacuo to give a colourless solid which was dissolved in DCM for purification using flash chromatography. A gradient of 2.4% to 12.4% 2M methanolic ammonia in DCM was used and the appropriate fractions were reduced in vacuo to give the desired product as a colourless solid (54 mg).

LCMS (Method A): Rt=0.90, MH+=479

Example 20

1-methylethyl {(cis)-1-acetyl-2-methyl-6-[4-({[2-(1-pyrrolidinyl)ethyl]amino}methyl)phenyl]-1,2,3,4-tetrahydro-4-quinolinyl}carbamate dihydrochloride

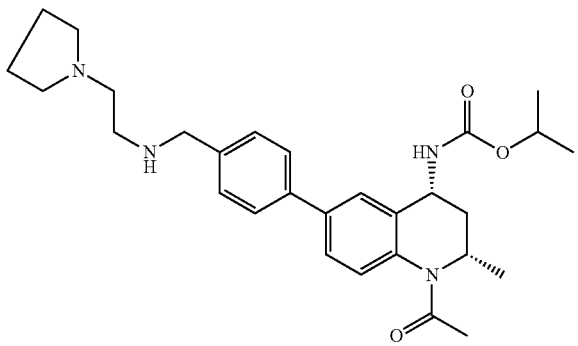

(±)  •HCl

This was prepared in a similar manner to Example 19, using [2-(1-pyrrolidinyl)ethyl]amine (27.4 mg, 0.24 mmol, available from Aldrich) to give the desired product (45 mg).

LCMS (Method A): Rt=0.98, MH+=493

Example 21

1-methylethyl[(cis)-1-acetyl-6-(4-{[(2-hydroxy-2-methylpropyl)amino]methyl}phenyl)-2-methyl-1,2,3,4-tetrahydro-4-quinolinyl]carbamate hydrochloride

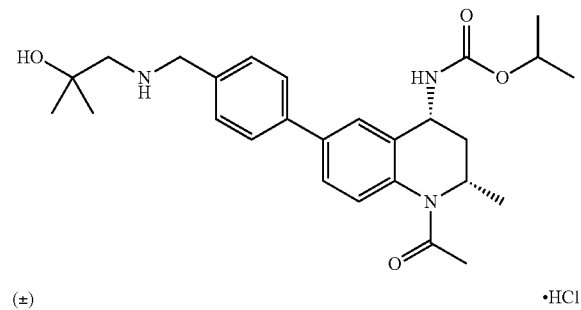 [SMILES: CC(=O)N1c2ccc(-c3ccc(CNCC(C)(C)O)cc3)cc2[C@H](NC(=O)OC(C)C)C[C@@H]1C ; Cl]

(±)  •HCl

This was prepared in a similar manner to Example 19, using 1-amino-2-methyl-2-propanol (27.4 mg, 0.24 mmol, available from Tyger Scientific Ltd.) to give the desired product (45 mg). LCMS (Method A): Rt=0.99, MH+=468

Example 22

1-methylethyl {(cis)-1-acetyl-2-methyl-6-[5-(1-piperidinylmethyl)-2-furanyl]-1,2,3,4-tetrahydro-4-quinolinyl}carbamate (formic acid salt)

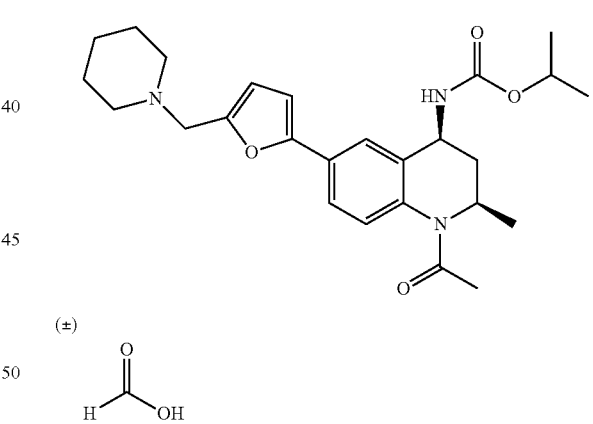

(±)

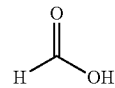

1-Methylethyl[(cis)-1-acetyl-6-(5-formyl-2-furanyl)-2-methyl-1,2,3,4-tetrahydro-4-quinolinyl]carbamate (for a preparation see Intermediate 21) (18 mg, 0.047 mmol) was dissolved in dichloromethane (DCM) (1 mL), mixed with acetic acid (8.04 µL, 0.140 mmol) and piperidine (9.27 µL, 0.094 mmol) and stirred under nitrogen for 30 minutes. sodium triacetoxyborohydride (12.90 mg, 0.061 mmol) was added and the reaction was stirred again under nitrogen. After 17 hours reaction time a second quantity of sodium triacetoxyborohydride (12.90 mg, 0.061 mmol) was added. 1 hour after this another sample of sodium triacetoxyborohydride (12.90 mg, 0.061 mmol) was added. After 2 further hours the reaction was loaded onto a 2 g Flash SCX-column, eluting with MeOH (60 mL) followed by 2M MeOH/NH3 (60 mL).

The product-containing fraction was evaporated to dryness to give a brown solid which was purified by MDAP. Product-containing fractions were evaporated to dryness to give a clear, colourless solid (3 mg).
LCMS (Method C): Rt=0.74, MH+=454

Example 23 sodium 5-[(cis)-1-acetyl-2-methyl-4-({[(1-methyl-ethyl)oxy]carbonyl}amino)-1,2,3,4-tetrahydro-6-quinolinyl]-3-furancarboxylate

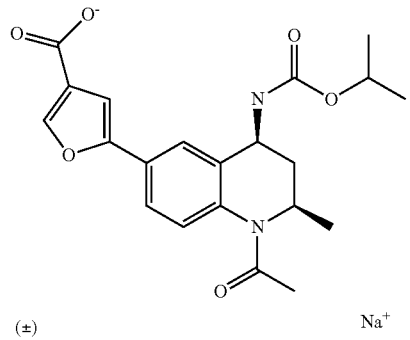 [SMILES: CC(=O)N1c2ccc(-c3cc(C(=O)[O-])co3)cc2[C@@H](NC(=O)OC(C)C)C[C@H]1C ; [Na+]]

(±)    Na+

1-Methylethyl((cis)-1-acetyl-6-bromo-2-methyl-1,2,3,4-tetrahydro-4-quinolinyl)carbamate (for a preparation see Example 61) (100 mg, 0.271 mmol) was dissolved in ethanol (1 mL) and Toluene (1 mL), mixed with potassium carbonate (74.9 mg, 0.542 mmol), 5-(4,4,5,5-tetramethyl-1,3,2-dioxaborolan-2-yl)-3-furancarboxylic acid (77 mg, 0.325 mmol, available from Frontier Scientific), followed by tetrakis(triphenylphosphine)palladium(0) (15.65 mg, 0.014 mmol) and refluxed under nitrogen at 90° C. After 30 minutes heating was stopped and the reaction mixture was left to stand overnight then partitioned between 2M HCl (40 mL) and EtOAc (40 mL). The aqueous and organic layers were run off and the former extracted twice more with EtOAc (2×40 mL). The organic layers were combined, washed (brine (80 mL), dried (sodium sulfate), filtered and evaporated to dryness to give a bright yellow solid (150 mg). This was purified using MDAP. Product-containing fractions were evaporated to dryness to give a white solid which was dissolved in methanol, treated with sodium hydroxide (2N, 106.5 µL, 0.213 mmol) and concentrated to afford a cream-coloured solid (90 mg) LCMS (Method C): Rt=0.84, MH+=401

Example 24

1-methylethyl((cis)-1-acetyl-2-methyl-6-{1-[2-(4-morpholinyl)ethyl]-1H-pyrazol-4-yl}-1,2,3,4-tetrahydro-4-quinolinyl)carbamate

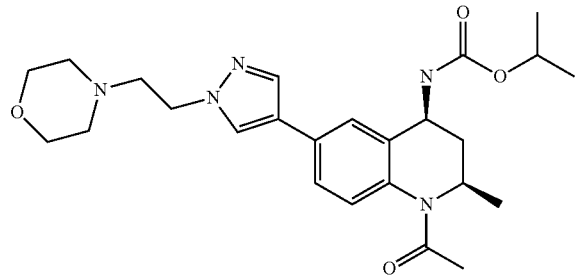

(±)

This was prepared in a similar manner to Example 23, using 4-{2-[4-(4,4,5,5-tetramethyl-1,3,2-dioxaborolan-2-yl)-1H-pyrazol-1-yl]ethyl}morpholine (100 mg, 0.325 mmol, available from Boron Molecular), and working up by loading the reaction mixture onto a 5 g SCX-column, eluting with MeOH (70 mL) followed by 2M MeOH/NH3 (70 mL). Product-containing fractions were evaporated to dryness to give a pale white solid (81 mg) which was purified on a 12+M Biotage silica column, eluting with DCM:2M MeOH/NH3 (1:0 to 24:1). Product-containing fractions were evaporated to dryness to give a clear, colourless solid (72 mg). LCMS (Method C): Rt=0.67, MH+=470

Example 25 sodium 4-[(cis)-1-acetyl-2-methyl-4-({[(1-methyl-ethyl)oxy]carbonyl}amino)-1,2,3,4-tetrahydro-6-quinolinyl]benzoate

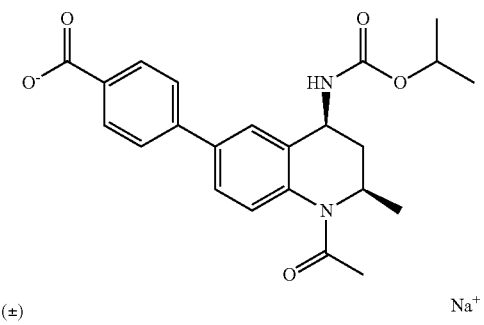 [SMILES: CC(=O)N1c2ccc(-c3ccc(C(=O)[O-])cc3)cc2[C@@H](NC(=O)OC(C)C)C[C@H]1C ; [Na+]]

(±)    Na+

This was prepared in a similar manner to Example 23, using 4-Carboxyphenylboronic acid (53.9 mg, 0.325 mmol, available from Frontier Scientific) with 23.5 hours reaction time. After initial purification as described in Example 23 the material was loaded onto a 12+M Biotage silica column, eluting with EtOAc:20% MeOH/AcOH (9:1) in DCM (1:0 to 19:1). Product-containing fractions were evaporated to dryness to give a clear, colourless solid. This was further purified using MDAP. Product containing fractions were concentrated, dissolved in methanol and treated with sodium hydroxide (2N aqueous, 19.5 µL, 0.039 mmol) to convert the product to the sodium salt which was isolated as a white solid after concentration (51 mg). LCMS (Method C): Rt=0.88, MH+=411

Example 26

Sodium {4-[(cis)-1-acetyl-2-methyl-4-({[(1-methyl-ethyl)oxy]carbonyl}amino)-1,2,3,4-tetrahydro-6-quinolinyl]-1H-pyrazol-1-yl}acetate

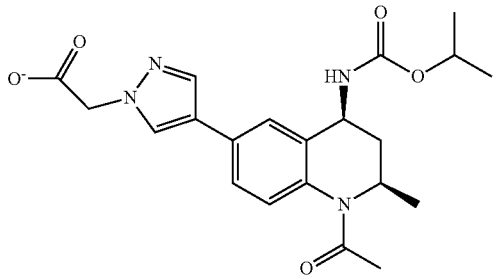

(±)    Na+

1-Methylethyl((cis)-1-acetyl-6-bromo-2-methyl-1,2,3,4-tetrahydro-4-quinolinyl)carbamate (for a preparation see Example 61) (100 mg, 0.271 mmol) was dissolved in (1 mL) and toluene (1 mL), mixed with potassium carbonate (74.9 mg, 0.542 mmol) and 1-(Ethoxycarbonylmethyl)-1H-pyrazole-4-boronic acid pinacol ester (91 mg, 0.325 mmol, Aldrich) followed by tetrakis(triphenylphosphine)palladium(0) (15.65 mg, 0.014 mmol) and refluxed under nitrogen at 90° C. After 18.5 hours reaction time additional tetrakis(triphenylphosphine)palladium(0) (15.65 mg, 0.014 mmol) was added to the reactions. After 23.5 hours total reaction time the reaction was left to stand to cool. The reaction mixture was partitioned between 2M HCl (50 mL) and EtOAc (50 mL) The organic and aqueous layers were run off and the latter extracted twice more with EtOAc (2×50 mL). Organic fractions were combined, dried (brine (100 mL) and sodium sulfate), filtered and evaporated to dryness to give a bright yellow solid (150 mg). This was purified using MDAP. Product-containing fractions were evaporated to dryness to give a white solid which was converted to the sodium salt by dissolving in methanol and adding NaOH (2N aqueous, 91.5 µL, 0.183 mmol) to give the desired sodium salt after concentration (81 mg). LCMS (Method C): Rt=0.74, MH+=415

Example 27

1-methylethyl[(cis)-1-acetyl-6-(6-amino-3-pyridinyl)-2-methyl-1,2,3,4-tetrahydro-4-quinolinyl]carbamate hydrochloride

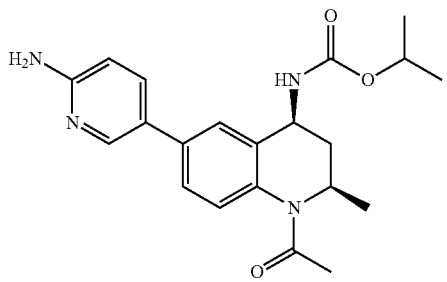

(±) •HCl

1-Methylethyl((cis)-1-acetyl-6-bromo-2-methyl-1,2,3,4-tetrahydro-4-quinolinyl)carbamate (for a preparation see Example 61) (100 mg, 0.271 mmol) was mixed with potassium carbonate (74.9 mg, 0.542 mmol), 5-(4,4,5,5-tetramethyl-1,3,2-dioxaborolan-2-yl)-2-pyridinamine (71.5 mg, 0.325 mmol, available from Aldrich) and dissolved in ethanol (1 mL) and toluene (1 mL). tetrakis(triphenylphosphine)palladium(0) (15.65 mg, 0.014 mmol) was added and the mixture was refluxed under nitrogen at 90° C. The reaction was left to stir overnight under nitrogen. After 16 hours reaction time the mixture was run down a 10 g SCX-column, eluting with MeOH (70 mL) followed by 2M MeOH/NH₃ (70 mL). Product-containing fractions were evaporated to dryness to give a brown/orange solid (188 mg). The residue was purified on a 12+M Biotage silica column, eluting with EtOAc:2M MeOH/NH₃ (1:0 to 97:3). Product-containing fractions were evaporated to dryness to give an orange/brown solid which was converted to a mono-HCl salt using 2M HCl (130.5 µL, 0.261 mmol) and concentrated to give an orange/brown solid (97 mg).

LCMS (Method C): Rt=0.64, MH+=383

Example 28

1-methylethyl {(cis)-1-acetyl-2-methyl-6-[4-(1-piperazinylmethyl)phenyl]-1,2,3,4-tetrahydro-4-quinolinyl}carbamate dihydrochloride

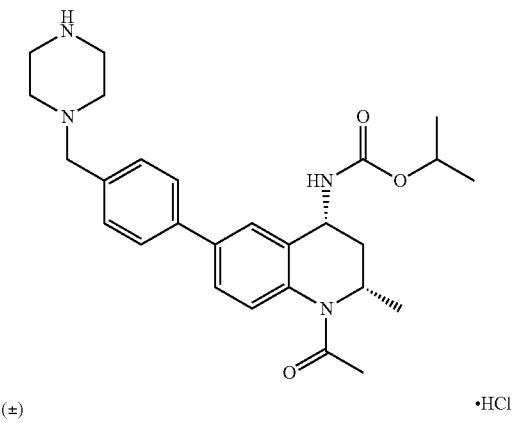 [SMILES: CC(=O)N1c2ccc(-c3ccc(CN4CCNCC4)cc3)cc2[C@H](NC(=O)OC(C)C)C[C@@H]1C ; Cl]

(±) •HCl 1,1-Dimethylethyl-4-({-4-[(cis)-1-acetyl-2-methyl-4-({[(1-methylethyl)oxy]carbonyl}amino)-1,2,3,4-tetrahydro-6-quinolinyl]phenyl}methyl)-1-piperazinecarboxylate (for a preparation see Intermediate 8) (98 mg, 0.174 mmol) was dissolved in methanol (2 mL) and to this was added 1.25M HCl in methanol. (0.305 mL, 0.382 mmol) and stirred overnight. 1.25M HCl in methanol. (0.305 mL, 0.382 mmol) was added and the reaction was heated in a sealed vessel to 70° C. in an optimiser microwave for 15 min followed by a further 30 min. 2 eqv of 1.25M HCl in methanol was added and the reaction mixture heated in the microwave under the same conditions for a further 1 hr. The reaction mixture was reduced in vacuo to give a white solid (86 mg). LCMS (Method A): Rt=0.92, MH+=465

Example 29

1-methylethyl[(cis)-1-acetyl-2-methyl-6-(1H-pyrazol-4-yl)-1,2,3,4-tetrahydro-4-quinolinyl]carbamate

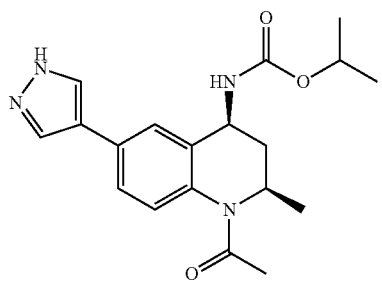

(±)

1-Methylethyl((cis)-1-acetyl-6-bromo-2-methyl-1,2,3,4-tetrahydro-4-quinolinyl)carbamate (for a preparation see Example 61) (100 mg, 0.271 mmol) was dissolved in ethanol (1 mL) and Toluene (1 mL), mixed with potassium carbonate (74.9 mg, 0.542 mmol), 1,1-dimethylethyl 4-(4,4,5,5-tetramethyl-1,3,2-dioxaborolan-2-yl)-1H-pyrazole-1-carboxylate (96 mg, 0.325 mmol, available from Aldrich) and tetrakis(triphenylphosphine)palladium(0) (15.65 mg, 0.014 mmol) and refluxed under nitrogen at 90° C. for 22 hours reaction time. The reaction was left to stand at room temperature for 2.5 days. It was refluxed again at 90° C. for 24 hours. A second sample of 1,1-dimethylethyl 4-(4,4,5,5-tetramethyl-1,3,2-dioxaborolan-2-yl)-1H-pyrazole-1-carboxylate (96 mg, 0.325 mmol) was added to the reaction mixture after this time and heating continued. A third sample of 1,1-dimethylethyl 4-(4,4,5,5-tetramethyl-1,3,2-dioxaborolan-2-yl)-1H-pyrazole-1-carboxylate (96 mg, 0.325 mmol) was added to the reaction mixture after 102.5 hours reaction time and the mixture was allowed to stir overnight under nitrogen at the same temperature. Another sample of 1,1-dimethylethyl 4-(4,4,5,5-tetramethyl-1,3,2-dioxaborolan-2-yl)-1H-pyrazole-1-carboxylate (96 mg, 0.325 mmol) was added after 199 hours total reaction time. After 248 hours reaction time the mixture was cooled to room temperature and partitioned between distilled water (40 mL) and EtOAc (40 mL). The organic and aqueous layers were run off and the latter was extracted 3 more times using EtOAc (3×40 mL). Organic fractions were combined, washed (brine (50 mL), dried (sodium sulfate), filtered and evaporated to dryness to give an orange/brown oil (248 mg). The residue was purified by SP4 on a 25+S silica cartridge using a gradient of 0 to 2.5% 2M methanloic ammonia in ethyl acetate. Product-containing fractions were evaporated to dryness and purified again using MDAP. Product-containing fractions were evaporated to dryness to give a clear, colourless solid (18 mg). LCMS (Method C): Rt=0.73, MH+=357

Example 30

1-methylethyl {(cis)-1-acetyl-2-methyl-6-[4-(1-pyrrolidinylmethyl)phenyl]-1,2,3,4-tetrahydro-4-quinolinyl}carbamate hydrochloride

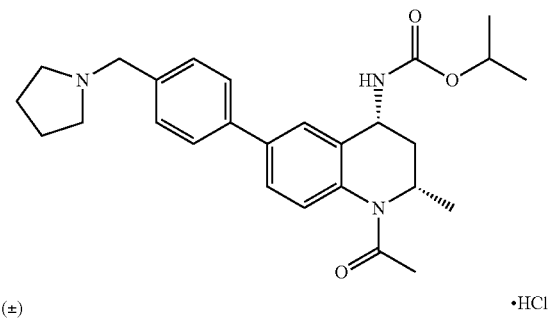 [SMILES: CC(=O)N1c2ccc(-c3ccc(CN4CCCC4)cc3)cc2[C@H](NC(=O)OC(C)C)C[C@@H]1C ; Cl]

(±)    ·HCl

1-Methylethyl[(cis)-1-acetyl-6-(4-formylphenyl)-2-methyl-1,2,3,4-tetrahydro-4-quinolinyl]carbamate (for a preparation see Intermediate 7) (34 mg, 0.086 mmol) was dissolved in Dichloromethane (DCM) (2 mL) and to this was added pyrrolidine (10.69 µL, 0.129 mmol). This was stirred for 40 min under nitrogen. Sodium triacetoxyborohydride (23.75 mg, 0.112 mmol) was added and stirred overnight. The reaction was quenched with the addition of ammonium chloride (3 ml) and water (5 ml) was added. The two layers were separated and the organics passed through a phase separation cartridge and reduced in vacuo to give a colourless film (50 mg). The film was dissolved in DCM and purified by SP4 on a 12+S silica cartridge using a gradient of 16 to 81% ethyl acetate in cyclohexane followed by a gradient of 0-20% 2M methanolic ammonia in ethyl acetate. Product containing fractions were combined and reduced in vacuo to give a colourless oil (23 mg). The oil was dissolved in methanol and to this was added 1.25M HCl in methanol (0.0408 ml) and reduced. to give a colourless solid (25 mg). LCMS (Method A): Rt=1.18, MH+=450

Example 31

1-methylethyl[(cis)-1-acetyl-2-methyl-6-(1H-pyrazol-5-yl)-1,2,3,4-tetrahydro-4-quinolinyl]carbamate

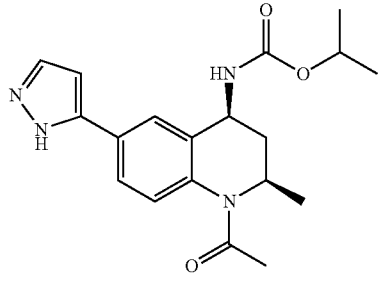

(±)

1-Methylethyl((cis)-1-acetyl-6-bromo-2-methyl-1,2,3,4-tetrahydro-4-quinolinyl)carbamate (for a preparation see Example 61) (100 mg, 0.271 mmol) was dissolved in ethanol (1 mL) and Toluene (1 mL), mixed with potassium carbonate (74.9 mg, 0.542 mmol), 1H-pyrazol-5-ylboronic acid (36.4 mg, 0.325 mmol, available from Frontier Scientific) followed by tetrakis(triphenylphosphine)palladium(0) (15.65 mg, 0.014 mmol) and refluxed under nitrogen at 90° C. After 21 hours a sample of tetrakis(triphenylphosphine)palladium(0) (15.65 mg, 0.014 mmol) was added to the reaction which was left to stir under nitrogen at the same temperature. Another sample of 1H-pyrazol-5-ylboronic acid (36.4 mg, 0.325 mmol) was added after 171 hours total reaction time and heating and stirring continued. Another sample of 1H-pyrazol-5-ylboronic acid (36.4 mg, 0.325 mmol) was added to the mixture after 345 hours. After 391 hours total reaction time the reaction was partitioned between distilled water (40 mL) and EtOAc (40 mL). The organic and aqueous layers were run off and the latter was extracted twice more using EtOAc (2×40 mL). Organic fractions were combined, washed (brine (80 mL), dried (sodium sulfate), filtered and evaporated to dryness to give a clear, colourless solid (110 mg). This was purified on a 12+M Biotage silica column, eluting with 0 to 100% EtOAc in cyclohexane. Product-containing fractions were evaporated to dryness to give a clear, colourless solid (6 mg).
LCMS (Method C): Rt=0.76, MH+=357

Example 32

1-methylethyl[(cis)-1-acetyl-6-(2,4-dimethyl-1,3-thiazol-5-yl)-2-methyl-1,2,3,4-tetrahydro-4-quinolinyl]carbamate

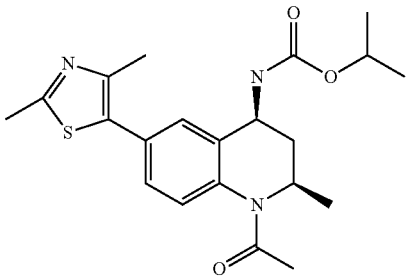

(±)

1-Methylethyl((cis)-1-acetyl-6-bromo-2-methyl-1,2,3,4-tetrahydro-4-quinolinyl)carbamate (for a preparation see Example 61) (100 mg, 0.271 mmol) were dissolved in ethanol (1 mL) and Toluene (1 mL), mixed with potassium carbonate (74.9 mg, 0.542 mmol), 2,4-dimethyl-5-(4,4,5,5-tetramethyl-1,3,2-dioxaboroian-2-yl)-1,3-thiazole (78 mg, 0.325 mmol, available from Maybridge), followed by tetrakis(triphenylphosphine)palladium(0) (15.65 mg, 0.014 mmol) and refluxed under nitrogen at 90° C. for 18.5 hours reaction time. The reaction mixture was partitioned between distilled water (40 mL) and EtOAc (40 mL). The organic and aqueous layers were run off and the latter extracted twice more using EtOAc (2×40 mL). Organic fractions were combined, dried (brine (80 mL) and sodium sulfate), filtered and evaporated to dryness to give a pale white solid (0.123 g). This was purified on a 25+M Biotage silica column, eluting with cyclohexane:EtOAc (1:0 to 1:3). Product-containing fractions were evaporated to dryness to give a clear, colourless solid which was repurified on a 12+M column using the same solvent system. Analysis of the product still showed contamination and it was further purified using MDAP. Product-containing fractions were evaporated to dryness to give a clear, colourless solid (41 mg). LCMS (Method C): Rt=0.76, MH+=402

Example 33 cyclobutyl[(cis)-1-acetyl-6-bromo-2-methyl-1,2,3,4-tetrahydro-4-quinolinyl]carbamate

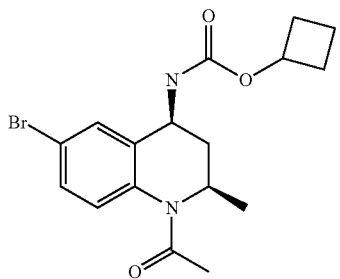

(±)

(cis)-1-Acetyl-6-bromo-2-methyl-1,2,3,4-tetrahydro-4-quinolinamine (for a preparation see Intermediate 4) (200 mg, 0.706 mmol) was dissolved in dichloromethane (DCM) (5 mL), mixed with DIPEA (0.370 mL, 2.119 mmol) followed by 4-nitrophenyl chloridocarbonate (157 mg, 0.777 mmol, available from Fluka) and stirred under nitrogen. Cyclobutanol (0.082 mL, 1.059 mmol) was added after 1.75 hours. The reaction was allowed to stir under nitrogen for 17 hours. The reaction was partitioned between distilled water (20 mL) and EtOAc (60 mL). The aqueous layer was extracted with EtOAc (60 mL) and the organic fractions were combined, washed (brine (50 mL)), dried (sodium sulfate) and evaporated to dryness to give a yellow solid (346 mg). The residue was purified by SP4 on a 25+M Biotage silica column, eluting with a gradient of 0 to 50% ethyl acetate in cyclohexane. Product-containing fractions were evaporated to dryness to give a clear, colourless solid (39 mg). LCMS (Method C): Rt=1.05, MH+=383

Example 34 ethyl {(cis)-1-acetyl-2-methyl-6-[4-(1-piperidinylmethyl)phenyl]-1,2,3,4-tetrahydro-4-quinolinyl}carbamate

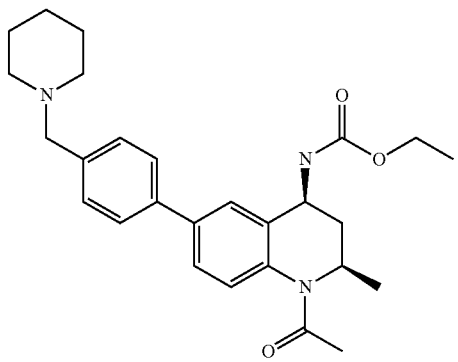

(±)

(cis)-1-Acetyl-2-methyl-6-[4-(1-piperidinylmethyl)phenyl]-1,2,3,4-tetrahydro-4-quinolinamine (for a preparation see Intermediate 2) (50 mg, 0.132 mmol) was dissolved in dichloromethane (DCM) (2 mL), mixed with ethyl chloridocarbonate (0.015 mL, 0.159 mmol), and DIPEA (0.046 mL, 0.265 mmol) and stirred under nitrogen for 2.5 days. Another sample of ethyl chloridocarbonate (0.015 mL, 0.159 mmol) was added to the reaction, along with a sample of DIPEA (0.046 mL, 0.265 mmol). LCMS analysis after 73 hours reaction time indicated that the reaction had produced a side-product. The reaction was allowed to stir overnight. The reaction mixture was loaded onto a 5 g SCX-column, eluting with MeOH (70 mL) followed by 2M MeOH/NH₃ (70 mL). Fractions were evaporated to dryness to give a solid which was further purified on a 12+M Biotage silica columns, eluting with cyclohexane:EtOAc (1:0 to 1:1). Product-containing fractions were evaporated to dryness to give a white solid (38 mg) that was characterised as ethyl {1-acetyl-6-[4-(chloromethyl)phenyl]-2-methyl-1,2,3,4-tetrahydro-4-quinolinyl}carbamate. Some of this material (24 mg, 0.060 mmol) was added to a solution of piperidine (0.036 mL, 0.363 mmol) mixed with acetonitrile (4 mL), along with six equivalents of potassium carbonate (60.2 mg, 0.435 mmol) and the solution was refluxed under nitrogen at 85° C. for 15 hours then cooled and loaded onto a 5 g SCX-column, eluting with MeOH (70 mL) followed by 2M MeOH/NH₃ (70 mL). Product-containing fractions were evaporated to dryness to give a clear, colourless solid (35 mg). This was purified on a 12+M Biotage silica column, eluting with DCM:2M MeOH/NH3 (1:0 to 49:1). Product-containing fractions were evaporated to dryness to give a clear, colourless solid (21 mg).

LCMS (Method C): Rt=0.72, MH+=450

Example 35 methyl {(cis)-1-acetyl-2-ethyl-6-[4-(1-piperidinylmethyl)phenyl]-1,2,3,4-tetrahydro-4-quinolinyl}carbamate

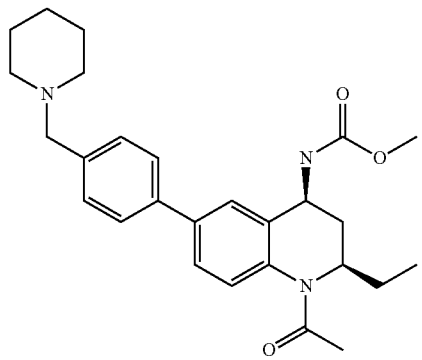

(±)

This was prepared in a similar manner to Example 34, omitting the final silica purification step, using (cis)-1-acetyl-2-ethyl-6-[4-(1-piperidinylmethyl)phenyl]-1,2,3,4-tetrahydro-4-quinolinamine (for a preparation see Intermediate 5) (50 mg, 0.128 mmol) and Methyl chloroformate (0.013 mL, 0.166 mmol) to give the desired product as a colourless solid (19 mg) LCMS (Method C): Rt=0.78, MH+=450

Example 36 cyclopentyl {(cis)-1-acetyl-2-methyl-6-[4-(1-piperidinylmethyl)phenyl]-1,2,3,4-tetrahydro-4-quinolinyl}carbamate

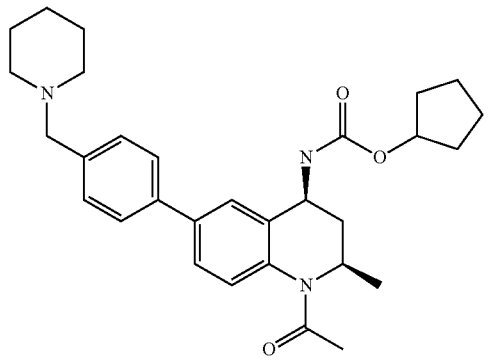

(±)

This was prepared in a similar manner to Example 34, omitting the final silica purification step, using cyclopentyl chloridocarbonate (0.024 mL, 0.159 mmol, Apollo), to give the desired product as a colourless solid (17 mg). LCMS (Method C): Rt=0.91, MH+=490

Example 37

2-methylpropyl {(cis)-1-acetyl-2-methyl-6-[4-(1-piperidinylmethyl)phenyl]-1,2,3,4-tetrahydro-4-quinolinyl}carbamate

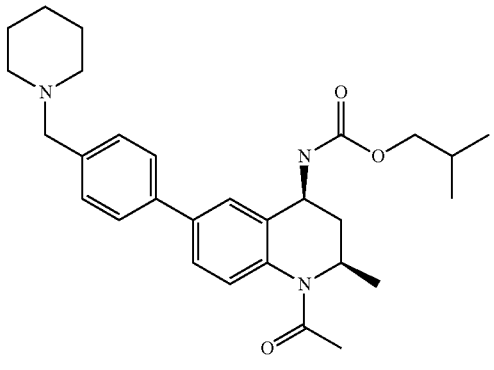

(±)

This was prepared in a similar manner to Example 34, omitting the final silica purification step, using 2-methylpropyl chloridocarbonate (0.021 mL, 0.159 mmol), to give the desired product as a colourless solid (2 mg). LCMS (Method C): Rt=0.91, MH+=478

Example 38 propyl {(cis)-1-acetyl-2-ethyl-6-[4-(1-piperidinylmethyl)phenyl]-1,2,3,4-tetrahydro-4-quinolinyl}carbamate

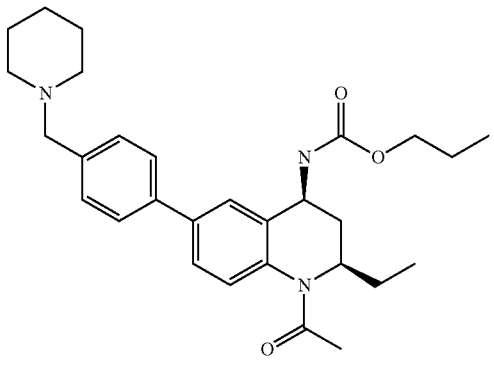

(±)

(cis)-1-Acetyl-2-ethyl-6-[4-(1-piperidinylmethyl)phenyl]-1,2,3,4-tetrahydro-4-quinolinamine (for a preparation see Intermediate 5) (50 mg, 0.128 mmol) was dissolved in dichloromethane (DCM) (2 mL), mixed with DIPEA (0.045 mL, 0.255 mmol) and propylchloroformate (0.019 mL, 0.166 mmol, Aldrich) and stirred under nitrogen. After 40 minutes the reaction was loaded onto a 5 g SCX-column, eluting with MeOH (70 mL) followed by 2M MeOH/NH$_3$ (70 mL). Product-containing fractions were evaporated to dryness to give a colourless solid (38 mg). This was purified on a 12+M Biotage silica column, eluting with 0 to 8% 2M methanolic ammonia in DCM. Product-containing fractions were evaporated to dryness to give a clear, colourless solid (16 mg). LCMS (Method C): Rt=0.83, MH+=478

Example 39

1-methylethyl((cis)-1-acetyl-6-{1-[2-(4-amino-1-piperidinyl)ethyl]-1H-pyrazol-4-yl}-2-methyl-1,2,3,4-tetrahydro-4-quinolinyl)carbamate dihydrochloride

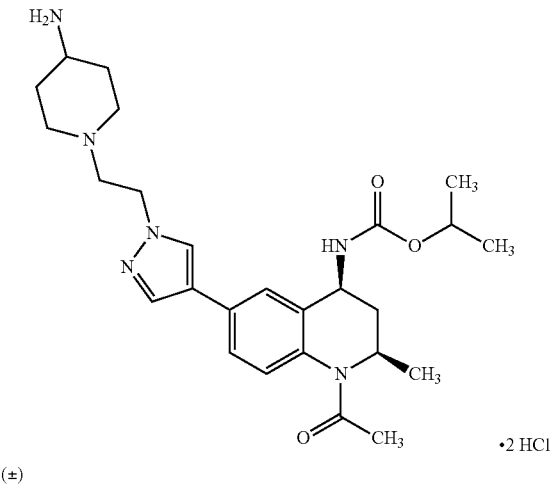 [SMILES: CC(=O)N1c2ccc(-c3cnn(CCN4CCC(N)CC4)c3)cc2[C@@H](NC(=O)OC(C)C)C[C@H]1C]

(±)

1-Methylethyl[(cis)-1-acetyl-6-(1-{2-[4-({[(1,1-dimethylethyl)oxy]carbonyl}amino)-1-piperidinyl]ethyl}-1H-pyrazol-4-yl)-2-methyl-1,2,3,4-tetrahydro-4-quinolinyl]carbamate (for a preparation see Intermediate 37) (130 mg, 0.223 mmol) was dissolved in dichloromethane (DCM) (1 mL), mixed with trifluoroacetic acid (0.5 mL, 6.49 mmol) and stirred under nitrogen. The crude product was concentrated and purified on MDAP. The product-containing fractions were evaporated to dryness, loaded onto a 2 g SCX cartridge and eluted with MeOH (15 ml) and 2M methanolic ammonia (15 ml). The basic fractions were evaporated to give a white solid which was dissolved in MeOH (1 ml) and 1.25M HCl in MeOH was added (0.1 ml). The mixture was dried to give a white solid (47 mg).

LCMS (Method C): Rt=0.59, MH+=483

Example 40

1-methylethyl((cis)-1-acetyl-2-methyl-6-{1-[2-(1-piperazinyl)ethyl]-1H-pyrazol-4-yl}-1,2,3,4-tetrahydro-4-quinolinyl)carbamate hydrochloride

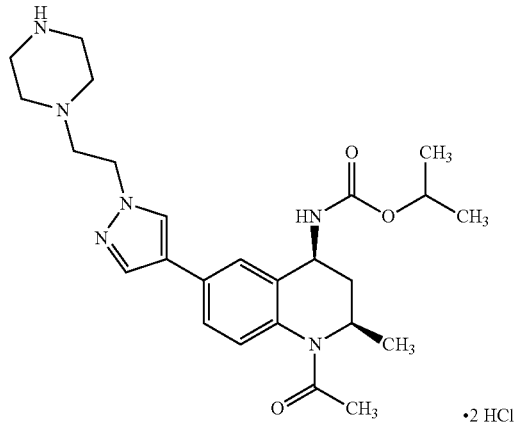

(±)

1,1-Dimethylethyl 4-(2-{4-[(cis)-1-acetyl-2-methyl-4-({[(1-methylethyl)oxy]carbonyl}amino)-1,2,3,4-tetrahydro-6-quinolinyl]-1H-pyrazol-1-yl}ethyl)-1-piperazinecarboxylate (for a preparation see Intermediate 38) (65 mg, 0.114 mmol) was dissolved in dichloromethane (DCM) (1 mL), mixed with trifluoroacetic acid (0.5 mL, 6.49 mmol) and stirred under nitrogen. The product was concentrated, dissolved in MeOH (1.5 mL), mixed with 1.25M HCl (157 μL) and blown down to dryness to give a white solid (41 mg).

LCMS (Method C): Rt=0.61, MH+=469

Example 41

1-methylethyl {(cis)-1-acetyl-2-methyl-6-[2-(1-piperidinylmethyl)-1,3-thiazol-4-yl]-1,2,3,4-tetrahydro-4-quinolinyl}carbamate

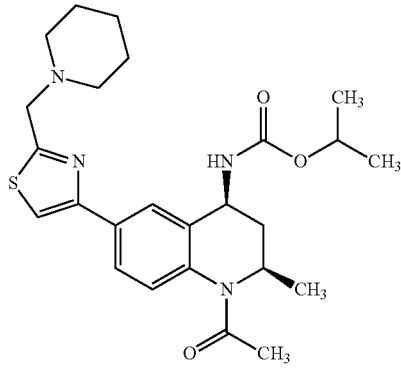

(±)

1-Methylethyl[(cis)-1-acetyl-6-(2-formyl-1,3-thiazol-4-yl)-2-methyl-1,2,3,4-tetrahydro-4-quinolinyl]carbamate (for a preparation see Intermediate 39) (21 mg, 0.052 mmol) was dissolved in dichloromethane (DCM) (1 mL), mixed with piperidine (7.77 μL, 0.078 mmol) and acetic acid (7.49 μL, 0.131 mmol) and stirred under nitrogen for 30 minutes. Sodium triacetoxyborohydride (16.63 mg, 0.078 mmol) was added and the mixture was allowed to stir under nitrogen. The mixture was loaded onto a 2 g SCX-column, eluting with MeOH (25 mL) followed by 2M MeOH/NH$_3$ (25 mL). Product-containing fractions were evaporated to dryness to give a solid (18 mg). This was purified on a 12+M Biotage silica column, eluting with 0 to 4% 2N methanolic ammonia in DCM. Product-containing fractions were evaporated to dryness to give a clear, colourless solid (16 mg).

LCMS (Method C): Rt=0.71, MH+=471

Example 42 formic acid-1-methylethyl {(cis)-1-acetyl-2-methyl-6-[4-(1-piperidinylmethyl)phenyl]-1,2,3,4-tetrahydro-4-quinolinyl}methylcarbamate (1:1)

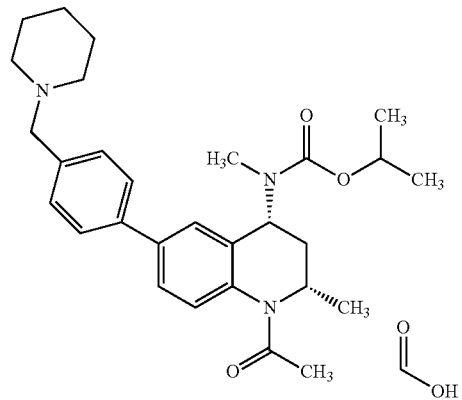

(±)

[4-(1-Piperidinylmethyl)phenyl]boronic acid (135 mg, 0.475 mmol), 1-methylethyl[(cis)-1-acetyl-6-bromo-2-methyl-1,2,3,4-tetrahydro-4-quinolinyl]methylcarbamate (for a preparation see Intermediate 40) (104 mg, 0.271 mmol), Tetrakis(triphenylphosphine)palladium(0) (15.68 mg, 0.014 mmol) and potassium carbonate (150 mg, 1.085 mmol) were placed in a round-bottomed flask with ethanol (1.8 mL) and Toluene (1.800 mL). The reaction mixture was stirred at 90° C. under N2 overnight. The brown reaction mixture was concentrated down and partitioned between EtOAc (10 mL) and water (10 mL). Further EtOAc (15 mL) was used to extract the product from the aqueous layer and the organics were combined, washed with saturated sodium bicarbonate solution (10 mL), dried (phase separator) and concentrated to yield a brown oil. This was purified by SP4 on a 12+M silica column using a gradient of 0.6-6% 2M methanolic ammonia in DCM. The relevant fractions were concentrated down to obtain a yellow oil (121 mg). Further purification was carried out using MDAP to give the desired compound (70 mg). LCMS (Method B): Rt=0.73, MH+=478

Example 43

1-methylethyl {(cis)-1-acetyl-2-methyl-6-[5-(1-piperazinyl)-2-pyrazinyl]-1,2,3,4-tetrahydro-4-quinolinyl}carbamate hydrochloride

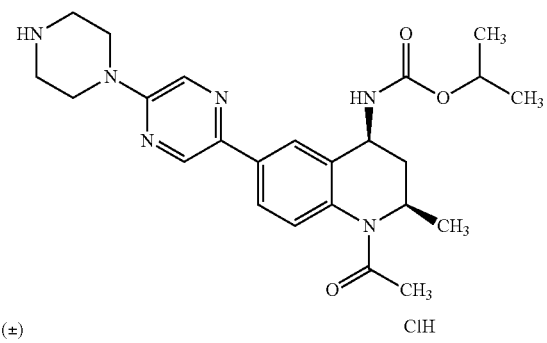 [SMILES: CC(=O)N1c2ccc(-c3cnc(N4CCNCC4)cn3)cc2[C@@H](NC(=O)OC(C)C)C[C@H]1C ; Cl]

(±) ClH

In a carousel tube, 1-methylethyl[(cis)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 12) (80 mg, 0.192 mmol), potassium carbonate (53.1 mg, 0.384 mmol), tetrakis(triphenylphosphine)palladium(0) (11.10 mg, 9.61 µmol) and 1,1-dimethylethyl 4-(5-iodo-2-pyrazinyl)-1-piperazinecarboxylate (for a preparation see Intermediate 13) (90 mg, 0.231 mmol) were dissolved in Ethanol (0.5 mL) and Toluene (0.5 mL). The tube was placed in a carousel and heated under nitrogen for 18 hr at 90° C. The reaction mixture was filtered and the solvent evaporated before being taken up in DCM and purified by SP4 on a 12+M silica cartridge using a gradient of 10-60% EtOAc in cyclohexane. Appropriate fractions were collected and concentrated. The samples were dissolved in 1:1 MeOH:DMSO 1 mL and purified by MDAP. The solvent was evaporated in vacuo to give the protected product. The sample was then dissolved in MeOH and acetyl chloride (0.015 mL, 0.211 mmol) was added. The solvent was then evaporated via nitrogen blow down to give the final product (63.9 mg) as an HCl salt. LCMS (Method C): Rt=0.65, MH+=453

Example 44

1-methylethyl {(cis)-1-acetyl-2-methyl-6-[2-(1-piperazinyl)-5-pyrimidinyl]-1,2,3,4-tetrahydro-4-quinolinyl}carbamate hydrochloride

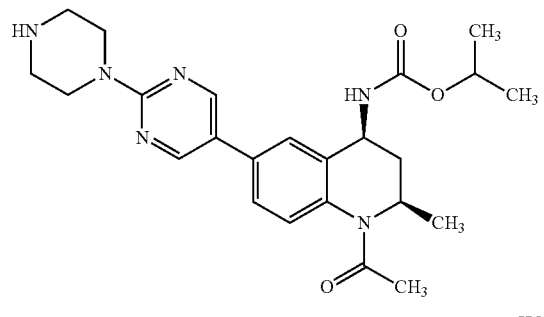

(±) •HCl

This was prepared by a similar method as Example 43, using 1,1-dimethylethyl 4-(5-bromo-2-pyrimidinyl)-1-piperazinecarboxylate (for a preparation see Intermediate 19) (79 mg, 0.231 mmol). LCMS (Method C): Rt 0.66, MH+=453

Example 45

1-methylethyl {(cis)-1-acetyl-2-methyl-6-[6-(1-piperazinyl)-3-pyridazinyl]-1,2,3,4-tetrahydro-4-quinolinyl}carbamate hydrochloride

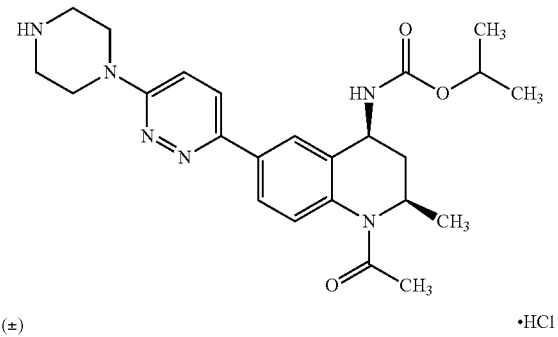 [SMILES: CC(=O)N1c2ccc(-c3ccc(N4CCNCC4)nn3)cc2[C@@H](NC(=O)OC(C)C)C[C@H]1C ; Cl]

(±) •HCl

This was prepared by a similar method as Example 43, using 1,1-dimethylethyl 4-(6-chloro-3-pyridazinyl)-1-piperazinecarboxylate (Intermediate 14, 68.9 mg, 0.231 mmol).

LCMS (Method C): Rt 0.57, MH+=453

Example 46

1-methylethyl((cis)-1-acetyl-2-methyl-6-{1-[2-(1-piperidinyl)ethyl]-1H-pyrazol-4-yl}-1,2,3,4-tetrahydro-4-quinolinyl)carbamate hydrochloride

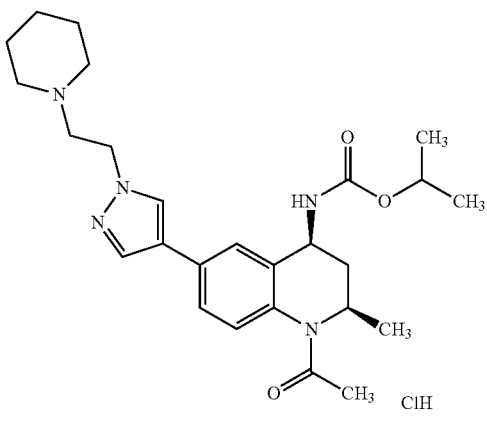

(±)

1-Methylethyl[(cis)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 12) (120 mg, 0.288 mmol) was mixed with 1-[2-(4-bromo-1H-pyrazol-1-yl)ethyl]piperidine (for a preparation see Intermediate 16) (101 mg, 0.391 mmol), potassium carbonate (80 mg, 0.576 mmol) and tetrakis(triphenylphosphine)palladium(0) (16.65 mg, 0.014 mmol), dissolved in Ethanol (1 mL) and Toluene (1 mL) and stirred under nitrogen at 90° C. for 19.5 hours. The reaction was loaded onto a 5 g-SCX-column, eluting with MeOH (30 mL) followed by 2M MeOH/NH$_3$ (30 mL). Product-containing fractions were evaporated to dryness to give a yellow solid (134 mg). This was purified on a 12+M Biotage silica column, eluting with 0 to 4% 2M methanolic ammonia in DCM. Product-containing fractions were evaporated to dryness to give a clear, colourless solid. This was dissolved in MeOH (0.5 mL) and mixed with 1.25M HCl (115 µL, 0.14 mmol) to give a light brown solid. This solid was purified further by MDAP. The product containing fractions were evaporated to dryness, loaded on to a 2 g SCX cartridge and eluted with MeOH (15 ml) and 2M methanolic ammonia (15 ml). The basic fractions were evaporated to give a white solid which was dissolved in MeOH and treated with 1.25M HCl in methanol (0.050 ml) and evaporated to give a white solid (34 mg). LCMS (Method C): Rt=0.70, MH+=468

Example 47 formic acid-1-methylethyl {(cis)-1-acetyl-6-[1-(2-aminoethyl)-1H-pyrazol-4-yl]-2-methyl-1,2,3,4-tetrahydro-4-quinolinyl}carbamate (1:1)

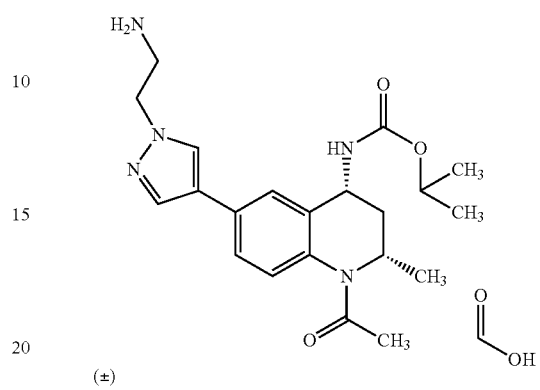

(±)

1-Methylethyl((cis)-1-acetyl-6-{1-[2-(1,3-dioxo-1,3-dihydro-2H-isoindol-2-yl)ethyl]-1H-pyrazol-4-yl}-2-methyl-1,2,3,4-tetrahydro-4-quinolinyl)carbamate (for a preparation see Intermediate 22) (39 mg, 0.074 mmol) was dissolved in Methanol (2 mL) and hydrazine monohydrate (7.14 µL, 0.147 mmol) was added. The reaction mixture was stirred under nitrogen at 65° C. for 6 hours. The reaction mixture was applied to an SCX cartridge (1 g) and washed with MeOH (2 CV) followed by 2M NH$_3$-MeOH (3 CV). The basic fractions were concentrated down to yield product. This was purified further by MDAP Concentration of the resulting fraction gave 1-methylethyl {cis-1-acetyl-6-[1-(2-aminoethyl)-1H-pyrazol-4-yl]-2-methyl-1,2,3,4-tetrahydro-4-quinolinyl}carbamate (21 mg, 0.044 mmol, 60.2% yield) as the formate salt (21 mg). LCMS (Method B): Rt=0.56, MH+=400

Example 48

1-methylethyl {(cis)-1-acetyl-6-[6-(dimethylamino)-3-pyridinyl]-2-methyl-1,2,3,4-tetrahydro-4-quinolinyl}carbamate hydrochloride

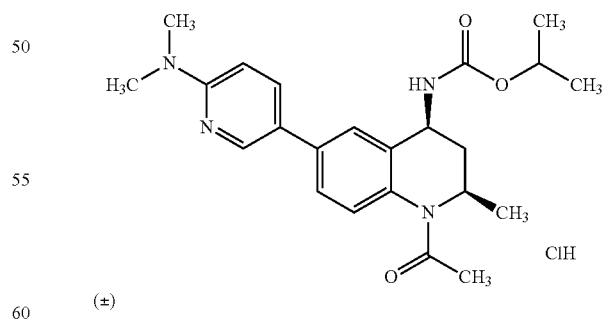

(±)

In a carousel tube, 1-methylethyl[(cis)-1-acetyl-6-bromo-2-methyl-1,2,3,4-tetrahydro-4-quinolinyl]carbamate (for a preparation see Example 61) (80 mg, 0.217 mmol), potassium carbonate (59.9 mg, 0.433 mmol), tetrakis(triphenylphosphine)palladium(0) (12.52 mg, 10.83 µmol) and [6-(dimethylamino)-3-pyridinyl]boronic acid hydrate (47.8 mg, 0.26 mmol, available from Apollo) were dissolved in Ethanol (0.5 mL) and Toluene (0.5 mL). The tube was placed in a carousel and heated under nitrogen for 18 hr at 90° C. The reaction mixture was filtered and the solvent evaporated before being taken up in DCM and purified by SP4 on a 12+M silica cartridge using a gradient of 20-100% EtOAc in cyclohexane. Appropriate fractions were collected and concentrated. The sample was dissolved in 1:1 MeOH:DMSO 1 mL and purified by MDAP. The solvent was evaporated in vacuo. To form a salt, the product was dissolved in MeOH and HCl (0.217 mL, 0.217 mmol) 1M in ether was added. Solvent was evaporated to yield the product as a pale yellow solid (76 mg). LCMS (Method C): Rt=0.66, MH+=411

Example 49

1-methylethyl {(cis)-1-acetyl-2-methyl-6-[2-(1-piperidinyl)-5-pyrimidinyl]-1,2,3,4-tetrahydro-4-quinolinyl}carbamate hydrochloride

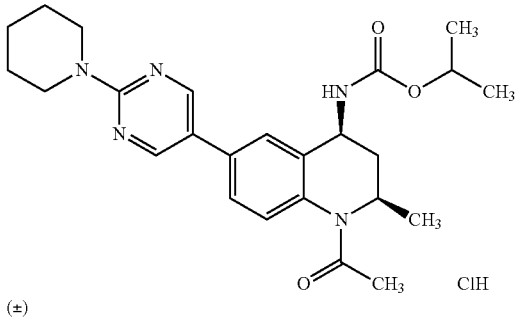 [SMILES: CC(=O)N1c2ccc(-c3cnc(N4CCCCC4)nc3)cc2[C@@H](NC(=O)OC(C)C)C[C@H]1C ; Cl]

This was prepared by a similar method as Example 48, using 2-(1-piperidinyl)-5-(4,4,5,5-tetramethyl-1,3,2-dioxaborolan-2-yl)pyrimidine (75 mg, 0.26 mmol, available from Frontier Scientific), to give the product as a pale yellow solid (50 mg).
LCMS (Method C): Rt=1.00, MH+=452

Example 50

1-methylethyl[(cis)-1-acetyl-6-(2-amino-5-pyrimidinyl)-2-methyl-1,2,3,4-tetrahydro-4-quinolinyl]carbamate hydrochloride

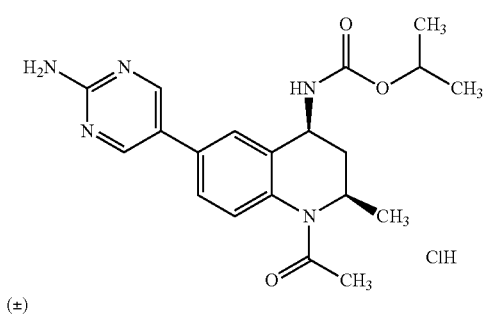 [SMILES: CC(=O)N1c2ccc(-c3cnc(N)nc3)cc2[C@@H](NC(=O)OC(C)C)C[C@H]1C ; Cl]

This was prepared by a similar method as Example 48, using 5-(4,4,5,5-tetramethyl-1,3,2-dioxaborolan-2-yl)-2-pyrimidinamine (57.5 mg, 0.26 mmol, available from Frontier Scientific), omitting the MDAP purification step, to give the product as a pale yellow solid (80 mg). LCMS (Method C): Rt=0.62, MH+=384

Example 51

1-methylethyl {(cis)-1-acetyl-2-methyl-6-[2-(4-morpholinyl)-5-pyrimidinyl]-1,2,3,4-tetrahydro-4-quinolinyl}carbamate hydrochloride

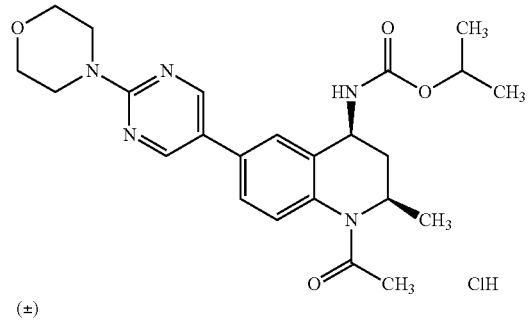 [SMILES: CC(=O)N1c2ccc(-c3cnc(N4CCOCC4)nc3)cc2[C@@H](NC(=O)OC(C)C)C[C@H]1C ; Cl]

This was prepared by a similar method as Example 48, using 4-[5-(4,4,5,5-tetramethyl-1,3,2-dioxaborolan-2-yl)-2-pyrimidinyl]morpholine (57.5 mg, 0.26 mmol, commercially available from Frontier Scientific), omitting the MDAP purification step, to give the product as a pale yellow solid (92 mg). LCMS (Method C): Rt=0.89, MH+=454

Example 52

1-methylethyl {(cis)-1-acetyl-2-methyl-6-[5-(1-piperidinylmethyl)-1,3-thiazol-2-yl]-1,2,3,4-tetrahydro-4-quinolinyl}carbamate hydrochloride

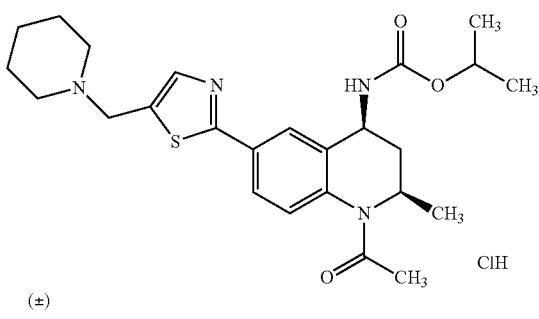 [SMILES: CC(=O)N1c2ccc(-c3ncc(CN4CCCCC4)s3)cc2[C@@H](NC(=O)OC(C)C)C[C@H]1C ; Cl]

1-[(2-Bromo-1,3-thiazol-5-yl)methyl]piperidine (for a preparation see Intermediate 12) (130 mg, 0.498 mmol) was mixed with potassium carbonate (138 mg, 0.995 mmol), 1-methylethyl[1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 27) (249 mg, 0.597 mmol) and dissolved in Ethanol (2 mL) and Toluene (2 mL). Tetrakis(triphenylphosphine)palladium(0) (28.8 mg, 0.025 mmol) was added and the reaction was stirred under nitrogen at 90° C. After 3.5 hours the reaction was left to cool to room temperature overnight and partitioned between sodium bicarbonate (20 mL) and EtOAc (60 mL). The aqueous layer was extracted with EtOAc (40 mL) and organic fractions were combined, washed (brine (50 mL)), dried (sodium sulfate), filtered and evaporated to dryness to give a black solid (342 mg). This was purified on a 25+M Biotage silica column, eluting with cyclohexane:EtOAc (9:1 to 0:1). Product-containing fractions were evaporated to dryness to give a brown/orange solid (210 mg). The product was purified by MDAP. Product-containing fractions were evaporated to dryness to give a clear, colourless solid, which was loaded onto a 5 g SCX-column, eluting with MeOH (25 mL) followed by 2M MeOH/NH$_3$ (25 mL). Product-containing fractions were evaporated to dryness to give a clear, colourless solid. This was dissolved in MeOH (0.5 mL), mixed with 1.25M HCl (107.1 μL, 0.134 mmol) and evaporated to dryness to give a colourless solid (63 mg). LCMS (Method C): Rt=0.68, MH+=471

Example 53

1-methylethyl {(cis)-1-acetyl-2-methyl-6-[6-(methylamino)-3-pyridinyl]-1,2,3,4-tetrahydro-4-quinolinyl}carbamate hydrochloride

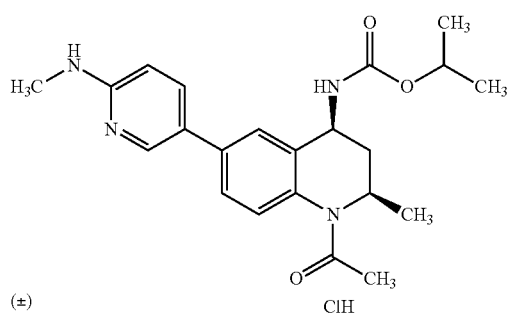 [SMILES: CNc1ccc(-c2ccc3c(c2)[C@@H](NC(=O)OC(C)C)C[C@@H](C)N3C(C)=O)cn1 ; Cl]

1-Methylethyl[(cis)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 12) (80 mg, 0.192 mmol), potassium carbonate (53.1 mg, 0.384 mmol), tetrakis(triphenylphosphine)palladium(0) (11.10 mg, 9.61 μmol) and 5-bromo-N-methyl-2-pyridinamine (43.1 mg, 0.231 mmol, Intermediate 3) were dissolved in Ethanol (0.5 mL) and toluene (0.5 mL). The reaction mixture was stirred heated under nitrogen for 18 hr at 90° C. The reaction mixture was filtered and the solvent evaporated before being taken up in DCM and purified by SP4 on a 12+M silica cartridge using a gradient of 0-10% MeOH in DCM. Appropriate fractions were collected and concentrated but remained impure. The sample was dissolved in 1:1 MeOH:DMSO 1 mL and purified by MDAP then repurified by loading onto a 10 g SCX column, washed with MeOH (100 mL) and eluted with 10% 2M NH$_3$ in MeOH (70 mL). The solvent was evaporated in vacuo. 2M HCl in ether (0.5 mL) was added to the residue to form the salt and the solvent was evaporated via nitrogen blow down to yield the desired product as a white/pale yellow solid (27.7 mg) LCMS (Method C): Rt=0.65, MH+=397

Example 54

1-methylethyl((cis)-1-acetyl-6-{1-[2-(dimethylamino)ethyl]-1H-pyrazol-4-yl}-2-methyl-1,2,3,4-tetrahydro-4-quinolinyl)carbamate hydrochloride

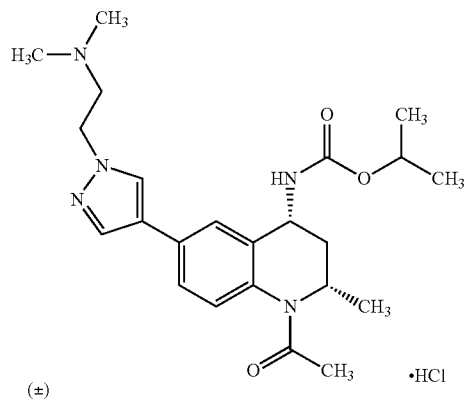 [SMILES: CC(=O)N1c2ccc(-c3cnn(CCN(C)C)c3)cc2[C@H](NC(=O)OC(C)C)C[C@@H]1C ; Cl]

1-Methylethyl[(cis)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 12) (120 mg, 0.288 mmol), [2-(4-bromo-1H-pyrazol-1-yl)ethyl]dimethylamine (for a preparation see Intermediate 15) (85 mg, 0.390 mmol) and potassium carbonate (51.8 mg, 0.375 mmol) were stirred in ethanol (1.5 ml) and toluene (1.5 ml) and the mixture degassed. Tetrakis(triphenylphosphine)palladium(0) (16.65 mg, 0.014 mmol) was added, the mixture degassed again and heated to reflux (85° C.) overnight. The mixture was cooled to room temperature, partitioned between ethyl acetate (35 ml) and sat. sodium hydrogen carbonate: water (1:1, 10 ml). The aqueous layer was run off and the organic washed (sat. sodium hydrogen carbonate:water (1:1, 10 ml)), dried (magnesium sulfate) and evaporated to an orange residue. The residue was loaded on to a 12+M Biotage silica column and eluted with DCM:2M Methanolic ammonia (0 to 15%). The product containing fractions were evaporated to dryness then dissolved in MeOH (1 ml) and 1.25M HCl in MeOH (0.128 ml, 0.159 mmol) was added and the mixture evaporated to an off white solid (59 mg). LCMS (Method C): Rt=0.64, MH+=428

Example 55

1-methylethyl {(cis)-1-acetyl-6-[4-(aminomethyl)phenyl]-2-methyl-1,2,3,4-tetrahydro-4-quinolinyl}carbamate hydrochloride

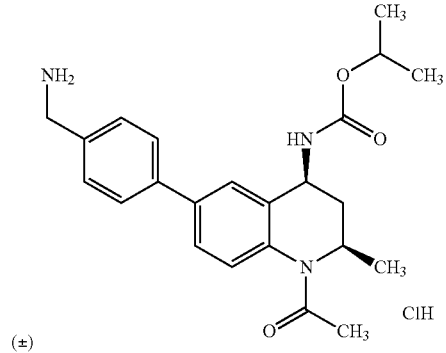 [SMILES: CC(=O)N1c2ccc(-c3ccc(CN)cc3)cc2[C@@H](NC(=O)OC(C)C)C[C@H]1C ; Cl]

1-Methylethyl[(cis)-1-acetyl-6-bromo-2-methyl-1,2,3,4-tetrahydro-4-quinolinyl]carbamate (for a preparation see Example 61) (212 mg, 0.574 mmol), potassium carbonate (159 mg, 1.148 mmol), tetrakis(triphenylphosphine)palladium(0) (33.2 mg, 0.029 mmol) and {4-[({[(1,1-dimethylethyl)oxy]carbonyl}amino)methyl]phenyl}boronic acid (173 mg, 0.689 mmol, available from Apollo) were dissolved in ethanol (1.5 mL) and toluene (1.5 mL). The reaction mixture was degassed for 20 min then stirred and heated under nitrogen for 1 hr at 100° C. The reaction mixture was concentrated under vacuum. The residue was partitioned between dichloromethane (10 ml) and water (10 ml). The organic layer was dried through a hydrophobic frit and concentrated in vacuo, then dissolved in DCM and purified by SP4 on a 25+M silica cartridge using a gradient of 0-50% EtOAc in cyclohexane. The appropriate fractions were combined and evaporated in vacuo to give the boc-protected product (250 mg). This was dissolved with 5 ml of methanol and treated with 1 ml of acetyl chloride. After 1 h the reaction mixture was loaded on a 20 g NH$_2$ cartridge, which was previously conditioned with methanol. Column was washed with methanol (3 CV). The appropriate fractions were combined and evaporated in vacuo to give the free base product (197 mg). The product was dissolved with 3 ml of methanol and treated with 1.1 eq of 2M HCl in to give a yellow solid (181 mg)

LCMS (Method B): Rt=0.63, MH+=396

Example 56

1-methylethyl {(cis)-1-acetyl-2-methyl-6-[5-(1-piperidinylmethyl)-2-pyridinyl]-1,2,3,4-tetrahydro-4-quinolinyl}carbamate

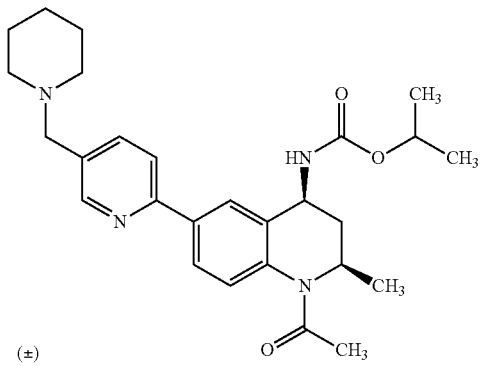 [SMILES: CC(=O)N1c2ccc(-c3ccc(CN4CCCCC4)cn3)cc2[C@@H](NC(=O)OC(C)C)C[C@H]1C]

(±)

2-bromo-5-(1-piperidinylmethyl)pyridine (for a preparation see Intermediate 24) (98 mg, 0.384 mmol) was mixed with 1-methylethyl[(cis)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 12) (100 mg, 0.240 mmol), potassium carbonate (66.4 mg, 0.480 mmol) and tetrakis(triphenylphosphine)palladium(0) (13.88 mg, 0.012 mmol), dissolved in ethanol (1 mL) and toluene (1 mL) and stirred under nitrogen at 90° C. The reaction mixture was loaded onto a 5 g SCX column, eluting with MeOH (30 mL) followed by 2M MeOH/NH$_3$ (30 mL). Product-containing fractions were evaporated to dryness to give a yellow solid (155 mg). This was purified by MDAP. Product-containing fractions were evaporated to dryness to give a clear, colourless solid (55 mg). LCMS (Method C): Rt=0.67, MH+=465

Example 57

1-methylethyl {(cis)-1-acetyl-2-methyl-6-[6-(1-piperidinylmethyl)-3-pyridinyl]-1,2,3,4-tetrahydro-4-quinolinyl}carbamate

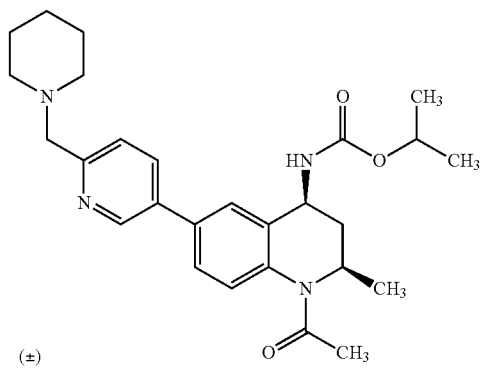

(±)

This was prepared by a similar method as Example 56, using 5-bromo-2-(1-piperidinylmethyl)pyridine (Intermediate 23, 61.3 mg, 0.240 mmol), to give the product as a clear, colourless solid (34 mg). LCMS (Method C): Rt=0.69, MH+=465

Example 58 cyclobutyl {(cis)-1-acetyl-2-methyl-6-[4-(1-piperidinylmethyl)phenyl]-1,2,3,4-tetrahydro-4-quinolinyl}carbamate hydrochloride

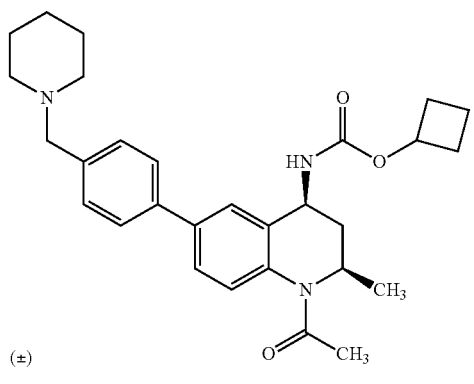

(±)

ClH

Cyclobutyl((cis)-1-acetyl-6-bromo-2-methyl-1,2,3,4-tetrahydro-4-quinolinyl)carbamate (for a preparation see Example 33) (29 mg, 0.076 mmol) was mixed with [4-(1-piperidinylmethyl)phenyl]boronic acid (for a preparation see Intermediate 1) (29.2 mg, 0.114 mmol), potassium carbonate (42.0 mg, 0.304 mmol) and dissolved in ethanol (0.5 mL) and toluene (0.5 mL). tetrakis(triphenylphosphine)palladium(0) (4.39 mg, 3.80 µmol) was added and the reaction was stirred under nitrogen at 90° C. for 16 hours. The reaction mixture was run down a 2 g-Flash SCX-column eluting with MeOH (50 mL) followed by 2M MeOH/NH₃ (50 mL). Product-containing fractions were evaporated to dryness to give a yellow solid (37 mg). The residue was purified on a 12+M Biotage silica column, eluting with DCM:2M MeOH/NH₃ (1:0 to 24:1). Pure product-containing fractions were evaporated to dryness to give a clear, colourless solid (10 mg). Impure fractions (totalling 28 mg) were evaporated to dryness giving a clear, colourless solid and were purified using MDAP. Product-containing fractions were evaporated to dryness to give a clear, colourless solid. These were combined with the pure fractions obtained earlier, dissolved in MeOH (1 mL), mixed with 1.25M HCl in MeOH (40 µL, 0.05 mmol) and blown down to give a white solid (18 mg). LCMS (Method C): Rt 0.79, MH+=476

Example 59

1-methylethyl((cis)-1-acetyl-2-methyl-6-{4-[(4-methyl-1-piperazinyl)methyl]phenyl}-1,2,3,4-tetrahydro-4-quinolinyl)carbamate hydrochloride

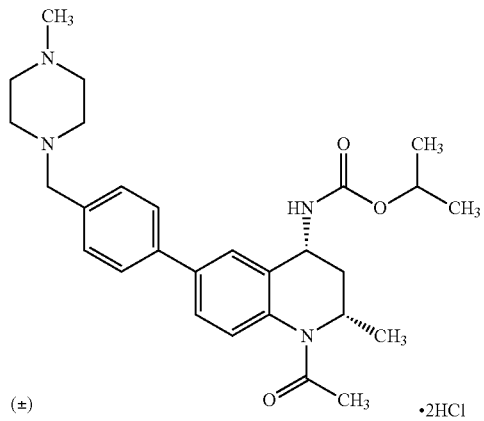 [SMILES: CC(=O)N1c2ccc(-c3ccc(CN4CCN(C)CC4)cc3)cc2[C@H](NC(=O)OC(C)C)C[C@@H]1C ; "·2HCl"]

1-Methylethyl[(cis)-1-acetyl-6-(4-formylphenyl)-2-methyl-1,2,3,4-tetrahydro-4-quinolinyl]carbamate (for a preparation see Intermediate 7) (95 mg, 0.241 mmol) was dissolved in dichloromethane (DCM) (2 mL) and to this was added 1-methylpiperazine (0.040 mL, 0.361 mmol, Aldrich) as a liquid and the resulting solution stirred under nitrogen for 5 min. sodium triacetoxyborohydride (66.4 mg, 0.313 mmol) was added and stirred as a suspension over the weekend. The reaction was quenched with ammonium chloride (2 ml). The organics were separated and the aqueous reextracted with DCM (5 ml). The combined organics were washed with water (5 ml) and reduced in vacuo to give a colourless solid (103 mg). The solid was dissolved in DCM and purified by SP4 on a 12+M silica cartridge eluting with a gradient of 2.5 to 12.5% 2M methanolic ammonia in ethyl acetate to give a colourless oil (89 mg). This was dissolved in methanol and to this was added 2 equivalents of 1.25M HCl and reduced in vacuo to give a white solid.

LCMS (Method A): Rt 1.01, MH+=479

Example 60

1-methylethyl {(cis)-1-acetyl-2-methyl-6-[4-(4-morpholinylmethyl)phenyl]-1,2,3,4-tetrahydro-4-quinolinyl}carbamate hydrochloride

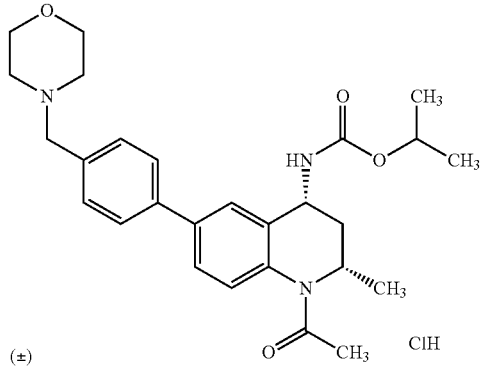 [SMILES: CC(=O)N1c2ccc(-c3ccc(CN4CCOCC4)cc3)cc2[C@H](NC(=O)OC(C)C)C[C@@H]1C ; Cl]

1-Methylethyl[(cis)-1-acetyl-6-(4-formylphenyl)-2-methyl-1,2,3,4-tetrahydro-4-quinolinyl]carbamate (for a preparation see Intermediate 7) (97 mg, 0.246 mmol) was dissolved in dichloromethane (DCM) (2 mL) and to this was added morpholine (0.032 mL, 0.369 mmol, Aldrich) as a liquid and the resulting solution stirred under nitrogen for 5 min. sodium triacetoxyborohydride (67.8 mg, 0.320 mmol) was added and stirred as a suspension over the weekend. The solvent had evaporated so dichloromethane (DCM) (2 mL) was added. The reaction was quenched with ammonium chloride (2 ml). The organics were separated and the aqueous reextracted with DCM (5 ml). The combined organics were washed with water (5 ml) and reduced in vacuo to give a colourless solid (128 mg). The solid was dissolved in DCM and purified by SP4 on a 12+M silica cartridge eluting with a gradient of 0.5 to 3% 2M methanolic ammonia in ethyl acetate to give a colourless oil. The colourless oil was dissolved in methanol and to this was added 2 eqv. of 1.25M HCl in methanol and reduced in vacuo to give a white solid. LCMS (Method A): Rt 1.07, MH+=466

Example 61

1-methylethyl[(cis)-1-acetyl-6-bromo-2-methyl-1,2,3,4-tetrahydro-4-quinolinyl]carbamate

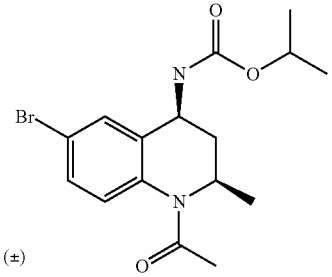 [SMILES: CC(=O)N1c2ccc(Br)cc2[C@@H](NC(=O)OC(C)C)C[C@H]1C]

(cis)-1-acetyl-6-bromo-2-methyl-1,2,3,4-tetrahydro-4-quinolinamine (for a preparation see Intermediate 4) (3.165 g, 9.90 mmol) and DIPEA (5.19 ml, 29.7 mmol) were stirred in dichloromethane (DCM) (66.0 ml) under nitrogen. 1M isopropyl chloroformate in toluene (14.85 ml, 14.85 mmol) was added, the mixture stirred for 2 hours, evaporated to dryness, partitioned between ethyl acetate (200 ml) water (70 ml) and the aqueous layer run off. The organic layer was washed (water (50 ml), brine (20 ml)), dried (sodium sulfate), evaporated to dryness, loaded on to a 40+M Biotage silica column and eluted with cyclohexane:ethyl acetate (9:1 to 1:1). The product containing fractions were evaporated to a white solid (3.23 g). LCMS (Method B): Rt=1.03, MH+=371

Example 62

1-methylethyl((2S,4R)-1-acetyl-2-methyl-6-{1-[2-(methylamino)ethyl]-1H-pyrazol-4-yl}-1,2,3,4-tetrahydro-4-quinolinyl)carbamate hydrochloride

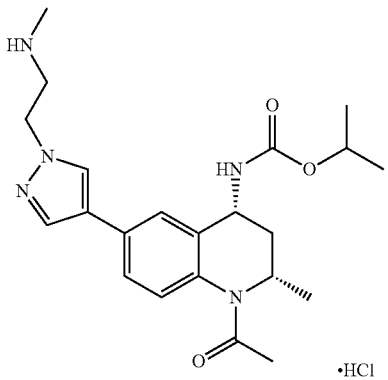 [SMILES: CNCCn1cc(-c2ccc3c(c2)[C@H](NC(=O)OC(C)C)C[C@H](C)N3C(C)=O)cn1 ; Cl]

1-Methylethyl[(2S,4R)-1-acetyl-2-methyl-6-(1-{2-[methyl(phenylmethyl)amino]ethyl}-1H-pyrazol-4-yl)-1,2,3,4-tetrahydro-4-quinolinyl]carbamate (223 mg, 0.443 mmol, for a preparation see Intermediate 51) was dissolved in methanol (9 ml) and hydrogenated using the Thales H-Cube (flow rate 1 ml/min, 20° C. temperature, Full Hydrogen setting) and the mixture sampled for LCMS (N11804-16-R1, TFA). The resulting eluent was hydrogenated using the Thales H-Cube (flow rate 1 ml/min, 60° C. temperature, Full Hydrogen setting). The reaction mixture was evaporated to dryness, loaded on to a 12+M Biotage silica column and eluted with DCM:2M methanolic ammonia (0 to 6%, 22 CV). The clean, product containing fractions were evaporated to a colourless gum which was purified by MDAP and the product containing fractions evaporated to dryness. The residue was loaded on to a 2 g SCX cartridge and eluted with MeOH (25 ml) and 2M methanolic ammonia (12 mL). The basic fractions were evaporated to a white solid which was diluted in CDCl$_3$ (0.5 ml) and MeOH (0.5 ml) and 1.25M HCl in MeOH added (0.120 ml, 0.15 mmol) and evaporated to a white powder (52 mg).

LCMS (Method C): Rt=0.66, MH+=414

Example 63

(2S,4R)-1-Acetyl-6-bromo-2-methyl-1,2,3,4-tetrahydro-4-quinolinamine

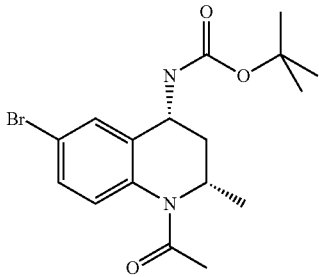 [SMILES: CC(=O)N1c2ccc(Br)cc2[C@H](NC(=O)OC(C)(C)C)C[C@@H]1C]

To a solution of (2S,4R)-1-acetyl-6-bromo-2-methyl-1,2,3,4-tetrahydro-4-quinolinamine hydrochloride (for a preparation, see Intermediate 55) (5.36 g, 16.77 mmol) in dichloromethane (DCM) (100 mL) at room temperature was added triethylamine (7.01 mL, 50.3 mmol) then bis(1,1-dimethylethyl) dicarbonate (4.28 mL, 18.45 mmol). After 90 min, triethylamine (1.75 mL, 12.6 mmol) then bis(1,1-dimethylethyl) dicarbonate (1.07 mL, 4.61 mmol) were further added and the resulting mixture was stirred at room temperature for another 30 min. The reaction mixture was then washed with water. The aqueous phase was extracted with DCM and the combined organic phases were washed with water then dried using a phase separator and concentrated in vacuo. Purification of the residue by SP4 using a 100 G silica cartridge (gradient: 13 to 63% AcOEt in Hexanes) gave 1,1-dimethylethyl[(2S,4R)-1-acetyl-6-bromo-2-methyl-1,2,3,4-tetrahydro-4-quinolinyl]carbamate (5.27 g, 13.75 mmol, 82% yield) as a white foam.

LCMS (method A): Retention time 1.14 min, [M−H]−=383.09 (1 Br)

Example 64

1-Methylethyl[(2S,4R)-1-acetyl-2-methyl-6-(5-methyl-1,2,4-oxadiazol-3-yl)-1,2,3,4-tetrahydro-4-quinolinyl]carbamate

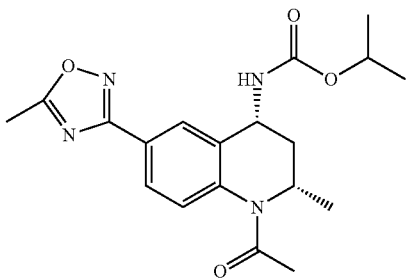 [SMILES: CC(=O)N1c2ccc(-c3noc(C)n3)cc2[C@H](NC(=O)OC(C)C)C[C@@H]1C]

To a solution of 1-methylethyl {(2S,4R)-1-acetyl-6-[(hydroxyamino)(imino)methyl]-2-methyl-1,2,3,4-tetrahydro-4-quinolinyl}carbamate (for a preparation, see Intermediate 56) (130 mg, 0.373 mmol) in toluene (2 mL) and pyridine (2 mL) was added acetyl chloride (a solution 0.34 mL of acetyl chloride in 5 mL of toluene was made and 0.52 mL was used, 0.485 mmol) dropwise and the resulting mixture was stirred at room temperature under nitrogen for 30 min. The mixture was then warmed to 110° C. and stirred at this temperature for 16 h then cooled to room temperature. Most of the solvents were removed in vacuo and the residue was partitioned between AcOEt and water (acidified to pH 1 with a 2N HCl aqueous solution). The two layers were separated and the aqueous phase was extracted with AcOEt. The combined organic phases were washed with a saturated NaHCO$_3$ aqueous solution then brine, dried over MgSO$_4$ and concentrated in vacuo. Purification of the residue on SP4 using a 10 G silica cartridge (gradient: 13 to 63% AcOEt in hexanes) gave 1-methylethyl[(2S,4R)-1-acetyl-2-methyl-6-(5-methyl-1,2,4-oxadiazol-3-yl)-1,2,3,4-tetrahydro-4-quinolinyl]carbamate (120 mg, 0.322 mmol, 86% yield) as a white foam. LCMS (method A): Retention time 0.94 min, [M+H]+=373.05

Example 65

1-Methylethyl[(2S,4R)-1-acetyl-2-methyl-6-(1H-1,2,3-triazol-4-yl)-1,2,3,4-tetrahydro-4-quinolinyl]carbamate

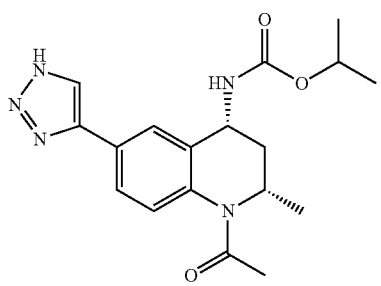 [SMILES: CC(=O)N1c2ccc(-c3c[nH]nn3)cc2[C@H](NC(=O)OC(C)C)C[C@@H]1C]

A flask was charged with 1-methylethyl[(2S,4R)-1-acetyl-6-ethynyl-2-methyl-1,2,3,4-tetrahydro-4-quinolinyl]carbamate (for a preparation, see Intermediate 58) (80 mg, 0.254 mmol) and copper(I) iodide (2.423 mg, 0.013 mmol) then filled with N,N-dimethylformamide (DMF) (1.8 mL) and Methanol (0.200 mL). Trimethylsilyl azide (0.059 mL, 0.509 mmol) was added and the resulting mixture was stirred under microwave irradiation at 100° C. for 5 h then cooled to room temperature. The solution was partitioned between AcOEt and water/brine (1/1) and the layers were separated. The aqueous phase was extracted three times with AcOEt and the combined organic phases were washed with water then brine, dried over MgSO$_4$ and concentrated in vacuo. The residue was purified using MDAP (modifier: ammonium bicarbonate). The appropriate fractions were concentrated in vacuo and the residue dissolved in DCM. The organic phase was dried using a phase separator then concentrated in vacuo to give 1-methylethyl[(2S,4R)-1-acetyl-2-methyl-6-(1H-1,2,3-triazol-4-yl)-1,2,3,4-tetrahydro-4-quinolinyl]carbamate (30 mg, 0.084 mmol, 33.0% yield) as a white foam.

LCMS (method A): Retention time 0.65 min, [M+H]+= 358.15

Example 66

1-Methylethyl {(2S,4R)-1-acetyl-6-[5-(aminomethyl)-1,2,4-oxadiazol-3-yl]-2-methyl-1,2,3,4-tetrahydro-4-quinolinyl}carbamate hydrochloride

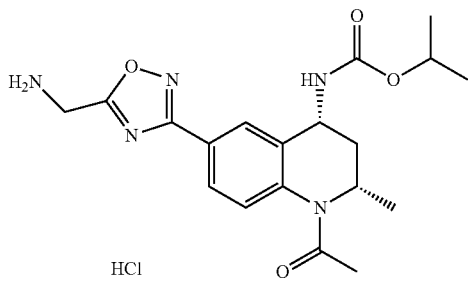 [SMILES: CC(=O)N1c2ccc(-c3noc(CN)n3)cc2[C@H](NC(=O)OC(C)C)C[C@@H]1C ; Cl]

To a solution of 1-methylethyl((2S,4R)-1-acetyl-6-{5-[({[(1,1-dimethylethyl)oxy]carbonyl}amino)methyl]-1,2,4-oxadiazol-3-yl}-2-methyl-1,2,3,4-tetrahydro-4-quinolinyl)carbamate (for a preparation, see Intermediate 60) (132 mg, 0.271 mmol) in 1,4-dioxane (2 mL) at room temperature was added HCl (4N in 1,4-dioxane, 2 mL, 8.00 mmol) and the resulting mixture was stirred at this temperature for 5 h then left standing at 4° C. for 16 h. The mixture was warmed to room temperature and most of the solvent was removed in vacuo. The residue was loaded on a 2 G SCX cartridge and eluted with MeOH then with a 2N NH$_3$ solution in MeOH. The ammonia fractions were collected and concentrated in vacuo, The residue was dissolved in 1,4-dioxane (3 mL) and the solution was treated with 0.5 ml of HCl (4N in 1,4-dioxane) then concentrated in vacuo. Trituration of the residue with Et$_2$O gave 1-methylethyl {(2S,4R)-1-acetyl-6-[5-(aminomethyl)-1,2,4-oxadiazol-3-yl]-2-methyl-1,2,3,4-tetrahydro-4-quinolinyl}carbamate hydrochloride (71 mg, 0.167 mmol, 61.9% yield) as a pale red solid.

LCMS (method A): Retention time 1.98 min, [M+H]+= 388.1

Example 67

{4-[(2S,4R)-1-Acetyl-2-methyl-4-({[(1-methylethyl)oxy]carbonyl}amino)-1,2,3,4-tetrahydro-6-quinolinyl]phenyl}acetic acid

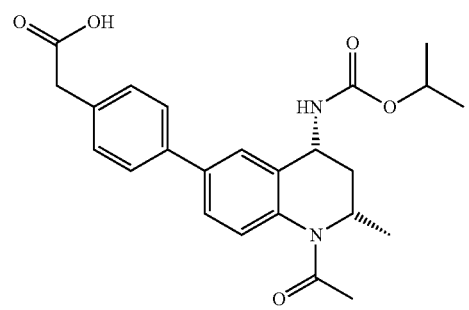

To a solution of ethyl {4-[(2S,4R)-1-acetyl-2-methyl-4-({[(1-methylethyl)oxy]carbonyl}amino)-1,2,3,4-tetrahydro-6-quinolinyl]phenyl}acetate (for a preparation, see Intermediate 61) (270 mg, 0.597 mmol) in methanol (6 mL) and water (2 mL) at room temperature was added sodium hydroxide (2N in water, 0.597 mL, 1.193 mmol) and the resulting mixture was stirred at this temperature for 6 h. 0.5 ml of 2N sodium hydroxide in water were then added and the resulting mixture was left standing for 16 h. Most of the methanol was then removed in vacuo and the residue was partitioned between water and Et$_2$O. The layers were separated. The aqueous layer was acidified with 2 mL of 2N HCl in water and extracted twice with AcOEt. The combined AcOEt fractions were dried over MgSO$_4$ and concentrated in vacuo to give {4-[(2S,4R)-1-acetyl-2-methyl-4-({[(1-methylethyl)oxy]carbonyl}amino)-1,2,3,4-tetrahydro-6-quinolinyl]phenyl}acetic acid (200 mg, 0.471 mmol, 79% yield) as a brown foam.

LCMS (method A): Retention time 0.65 min, [M+H]+= 425.21

Example 68

1-Methylethyl[(2S,4R)-1-acetyl-2-methyl-6-(5-methyl-1,3,4-thiadiazol-2-yl)-1,2,3,4-tetrahydro-4-quinolinyl]carbamate

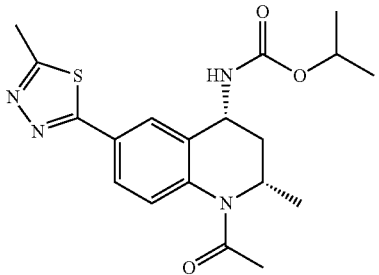 [SMILES: CC(=O)N1c2ccc(-c3nnc(C)s3)cc2[C@H](NC(=O)OC(C)C)C[C@@H]1C]

A flask was charged with 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation, see Intermediate 52) (223 mg, 0.536 mmol), potassium carbonate (222 mg, 1.607 mmol), tetrakis(triphenylphosphine)palladium(0) (61.9 mg, 0.054 mmol) and 2-bromo-5-methyl-1,3,4-thiadiazole (125 mg, 0.696 mmol) then filled with ethanol (3 mL) and toluene (3 mL). The resulting mixture was degassed for 15 min under house vacuum (with several quenches with nitrogen) then stirred at 100° C. for 2 h before being cooled to room temperature and left stand still for 16 h. The insoluble material was filtered off and rinsed with AcOEt. Most of the solvent was removed in vacuo and the residue was dissolved in AcOEt. The organic phase was washed with brine, dried over $MgSO_4$ and concentrated in vacuo. Purification of the residue by SP4 using a 25 G silica cartridge (gradient: 25 to 100% AcOEt in hexanes) gave a material which was then further purified by MDAP (modifier: ammonium bicarbonate) to give 1-methylethyl[(2S,4R)-1-acetyl-2-methyl-6-(5-methyl-1,3,4-thiadiazol-2-yl)-1,2,3,4-tetrahydro-4-quinolinyl]carbamate (60 mg, 0.154 mmol, 28.8% yield) as a white foam.

LCMS (method A): Retention time 0.89 min, [M+H]+= 389.06.

Example 69

1-Methylethyl {(2S,4R)-1-acetyl-6-[3-(aminomethyl)-1,2,4-oxadiazol-5-yl]-2-methyl-1,2,3,4-tetrahydro-4-quinolinyl}carbamate hydrochloride

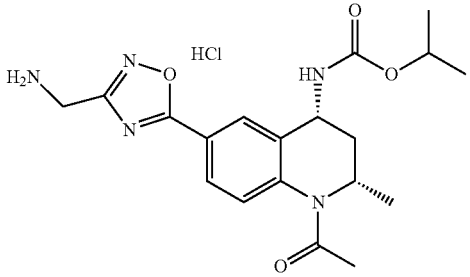 [SMILES: CC(=O)N1c2ccc(-c3nc(CN)no3)cc2[C@H](NC(=O)OC(C)C)C[C@@H]1C ; Cl]

To a solution of 1-methylethyl((2S,4R)-1-acetyl-6-{3-[({[(1,1-dimethylethyl)oxy]carbonyl}amino)methyl]-1,2,4-oxadiazol-5-yl}-2-methyl-1,2,3,4-tetrahydro-4-quinolinyl)carbamate (for a preparation, see Intermediate 62) (100 mg, 0.205 mmol) in 1,4-dioxane (0.5 mL) at room temperature was added HCl (4N in 1,4-dioxane, 2 mL, 8 mmol) and the resulting mixture was stirred at this temperature for 3 h than at 4° C. for 16 h before being warmed to room temperature. The residue was triturated with $Et_2O$ then purified using MDAP (modifier: ammonium bicarbonate). The residue obtained was dissolved in 1,4-dioxane (2 mL) and treated with HCl (4N in dioxane, 1 mL). The resulting mixture was concentrated in vacuo and the residue triturated with $Et_2O$ to give 1-methylethyl {(2S,4R)-1-acetyl-6-[3-(aminomethyl)-1,2,4-oxadiazol-5-yl]-2-methyl-1,2,3,4-tetrahydro-4-quinolinyl}carbamate hydrochloride (9 mg, 0.021 mmol, 10.35% yield).

LCMS (method A): Retention time 0.75 min, [M+H]+= 388.12

Example 70

1-Methylethyl {(2S,4R)-1-acetyl-6-[3-(2-aminoethyl)-1,2,4-oxadiazol-5-yl]-2-methyl-1,2,3,4-tetrahydro-4-quinolinyl}carbamate hydrochloride

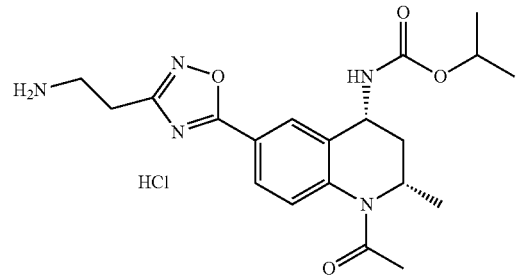 [SMILES: CC(=O)N1c2ccc(-c3nc(CCN)no3)cc2[C@H](NC(=O)OC(C)C)C[C@@H]1C ; Cl]

To a solution of 1-methylethyl((2S,4R)-1-acetyl-6-{3-[2-({[(1,1-dimethylethyl)oxy]carbonyl}amino)ethyl]-1,2,4-oxadiazol-5-yl}-2-methyl-1,2,3,4-tetrahydro-4-quinolinyl)carbamate (for a preparation, see Intermediate 66) (100 mg, 0.199 mmol) in 1,4-dioxane (0.5 mL) at room temperature was added HCl (4N in 1,4-dioxane, 2 mL, 8.00 mmol) and the resulting mixture was stirred at this temperature for 3 h then was left standing at 4° C. for 16 h before being warmed to room temperature. The residue was triturated with $Et_2O$ then purified using MDAP (modifier: ammonium bicarbonate). The residue obtained was dissolved in 1,4-dioxane (2 mL) and treated with HCl (4N in 1,4-dioxane, 1 mL). The resulting mixture was concentrated in vacuo and the residue triturated with $Et_2O$ to give 1-methylethyl {(2S,4R)-1-acetyl-6-[3-(2-aminoethyl)-1,2,4-oxadiazol-5-yl]-2-methyl-1,2,3,4-tetrahydro-4-quinolinyl}carbamate hydrochloride (10 mg, 0.023 mmol, 11.45% yield) as a colourless solid.

LCMS (method A): Retention time 0.77 min, [M+H]+= 402.13

Example 71

1-Methylethyl((2S,4R)-1-acetyl-2-methyl-6-{3-[2-(methylamino)ethyl]-1,2,4-oxadiazol-5-yl}-1,2,3,4-tetrahydro-4-quinolinyl)carbamate hydrochloride

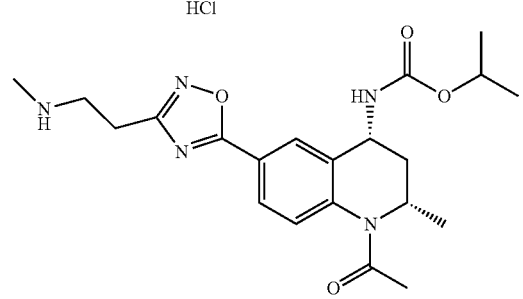 [SMILES: Cl ; CNCCc1noc(-c2ccc3c(c2)[C@H](NC(=O)OC(C)C)C[C@H](C)N3C(C)=O)n1]

To a solution of 1-methylethyl[(2S,4R)-1-acetyl-6-(3-{2-[{[(1,1-dimethylethyl)oxy]carbonyl}(methyl)amino]ethyl}-1,2,4-oxadiazol-5-yl)-2-methyl-1,2,3,4-tetrahydro-4-quinolinyl]carbamate (for a preparation, see Intermediate 68) (4.125 g, 8.00 mmol) in 1,4-dioxane (0.5 mL) at room temperature was added HCl (4N in 1,4-dioxane, 2 mL, 8.00 mmol) and the resulting mixture was stirred at this temperature for 3 h then was left standing at 4° C. for 16 h before being warmed to room temperature. The residue was triturated with Et₂O then purified using MDAP (modifier: ammonium bicarbonate). The residue obtained was dissolved in 1,4-dioxane (2 mL) and treated with HCl (4N in 1,4-dioxane, 1 mL). The resulting mixture was concentrated in vacuo and the residue triturated with Et₂O to give 1-methylethyl((2S,4R)-1-acetyl-2-methyl-6-{3-[2-(methylamino)ethyl]-1,2,4-oxadiazol-5-yl}-1,2,3,4-tetrahydro-4-quinolinyl)carbamate hydrochloride (14 mg, 0.031 mmol, 0.387% yield) as a colourless solid.

LCMS (method A): Retention time 0.83 min, [M+H]+= 416.14

Example 72

1-Methylethyl[(2S,4R)-1-acetyl-6-(4-aminophenyl)-2-methyl-1,2,3,4-tetrahydro-4-quinolinyl]carbamate

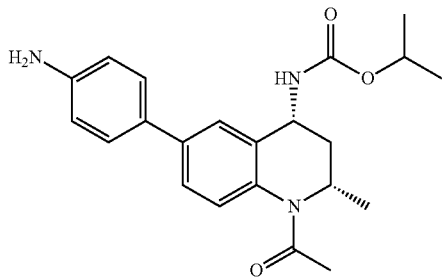

A flask was charged with 1-methylethyl[(2S,4R)-1-acetyl-6-bromo-2-methyl-1,2,3,4-tetrahydro-4-quinolinyl]carbamate (for a preparation, see example 4) (739 mg, 2 mmol), [4-(4,4,5,5-tetramethyl-1,3,2-dioxaborolan-2-yl)phenyl]amine (570 mg, 2.60 mmol), potassium carbonate (691 mg, 5.00 mmol) and [1,1'-bis(diphenylphosphino)ferrocene]dichloropalladium(II) (146 mg, 0.200 mmol) then filled with 1,4-dioxane (9 mL) and water (3 mL) and purged with nitrogen. The mixture was stirred under microwave irradiation for 30 min at 120° C. then cooled to room temperature. Most of the 1,4-dioxane was removed in vacuo and the residue was partitioned between water and AcOEt. The layers were separated and the aqueous phase extracted twice with AcOEt. The combined organic phases were washed twice with brine, dried over MgSO₄ and concentrated in vacuo. Purification of the residue by SP4 using a 25 G silica cartridge (gradient: 13 to 63% AcOEt in Hexanes) gave 1-methylethyl[(2S,4R)-1-acetyl-6-(4-aminophenyl)-2-methyl-1,2,3,4-tetrahydro-4-quinolinyl]carbamate (660 mg, 1.730 mmol, 87% yield) as a pale yellow foam.

LCMS (method A): Retention time 0.92 min, [M+H]+= 382.19

Example 73

1-Methylethyl((2S,4R)-1-acetyl-2-methyl-6-{4-[(2-oxo-1-piperazinyl)methyl]phenyl}-1,2,3,4-tetrahydro-4-quinolinyl)carbamate hydrochloride

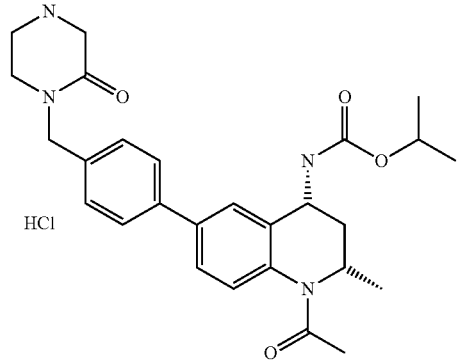

To a solution of 1,1-dimethylethyl 4-({4-[(2S,4R)-1-acetyl-2-methyl-4-({[(1-methylethyl)oxy]carbonyl}amino)-1,2,3,4-tetrahydro-6-quinolinyl]phenyl}methyl)-3-oxo-1-piperazinecarboxylate (for a preparation, see Intermediate 71) (180 mg, 0.311 mmol) in 1,4-dioxane (2 mL) was added HCl (4N in 1,4-dioxane, 2 mL, 8.00 mmol) and the resulting mixture was stirred at room temperature for 2 h then concentrated in vacuo. The residue was purified by MDAP (modifier: ammonium bicarbonate) and the adduct obtained was dissolved in 1,4-dioxane (2 mL) and treated with HCl (4N in Et₂O, 1 mL). The mixture was concentrated in vacuo to give 1-methylethyl((2S,4R)-1-acetyl-2-methyl-6-{4-[(2-oxo-1-piperazinyl)methyl]phenyl}-1,2,3,4-tetrahydro-4-quinolinyl)carbamate hydrochloride (160 mg, 0.311 mmol, 100% yield) as a white solid.

LCMS (method A): Retention time 0.82 min, [M+H]+= 479.16

Example 74

1-Methylethyl {(2S,4R)-1-acetyl-6-[1-(3-aminopropyl)-1H-1,2,3-triazol-4-yl]-2-methyl-1,2,3,4-tetrahydro-4-quinolinyl}carbamate hydrochloride

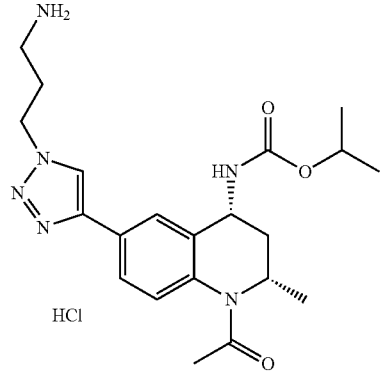 [SMILES: CC(=O)N1c2ccc(-c3cn(CCCN)nn3)cc2[C@H](NC(=O)OC(C)C)C[C@@H]1C ; Cl]

A solution of 1-methylethyl((2S,4R)-1-acetyl-6-{1-[3-({[(1,1-dimethylethyl)oxy]carbonyl}amino)propyl]-1H-1,2,3-triazol-4-yl}-2-methyl-1,2,3,4-tetrahydro-4-quinolinyl)carbamate (for a preparation, see Intermediate 73) (543 mg, 1.055 mmol) in 1,4-dioxane (1 mL) was treated with HCl (4N in 1,4-dioxane, 4.00 mL, 16 mmol) and the resulting mixture was stirred for 2 h at room temperature then concentrated in vacuo. The residue was co-evaporated twice with toluene then triturated with Et₂O and filtered off to give 1-methylethyl {(2S,4R)-1-acetyl-6-[1-(3-aminopropyl)-1H-1,2,3-triazol-4-yl]-2-methyl-1,2,3,4-tetrahydro-4-quinolinyl}carbamate hydrochloride (370 mg, 0.771 mmol, 73% yield) as a brown solid.

LCMS (method A): Retention time 0.59 min, [M+H]+= 415.22

Example 75

1-Methylethyl {(2S,4R)-1-acetyl-6-[1-(2-hydroxyethyl)-1H-1,2,3-triazol-4-yl]-2-methyl-1,2,3,4-tetrahydro-4-quinolinyl}carbamate

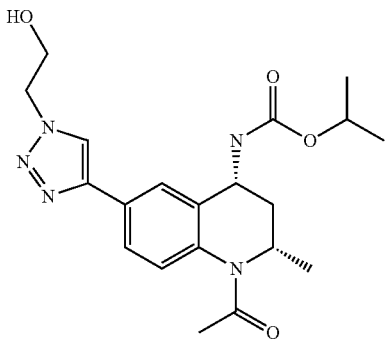 [SMILES: CC(=O)N1c2ccc(-c3cn(CCO)nn3)cc2[C@H](NC(=O)OC(C)C)C[C@@H]1C]

To a solution of 1-methylethyl[(2S,4R)-1-acetyl-6-ethynyl-2-methyl-1,2,3,4-tetrahydro-4-quinolinyl]carbamate (for a preparation, see Intermediate 58) (100 mg, 0.318 mmol) in a mixture of N,N-dimethylformamide (DMF) (1.8 mL) and methanol (0.200 mL) were successively added 2-azidoethanol (55.4 mg, 0.636 mmol) and copper(I) iodide (3.03 mg, 0.016 mmol). The resulting mixture was stirred at 100° C. under microwave irradiation for 2 h then cooled to room temperature. The reaction mixture was partitioned between EtOAc and brine and the layers were separated. The aqueous phase was extracted with EtOAc (3×) and the combined organic layers were washed with brine, dried over a Na₂SO₄ cartridge and concentrated in vacuo. Purification of the residue on SP4 using a 10 G silica cartridge (gradient: 2 to 10% MeOH in DCM) gave 1-methylethyl {(2S,4R)-1-acetyl-6-[1-(2-hydroxyethyl)-1H-1,2,3-triazol-4-yl]-2-methyl-1,2,3,4-tetrahydro-4-quinolinyl}carbamate (83 mg, 0.198 mmol, 62%) as an off white solid.

LCMS (method A): Retention time 0.69 min, [M+H]+= 402.16

Example 76

{4-[(2S,4R)-1-Acetyl-2-methyl-4-({[(1-methylethyl)oxy]carbonyl}amino)-1,2,3,4-tetrahydro-6-quinolinyl]-1H-1,2,3-triazol-1-yl}acetic acid

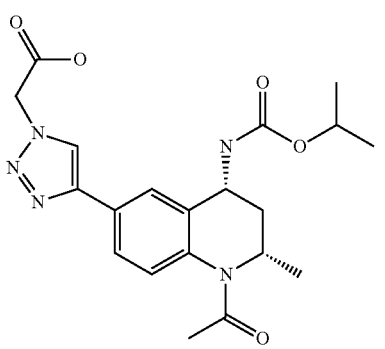 [SMILES: CC(=O)N1c2ccc(-c3cn(CC(=O)O)nn3)cc2[C@H](NC(=O)OC(C)C)C[C@@H]1C]

To a solution of methyl {4-[(2S,4R)-1-acetyl-2-methyl-4-({[(1-methylethyl)oxy]carbonyl}amino)-1,2,3,4-tetrahydro-6-quinolinyl]-1H-1,2,3-triazol-1-yl}acetate (for a preparation, see Intermediate 75) (250 mg, 0.582 mmol) in methanol (5 mL) was added a 2M NaOH aqueous solution (0.873 mL, 1.746 mmol). The reaction mixture was stirred at 50° C. for 1 hour, then cooled to room temperature and concentrated in vacuo. The residue was partitioned between AcOEt and a 2M NaOH aqueous solution. The layers were separated and the organic phase was further extracted with a 2M NaOH aqueous solution. The combined aqueous layers were acidified to pH=3 using a 2M HCl aqueous solution. then extracted with EtOAc (3×). The combined organic layers were washed with brine, dried over a Na₂SO₄ cartridge and concentrated in vacuo to give {4-[(2S,4R)-1-acetyl-2-methyl-4-({[(1-methylethyl)oxy]carbonyl}amino)-1,2,3,4-tetrahydro-6-quinolinyl]-1H-1,2,3-triazol-1-yl}acetic acid (245 mg, 0.566 mmol, 97%) as a white solid.

LCMS (method A): Retention time 0.67 min, [M+H]+= 416.3

Example 77

1-Methylethyl {(2S,4R)-1-acetyl-6-[5-(2-aminoethyl)-1,2,4-oxadiazol-3-yl]-2-methyl-1,2,3,4-tetrahydro-4-quinolinyl}carbamate hydrochloride

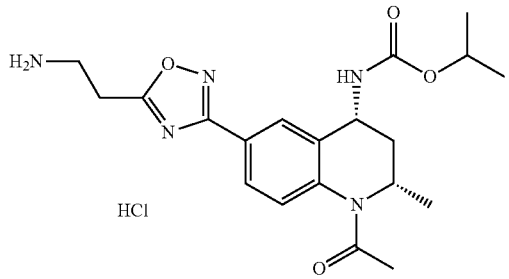 [SMILES: CC(=O)N1c2ccc(-c3noc(CCN)n3)cc2[C@H](NC(=O)OC(C)C)C[C@@H]1C ; Cl]

A solution of 1-methylethyl((2S,4R)-1-acetyl-6-{5-[2-({[(1,1-dimethylethyl)oxy]carbonyl}amino)ethyl]-1,2,4-oxadiazol-3-yl}-2-methyl-1,2,3,4-tetrahydro-4-quinolinyl)carbamate (for a preparation, see Intermediate 76) (260 mg, 0.518 mmol) in 1,4-Dioxane (1 mL) was treated with HCl (4N in 1,4-dioxane, 1.00 mL, 4 mmol) and the resulting mixture was stirred at room temperature for 16 h. Et₂O (10 mL) was then added and the precipitate formed was triturated then filtered off to give 1-methylethyl {(2S,4R)-1-acetyl-6-[5-(2-aminoethyl)-1,2,4-oxadiazol-3-yl]-2-methyl-1,2,3,4-tetrahydro-4-quinolinyl}carbamate hydrochloride (195 mg, 0.446 mmol, 86%) as an off white solid.

LCMS (method G): Retention time 0.59 min, [M+H]+= 402.10

Example 78

1-Methylethyl((2S,4R)-1-acetyl-6-{5-[2-(dimethylamino)ethyl]-1,2,4-oxadiazol-3-yl}-2-methyl-1,2,3,4-tetrahydro-4-quinolinyl)carbamate hydrochloride

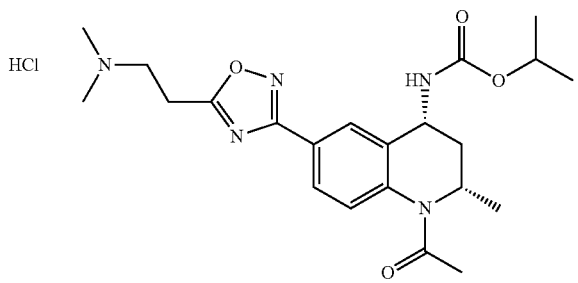 [SMILES: Cl ; CC(=O)N1c2ccc(-c3noc(CCN(C)C)n3)cc2[C@H](NC(=O)OC(C)C)C[C@@H]1C]

A flask was charged with 1-methylethyl {(2S,4R)-1-acetyl-6-[5-(2-aminoethyl)-1,2,4-oxadiazol-3-yl]-2-methyl-1,2,3,4-tetrahydro-4-quinolinyl}carbamate hydrochloride (for a preparation see Example 77) (75 mg, 0.17 mmol) then filled with formic acid (0.5 mL) and 37% w/w aqueous formaldehyde solution (0.5 mL). The reaction mixture was heated at 110° C. for 15 min under microwave irradiation then cooled to room temperature. The reaction mixture was diluted with AcOEt (10 mL) and washed with a saturated NaHCO₃ aqueous solution (×2). The organic phase was dried over MgSO₄ then concentrated in vacuo. Purification of the residue by flash chromatography on silica gel (gradient: 0 to 6% MeOH in DCM) provided a product which was then treated with 1M HCl in Et₂O (0.25 mL). The solvent was evaporated to give 1-methylethyl((2S,4R)-1-acetyl-6-{5-[2-(dimethylamino)ethyl]-1,2,4-oxadiazol-3-yl}-2-methyl-1,2,3,4-tetrahydro-4-quinolinyl)carbamate hydrochloride (25 mg, 0.054 mmol, 31%) as a colourless solid.

LCMS (method G): Retention time 0.62 min, [M+H]+= 430.1

Example 79

1-Methylethyl {(2S,4R)-1-acetyl-6-[1-(2-aminoethyl)-1H-1,2,3-triazol-4-yl]-2-methyl-1,2,3,4-tetrahydro-4-quinolinyl}carbamate hydrochloride

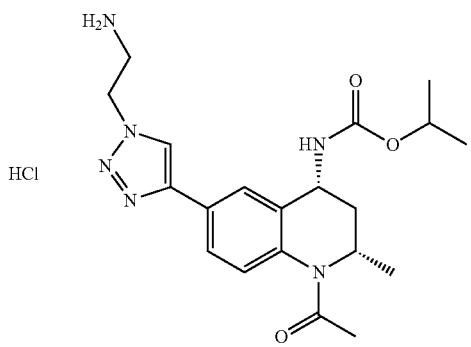 [SMILES: Cl ; CC(=O)N1c2ccc(-c3cn(CCN)nn3)cc2[C@H](NC(=O)OC(C)C)C[C@@H]1C]

HCl (4M in 1,4-dioxane, 2 mL, 8 mmol) was added to a solution of 1-methylethyl((2S,4R)-1-acetyl-6-{1-[2-({[(1,1-dimethylethyl)oxy]carbonyl}amino)ethyl]-1H-1,2,3-triazol-4-yl}-2-methyl-1,2,3,4-tetrahydro-4-quinolinyl)carbamate (for a preparation, see intermediate 77) (108 mg, 0.22 mmol) in 1,4-dioxane (0.5 mL). The mixture was stirred at room temperature for 16 h. Et₂O (5 mL) was added and the mixture stirred for 1 h. The solid formed was filtered off, washed with Et₂O and dried under house vacuum to give 1-methylethyl {(2S,4R)-1-acetyl-6-[1-(2-aminoethyl)-1H-1,2,3-triazol-4-yl]-2-methyl-1,2,3,4-tetrahydro-4-quinolinyl}carbamate hydrochloride (75 mg, 0.172 mmol, 80%) as a colourless solid. LCMS (method G): Retention time 0.55 min, [M+H]+= 401.1

Example 80

1-Methylethyl((2S,4R)-1-acetyl-6-{1-[2-(dimethylamino)ethyl]-1H-1,2,3-triazol-4-yl}-2-methyl-1,2,3,4-tetrahydro-4-quinolinyl)carbamate formate salt

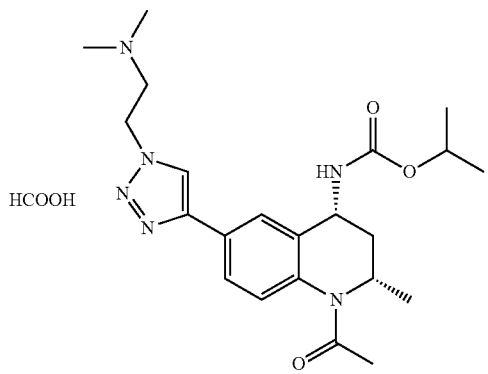 [SMILES: "HCOOH" ; CC(=O)N1c2ccc(-c3cn(CCN(C)C)nn3)cc2[C@H](NC(=O)OC(C)C)C[C@@H]1C]

A flask was charged with 1-methylethyl {(2S,4R)-1-acetyl-6-[1-(2-aminoethyl)-1H-1,2,3-triazol-4-yl]-2-methyl-1,2,3,4-tetrahydro-4-quinolinyl}carbamate hydrochloride (for a preparation see Example 79) (30 mg, 0.075 mmol) then filled with formic acid (0.5 mL) and 37% w/w aqueous formaldehyde solution (0.5 mL). The reaction mixture was heated at 110° C. for 15 min under microwave irradiation then cooled to room temperature. The reaction mixture was diluted with AcOEt (10 mL) and washed with a saturated NaHCO₃ aqueous solution (×2). The organic phase was dried over MgSO₄ then concentrated in vacuo. Purification of the residue by MDAP (modifier: formic acid) gave 1-methylethyl((2S,4R)-1-acetyl-6-{1-[2-(dimethylamino)ethyl]-1H-1,2,3-triazol-4-yl}-2-methyl-1,2,3,4-tetrahydro-4-quinolinyl)carbamate formate salt (17 mg, 0.036 mmol, 48%) as a colourless glass. LCMS (method A): Retention time 0.59 min, [M+H]+=429.19

Example 81

1-Methylethyl((2S,4R)-1-acetyl-6-{1-[3-(dimethylamino)propyl]-1H-1,2,3-triazol-4-yl}-2-methyl-1,2,3,4-tetrahydro-4-quinolinyl)carbamate formate salt

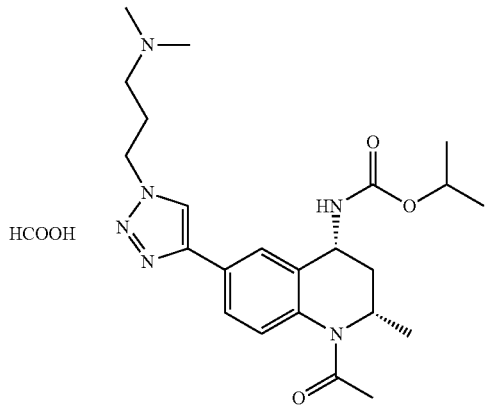 [SMILES: "HCOOH" ; CC(=O)N1c2ccc(-c3cn(CCCN(C)C)nn3)cc2[C@H](NC(=O)OC(C)C)C[C@@H]1C]

A flask was charged with 1-methylethyl {(2S,4R)-1-acetyl-6-[1-(3-aminopropyl)-1H-1,2,3-triazol-4-yl]-2-methyl-1,2,3,4-tetrahydro-4-quinolinyl}carbamate hydrochloride (for a preparation see Example 74) (40 mg, 0.097 mmol) then filled with formic acid (0.5 mL) and 37% w/w aqueous formaldehyde solution (0.5 mL). The reaction mixture was heated at 110° C. for 15 min under microwave irradiation then cooled to room temperature. The reaction mixture was diluted with AcOEt (10 mL) and washed with a saturated NaHCO₃ aqueous solution (×2). The organic phase was dried over MgSO₄ then concentrated in vacuo. Purification of the residue by MDAP (modifier: formic acid) gave 1-methylethyl ((2S,4R)-1-acetyl-6-{1-[3-(dimethylamino)propyl]-1H-1,2,3-triazol-4-yl}-2-methyl-1,2,3,4-tetrahydro-4-quinolinyl) carbamate formate salt (18 mg, 0.037 mmol, 38%) as a colourless glass. LCMS (method A): Retention time 0.60 min, [M+H]+=443.12

Example 82

1-Methylethyl[(2S,4R)-1-acetyl-2-methyl-6-(1-methyl-1H-imidazol-5-yl)-1,2,3,4-tetrahydro-4-quinolinyl]carbamate

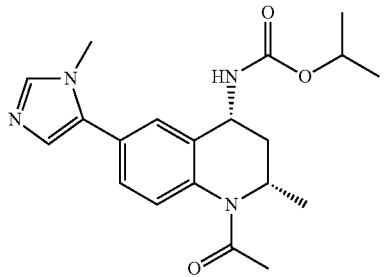 [SMILES: CC(=O)N1c2ccc(-c3cncn3C)cc2[C@H](NC(=O)OC(C)C)C[C@@H]1C]

A mixture of 1-methyl-5-(tributylstannyl)-1H-imidazole (200 mg, 0.54 mmol), 1-methylethyl [(2S,4R)-1-acetyl-6-bromo-2-methyl-1,2,3,4-tetrahydro-4-quinolinyl]carbamate (for a preparation, see Example 4) (199 mg, 0.54 mmol) and tetrakis(triphenylphosphine)palladium(0) (31 mg, 0.027 mmol) in dry, degassed DMF (5 mL) was stirred at 140° C. under nitrogen for 16 h then was cooled to room temperature and diluted with AcOEt (20 mL). The solution was washed with water (×2) then brine. The organic phase was dried over MgSO₄ and concentrated in vacuo. Purification of the residue by flash chromatography on silica gel (gradient: 0 to 6% MeOH in DCM) gave 1-methylethyl[(2S,4R)-1-acetyl-2-methyl-6-(1-methyl-1H-imidazol-5-yl)-1,2,3,4-tetrahydro-4-quinolinyl]carbamate (27 mg, 0.073 mmol, 13%) as a colourless solid after trituration with AcOEt/hexane. LCMS (method G): Retention time 0.59 min, [M+H]+=402.1

Example 83

1-Methylethyl[(2S,4R)-1-acetyl-2-methyl-6-(1-methyl-1H-imidazol-4-yl)-1,2,3,4-tetrahydro-4-quinolinyl]carbamate hydrochloride

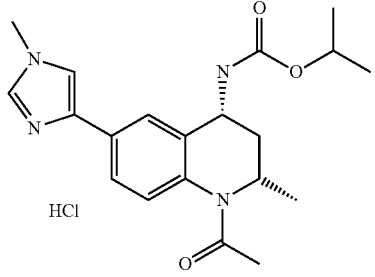

A mixture of 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation, see Intermediate 52) (150 mg, 0.36 mmol), 4-bromo-1-methylimidazole (0.43 mmol), tetrakis(triphenylphosphine) palladium(0) (42 mg, 10 mol %) and potassium carbonate (199 mg, 1.44 mmol) in toluene (2 mL) and ethanol (2 mL) was refluxed for 16 h then cooled to room temperature and concentrated in vacuo. The residue was partitioned between AcOEt (10 mL) and water (10 mL) and the layers were separated. The organic phase was dried over MgSO₄ and concentrated in vacuo. Purification of the residue by flash chromatography on silica gel (gradient: 0 to 6% MeOH in DCM) gave a residue which was treated with 1M HCl in Et₂O (0.5 mL, slight excess). The solvent was evaporated and the residue triturated with Et₂O to give 1-methylethyl[(2S,4R)-1-acetyl-2-methyl-6-(1-methyl-1H-imidazol-4-yl)-1,2,3,4-tetrahydro-4-quinolinyl]carbamate hydrochloride (8 mg, 0.02 mmol, 5%) as a colourless solid.

LCMS (method G): Retention time 0.56 min, [M+H]+=371.1

Example 84

1-Methylethyl[(2S,4R)-1-acetyl-2-methyl-6-(4-methyl-1H-imidazol-1-yl)-1,2,3,4-tetrahydro-4-quinolinyl]carbamate

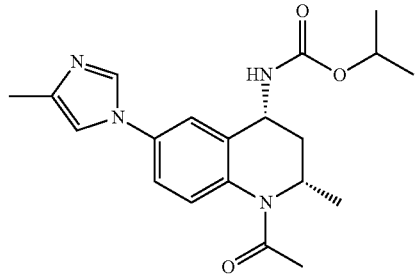 [SMILES: CC(=O)N1c2ccc(-n3cnc(C)c3)cc2[C@H](NC(=O)OC(C)C)C[C@@H]1C]

A stock solution of tert-butanol (5 mL) and water (10 μl) was prepared and degassed under house vacuum and quenched several times with nitrogen. A mixture of palladium (II) acetate (6 mg, 5 mmol) and Xantphos (38 mg, 0.081 mmol) in the stock solvent (4 mL) was heated at 80° C. for 1 min under microwave irradiation then cooled to room temperature. The solution was then added to a mixture of 4-methylimidazole (53 mg, 0.65 mmol), 1-methylethyl[(2S,4R)-1-acetyl-6-bromo-2-methyl-1,2,3,4-tetrahydro-4-quinolinyl]carbamate (for a preparation, see Example 4) (200 mg, 0.54 mmol) and potassium carbonate (112 mg, 0.81 mmol). The resulting mixture was stirred at 110° C. for 15 h under microwave irradiation then cooled to room temperature and the insoluble were filtered off. Most of the solvents were removed in vacuo. Purification of the residue by flash chromatography on silica gel (gradient: 0 to 6% MeOH in DCM) gave 1-methylethyl [(2S,4R)-1-acetyl-2-methyl-6-(4-methyl-1H-imidazol-1-yl)-1,2,3,4-tetrahydro-4-quinolinyl]carbamate (3 mg, 0.0081 mmol, 1.5%)

LCMS (method G): Retention time 0.58 min, [M+H]+=371.1

Example 84

Alternative Procedure

1-Methylethyl[(2S,4R)-1-acetyl-2-methyl-6-(4-methyl-1H-imidazol-1-yl)-1,2,3,4-tetrahydro-4-quinolinyl]carbamate A mixture of palladium(II) acetate (60 mg, 0.267 mmol) and Xantphos (380 mg, 0.797 mmol) in t-butanol (50 mL) and water (100 μL) was heated at 90° C. for 5 min. The hot solution was then added to a mixture of 4-methylimidazole (530 mg, 6.46 mmol), 1-methylethyl[(2S,4R)-1-acetyl-6-bromo-2-methyl-1,2,3,4-tetrahydro-4-quinolinyl]carbamate (for a preparation, see Example 4) (2.0 g, 5.4 mmol) and potassium carbonate (1.12 g, 8.1 mmol). The resulting mixture was refluxed for 24 h then cooled to room temperature and the insoluble were filtered off. Most of the solvents were removed in vacuo. Purification of the residue by flash chromatography on silica gel (gradient: 0 to 6% MeOH in DCM) gave 1-methylethyl[(2S,4R)-1-acetyl-2-methyl-6-(4-methyl-1H-imidazol-1-yl)-1,2,3,4-tetrahydro-4-quinolinyl]carbamate (189 mg, 0.51 mmol, 9%)

LCMS (method G): Retention time 0.58 min, [M+H]+= 371.1

Example 85

1-Methylethyl {(2S,4R)-1-acetyl-6-[1-(2-aminoethyl)-1H-imidazol-4-yl]-2-methyl-1,2,3,4-tetrahydro-4-quinolinyl}carbamate hydrochloride

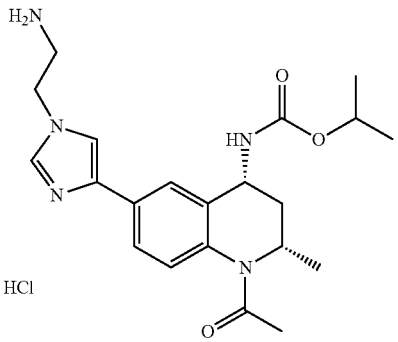 [SMILES: Cl ; CC(=O)N1c2ccc(-c3cn(CCN)cn3)cc2[C@H](NC(=O)OC(C)C)C[C@@H]1C]

A solution of 1-methylethyl((2S,4R)-1-acetyl-6-{1-[2-({[(1,1-dimethylethyl)oxy]carbonyl}amino)ethyl]-1H-imidazol-4-yl}-2-methyl-1,2,3,4-tetrahydro-4-quinolinyl)carbamate (for a preparation, see Intermediate 79) (47 mg, 0.094 mmol) in 1,4-dioxane (0.5 mL) was treated with HCl (4M in 1,4-dioxane, 2 mL, 8 mmol) and the resulting mixture was stirred at room temperature for 4 h. Et₂O (10 mL) was added and the resulting mixture stirred for 15 min. The solid formed was filtered off, washed with Et₂O and dried under house vacuum to give 1-methylethyl {(2S,4R)-1-acetyl-6-[1-(2-aminoethyl)-1H-imidazol-4-yl]-2-methyl-1,2,3,4-tetrahydro-4-quinolinyl}carbamate hydrochloride (25 mg, 0.057 mmol, 61%) as a brown solid.

LCMS (method G): Retention time 0.45 min, [M+H]+= 400.0

Example 86

1-Methylethyl[(2S,4R)-1-acetyl-6-(1H-imidazol-2-yl)-2-methyl-1,2,3,4-tetrahydro-4-quinolinyl]carbamate

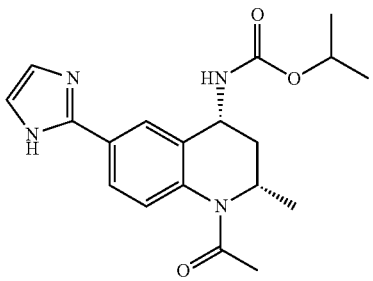 [SMILES: CC(=O)N1c2ccc(-c3ncc[nH]3)cc2[C@H](NC(=O)OC(C)C)C[C@@H]1C]

Sodium hydride (60% in mineral oil, 50 mg, 1.25 mmol) was added portionwise to a stirred solution of 1-methylethyl [(2S,4R)-1-acetyl-6-cyano-2-methyl-1,2,3,4-tetrahydro-4-quinolinyl]carbamate (for a preparation see Intermediate 57) (350 mg, 1.1 mmol) in dry methanol (10 mL). The resulting mixture was stirred at room temperature for 48 h then was treated with aminoacetaldehyde dimethyl acetaldehyde (233 mg, 2.2 mmol) and acetic acid (1 mL, excess). The resulting mixture was refluxed for 2 h then was cooled to room temperature and treated with HCl (1M in water, 5 mL). The resulting mixture was refluxed for 1 h, cooled to room temperature and most of the methanol was removed in vacuo. The residue was diluted with water (10 mL) and basified by the addition of solid potassium carbonate (CARE: gas evolved). The resulting aqueous phase was extracted with AcOEt (3×10 mL). The combined organic phases were washed with brine, dried over MgSO₄ and concentrated in vacuo. Purification of the residue by flash chromatography on silica gel (gradient: 0 to 6% MeOH in DCM) followed by trituration of the adduct obtained with Et₂O gave 1-methylethyl[(2S,4R)-1-acetyl-6-(1H-imidazol-2-yl)-2-methyl-1,2,3,4-tetrahydro-4-quinolinyl]carbamate (14 mg, 0.039 mmol, 3.5%) as an off white solid.

LCMS (method G): Retention time 0.54 min, [M+H]+= 357.0

Example 87

1-[(Cis)-1-acetyl-2-methyl-4-({[(1-methylethyl)oxy]carbonyl}amino)-1,2,3,4-tetrahydro-6-quinolinyl]-1H-imidazole-4-carboxylic acid

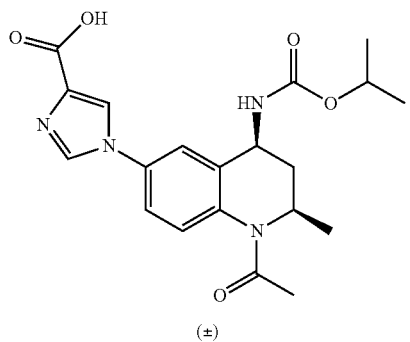 [SMILES: CC(=O)N1c2ccc(-n3cnc(C(=O)O)c3)cc2[C@@H](NC(=O)OC(C)C)C[C@H]1C]

A mixture of ethyl 1-[(cis)1-acetyl-2-methyl-4-({[(1-methylethyl)oxy]carbonyl}amino)-1,2,3,4-tetrahydro-6-quinolinyl]-1H-imidazole-4-carboxylate (for a preparation see Intermediate 82) (1.8 g, 4.2 mmol), methanol (15 mL), and lithium hydroxide (1M in water, 15 mL) was stirred at room temperature for 6 h then most of the methanol was removed in vacuo. The residue was diluted with water (15 mL) and acidified with glacial acetic acid. The resulting aqueous phase was extracted with AcOEt (3×30 mL). The combined organic phases were washed with brine, dried over MgSO₄ and concentrated in vacuo to give 1-[(cis)-1-acetyl-2-methyl-4-({[(1-methylethyl)oxy]carbonyl}amino)-1,2,3,4-tetrahydro-6-quinolinyl]-1H-imidazole-4-carboxylic acid (1.1 g, 2.75 mmol, 65%) as a colourless solid.

LCMS (method G): Retention time 0.62 min, [M+H]+= 401.1

Example 88

1-Methylethyl[(2S,4R)-1-acetyl-2-methyl-6-(2-methyl-1H-imidazol-1-yl)-1,2,3,4-tetrahydro-4-quinolinyl]carbamate

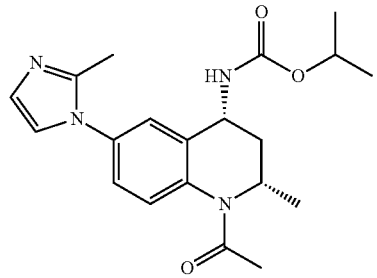 [SMILES: CC(=O)N1c2ccc(-n3ccnc3C)cc2[C@H](NC(=O)OC(C)C)C[C@@H]1C]

A mixture of 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 52) (500 mg, 1.2 mmol), 2-methylimidazole (99 mg, 1.2 mmol) and copper(I) oxide (10 mg, 0.126 mmol) in methanol (10 mL) was stirred in air at room temperature for 24 h. A further portion of copper(I) oxide (10 mg, 0.126 mmol) was added and stirring was continued for 48 h. The reaction mixture was then filtered through celite and most of the solvent were removed in vacuo. Purification of the residue by flash chromatography on silica gel (gradient: 0 to 5% MeOH in DCM) gave 1-methylethyl[(2S,4R)-1-acetyl-2-methyl-6-(2-methyl-1H-imidazol-1-yl)-1,2,3,4-tetrahydro-4-quinolinyl]carbamate (167 mg, 0.451 mmol, 37%) as a colourless foam.

LCMS (method G): Retention time 0.55 min, [M+H]+= 371.3

Example 89

1-Methylethyl {(cis)-1-acetyl-6-[4-(hydroxymethyl)-1H-imidazol-1-yl]-2-methyl-1,2,3,4-tetrahydro-4-quinolinyl}carbamate

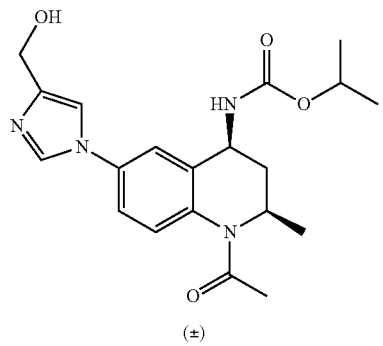 [SMILES: CC(=O)N1c2ccc(-n3cnc(CO)c3)cc2[C@@H](NC(=O)OC(C)C)C[C@H]1C]

A solution of ethyl 1-[(cis)-1-acetyl-2-methyl-4-({[(1-methylethyl)oxy]carbonyl}amino)-1,2,3,4-tetrahydro-6-quinolinyl]-1H-imidazole-4-carboxylate (for a preparation see Example 90) (857 mg, 2 mmol) in dry THF (10 mL) was cooled to 0° C. and treated with 2M lithium borohydride in THF (2 mL, 4 mmol). The reaction mixture was stirred at room temperature for 8 h then was partitioned between AcOEt (10 mL) and a saturated NH4Cl aqueous solution (10 mL). The layers were separated. The aqueous phase was extracted with AcOEt (2×10 mL). The combined organic phases were dried over MgSO4 and concentrated in vacuo. Purification of the residue by flash chromatography on silica gel (gradient: 0 to 10% MeOH in DCM) gave 1-methylethyl {(cis)-1-acetyl-6-[4-(hydroxymethyl)-1H-imidazol-1-yl]-2-methyl-1,2,3,4-tetrahydro-4-quinolinyl}carbamate (440 mg, 1.139 mmol, 57%) as a colourless foam.

LCMS (method A): Retention time 0.54 min, [M+H]+= 387.21

Example 90

{4-[(Cis)-1-acetyl-2-methyl-4-({[(1-methylethyl)oxy]carbonyl}amino)-1,2,3,4-tetrahydro-6-quinolinyl]-1H-imidazol-1-yl}acetic acid trifluoroacetate

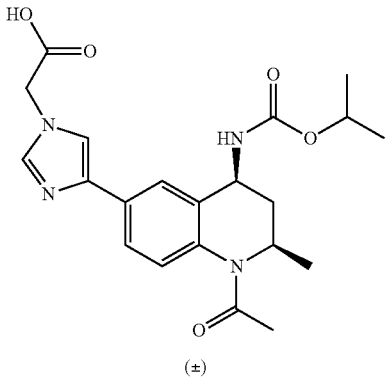 [SMILES: CC(=O)N1c2ccc(-c3cn(CC(=O)O)cn3)cc2[C@@H](NC(=O)OC(C)C)C[C@H]1C]

Trifluoracetic acid (1 mL) was added at room temperature to a solution of 1,1-dimethylethyl {(cis)-4-[1-acetyl-2-methyl-4-({[(1-methylethyl)oxy]carbonyl}amino)-1,2,3,4-tetrahydro-6-quinolinyl]-1H-imidazol-1-yl}acetate (for a preparation see Example 91) (1.26 g, 2.68 mmol) in DCM (5 mL). The reaction mixture was allowed to stand at room temperature for 16 h then concentrated in vacuo. The residue was co-evaporated twice with toluene then triturated with Et2O to give {4-[(cis)-1-acetyl-2-methyl-4-({[(1-methylethyl)oxy]carbonyl}amino)-1,2,3,4-tetrahydro-6-quinolinyl]-1H-imidazol-1-yl}acetic acid trifluoroacetate (1.19 g, 2.252 mmol, 84%) as an off-white solid.

LCMS (method G): Retention time 0.56 min, [M+H]+= 415.3

Example 91

1,1-Dimethylethyl 3-{-(cis)-4-[1-acetyl-2-methyl-4-({[(1-methylethyl)oxy]carbonyl}amino)-1,2,3,4-tetrahydro-6-quinolinyl]-1H-imidazol-1-yl}propanoate

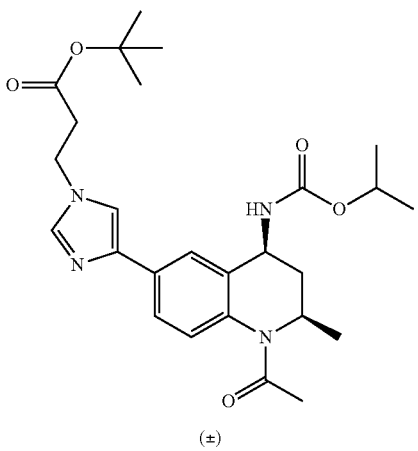 [SMILES: CC(=O)N1c2ccc(-c3cn(CCC(=O)OC(C)(C)C)cn3)cc2[C@@H](NC(=O)OC(C)C)C[C@H]1C]

A solution of 1,1-dimethylethyl 3-{-4-[2-methyl-4-({[(1-methylethyl)oxy]carbonyl}amino)-1,2,3,4-tetrahydro-6- quinolinyl]-1H-imidazol-1-yl}propanoate (for a preparation see Intermediate 93) (1.46 g, 3.3 mmol) in acetic anhydride (3 mL) was allowed to stand at room temperature for 16 h then most of the solvent was removed in vacuo. The residue was co-evaporated twice with toluene. Its purification by flash chromatography on silica gel (gradient: 0 to 2% MeOH in DCM) gave 1,1-dimethylethyl 3-{(cis)-4-[1-acetyl-2-methyl-4-({[(1-methylethyl)oxy]carbonyl}amino)-1,2,3,4-tetrahydro-6-quinolinyl]-1H-imidazol-1-yl}propanoate (1.055 g, 2.177 mmol, 66%) as a colourless solid.

LCMS (method A): Retention time 0.80 min, [M+H]+= 485.25

Example 92

1-Methylethyl[(cis)-1-acetyl-6-(4-{[(2-hydroxyethyl)amino]methyl}-1H-imidazol-1-yl)-2-methyl-1,2,3,4-tetrahydro-4-quinolinyl]carbamate

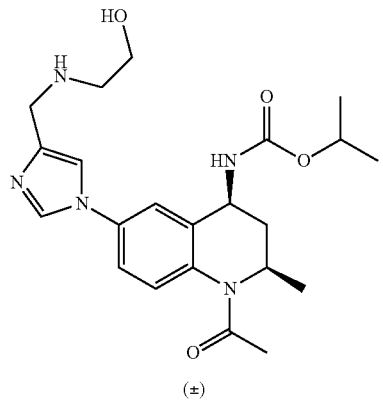 [SMILES: CC(=O)N1c2ccc(-n3cnc(CNCCO)c3)cc2[C@@H](NC(=O)OC(C)C)C[C@H]1C]

(±)

Dess-Martin periodinane (132 mg, 0.31 mmol) was added portionwise to a stirred suspension of 1-methylethyl {(cis)-1-acetyl-6-[4-(hydroxymethyl)-1H-imidazol-1-yl]-2-methyl-1,2,3,4-tetrahydro-4-quinolinyl}carbamate (for a preparation see example 89) (100 mg, 0.26 mmol) in DCM (5 mL) and the resulting mixture was stirred at room temperature for 30 min. 5 mL of a saturated NaHCO₃ aqueous solution was added and the mixture stirred for 15 min. The layers were separated and the aqueous phase was extracted with DCM (5 mL). The combined organic phases (DCM+AcOEt) were dried over MgSO₄ and concentrated in vacuo. The residue was dissolved in DCM (5 mL) and Methanol (1 mL). Ethanolamine (63 mg, 1.03 mmol) and glacial acetic acid (15 mg, 15 µl, 0.26 mmol) were added. The reaction mixture was stirred at room temperature for 30 min then sodium triacetoxyborohydride (110 mg, 0.52 mmol) was added. The resulting mixture was stirred at room temperature for 16 h then treated with a saturated NaHCO₃ aqueous solution. The layers were separated and the organic phase was washed with water, dried over MgSO₄ and concentrated in vacuo. The residue was purified by MDAP (modifier: formic acid). The appropriate fractions were collected and concentrated in vacuo. The residue obtained was dissolved in water and the aqueous layer was basified with K₂CO₃ then extracted with DCM (4×10 mL). The combined organic phases were dried over MgSO₄ and concentrated in vacuo to give 1-methylethyl [(cis)-1-acetyl-6-(4-{[(2-hydroxyethyl)amino]methyl}-1H-imidazol-1-yl)-2-methyl-1,2,3,4-tetrahydro-4-quinolinyl] carbamate (13 mg, 0.030 mmol, 12%) as a colourless foam.

LCMS (method G): Retention time 0.55 min, [M+H]+= 430.4

Example 93

1-Methylethyl[(2S,4R)-1-acetyl-2-methyl-6-(2-methylphenyl)-1,2,3,4-tetrahydro-4-quinolinyl]carbamate

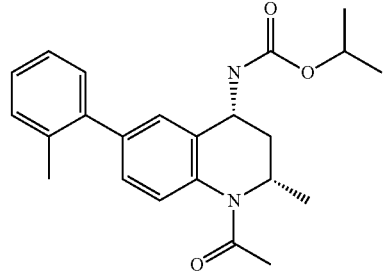 [SMILES: CC(=O)N1c2ccc(-c3ccccc3C)cc2[C@H](NC(=O)OC(C)C)C[C@@H]1C]

A mixture of 1-methylethyl[(2S,4R)-1-acetyl-6-bromo-2-methyl-1,2,3,4-tetrahydro-4-quinolinyl]carbamate (for a preparation see Example 4) (25 mg, 0.068 mmol), (2-methylphenyl)boronic acid (11.97 mg, 0.088 mmol), potassium carbonate (28.1 mg, 0.203 mmol) and tetrakis(triphenylphosphine)palladium(0) (3.91 mg, 3.39 µmol) in ethanol (1 mL) and toluene (1 mL) was degassed under house vacuum and quenched several times with nitrogen, and then was heated at 100° C. for 30 min before being cooled to room temperature. The mixture was filtered through celite and the insoluble washed with EtOH. Most of the solvent was concentrated in vacuo. Purification of the residue by flash chromatography on silica gel (gradient: 30 to 60% AcOEt in hexanes) gave 1-methylethyl [(2S,4R)-1-acetyl-2-methyl-6-(2-methylphenyl)-1,2,3,4-tetrahydro-4-quinolinyl]carbamate (24 mg, 0.063 mmol, 93%) as a colourless solid.

LCMS (method A): Retention time 1.20 min, [M+H]+= 381.14

Example 94

1-Methylethyl[(2S,4R)-1-acetyl-2-methyl-6-phenyl-1,2,3,4-tetrahydro-4-quinolinyl]carbamate

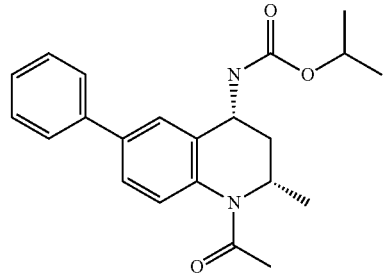 [SMILES: CC(=O)N1c2ccc(-c3ccccc3)cc2[C@H](NC(=O)OC(C)C)C[C@@H]1C]

A mixture of 1-methylethyl[(2S,4R)-1-acetyl-6-bromo-2-methyl-1,2,3,4-tetrahydro-4-quinolinyl]carbamate (for a preparation see example 4) (78.6 mg, 0.213 mmol), phenyl boronic acid (31.1 mg, 0.255 mmol), potassium carbonate (73.5 mg, 0.532 mmol) and tetrakis(triphenylphosphine)palladium(0) (12.30 mg, 10.64 µmol) in ethanol (2.5 mL) and toluene (2.5 mL) was degassed under house vacuum and quenched several times with nitrogen, and then was heated at 100° C. for 30 min before being cooled to room temperature. The mixture was filtered through celite and the insoluble washed with EtOH. Most of the solvent was concentrated in vacuo. Purification of the residue by flash chromatography on silica gel (gradient: 25 to 55% AcOEt in hexanes) gave 1-methylethyl [(2S,4R)-1-acetyl-2-methyl-6-phenyl-1,2,3,4-tetrahydro-4-quinolinyl]carbamate (71.6 mg, 0.195 mmol, 92%) as a white solid.

LCMS (method A): Retention time 1.15 min, [M+H]+= 367.13

Example 95

1-Methylethyl {(2S,4R)-1-acetyl-6-[4-(2-hydroxyethyl)phenyl]-2-methyl-1,2,3,4-tetrahydro-4-quinolinyl}carbamate

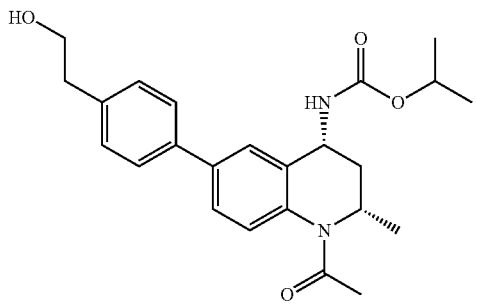 [SMILES: CC(=O)N1c2ccc(-c3ccc(CCO)cc3)cc2[C@H](NC(=O)OC(C)C)C[C@@H]1C]

A mixture of 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 52) (136. mg, 0.327 mmol), 2-(4-bromophenyl)ethanol (79 mg, 0.392 mmol), potassium carbonate (113 mg, 0.817 mmol) and tetrakis(triphenylphosphine)palladium(0) (18.87 mg, 0.016 mmol) was degassed under house vacuum for 15 min and quenched several times with nitrogen, then was then stirred at 100° C. under nitrogen for 50 min before being cooled to room temperature. Most of the solvent was removed in vacuo and the residue was partitioned between AcOEt (20 mL) and water (15 mL). The layers were separated and the aqueous phase was extracted with AcOEt (15 mL). The combined organic layers were washed with brine (15 mL), dried over MgSO$_4$, concentrated in vacuo. Purification of the residue by flash chromatography on silica gel (gradient: 50 to 80% AcOEt in Hexanes) gave a residue which was further purified by MDAP (modifier ammonium formate) to give 1-methylethyl {(2S,4R)-1-acetyl-6-[4-(2-hydroxyethyl)phenyl]-2-methyl-1,2,3,4-tetrahydro-4-quinolinyl}carbamate (42 mg, 0.102 mmol, 31%).

LCMS (method G): Retention time 0.90 min, [M+H]+= 411.1

Example 96

1-Methylethyl {(2S,4R)-1-acetyl-6-[4-(2-aminoethyl)phenyl]-2-methyl-1,2,3,4-tetrahydro-4-quinolinyl}carbamate hydrochloride

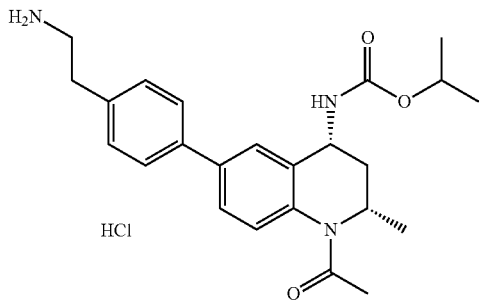 [SMILES: CC(=O)N1c2ccc(-c3ccc(CCN)cc3)cc2[C@H](NC(=O)OC(C)C)C[C@@H]1C ; Cl]

Trifluoroacetic acid (TFA) (3 mL) was added to a solution of 1-methylethyl((2S,4R)-1-acetyl-6-{4-[2-({[(1,1-dimethylethyl)oxy]carbonyl}amino)ethyl]phenyl}-2-methyl-1,2,3,4-tetrahydro-4-quinolinyl)carbamate (for a preparation see Intermediate 87) (50 mg, 0.098 mmol) in dichloromethane (DCM) (3.00 mL) and the resulting mixture was stirred at room temperature under nitrogen for 3 h then concentrated in vacuo. The residue obtained was co-evaporated with toluene then purified using a SCX column (5 g, elution 5 column volume (CV) methanol, then 5 CV 2M NH$_3$ in methanol). The ammonia fractions were collected and concentrated in vacuo to give a residue which was treated with HCl (1.0 M in Et$_2$O, 2 mL, 2 mmol). The resulting mixture was concentrated in vacuo to give 1-methylethyl((2S,4R)-1-acetyl-6-{4-[2-({[(1,1-dimethylethyl)oxy]carbonyl}amino)ethyl]phenyl}-2-methyl-1,2,3,4-tetrahydro-4-quinolinyl)carbamate hydrochloride (50 mg, 0.098 mmol, 80%) as a white solid.

LCMS (method G): Retention time 0.68 min, [M+H]+= 410.3

Example 97

1,1-Dimethylethyl {(cis)-4-[1-acetyl-2-methyl-4-({[(1-methylethyl)oxy]carbonyl}amino)-1,2,3,4-tetrahydro-6-quinolinyl]-1H-imidazol-1-yl}acetate

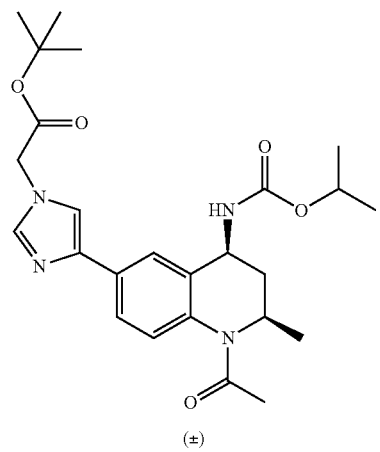 [SMILES: CC(=O)N1c2ccc(-c3cn(CC(=O)OC(C)(C)C)cn3)cc2[C@@H](NC(=O)OC(C)C)C[C@H]1C]

(±)

A solution of 1,1-dimethylethyl {(cis)-4-[2-methyl-4-({[(1-methylethyl)oxy]carbonyl}amino)-1,2,3,4-tetrahydro-6-quinolinyl]-1H-imidazol-1-yl}acetate (for a preparation see Intermediate 88) (1.0 g, 2.33 mmol) in acetic anhydride (2 mL) was allowed to stand at room temperature for 16 h then most of the solvent was concentrated in vacuo. The residue was co-evaporated twice with toluene. Purification of the resulting residue by flash chromatography on silica gel (gradient: 0 to 2% MeOH in DCM) gave 1,1-dimethylethyl {(cis)-4-[1-acetyl-2-methyl-4-({[(1-methylethyl)oxy]carbonyl}amino)-1,2,3,4-tetrahydro-6-quinolinyl]-1H-imidazol-1-yl}acetate (862 mg, 1.832 mmol, 78%) as a pale yellow solid.

LCMS (method G): Retention time 0.77 min, [M+H]+= 471.4

Example 98

1-Methylethyl((2S,4R)-1-acetyl-2-methyl-6-{4-[2-(methylamino)ethyl]phenyl}-1,2,3,4-tetrahydro-4-quinolinyl)carbamate hydrochloride

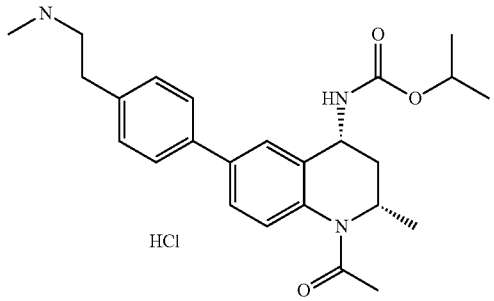 [SMILES: CNCCc1ccc(-c2ccc3c(c2)[C@H](NC(=O)OC(C)C)C[C@H](C)N3C(C)=O)cc1 ; Cl]

A solution of 1-methylethyl[(2S,4R)-1-acetyl-6-(4-{2-[{[(1,1-dimethylethyl)oxy]carbonyl}(methyl)amino]ethyl}phenyl)-2-methyl-1,2,3,4-tetrahydro-4-quinolinyl]carbamate (for a preparation see Intermediate 116) (41.5 mg, 0.079 mmol) in dichloromethane (DCM) (3 mL) was treated with HCl (4N in 1,4-dioxane, 3 mL, 12.00 mmol) and the resulting mixture was stirred at room temperature under nitrogen for 4 h.

Most of the solvent was removed in vacuo the residue was triturated with Et₂O to give 1-methylethyl((2S,4R)-1-acetyl-2-methyl-6-{4-[2-(methylamino)ethyl]phenyl}-1,2,3,4-tetrahydro-4-quinolinyl)carbamate hydrochloride (36 mg, 0.078 mmol, 99%) as a white solid. LCMS (method G): Retention time 0.68 min, [M+H]+=424.1

Example 99

3-{(Cis)-4-[1-acetyl-2-methyl-4-({[(1-methylethyl)oxy]carbonyl}amino)-1,2,3,4-tetrahydro-6-quinolinyl]-1H-imidazol-1-yl}propanoic acid trifluoroacetate

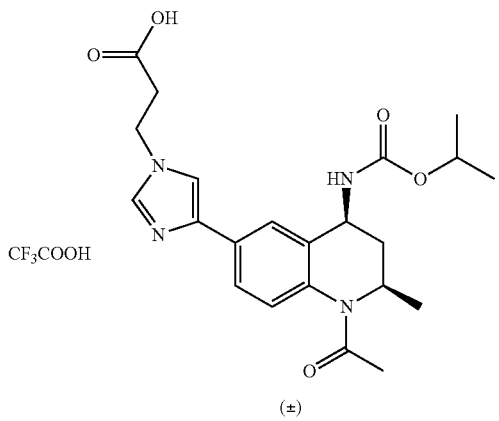 [SMILES: "CF3COOH" ; CC(=O)N1c2ccc(-c3cn(CCC(=O)O)cn3)cc2[C@@H](NC(=O)OC(C)C)C[C@H]1C]

Trifluoracetic acid (1 ml) was added to a solution of 1,1-dimethylethyl 3-{(cis)-4-[1-acetyl-2-methyl-4-({[(1-methylethyl)oxy]carbonyl}amino)-1,2,3,4-tetrahydro-6-quinolinyl]-1H-imidazol-1-yl}propanoate (for a preparation see Example 91) (1.06 g, 2.19 mmol) in DCM (5 mL). The reaction mixture was allowed to stand at room temperature for 16 h and then most of the solvent were removed in vacuo. The residue was co-evaporated twice with toluene then triturated with Et₂O to give 3-{(cis)-4-[1-acetyl-2-methyl-4-({[(1-methylethyl)oxy]carbonyl}amino)-1,2,3,4-tetrahydro-6-quinolinyl]-1H-imidazol-1-yl}propanoic acid trifluoroacetate (920 mg, 1.696 mmol, 78%) as an off-white solid.

LCMS (method G): Retention time 0.57 min, [M+H]+= 429.3

Example 100

{4-[(2S,4R)-1-Acetyl-2-methyl-4-({[(1-methylethyl)oxy]carbonyl}amino)-1,2,3,4-tetrahydro-6-quinolinyl]phenyl}acetic acid

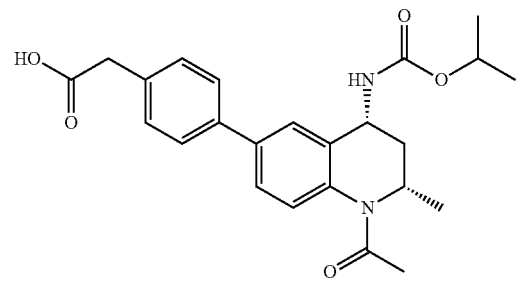 [SMILES: CC(=O)N1c2ccc(-c3ccc(CC(=O)O)cc3)cc2[C@H](NC(=O)OC(C)C)C[C@@H]1C]

Lithium hydroxide (4N in water, 1 mL, 4.00 mmol) was added to a solution of ethyl {4-[(2S,4R)-1-acetyl-2-methyl-4-({[(1-methylethyl)oxy]carbonyl}amino)-1,2,3,4-tetrahydro-6-quinolinyl]phenyl}acetate (for a preparation see Intermediate 100) (32.6 mg, 0.072 mmol) in methanol (3 mL). The resulting mixture was stirred under nitrogen at room temperature for 12 h then most of the solvent was removed in vacuo. The residue was partitioned between AcOEt (30 mL) and water (15 mL) and the layers were separated. The aqueous phase was extracted with AcOEt (15 mL). The combined organic phases were washed with brine (20 mL), dried over MgSO₄ and concentrated in vacuo. Purification of the residue by MDAP (modifier: formic acid) gave {4-[(2S,4R)-1-acetyl-2-methyl-4-({[(1-methylethyl)oxy]carbonyl}amino)-1,2,3,4-tetrahydro-6-quinolinyl]phenyl}acetic acid (23.8 mg, 0.056 mmol, 78%) as a white solid.

LCMS (method G): Retention time 0.66 min, [M+H]+= 425.13

Example 101

1-Methylethyl[(2S,4R)-1-acetyl-2-methyl-6-(2-pyridinyl)-1,2,3,4-tetrahydro-4-quinolinyl]carbamate

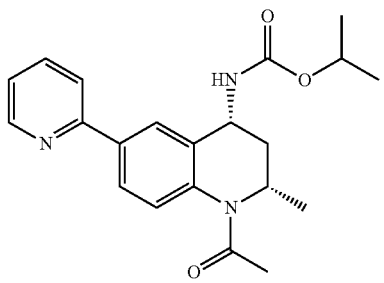 [SMILES: CC(=O)N1c2ccc(-c3ccccn3)cc2[C@H](NC(=O)OC(C)C)C[C@@H]1C]

A mixture of 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 52) (108 mg, 0.259 mmol), 2-chloropyridine (35.3 mg, 0.311 mmol), potassium carbonate (108 mg, 0.778 mmol) and tetrakis(triphenylphosphine)palladium(0) (14.99 mg, 0.013 mmol) in ethanol (2.5 mL) and toluene (2.5 mL) was degassed for 15 min under house vacuum and quenched several times with nitrogen, and then was heated at 100° C. for 1 h before being cooled to room temperature and partitioned between AcOEt (30 mL) and water (15 mL). The layers were separated and the aqueous phase was extracted with AcOEt (15 mL). The combined organic phases were washed with brine (15 mL), dried over MgSO₄ and concentrated in vacuo. Purification of the residue by MDAP (reversed phase, water/acetonitrile, modifier: ammonium bicarbonate) gave 1-methylethyl [(2S,4R)-1-acetyl-2-methyl-6-(2-pyridinyl)-1,2,3,4-tetrahydro-4-quinolinyl]carbamate (32.1 mg, 0.087 mmol, 34%) as a white solid.

LCMS (method G): Retention time 0.95 min, [M+H]+= 368.11

Example 102

3-{4-[(2S,4R)-1-Acetyl-2-methyl-4-({[(1-methylethyl)oxy]carbonyl}amino)-1,2,3,4-tetrahydro-6-quinolinyl]phenyl}propanoic acid

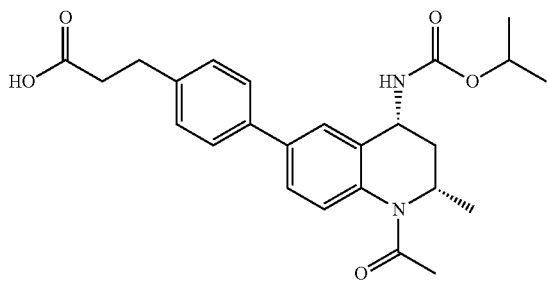 [SMILES: CC(=O)N1c2ccc(-c3ccc(CCC(=O)O)cc3)cc2[C@H](NC(=O)OC(C)C)C[C@@H]1C]

Lithium hydroxide (1N in water, 2 mL, 2.000 mmol) was added to a solution of ethyl 3-{4-[(2S,4R)-1-acetyl-2-methyl-4-({[(1-methylethyl)oxy]carbonyl}amino)-1,2,3,4-tetrahydro-6-quinolinyl]phenyl}propanoate (for a preparation see Intermediate 101) (39.7 mg, 0.085 mmol) in methanol (5 mL). The reaction mixture was stirred at room temperature for 12 h then most of the solvent was removed in vacuo. The residue was partitioned between AcOEt (30 mL), water (20 mL) and glacial acetic acid (0.5 mL). The layers were separated and the organic layer was washed with brine (20 mL). The combined aqueous phases were extracted with AcOEt (20 mL). The combined organic phases were dried over MgSO₄ and concentrated in vacuo to give 3-{4-[(2S,4R)-1-acetyl-2-methyl-4-({[(1-methylethyl)oxy]carbonyl}amino)-1,2,3,4-tetrahydro-6-quinolinyl]phenyl}propanoic acid (35.8 mg, 0.082 mmol, 96%) as a white solid.

LCMS (method G): Retention time 0.68 min, [M+H]+= 439.17

Example 103 and 104

1-Methylethyl[(2S,4R)-1-acetyl-2-methyl-6-(4-methyl-1H-imidazol-1-yl)-1,2,3,4-tetrahydro-4-quinolinyl]carbamate and 1-methylethyl[(2S,4R)-1-acetyl-2-methyl-6-(5-methyl-1H-imidazol-1-yl)-1,2,3,4-tetrahydro-4-quinolinyl]carbamate

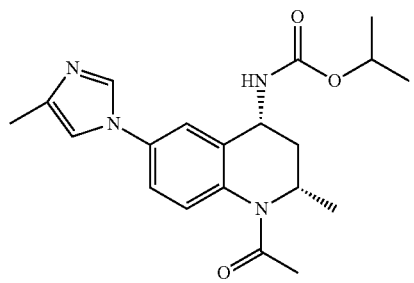

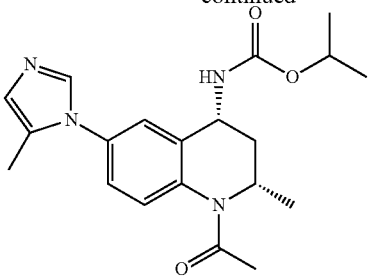

A mixture of 1-methylethyl[(2S,4R)-1-acetyl-2-methyl-6-(4,4,5,5-tetramethyl-1,3,2-dioxaborolan-2-yl)-1,2,3,4-tetrahydro-4-quinolinyl]carbamate (for a preparation see Intermediate 52) (2.42 g, 5.81 mmol), 4-methyl-1H-imidazole (0.716 g, 8.72 mmol) and copper(I) oxide (0.166 g, 1.163 mmol) was stirred in methanol (15 mL) under air for 24 h at room temperature. An extra portion of copper(I) oxide (0.166 g, 1.163 mmol) was added and the resulting mixture was stirred under air at the same temperature for 60 h then was concentrated in vacuo. The residue was partitioned between AcOEt (100 mL) and a saturated NaHCO₃ aqueous solution and the layers were separated. The aqueous layer was extracted with AcOEt (50 mL) and the combined organic phases were dried over MgSO₄ and concentrated in vacuo. Purification of the residue by flash chromatography on silica gel (gradient: 0-20% i-propanol in hexanes) gave a residue (1.1 g) which was further purified by chromatography: Prep Method: Approx 200 mg dissolved in 2 mL of EtOH and 2 mL of Heptane; Injection; 4 mL of the above sample solution was injected onto the column. 50% EtOH/Heptane, f=75 ml/min, wavelength 215 nm, 4. Ref 550,100. Column 5 cm×20 cm Chiralpak IC (20 um) Total number of injections 7; Fraction Collection: Fractions from 12-16 mins were bulked and labelled isomer 1; Fractions from 18-25 mins were bulked and labelled isomer 2. Both bulked fractions of isomers 1 and 2 were then concentrated in vacuo and transferred to weighed flasks for final analysis as described by the analytical method above. Isomer 1 proved to be 1-methylethyl[(2S,4R)-1-acetyl-2-methyl-6-(4-methyl-1H-imidazol-1-yl)-1,2,3,4-tetrahydro-4-quinolinyl]carbamate (629 mg, 1.70 mmol, 28%) and Isomer 2 proved to be 1-methylethyl[(2S,4R)-1-acetyl-2-methyl-6-(5-methyl-1H-imidazol-1-yl)-1,2,3,4-tetrahydro-4-quinolinyl]carbamate (364 mg, 0.983 mmol, 17%)

LCMS (method G): 1-methylethyl[(2S,4R)-1-acetyl-2-methyl-6-(4-methyl-1H-imidazol-1-yl)-1,2,3,4-tetrahydro-4-quinolinyl]carbamate Retention time 0.83 min, [M+H]+= 371.23; 1-methylethyl[(2S,4R)-1-acetyl-2-methyl-6-(5-methyl-1H-imidazol-1-yl)-1,2,3,4-tetrahydro-4-quinolinyl]carbamate: Retention time 0.81 min, [M+H]+=371.16

Example 105

1-Methylethyl {(2S,4R)-1-acetyl-2-methyl-6-[5-(1-piperazinylmethyl)-1,3-thiazol-2-yl]-1,2,3,4-tetrahydro-4-quinolinyl}carbamate

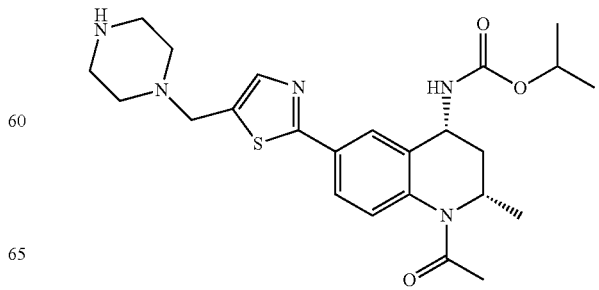

1,1-Dimethylethyl 1-piperazinecarboxylate (48.2 mg, 0.259 mmol), 1-methylethyl[(2S,4R)-1-acetyl-6-(5-formyl-1,3-thiazol-2-yl)-2-methyl-1,2,3,4-tetrahydro-4-quinolinyl]carbamate (for a preparation see Intermediate 106) (104 mg, 0.259 mmol) and sodium triacetoxyborohydride (220 mg, 1.036 mmol) were dissolved in dichloromethane (DCM) (4 mL) and the resulting mixture was stirred at room temperature under nitrogen for 16 h before being treated with a saturated NaHCO₃ aqueous solution. The two layers were separated using a phase separator cartridge and the organic phase was concentrated in vacuo. The residue was loaded on a 20 G SCX cartridge which was eluted with MeOH then with a 2M NH₃ solution in MeOH. The ammonia fractions were concentrated in vacuo to give a residue which was dissolved in DCM (3 mL) and treated with TFA (0.5 mL, 6.49 mmol). After 1 h, the mixture was concentrated in vacuo. Purification of the residue by flash chromatography on silica gel (gradient: 1 to 10% (2M NH3 in MeOH) in DCM) gave 1-methylethyl {(2S,4R)-1-acetyl-2-methyl-6-[5-(1-piperazinyl methyl)-1,3-thiazol-2-yl]-1,2,3,4-tetrahydro-4-quinolinyl}carbamate (70 mg, 0.148 mmol, 57.3% yield).

LCMS (method A): Retention time 0.64 min, [M+H]+= 472.13

Example 106

1-Methylethyl((2S,4R)-1-acetyl-2-methyl-6-{1-[(methyloxy)methyl]-1H-pyrazol-4-yl}-1,2,3,4-tetrahydro-4-quinolinyl)carbamate

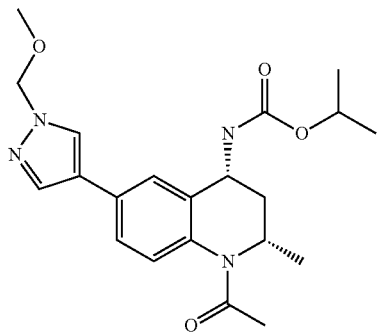 [SMILES: COCn1cc(-c2ccc3c(c2)[C@H](NC(=O)OC(C)C)C[C@H](C)N3C(C)=O)cn1]

A flask was charged with 1-methylethyl[(2S,4R)-1-acetyl-6-bromo-2-methyl-1,2,3,4-tetrahydro-4-quinolinyl]carbamate (0.185 g, 0.500 mmol) (for a preparation see Example 4), 1-[(methyloxy)methyl]-4-(4,4,5,5-tetramethyl-1,3,2-dioxaborolan-2-yl)-1H-pyrazole (for a preparation see Intermediate 94) (143 mg, 0.600 mmol), K₂CO₃ (90 mg, 0.650 mmol) and tetrakis(triphenylphosphine)palladium(0) (28.9 mg, 0.025 mmol) then filled with EtOH (1 mL) and toluene (1 mL) and the resulting mixture was stirred at 80° C. for 18 h then cooled to room temperature and concentrated in vacuo. The residue was partitioned between AcOEt (10 mL) and water (10 mL) and the layers were separated. The aqueous layer was extracted with AcOEt and the combined organic phases were washed with brine (25 mL), dried over Na₂SO₄ and concentrated in vacuo. Purification of the residue using MDAP (modifier: formic acid) gave 1-methylethyl((2S,4R)-1-acetyl-2-methyl-6-{1-[(methyloxy)methyl]-1H-pyrazol-4-yl}-1,2,3,4-tetrahydro-4-quinolinyl)carbamate (42.2 mg, 0.105 mmol, 20%) as an off-white foam.

LCMS (method A): Retention time 0.84 min, [M+H]+= 401.08

Example 107

1-Methylethyl((2S,4R)-1-acetyl-2-methyl-6-{1-[2-(methyloxy)ethyl]-1H-pyrazol-4-yl}-1,2,3,4-tetrahydro-4-quinolinyl)carbamate

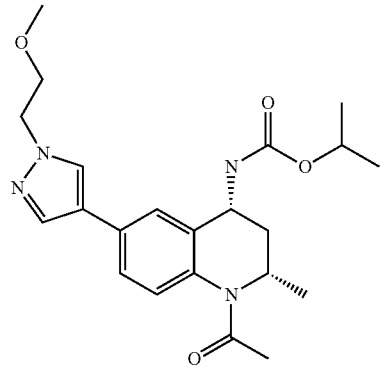 [SMILES: COCCn1cc(-c2ccc3c(c2)[C@H](NC(=O)OC(C)C)C[C@H](C)N3C(C)=O)cn1]

A flask was charged with 1-methylethyl[(2S,4R)-1-acetyl-6-bromo-2-methyl-1,2,3,4-tetrahydro-4-quinolinyl]carbamate (for a preparation see Example 4) (0.185 g, 0.500 mmol), 1-[2-(methyloxy)ethyl]-4-(4,4,5,5-tetramethyl-1,3,2-dioxaborolan-2-yl)-1H-pyrazole (for a preparation see Intermediate 117) (151 mg, 0.600 mmol), K₂CO₃ (90 mg, 0.650 mmol) and tetrakis(triphenylphosphine)palladium(0) (28.9 mg, 0.025 mmol) then filled with EtOH (1 mL) and toluene (1 mL) and the resulting mixture was stirred at 80° C. for 18 h then cooled to room temperature and concentrated in vacuo. The residue was partitioned between AcOEt (10 mL) and water (10 mL) and the layers were separated. The aqueous layer was extracted with AcOEt and the combined organic phases were washed with brine (25 mL), dried over Na₂SO₄ and concentrated in vacuo. Purification of the residue using MDAP (modifier: formic acid) gave an oil which was dissolved in 1,4-dioxane, freezed using an acetone bath cooled with solid CO₂ and left on a freeze drier for 16 h to give 1-methylethyl((2S,4R)-1-acetyl-2-methyl-6-{1-[2-(methyloxy)ethyl]-1H-pyrazol-4-yl}-1,2,3,4-tetrahydro-4-quinolinyl)carbamate (84.7 mg, 0.204 mmol, 37%) as a white solid. LCMS (method A): Retention time 0.84 min, [M+H]+=415.15

Example 108

1-Methylethyl {(2S,4R)-1-acetyl-6-[1-(2-hydroxyethyl)-1H-pyrazol-4-yl]-2-methyl-1,2,3,4-tetrahydro-4-quinolinyl}carbamate

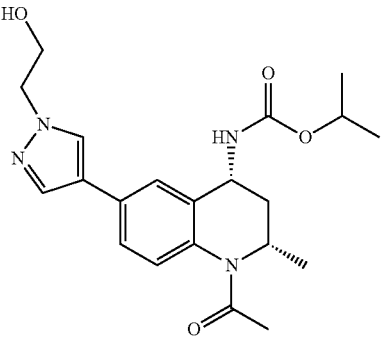 [SMILES: CC(=O)N1c2ccc(-c3cnn(CCO)c3)cc2[C@H](NC(=O)OC(C)C)C[C@@H]1C]

A flask was charged with 1-methylethyl[(2S,4R)-1-acetyl-6-bromo-2-methyl-1,2,3,4-tetrahydro-4-quinolinyl]carbamate (for a preparation see Example 4) (0.185 g, 0.500 mmol), 2-[4-(4,4,5,5-tetramethyl-1,3,2-dioxaborolan-2-yl)-1H-pyrazol-1-yl]ethanol (for a preparation see Intermediate 118) (143 mg, 0.600 mmol), K₂CO₃ (90 mg, 0.650 mmol) and tetrakis(triphenylphosphine)palladium(0) (28.9 mg, 0.025 mmol) then filled with EtOH (1 mL) and toluene (1 mL) and the resulting mixture was stirred at 80° C. for 18 h then cooled to room temperature and concentrated in vacuo. The residue was partitioned between AcOEt (10 mL) and water (10 mL) and the layers were separated. The aqueous layer was extracted with AcOEt and the combined organic phases were washed with brine (25 mL), dried over Na₂SO₄ and concentrated in vacuo. Purification of the residue using MDAP (modifier: formic acid) gave an oil which was dissolved in 1,4-dioxane, freezed using an acetone bath cooled with solid CO₂ and left on a freeze drier for 16 h to give 1-methylethyl {(2S,4R)-1-acetyl-6-[1-(2-hydroxyethyl)-1H-pyrazol-4-yl]-2-methyl-1,2,3,4-tetrahydro-4-quinolinyl}carbamate (33.3 mg, 0.083 mmol, 15%) as a white solid.

LCMS (method A): Retention time 0.73 min, [M+H]+= 401.15

Example 109

1-Methylethyl {(2S,4R)-1-acetyl-6-[1-(2-hydroxy-2-methylpropyl)-1H-pyrazol-4-yl]-2-methyl-1,2,3,4-tetrahydro-4-quinolinyl}carbamate

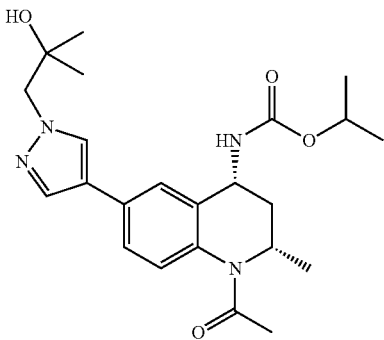 [SMILES: CC(=O)N1c2ccc(-c3cnn(CC(C)(C)O)c3)cc2[C@H](NC(=O)OC(C)C)C[C@@H]1C]

A flask was charged with 1-methylethyl[(2S,4R)-1-acetyl-6-bromo-2-methyl-1,2,3,4-tetrahydro-4-quinolinyl]carbamate (for a preparation see Example 4) (0.185 g, 0.500 mmol), 2-methyl-1-[4-(4,4,5,5-tetramethyl-1,3,2-dioxaborolan-2-yl)-1H-pyrazol-1-yl]-2-propanol (for a preparation see Intermediate 119) (160 mg, 0.600 mmol), K₂CO₃ (90 mg, 0.650 mmol) and tetrakis(triphenylphosphine)palladium(0) (28.9 mg, 0.025 mmol) then filled with EtOH (1 mL) and toluene (1 mL) and the resulting mixture was stirred at 80° C. for 18 h then cooled to room temperature and concentrated in vacuo. The residue was partitioned between AcOEt (10 mL) and water (10 mL) and the layers were separated. The aqueous layer was extracted with AcOEt and the combined organic phases were washed with brine (25 mL), dried over Na₂SO₄ and concentrated in vacuo. Purification of the residue using MDAP (modifier: formic acid) gave an oil which was dissolved in 1,4-dioxane, freezed using an acetone bath cooled with solid CO₂ and left on a freeze drier for 16 h to give 1-methylethyl {(2S,4R)-1-acetyl-6-[1-(2-hydroxy-2-methylpropyl)-1H-pyrazol-4-yl]-2-methyl-1,2,3,4-tetrahydro-4-quinolinyl}carbamate (73.4 mg, 0.171 mmol, 32%) as a white solid. LCMS (method A): Retention time 0.81 min, [M+H]+= 429.10

Example 110

1-Methylethyl[(2S,4R)-1-acetyl-6-bromo-2-methyl-1,2,3,4-tetrahydro-4-quinolinyl]carbamate

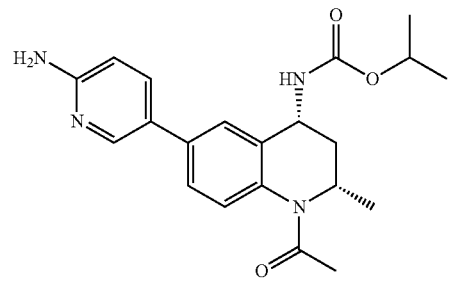 [SMILES: CC(=O)N1c2ccc(-c3ccc(N)nc3)cc2[C@H](NC(=O)OC(C)C)C[C@@H]1C]

1-Methylethyl[(2S,4R)-1-acetyl-6-bromo-2-methyl-1,2,3,4-tetrahydro-4-quinolinyl]carbamate (1 g, 2.71 mmol) (for a preparation see Example 4) and 5-(4,4,5,5-tetramethyl-1,3,2-dioxaborolan-2-yl)-2-pyridinamine (0.487 g, 2.213 mmol) were combined in ethanol (4.7 ml) and toluene (4.70 ml) to give a light yellow solution. K₂CO₃ (0.449 g, 3.25 mmol) followed by tetrakis(triphenylphosphine)palladium(0) (0.156 g, 0.135 mmol) were added and the resulted mixture was stirred at 90° C. under nitrogen for 16 h then was cooled to room temperature and concentrated in vacuo. The residue was partitioned between water (40 mL) and EtOAc (50 mL) and the layers were separated. The aqueous layer was extracted with EtOAc (50 mL) and the combined organic phases were washed with brine (100 mL), dried over Na₂SO₄ and concentrated in vacuo. Purification of the residue by flash chromatography on silica gel (gradient: 12 to 63% AcOEt in Hexanes followed by 10% (2M NH₃ in MeOH) in DCM) gave a residue which was further purified by flash chromatography on silica gel (gradient: 1 to 5% (2M NH₃ in MeOH) in DCM) to give 1-methylethyl[(2S,4R)-1-acetyl-6-(6-amino-3-pyridinyl)-2-methyl-1,2,3,4-tetrahydro-4-quinolinyl]carbamate (0.74 g, 1.885 mmol, 69.6% yield) as a yellow foam.

LCMS (method A): Retention time 0.61 min, [M+H]+= 383.12

Example 111

1-Methylethyl((2S,4R)-1-acetyl-2-methyl-6-{3-[(methylamino)methyl]phenyl}-1,2,3,4-tetrahydro-4-quinolinyl)carbamate hydrochloride

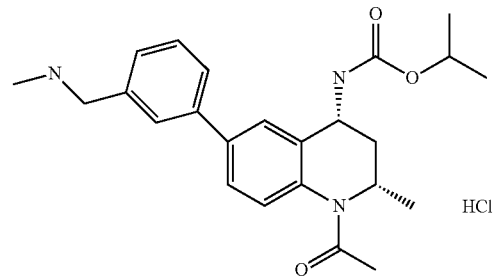 [SMILES: CNCc1cccc(-c2ccc3c(c2)[C@H](NC(=O)OC(C)C)C[C@H](C)N3C(C)=O)c1 ; Cl]

[(3-Bromophenyl)methyl]methylamine (0.059 ml, 0.432 mmol), 1-methylethyl[(2S,4R)-1-acetyl-2-methyl-6-(4,4,5,5-tetramethyl-1,3,2-dioxaborolan-2-yl)-1,2,3,4-tetrahydro- 4-quinolinyl]carbamate (for a preparation see Intermediate 52) (150 mg, 0.360 mmol), and potassium carbonate (74.7 mg, 0.540 mmol) were mixed together in ethanol (1.2 mL) and toluene (1.2 mL) and the reaction mixture was degassed using house vacuum and quenched several times with nitrogen tetrakis(triphenylphosphine)palladium(0) (20.82 mg, 0.018 mmol) was added and the reaction was degassed again and then stirred under nitrogen at 90° C. for 16 h then cooled to room temperature and concentrated in vacuo. The residue was partitioned between EtOAc (15 mL) and water (5 mL) and the layers were separated. The organic layer was washed with brine (5 mL), dried using phase separator and concentrated in vacuo to give a first residue. The aqueous phase was washed with further EtOAc (20 mL) and the organic phase was dried using a phase separator then concentrated in vacuo to give a second residue which was mixed with the first one. Purification of the combined residues by flash chromatography on silica gel (gradient: 5 to 25% (2M NH$_3$ in MeOH) in DCM) gave a residue which was further purified by flash chromatography on silica gel (gradient: 5 to 25% (2M NH$_3$ in MeOH) in AcOEt) to give a second residue. This residue was dissolved in DCM (3 mL) and HCl (1.25 M in MeOH, 0.129 ml, 0.161 mmol) was added. The resulting mixture was concentrated in vacuo to give 1-methylethyl((2S,4R)-1-acetyl-2-methyl-6-{3-[(methylamino)methyl]phenyl}-1,2,3,4-tetrahydro-4-quinolinyl)carbamate hydrochloride (50 mg, 0.107 mmol, 29.6% yield) as a white solid.

LCMS (method G): Retention time 0.69 min, [M+H]+= 410.1

Example 112

4-[(2S,4R)-1-Acetyl-2-methyl-4-({[(1-methylethyl)oxy]carbonyl}amino)-1,2,3,4-tetrahydro-6-quinolinyl]benzoic acid

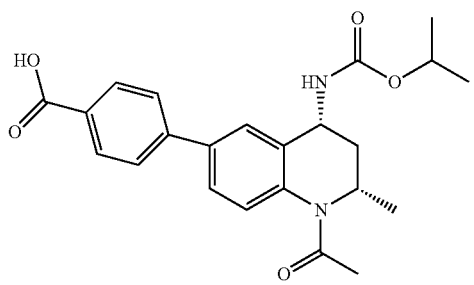 [SMILES: CC(=O)N1c2ccc(-c3ccc(C(=O)O)cc3)cc2[C@H](NC(=O)OC(C)C)C[C@@H]1C]

To a solution of methyl 4-[(2S,4R)-1-acetyl-2-methyl-4-({[(1-methylethyl)oxy]carbonyl}amino)-1,2,3,4-tetrahydro-6-quinolinyl]benzoate (for a preparation see Intermediate 107) (20 mg, 0.047 mmol) in ethanol (0.5 mL) was added NaOH (1M in water, 0.188 mL, 0.188 mmol) and the resulting mixture was stirred at room temperature for 3 h then concentrated in vacuo. Purification of the residue using MDAP gave 4-[(2S,4R)-1-acetyl-2-methyl-4-({[(1-methylethyl)oxy]carbonyl}amino)-1,2,3,4-tetrahydro-6-quinolinyl]benzoic acid (12 mg, 0.029 mmol, 62%) as a white solid.

LCMS (method A): Retention time 0.88 min, [M+H]+= 411.21

Example 113

1-Methylethyl {(2S,4R)-1-acetyl-6-[3,4-bis(methyloxy)phenyl]-2-methyl-1,2,3,4-tetrahydro-4-quinolinyl}carbamate

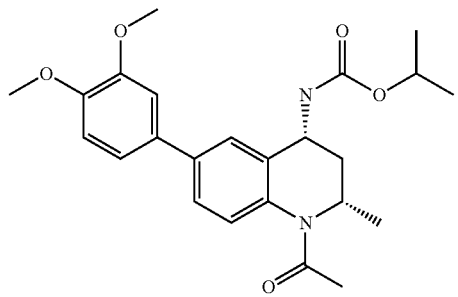 [SMILES: COc1ccc(-c2ccc3c(c2)[C@H](NC(=O)OC(C)C)C[C@H](C)N3C(C)=O)cc1OC]

A flask was charged with 2-[3,4-bis(methyloxy)phenyl]-4,4,5,5-tetramethyl-1,3,2-dioxaborolane (0.429 g, 1.625 mmol), 1-methylethyl[(2S,4R)-1-acetyl-6-bromo-2-methyl-1,2,3,4-tetrahydro-4-quinolinyl]carbamate (for a preparation see Example 4) (0.5 g, 1.354 mmol), a saturated NaHCO$_3$ aqueous solution (1.5 mL, 1.354 mmol) and bis(diphenylphosphino)ferrocene]dichloropalladium(II)-DCM adduct (0.111 g, 0.135 mmol) then filled with 1,4-dioxane (7 mL). The resulting mixture was degassed by bubbling nitrogen in to it, stirred at 100° C. for 1 hr under microwave irradiation then cooled to room temperature. The reaction mixture was filtered through celite and concentrated in vacuo. The residue was partitioned between EtOAC (30 mL) and water (30 mL) and the layers were separated. The organic phase was washed with brine (25 mL) dried over MgSO$_4$ and concentrated in vacuo. Purification of the residue by flash chromatography on silica gel (gradient: 0 to 60% AcOEt in hexanes) gave 1-methylethyl {(2S,4R)-1-acetyl-6-[3,4-bis(methyloxy)phenyl]-2-methyl-1,2,3,4-tetrahydro-4-quinolinyl}carbamate (327 mg, 0.766 mmol, 56.6%). LCMS (method A): Retention time 1.02 min, [M+H]+=427.18

Example 114

4-[(2S,4R)-1-Acetyl-2-methyl-4-({[(1-methylethyl)oxy]carbonyl}amino)-1,2,3,4-tetrahydro-6-quinolinyl]-3-methylbenzoic acid

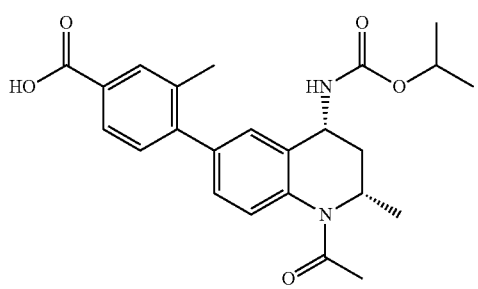 [SMILES: CC(=O)N1c2ccc(-c3ccc(C(=O)O)cc3C)cc2[C@H](NC(=O)OC(C)C)C[C@@H]1C]

A solution of methyl 4-[(2S,4R)-1-acetyl-2-methyl-4-({[(1-methylethyl)oxy]carbonyl}amino)-1,2,3,4-tetrahydro-6-quinolinyl]-3-methylbenzoate (for a preparation see Intermediate 108) (20 mg, 0.046 mmol) in ethanol (0.5 mL) was treated with NaOH (1M in water, 0.182 mL, 0.182 mmol) and the resulting mixture was stirred at room temperature for 30 min. It was then made up to 0.9 mL by addition of 1:1 solvent mixture of DMSO/CH₃CN and purified by MDAP to give 4-[(2S,4R)-1-acetyl-2-methyl-4-({[(1-methylethyl)oxy]carbonyl}amino)-1,2,3,4-tetrahydro-6-quinolinyl]-3-methylbenzoic acid (16 mg, 0.038 mmol, 83%) as a white solid. LCMS (method A): Retention time 0.91 min, [M+H]+= 425.18

Example 115

1-Methylethyl((2S,4R)-1-acetyl-2-methyl-6-{4-[(4-piperidinylamino)methyl]phenyl}-1,2,3,4-tetrahydro-4-quinolinyl)carbamate

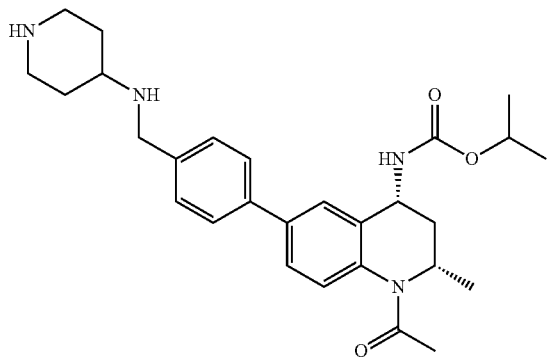 [SMILES: CC(=O)N1c2ccc(-c3ccc(CNC4CCNCC4)cc3)cc2[C@H](NC(=O)OC(C)C)C[C@@H]1C]

A solution of 1,1-dimethylethyl 4-[({4-[(2S,4R)-1-acetyl-2-methyl-4-({[(1-methylethyl)oxy]carbonyl}amino)-1,2,3,4-tetrahydro-6-quinolinyl]phenyl}methyl)amino]-1-piperidinecarboxylate (for a preparation see Intermediate 109) (605 mg, 1.045 mmol) in dichloromethane (DCM) (5 mL) was treated with TFA (1 mL, 12.98 mmol) and the resulting mixture was stirred at room temperature for 1.5 h then concentrated in vacuo. The residue was loaded on a 20 G SCX column and eluted with MeOH then with 2N NH₃ in MeOH). The ammonia fractions were combined and concentrated in vacuo to give 1-methylethyl((2S,4R)-1-acetyl-2-methyl-6-{4-[(4-piperidinylamino)methyl]phenyl}-1,2,3,4-tetrahydro-4-quinolinyl)carbamate (443 mg, 0.879 mmol, 84%) as a white glassy solid.

LCMS (method G): Retention time 0.55 min, [M+H]+= 479.2

Example 116

1-Methylethyl[(2S,4R)-1-acetyl-6-(2,4-dimethyl-1H-imidazol-1-yl)-2-methyl-1,2,3,4-tetrahydro-4-quinolinyl]carbamate

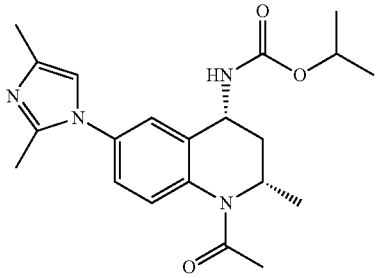 [SMILES: CC(=O)N1c2ccc(-n3cc(C)nc3C)cc2[C@H](NC(=O)OC(C)C)C[C@@H]1C]

A mixture of 1-methylethyl {(2S,4R)-1-acetyl-6-[acetyl(2-oxopropyl)amino]-2-methyl-1,2,3,4-tetrahydro-4-quinolinyl}carbamate (for a preparation see Intermediate 110) (130 mg, 0.322 mmol), ammonium acetate (124 mg, 1.611 mmol) and acetic acid (2 mL, 34.9 mmol) was stirred at 120° C. under nitrogen for 24 h then cooled to room temperature and basified with NaOH (2N in water). The mixture was then partitioned between AcOEt (10 mL) and water (5 mL) and the phases were separated. The organic layer was washed with a saturated NaHCO₃ aqueous solution, dried over Na₂SO₄ and concentrated in vacuo. Purification of the residue by flash chromatography on silica gel (gradient: 100% AcOEt then 0 to 10% MeOH in DCM) gave 1-methylethyl[(2S,4R)-1-acetyl-6-(2,4-dimethyl-1H-imidazol-1-yl)-2-methyl-1,2,3,4-tetrahydro-4-quinolinyl]carbamate (28 mg, 0.062 mmol, 19%) as a yellow gum.

LCMS (method G): Retention time 0.59 min, [M+H]+= 385.3

Example 117

Sodium 2-[(cis)-1-acetyl-2-methyl-4-({[(1-methylethyl)oxy]carbonyl}amino)-1,2,3,4-tetrahydro-6-quinolinyl]-3-furancarboxylate

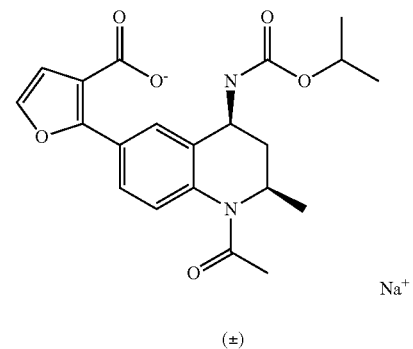 [SMILES: CC(=O)N1c2ccc(-c3occc3C(=O)[O-])cc2[C@@H](NC(=O)OC(C)C)C[C@H]1C ; [Na+]]

(±)

A flask was charged with 1-methylethyl (1-acetyl-6-bromo-2-methyl-1,2,3,4-tetrahydro-4-quinolinyl)carbamate (for a preparation see Example 61) (100 mg, 0.271 mmol), potassium carbonate (74.9 mg, 0.542 mmol), 2-(dihydroxyboranyl)-3-furancarboxylic acid (50.7 mg, 0.325 mmol) and tetrakis(triphenylphosphine)palladium(0) (15.65 mg, 0.014 mmol) then filled with ethanol (1 mL) and toluene (1 mL) and the resulting mixture was refluxed under nitrogen for 21 h then cooled to room temperature and partitioned between a 2M HCl aqueous solution (40 mL) and EtOAc (40 mL). The layers were separated and the aqueous phase was extracted with EtOAc (2×40 mL). The combined organic phases were washed with brine (80 mL), dried over Na₂SO₄ and concentrated in vacuo. Purification of the residue using MDAP (modifier; trifluoroacetic acid) gave a residue which was treated with a 2M NaOH aqueous solution (2.25×10⁻² mL, 4.50 mmol). The precipitate formed was filtered off and dried under house vacuum to give sodium 2-[(2R,4S)-1-acetyl-2-methyl-4-({[(1-methylethyl)oxy]carbonyl}amino)-1,2,3,4-tetrahydro-6-quinolinyl]-3-furancarboxylate (18 mg, 0.040 mmol, 15%) as a cream solid.

LCMS (method G): Retention time 0.86 min, [M+H]+= 400.95

Example 118

1-Methylethyl[(cis)-1-acetyl-6-(3,5-dimethyl-4-isoxazolyl)-2-methyl-1,2,3,4-tetrahydro-4-quinolinyl]carbamate

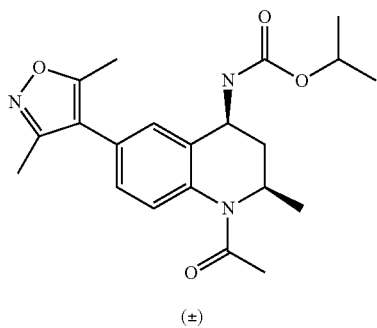 [SMILES: CC(=O)N1c2ccc(-c3c(C)noc3C)cc2[C@@H](NC(=O)OC(C)C)C[C@H]1C]

(±)

A flask was charged with 1-methylethyl (1-acetyl-6-bromo-2-methyl-1,2,3,4-tetrahydro-4-quinolinyl)carbamate (for a preparation see Example 61) (100 mg, 0.271 mmol), potassium carbonate (74.9 mg, 0.542 mmol), 3,5-dimethyl-4-isoxazolylboronic acid (45.8 mg, 0.325 mmol), and tetrakis(triphenylphosphine)palladium(0) (15.65 mg, 0.014 mmol) then filled with ethanol (1 mL) and toluene (1 mL) and the resulting mixture was refluxed under nitrogen for 20 h. tetrakis(triphenylphosphine)palladium(0) (15.65 mg, 0.014 mmol) was then added and the mixture refluxed for 40 h then cooled to room temperature and partitioned between water (40 mL) and EtOAc (40 mL). The layers were separated and the aqueous phase was extracted with EtOAc (40 mL). The combined organic phases were washed with brine, dried over MgSO$_4$ and concentrated in vacuo. Purification of the residue by flash chromatography on silica gel (gradient: 0 to 66% AcOEt in Hexanes) gave 1-methylethyl[(cis)-1-acetyl-6-(3,5-dimethyl-4-isoxazolyl)-2-methyl-1,2,3,4-tetrahydro-4-quinolinyl]carbamate (42 mg, 0.103 mmol, 38%) as a colourless solid.

LCMS (method G): Retention time 0.98 min, [M+H]+= 395.1

Example 119

1-Methylethyl[(cis)-1-acetyl-2-methyl-6-(1,3,5-trimethyl-1H-pyrazol-4-yl)-1,2,3,4-tetrahydro-4-quinolinyl]carbamate

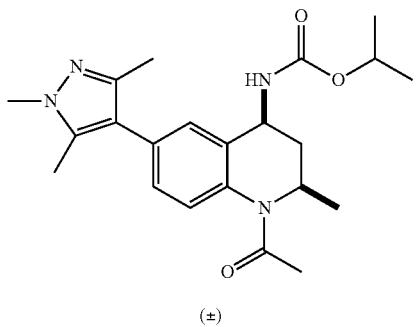 [SMILES: CC(=O)N1c2ccc(-c3c(C)nn(C)c3C)cc2[C@@H](NC(=O)OC(C)C)C[C@H]1C]

(±)

A flask was charged with 1-methylethyl (1-acetyl-6-bromo-2-methyl-1,2,3,4-tetrahydro-4-quinolinyl)carbamate (for a preparation see Example 61) (100 mg, 0.271 mmol), potassium carbonate (74.9 mg, 0.542 mmol), 1,3,5-trimethyl-4-(4,4,5,5-tetramethyl-1,3,2-dioxaborolan-2-yl)-1H-pyrazole (77 mg, 0.325 mmol) and tetrakis(triphenylphosphine)palladium(0) (15.65 mg, 0.014 mmol) then filled with ethanol (1 mL) and toluene (1 mL) and the resulting mixture was refluxed under nitrogen for 18 h then cooled to room temperature and partitioned between water (40 mL) and EtOAc (40 mL). The layers were separated and the aqueous phase was extracted with EtOAc (40 mL). The combined organic phases were washed with brine, dried over Na$_2$SO$_4$ and concentrated in vacuo. Purification of the residue by flash chromatography on silica gel (gradient: 0 to 50% AcOEt in Hexanes) gave 1-methylethyl[(cis)-1-acetyl-2-methyl-6-(1,3,5-trimethyl-1H-pyrazol-4-yl)-1,2,3,4-tetrahydro-4-quinolinyl]carbamate (33 mg, 0.078 mmol, 29%) as a dark yellow solid.

LCMS (method G): Retention time 0.73 min, [M+H]+= 399.03

Example 120

1-Methylethyl[(2S,4R)-1-acetyl-6-(4-cyanophenyl)-2-methyl-1,2,3,4-tetrahydro-4-quinolinyl]carbamate

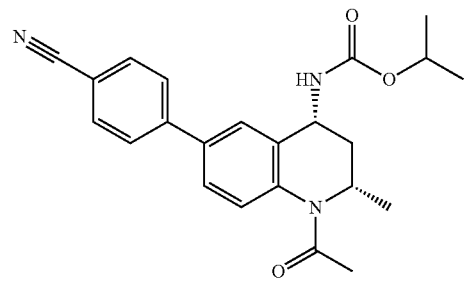 [SMILES: CC(=O)N1c2ccc(-c3ccc(C#N)cc3)cc2[C@H](NC(=O)OC(C)C)C[C@@H]1C]

A flask was charged with 1-methylethyl[(2S,4R)-1-acetyl-6-bromo-2-methyl-1,2,3,4-tetrahydro-4-quinolinyl]carbamate (for a preparation see Example 4) (200 mg, 0.542 mmol), potassium carbonate (150 mg, 1.083 mmol), tetrakis(triphenylphosphine)palladium(0) (6.26 mg, 5.42 μmol) and 4-(4,4,5,5-tetramethyl-1,3,2-dioxaborolan-2-yl)benzonitrile (149 mg, 0.650 mmol) then filled with ethanol (2 mL) and toluene (2 mL) and the resulting mixture was stirred under nitrogen at 90° C. for 16 h then cooled to room temperature and partitioned between water (20 mL) and EtOAc (60 mL). The layers were separated and the aqueous phase was extracted with EtOAc (30 mL). The combined organic phases were washed with brine (30 mL), dried over MgSO$_4$ and concentrated in vacuo. Purification of the residue by flash chromatography on silica gel (gradient: 10 to 55% AcOEt in hexanes) gave 1-methylethyl[(2S,4R)-1-acetyl-6-(4-cyanophenyl)-2-methyl-1,2,3,4-tetrahydro-4-quinolinyl]carbamate (176 mg, 0.45 mmol, 83%) as a white solid. LCMS (method G): Retention time 1.03 min, [M+H]+=392.0

Example 121

1,1-Dimethylethyl {(2S,4R)-1-acetyl-6-[1-(2-hydroxyethyl)-1H-1,2,3-triazol-4-yl]-2-methyl-1,2,3,4-tetrahydro-4-quinolinyl}carbamate

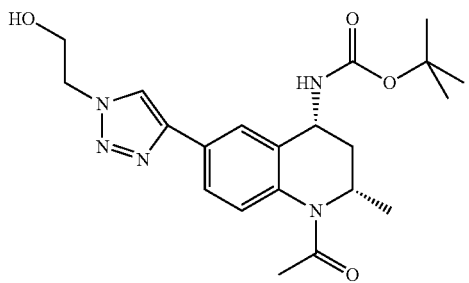 [SMILES: CC(=O)N1c2ccc(-c3cn(CCO)nn3)cc2[C@H](NC(=O)OC(C)(C)C)C[C@@H]1C]

A flask was charged with 2-azidoethanol (318 mg, 3.65 mmol) and copper(I) iodide (17.40 mg, 0.091 mmol) then filled with N,N-dimethylformamide (DMF) (13 mL) and methanol (1.5 mL). This mixture was treated with 1,1-dimethylethyl[(2S,4R)-1-acetyl-6-ethynyl-2-methyl-1,2,3,4-tetrahydro-4-quinolinyl]carbamate (for a preparation see Intermediate 113) (600 mg, 1.827 mmol) and the resulting mixture was at 100° C. for 2 h under microwave irradiation then cooled to room temperature and partitioned between EtOAc and water. The layers were separated and the aqueous phase was extracted three times with EtOAc. The combined organic layers were washed twice with brine, and then dried over MgSO₄ and concentrated in vacuo. Purification of the residue by flash chromatography on silica gel (gradient: 0 to 5% MeOH in DCM) gave 1,1-dimethylethyl {(2S,4R)-1-acetyl-6-[1-(2-hydroxyethyl)-1H-1,2,3-triazol-4-yl]-2-methyl-1,2,3,4-tetrahydro-4-quinolinyl}carbamate (659 mg, 1.523 mmol, 83% yield).

LCMS (method G): Retention time 0.76 min, [M+H]+= 416.3

Example 122

1-Methylethyl((2S,4R)-1-acetyl-6-{1-[2-(dimethylamino)ethyl]-1H-pyrazol-4-yl}-2-methyl-1,2,3,4-tetrahydro-4-quinolinyl)carbamate

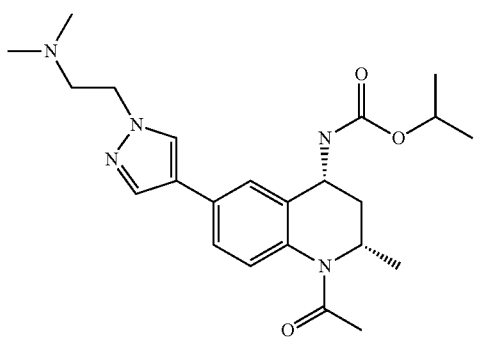 [SMILES: CC(=O)N1c2ccc(-c3cnn(CCN(C)C)c3)cc2[C@H](NC(=O)OC(C)C)C[C@@H]1C]

1-Methylethyl[(2S,4R)-1-acetyl-6-bromo-2-methyl-1,2,3,4-tetrahydro-4-quinolinyl]carbamate (for a preparation see Example 4) (0.24 g, 0.650 mmol), potassium hydroxide (1.300 mL, 1.300 mmol), N,N-dimethyl-2-[4-(4,4,5,5-tetramethyl-1,3,2-dioxaborolan-2-yl)-1H-pyrazol-1-yl]ethanamine (for a preparation see Intermediate 115) (0.190 g, 0.715 mmol) and (1,3-bis(2,6-diisopropylphenyl)imidazolidene)(3-chloropyridyl)palladium(II) dichloride (0.03 g, 0.044 mmol) were dissolved in ethanol (10 mL) and 1,2-dimethoxyethane (DME) (10.00 mL) and the resulting mixture was degassed under house vacuum with several quenches with nitrogen then refluxed for three hours, cooled to room temperature, allowed to stand for 16 h then concentrated in vacuo. The residue was partitioned between water (30 mL) and EtOAc (30 mL) and the layer were separated. The organic phase was dried over MgSO₄ and concentrated in vacuo. Purification of this residue by SP4 using a 25 G silica cartridge (gradient: 0 to 10% (2M NH₃ in MeOH) in DCM) gave 1-methylethyl((2S,4R)-1-acetyl-6-{1-[2-(dimethylamino)ethyl]-1H-pyrazol-4-yl}-2-methyl-1,2,3,4-tetrahydro-4-quinolinyl)carbamate (137 mg, 0.320 mmol, 49.3% yield) as an amber oil.

LCMS (method A): Retention time 0.87 min, [M+H]+= 428.20

Example 123

1,1-Dimethylethyl[(cis)-1-acetyl-2-methyl-6-(4-methyl-1H-imidazol-1-yl)-1,2,3,4-tetrahydro-4-quinolinyl]carbamate

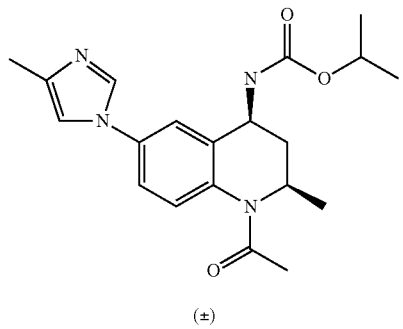 [SMILES: CC(=O)N1c2ccc(-n3cnc(C)c3)cc2[C@@H](NC(=O)OC(C)C)C[C@H]1C]

(±)

A mixture of 1,1-dimethylethyl[2-methyl-6-(4-methyl-1H-imidazol-1-yl)-1,2,3,4-tetrahydro-4-quinolinyl]carbamate (for a preparation see Intermediate 102) (273 mg, 0.797 mmol) and acetic anhydride (3 mL, 0.797 mmol) was stirred at room temperature under nitrogen for 24 h then concentrated in vacuo. The residue was dissolved in a saturated NaHCO₃ aqueous solution and left standing for 48 h. The aqueous phase was then extracted with AcOEt (50 mL). The organic phase was washed with brine. The combined aqueous phases were extracted with AcOEt (30 mL) and the combined organic layers were dried over MgSO₄ then concentrated in vacuo to give 1,1-dimethylethyl[(cis)-1-acetyl-2-methyl-6-(4-methyl-1H-imidazol-1-yl)-1,2,3,4-tetrahydro-4-quinolinyl]carbamate (255 mg, 0.663 mmol, 83%) as a white solid.

LCMS (method G): Retention time 0.89 min, [M+H]+= 385.21

REFERENCE COMPOUNDS

Reference Compound A 2-methyl-6-(methyloxy)-4H-3,1-benzoxazin-4-one

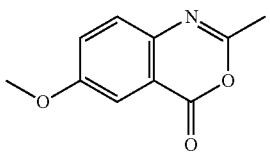

A solution of 5-methoxyanthranilic acid (Lancaster) (41.8 g, 0.25 mol) was refluxed in acetic anhydride (230 mL) for 3.5 h before being concentrated under reduced pressure. The crude compound was then concentrated twice in the presence of toluene before being filtered and washed twice with ether to yield to the title compound (33.7 g, 71% yield) as a brown solid. LC/MS (Method D): m/z 192 [M+H]$^+$, Rt 1.69 min.

Reference Compound B

[2-amino-5-(methyloxy)phenyl](4-chlorophenyl)methanone

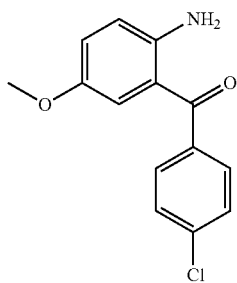 [SMILES: COc1ccc(N)c(C(=O)c2ccc(Cl)cc2)c1]

To a solution of 2-methyl-6-(methyloxy)-4H-3,1-benzoxazin-4-one (for a preparation see Reference compound A) (40.0 g, 0.21 mol) in a toluene/ether (2/1) mixture (760 mL) at 0° C. was added dropwise a solution of 4-chlorophenylmagnesium bromide (170 mL, 1M in Et$_2$O, 0.17 mol). The reaction mixture was allowed to warm to room temperature and stirred for 1 h before being quenched with 1N HCl (200 mL). The aqueous layer was extracted with EtOAc (3×150 mL) and the combined organics were washed with brine (100 mL), dried over Na$_2$SO$_4$, filtered and concentrated under reduced pressure. The crude compound was then dissolved in EtOH (400 mL) and 6N HCl (160 mL) was added. The reaction mixture was refluxed for 2 h before being concentrated to one-third in volume. The resulting solid was filtered and washed twice with ether before being suspended in EtOAc and neutralised with 1N NaOH. The aqueous layer was extracted with EtOAc (3×150 mL) and the combined organics were washed with brine (150 mL), dried over Na$_2$SO$_4$, filtered and concentrated under reduced pressure. The title compound was obtained as a yellow solid (39 g, 88% yield);

LC/MS (Method D): m/z 262 [M+H]$^+$, Rt 2.57 min.

Reference Compound C

Methyl N$^1$-[2-[(4-chlorophenyl)carbonyl]-4-(methyloxy)phenyl]-N$^2$-{[(9H-fluoren-9-ylmethyl)oxy]carbonyl}-L-α-asparaginate Methyl N-{[(9H-fluoren-9-ylmethyl)oxy]carbonyl}-L-α-aspartyl chloride (*Int. J. Peptide Protein Res.* 1992, 40, 13-18) (93 g, 0.24 mol) was dissolved in CHCl$_3$ (270 mL) and [2-amino-5-(methyloxy)phenyl](4-chlorophenyl)methanone (for a preparation see Reference compound B) (53 g, 0.2 mol) was added. The resulting mixture was stirred at 60° C. for 1 h before being cooled and concentrated to 60% in volume. Ether was added at 0° C. and the resulting precipitate was filtered and discarded. The filtrate was concentrated under reduced pressure and used without further purification.

Reference Compound D

Methyl[(3S)-5-(4-chlorophenyl)-7-(methyloxy)-2-oxo-2,3-dihydro-1H-1,4-benzodiazepin-3-yl]acetate To a solution of methyl N1-[2-[(4-chlorophenyl)carbonyl]-4-(methyloxy)phenyl]-N2-{[(9H-fluoren-9-ylmethyl)oxy]carbonyl}-L-α-asparaginate (for a preparation see Reference compound C) (assumed 0.2 mol) in DCM (500 mL) was added Et$_3$N (500 mL, 3.65 mol) and the resulting mixture was refluxed for 24 h before being concentrated. The resulting crude amine was dissolved in 1,2-DCE (1.5 L) and AcOH (104 mL, 1.8 mol) was added carefully. The reaction mixture was then stirred at 60° C. for 2 h before being concentrated in vacuo and dissolved in DCM. The organic layer was washed with 1N HCl and the aqueous layer was extracted with DCM (×3). The combined organic layers were washed twice with water, and brine, dried over Na$_2$SO$_4$, filtered and concentrated under reduced pressure. The crude solid was recrystallised in MeCN leading to the title compound (51 g) as a pale yellow solid. The filtrate could be concentrated and recrystallised in MeCN to give to another 10 g of the desired product $R_f$=0.34 (DCM/MeOH:95/5).

HRMS (M+H)$^+$ calculated for $C_{19}H_{18}{}^{35}ClN_2O_4$ 373.0955. found 373.0957.

Reference Compound E

Methyl[(3S)-5-(4-chlorophenyl)-7-(methyloxy)-2-thioxo-2,3-dihydro-1H-1,4-benzodiazepin-3-yl]acetate

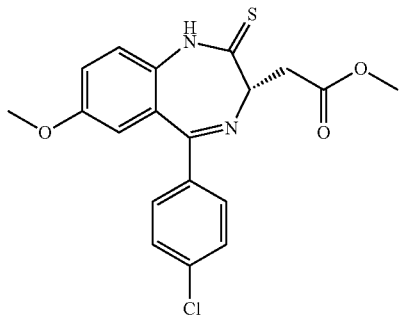

A suspension of $P_4S_{10}$ (36.1 g, 81.1 mmol) and $Na_2CO_3$ (8.6 g, 81.1 mmol) in 1,2-DCE (700 mL) at room temperature was stirred for 2 h before Methyl[(3S)-5-(4-chlorophenyl)-7-(methyloxy)-2-oxo-2,3-dihydro-1H-1,4-benzodiazepin-3-yl]acetate (for a preparation see Reference compound D) (16.8 g, 45.1 mmol) was added. The resulting mixture was stirred at 70° C. for 2 h before being cooled and filtered. The solid was washed twice with DCM and the filtrate washed with sat. NaHCO$_3$ and brine. The organic layer was dried over Na$_2$SO$_4$, filtered and concentrated under reduced pressure. The crude product was purified by flash-chromatography on silica gel (DCM/MeOH:99/1) to afford the title compound (17.2 g, 98% yield) as a yellowish solid. LC/MS (Method D): m/z 389 [M($^{35}$Cl)+H]$^+$, Rt 2.64 min HRMS (M+H)$^+$ calculated for $C_{19}H_{18}{}^{35}ClN_2O_3S$ 389.0727. found 389.0714.

Reference Compound F

Methyl[(3S)-2-[(1Z)-2-acetylhydrazino]-5-(4-chlorophenyl)-7-(methyloxy)-3H-1,4-benzodiazepin-3-yl]acetate

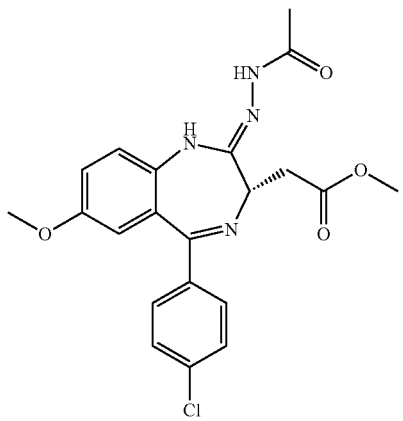

To a suspension of methyl[(3S)-5-(4-chlorophenyl)-7-(methyloxy)-2-thioxo-2,3-dihydro-1H-1,4-benzodiazepin-3-yl]acetate (for a preparation see Reference compound E (9.0 g, 23.2 mmol) in THF (300 mL) at 0° C. was added hydrazine monohydrate (3.4 mL, 69.6 mmol) dropwise. The reaction mixture was stirred for 5 h between 5° C. and 15° C. before being cooled at 0° C. Et$_3$N (9.7 mL, 69.6 mmol) was then added slowly and acetyl chloride (7.95 mL, 69.6 mmol) was added dropwise. The mixture was then allowed to warm to room temperature for 16 h before being concentrated under reduced pressure. The crude product was dissolved in DCM and washed with water. The organic layer was dried over Na$_2$SO$_4$, filtered and concentrated in vacuo to give the crude title compound (9.7 g, 98% yield) which was used without further purification. $R_f$=0.49 (DCM/MeOH:90/10).

Reference Compound G

Methyl[(4S)-6-(4-chlorophenyl)-1-methyl-8-(methyloxy)-4H-[1,2,4]triazolo[4,3-a][1,4]benzodiazepin-4-yl]acetate

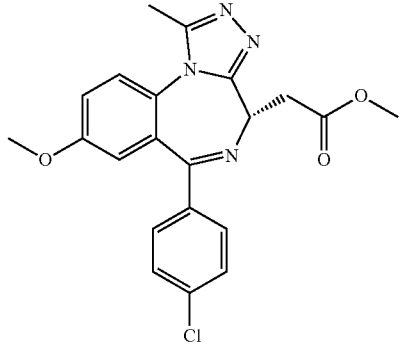

The crude methyl[(3S)-2-[(1Z)-2-acetylhydrazino]-5-(4-chlorophenyl)-7-(methyloxy)-3H-1,4-benzodiazepin-3-yl] acetate (for a preparation see Reference compound F) (assumed 9.7 g) was suspended in THF (100 ml) and AcOH (60 mL) was added at room temperature. The reaction mixture was stirred at this temperature for 2 days before being concentrated under reduced pressure. The crude solid was triturated in i-Pr$_2$O and filtered to give the title compound (8.7 g, 91% over 3 steps) as an off-white solid.

HRMS (M+H)$^+$ calculated for $C_{21}H_{20}ClN_4O_3$ 411.1229. found 411.1245.

Reference Compound H

[(4S)-6-(4-Chlorophenyl)-1-methyl-8-(methyloxy)-4H-[1,2,4]triazolo[4,3-a][1,4]benzodiazepin-4-yl] acetic acid

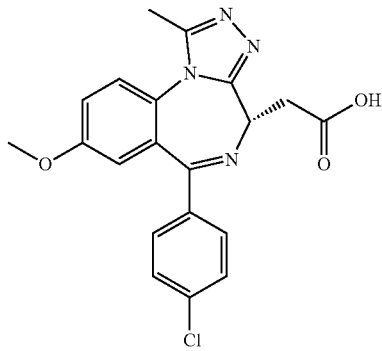 [SMILES: COc1ccc2c(c1)C(c1ccc(Cl)cc1)=N[C@@H](CC(=O)O)c1nnc(C)n1-2]

To a solution of methyl[(4S)-6-(4-chlorophenyl)-1-methyl-8-(methyloxy)-4H-[1,2,4]triazolo[4,3-a][1,4]benzodiazepin-4-yl]acetate (for a preparation see Reference compound G) (7.4 g, 18.1 mmol) in THF (130 mL) at room temperature was added 1N NaOH (36.2 mL, 36.2 mmol). The reaction mixture was stirred at this temperature for 5 h before being quenched with 1N HCl (36.2 mL) and concentrated in vacuo. Water is then added and the aqueous layer was extracted with DCM (×3) and the combined organic layers were dried over $Na_2SO_4$, filtered and concentrated under reduced pressure to give the title compound (7 g, 98% yield) as a pale yellow solid.

LC/MS (Method D): m/z 397 [M+H]$^+$

Reference Compound I 1,1-dimethylethyl[5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate

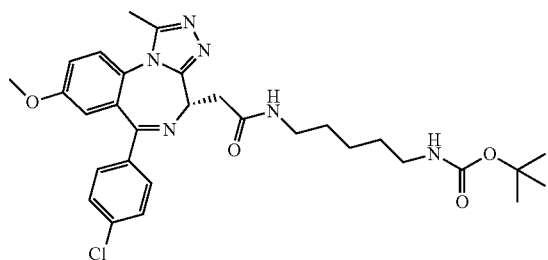 [SMILES: COc1ccc2c(c1)C(c1ccc(Cl)cc1)=N[C@@H](CC(=O)NCCCCCNC(=O)OC(C)(C)C)c1nnc(C)n1-2]

A mixture of [(4S)-6-(4-chlorophenyl)-1-methyl-8-(methyloxy)-4H-[1,2,4]triazolo[4,3-a][1,4]benzodiazepin-4-yl]acetic acid (for a preparation see Reference compound H) (1.0 g, 2.5 mmol), HATU (1.9 g, 5 mmol) and DIPEA (0.88 ml, 5 mmol) was stirred for 80 minutes at room temperature, to this was added 1,1-dimethylethyl (4-aminobutyl)carbamate (1.05 ml, 5.0 mmol, available from Aldrich). The reaction mixture was stirred at room temperature for 2 h before it was concentrated. The residue was taken up in dichloromethane and washed with 1N HCl. The aqueous layer was extracted with dichloromethane twice. Organic layer was washed with 1N sodium hydroxide, followed by a saturated solution of sodium chloride, dried over sodium sulphate and concentrated. The residue was purified by flash-chromatography on silica using dichloromethane/methanol 95/5 to give the title compound as a yellow solid (1.2 g). LC/MS (Method D): rt=3.04 min.

Reference Compound J

N-(5-aminopentyl)-2[(4S)-6-(4-chlorophenyl)-1-methyl-8-(methyloxy)-4H-[1,2,4]triazolo[4,3-a][1,4]benzodiazepin-4-yl]acetamide trifluoroacetate

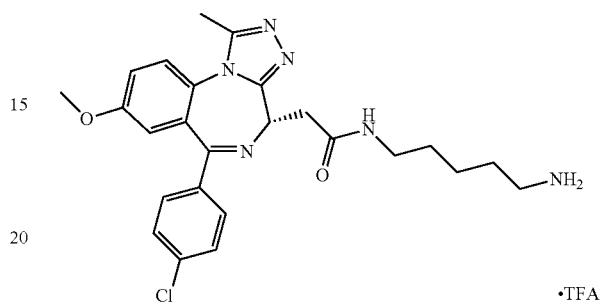

To a solution of 1,1-dimethylethyl[5-({[(4S)-6-(4-chlorophenyl)-1-methyl-8-(methyloxy)-4H-[1,2,4]triazolo[4,3-a][1,4]benzodiazepin-4-yl]acetyl}amino)pentyl]carbamate (for a preparation see Reference compound I) (0.2 g, 0.34 mmol) in dichloromethane (3 ml) was added trifluoroacetic acid (0.053 ml, 0.68 mmol) dropwise at 0° C. The reaction mixture was stirred for 3 h from 0° C. to room temperature. The reaction mixture was concentrated to dryness to afford the title compound as a hygroscopic yellow oil (200 mg)

LC/MS (Method D): rt=2.33 min.

HRMS (M+H)$^+$ calculated for $C_{25}H_{29}ClN_6O_2$ 481.2119. found 481.2162.

Reference Compound K

Mixture of 5- and 6-isomers of Alexa Fluor 488-N-(5-aminopentyl)-2-[(4S)-6-(4-chlorophenyl)-1-methyl-8-(methyloxy)-4H-[1,2,4]triazolo[4,3-a][1,4]benzodiazepin-4-yl]acetamide

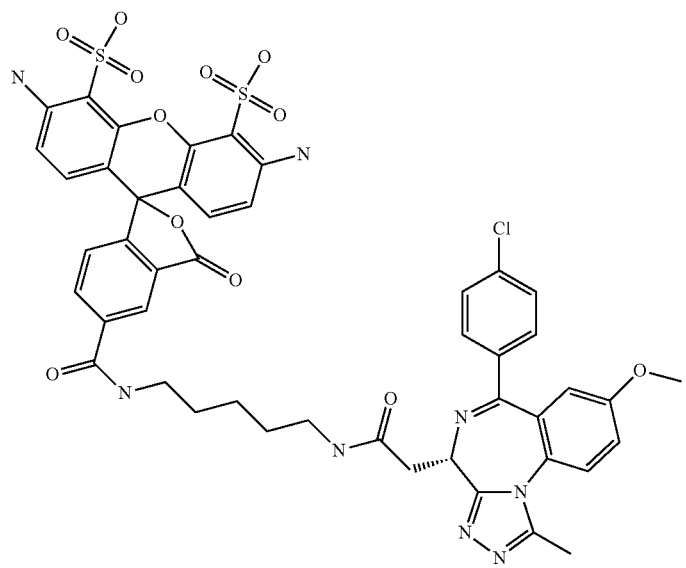

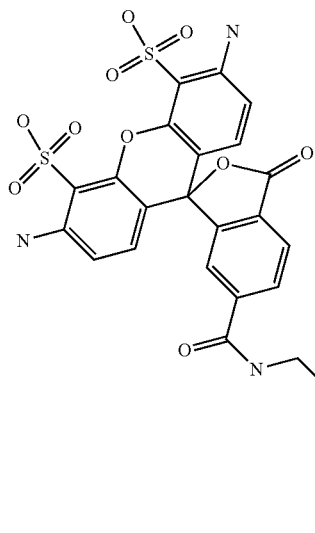
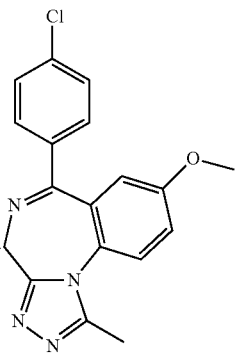

N-(5-Aminopentyl)-2-[(4S)-6-(4-chlorophenyl)-1-methyl-8-(methyloxy)-4H-[1,2,4]triazolo[4,3-a][1,4]benzodiazepin-4-yl]acetamide trifluoroacetate (for a preparation see Reference compound J) (7.65 mg, 0.013 mmol) was dissolved in N,N-Dimethylformamide (DMF) (300 μl) and added to Alexa Fluor 488 carboxylic acid succinimidyl ester (5 mg, 7.77 μmol, mixture of 5 and 6 isomers, available from Invitrogen, product number A-20100) in an Eppendorf centrifuge tube. Hunig's base (7.0 μl, 0.040 mmol) was added and the mixture vortex mixed overnight. After 18 h the reaction mixture was evaporated to dryness and the residue redissolved in DMSO/water (50%, <1 ml total), applied to a preparative Phenomenex Jupiter C18 column and eluted with a gradient of 95% A: 5% B to 100% B (A=0.1% trifluoroacetic acid in water, B=0.1% TFA/90% acetonitrile/10% water) at a flow rate of 10 ml/min over 150 minutes. Impure fractions were combined and re-purified using the same system. Fractions were combined and evaporated to yield the title product (2.8 mg) as a mixture of the 2 regioisomers shown.

LC/MS (Method F): MH+=999, rt=1.88 min.

Biological Test Methods

Fluorescence Anisotropy Binding Assay

The binding of the compounds of formula (I) to Bromodomains BRD2, BRD3 and BRD4 was assessed using a Fluorescence Anisotropy Binding Assay.

The Bromodomain protein, fluorescent ligand (Reference compound K see above) and a variable concentration of test compound are incubated together to reach thermodynamic equilibrium under conditions such that in the absence of test compound the fluorescent ligand is significantly (>50%) bound and in the presence of a sufficient concentration of a potent inhibitor the anisotropy of the unbound fluorescent ligand is measurably different from the bound value.

All data was normalized to the mean of 16 high and 16 low control wells on each plate. A four parameter curve fit of the following form was then applied:

$$y = a + ((b-a)/(1+(10^x/10^c)^d))$$

Where 'a' is the minimum, 'b' is the Hill slope, 'c' is the pIC50 and 'd' is the maximum.

Recombinant Human Bromodomains (BRD2 (1-473), BRD3 (1-435) and BRD4 (1-477)) were expressed in E. coli cells (in pET15b vector) with a six-His tag at the N-terminal. The His-tagged Bromodomain was extracted from E. coli cells using 0.1 mg/ml lysozyme and sonication. The Bromodomain was then purified by affinity chromatography on a HisTRAP HP column, eluting with a linear 10-500 mM Imidazole gradient, over 20 Cv. Further purification was completed by Superdex 200 prep grade size exclusion column. Purified protein was stored at −80 C in 20 mM HEPES pH 7.5 and 100 mM NaCl.

Protocol for Bromodomain BRD2: All components were dissolved in buffer composition of 50 mM HEPES pH7.4, 150 mm NaCl and 0.5 mM CHAPS with final concentrations of BRD2, 75 nM, fluorescent ligand 5 nM. 10 μl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision ($\lambda$x=485 nm, $\lambda$EM=530 nm; Dichroic −505 nM).

Protocol for Bromodomain BRD3: All components were dissolved in buffer of composition 50 mM HEPES pH7.4, 150 mm NaCl and 0.5 mM CHAPS with final concentrations of BRD3 75 nM, fluorescent ligand 5 nM. 10 μl of this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision ($\lambda$x=485 nm, $\lambda$EM=530 nm; Dichroic −505 nM).

Protocol for Bromodomain BRD4: All components were dissolved in buffer of composition 50 mM HEPES pH7.4, 150 mm NaCl and 0.5 mM CHAPS with final concentrations of BRD4 75 nM, fluorescent ligand 5 nM. 10 of μl this reaction mixture was added using a micro multidrop to wells containing 100 nl of various concentrations of test compound or DMSO vehicle (1% final) in Greiner 384 well Black low volume microtitre plate and equilibrated in dark 60 mins at room temperature. Fluorescence anisotropy was read in Envision ($\lambda$x=485 nm, $\lambda$EM=530 nm; Dichroic −505 nM).

All examples (with the exception of Examples 63, 72, 97, 112-114, 116, 121 and 122) were tested in the BRD2, BRD3 and BRD4 assays described above. All tested compounds had a pIC50 ≥5.0 in one or more of the BRD2, BRD3 and BRD4 assays described above.

Examples 1-36, 39-43, 46-60, 62, 64-69, 73-76, 78-81, 83-86, 90, 91, 94-96, 98, 99, 101, 102, 104-111, 115, 120 and 123 had a pIC50 ≥6.0 in one or more of the BRD2, BRD3 and BRD4 assays described above.

LPS Stimulated Whole Blood Measuring TNFα Levels Assay

Activation of monocytic cells by agonists of toll-like receptors such as bacterial lipopolysaccharide (LPS) results in production of key inflammatory mediators including TNFα. Such pathways are widely considered to be central to the pathophysiology of a range of auto-immune and inflammatory disorders.

Compounds to be tested are diluted to give a range of appropriate concentrations and 1 ul of the dilution stocks is added to wells of a 96 plate. Following addition of whole blood (130 ul) the plates are incubated at 37 degrees (5% CO2) for 30 min before the addition of 10 ul of 2.8 ug/ml lipopolysaccharides (LPS), diluted in complete RPMI 1640 (final concentration=200 ng/ml), to give a total volume of 140 ul per well. After further incubation for 24 hours at 37 degrees, 140 ul of PBS are added to each well. The plates are sealed, shaken for 10 minutes and then centrifuged (2500 rpm×10 min). 100 ul of the supernatant are removed and TNFα levels assayed by immunoassay (typically by MesoScale Discovery technology) either immediately or following storage at −20 degrees. Dose response curves for each compound was generated from the data and an IC50 value was calculated.

Examples 1-22, 24, 27-34, 36, 39-46, 48-60, 62, 111, 115 and 120 were tested in the above assay and were found to have a pIC50≥5.2. Examples 1-3, 5-7, 9, 12-14, 16, 19-21, 24, 27-29, 34, 40, 54-60 and 62 were found to have a pIC50≥6.5.

Measurement of LPS Induced IL-6 Secretion from Whole Blood

Activation of monocytic cells by agonists of toll-like receptors such as bacterial lipopolysaccharide (LPS) results in production of key inflammatory mediators including IL-6. Such pathways are widely considered to be central to the pathophysiology of a range of auto-immune and inflammatory disorders.

Compounds to be tested are diluted to give a range of appropriate concentrations of which 1 ul of the diluted stocks is added to a 96 well plate. Following addition of whole blood (130 ul) the plates are incubated at 37 degrees (5% CO2) for 30 min before the addition of 10 ul of 2.8 ug/ml LPS, diluted in complete RPMI 1640 (final concentration=200 ng/ml), to give a total volume of 140 ul per well. After further incubation for 24 hours at 37 degrees, 140 ul of PBS are added to each well. The plates are sealed, shaken for 10 minutes and then centrifuged (2500 rpm×10 min). 100 ul of the supernatant are removed and IL-6 levels assayed by immunoassay (typically by MesoScale Discovery technology) either immediately or following storage at −20 degrees. Concentration response curves for each compound was generated from the data and an $IC_{50}$ value was calculated.

Examples 1, 2, 12, 64-71, 73-90, 92-96, 98-110 and 123 were tested in the above assay and were found to have a pIC50≥4.5. Examples 1, 2, 12, 73, 75, 80, 98, 104, 105, 107 and 108 were found to have a pIC50≥6.0.

These data demonstrate that bromodomain inhibitors tested in the above two whole blood assays inhibited the production of key inflammatory mediators TNFα and/or IL-6.

All publications, including but not limited to patents and patent applications, cited in this specification are herein incorporated by reference as if each individual publication were specifically and individually indicated to be incorporated by reference herein as though fully set forth.

What is claimed is:

1. A compound of formula (I) or a salt thereof

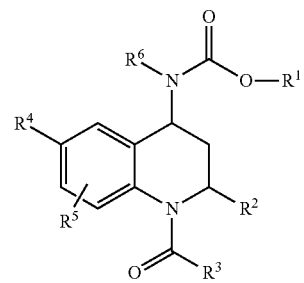

(I)

in which $R^1$ is $C_{1-6}$alkyl, $C_{3-7}$cycloalkyl or benzyl;

$R^2$ is $C_{1-4}$-alkyl;

$R^3$ is $C_{1-4}$alkyl;

$R^4$ is (i) halogen;
 (ii) hydroxy; or
 (iii) a group of formula (iii)

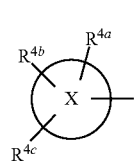

(iii)

in which

X is aryl or heteroaryl;

$R^{4a}$ is hydrogen, $C_{1-4}$alkyl or is a group L-Y in which L is a single bond or a $C_{1-6}$alkylene group and Y is OH, OMe, $CO_2H$, $CO_2C_{1-6}$alkyl, CN or $NR^7R^8$;

$R^7$ and $R^8$ are independently hydrogen, a heterocyclyl ring, $C_{1-6}$alkyl optionally substituted by hydroxy or a heterocyclyl ring; or $R^7$ and $R^8$ combine together to form a heterocyclyl ring optionally substituted by $C_{1-6}$alkyl, $CO_2C_{1-6}$alkyl, $NH_2$ or oxo;

$R^{4b}$ and $R^{4c}$ are independently hydrogen, halogen, $C_{1-6}$alkyl or $C_{1-6}$alkoxy;

$R^5$ is hydrogen, halogen, $C_{1-6}$alkyl or $C_{1-6}$alkoxy;

$R^6$ is hydrogen or $C_{1-4}$alkyl.

2. A compound or a salt thereof according to claim 1 which is a compound of formula (Ia)

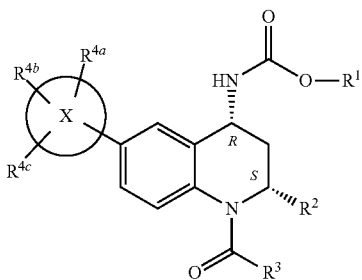

(Ia)

in which

R$^1$, R$^2$, R$^3$, R$^{4a-4c}$ and X are as defined in formula (I) and wherein S and R denote the stereochemistry at the adjacent chiral centre.

3. A compound or a salt thereof according to claim 1 in which X is phenyl or pyridyl.

4. A compound or a salt thereof according to claim 1 in which X is a heteroaryl group selected from the group consisting of furanyl, pyrazolyl, thiazolyl, pyridazinyl, pyrazinyl and pyrimidinyl.

5. A compound or a salt thereof according to claim 1 in which X is a heteroaryl group selected from the group consisting of imidazolyl, triazolyl, oxadiazolyl and thiadiazolyl.

6. A compound or a salt thereof according to claim 1 in which R$^1$ is isopropyl.

7. A compound or a salt thereof according claim 1 in which R$^2$ is methyl.

8. A compound or a salt thereof according to claim 1 in which R$^3$ is methyl.

9. A compound or a salt thereof according to claim 1 in which R$^4$ is a group of formula (iii) and R$^{4a}$ is a group L-Y wherein L is a single bond, CH$_2$ or CH$_2$CH$_2$ and Y is a group NR$^7$R$^8$ in which R$^7$ and R$^8$ are independently hydrogen or C$_{1-6}$alkyl.

10. A compound or a salt thereof according to claim 1 in which R$^4$ is a group of formula (iii) and R$^{4a}$ is a group L-Y wherein L is a single bond, CH$_2$ or CH$_2$CH$_2$ and Y is a group NR$^7$R$^8$ in which R$^7$ and R$^8$ combine together to form a heterocyclyl ring selected from the group consisting of pyrrolidinyl, piperidinyl, piperazinyl, morpholinyl, azepinyl and diazapinyl; said rings being optionally substituted by C$_{1-6}$alkyl, CO$_2$C$_{1-6}$alkyl, NH$_2$ or oxo.

11. A compound or a salt thereof according to claim 1 in which R$^4$ is a group of formula (iii) and R$^{4a}$ is a group L-Y wherein L is a single bond, CH$_2$ or CH$_2$CH$_2$ and Y is a CO$_2$H group.

12. A compound or a salt thereof according to claim 1 in which in R$^5$ is hydrogen.

13. A compound or a salt thereof according to claim 1 in which R$^6$ is hydrogen.

14. A compound or salt according to claim 1 wherein said compound or salt is any one of Examples 1-123 or a salt thereof.

15. A compound or salt according to claim 1 wherein said salt is a pharmaceutically acceptable salt.

16. A pharmaceutical composition which comprises a compound or a pharmaceutically acceptable salt thereof according to claim 15 and one or more pharmaceutically acceptable carriers, diluents or excipients.

17. A method for inhibiting a bromodomain which comprises contacting the bromodomain with a compound of formula (I) or a pharmaceutically acceptable salt thereof as defined in claim 15.

* * * * *